United States Patent
Choi-Sledeski et al.

(10) Patent No.: US 6,602,864 B1
(45) Date of Patent: *Aug. 5, 2003

(54) SULFONIC ACID OR SULFONYLAMINO N-(HETEROARALKYL)-AZAHETEROCYCLYLAMIDE COMPOUNDS

(75) Inventors: Yong Mi Choi-Sledeski, Collegeville, PA (US); Henry W. Pauls, Collegeville, PA (US); Jeffrey N. Barton, Philadelphia, PA (US); William R. Ewing, Downingtown, PA (US); Daniel M. Green, Ambler, PA (US); Michael R. Becker, Norristown, PA (US); Yong Gong, Norristown, PA (US)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/090,492

(22) Filed: Jun. 3, 1998

Related U.S. Application Data

(63) Continuation-in-part of application No. PCT/US97/22406, filed on Dec. 3, 1997
(60) Provisional application No. 60/033,159, filed on Dec. 13, 1996.

(51) Int. Cl.$^7$ .......................... A61K 31/55; A61K 31/47; C07D 217/00; C07D 223/00; C07D 205/08
(52) U.S. Cl. .................... 514/210.02; 514/210.04; 514/210.09; 514/210.16; 514/210.21; 514/212.07; 514/212.08; 514/213.01; 514/217.07; 514/307; 514/309; 514/310; 540/203; 540/354; 540/356; 540/363; 540/364; 540/523; 540/524; 540/593; 540/594; 540/595; 540/597; 546/139; 546/141; 546/142; 546/143; 546/145; 546/146

(58) Field of Search ................ 514/307, 309, 514/310, 210.02, 210.04, 210.09, 210.16, 210.21, 212.07, 212.08, 213.01, 217.07; 540/203, 354, 356, 363, 364, 523, 524, 593, 594, 595, 597; 546/139, 141, 142, 143, 145, 146

(56) References Cited

U.S. PATENT DOCUMENTS 6,194,409 B1 * 2/2001 Van Boeckel et al. ...... 514/243
6,281,227 B1 * 8/2001 Choi-Sledeski et al. .... 514/307

OTHER PUBLICATIONS

Bristol, James A., Ed., Thrombin and Factor Xa Inhibition, Annual Reports in Medicinal Chemistry, vol. 31, pp. 51–60, 1996.*

* cited by examiner

*Primary Examiner*—Brenda Coleman
(74) *Attorney, Agent, or Firm*—Raymond S. Parker, III; Irving Newman

(57) ABSTRACT

The compounds of formula I herein exhibit useful pharmacological activity and accordingly are incorporated into pharmaceutical compositions and used in the treatment of patients suffering from certain medical disorders. More specifically, they are inhibitors of the activity of Factor Xa. The present invention is directed to compounds of formula I, compositions containing compounds of formula I, and their use, which are for treating a patient suffering from, or subject to, physiological condition which can be ameliorated by the administration of an inhibitor of the activity of Factor Xa.

33 Claims, No Drawings

SULFONIC ACID OR SULFONYLAMINO N-(HETEROARALKYL)-AZAHETEROCYCLYLAMIDE COMPOUNDS

This application is a continuation-in-part of PCT patent application Ser. No. US97/22406, filed Dec. 3, 1997, which in turn is a nonprovisional application of U.S. Provisional Patent Application Ser. No. 60/033,159, filed Dec. 13, 1996, now abandoned.

FIELD OF THE INVENTION

The compounds of formula I exhibit useful pharmacological activity and accordingly are incorporated into pharmaceutical compositions and used in the treatment of patients suffering from certain medical disorders. More specifically, they are Factor Xa inhibitors. The present invention is directed to compounds of formula I, compositions containing compounds of formula I, and their use, which are for treating a patient suffering from, or subject to, conditions which can be ameliorated by the administration of an inhibitor of Factor Xa.

Factor Xa is the penultimate enzyme in the coagulation cascade. Both free factor Xa and factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to the pharmaceutical use of a compound of formula I below for treating a patient suffering from a physiological disorder capable of being modulated by inhibiting the activity of Factor Xa, where formula I is as follows:

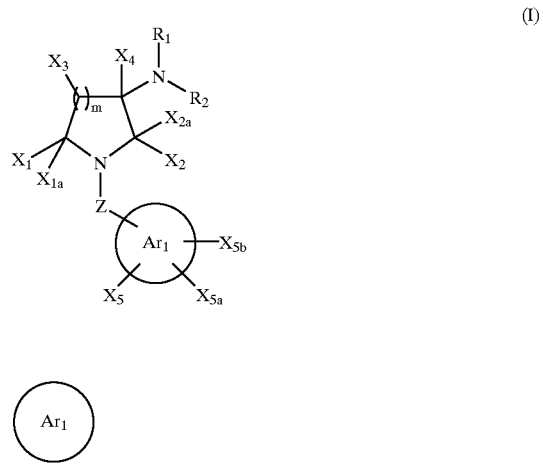

(I)

is a bicyclic heteroaryl containing at least one nitrogen atom in the distal ring thereof to the proximal ring thereof that is attached to Z;

Z is alkylenyl;

$R_1$ is hydrogen, optionally substituted alkyl, optionally substituted aralkyl, optionally substituted heteroaralkyl, $R'O(CH_2)_x-$, $R'O_2C(CH_2)_x-$, $Y^1Y^2NC(O)(CH_2)_x-$, or $Y^1Y^2N(CH_2)_x-$;

R' is hydrogen, optionally substituted alkyl, optionally substituted aralkyl or optionally substituted heteroaralkyl;

$R_2$ is $R_3S(O)_p-$ or $R_3R_4NS(O)_p-$;

$R_3$ is optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or $R_1$ and $R_3$ taken together with the $-N-S(O)_p-$ moiety or the $-N-S(O)_p-NR_4-$ moiety through which $R_1$ and $R_3$ are linked form a 5 to 7 membered optionally substituted heterocyclyl; and $R_4$ is optionally substituted alkyl, optionally substituted cycloalkyl or optionally substituted aryl, optionally substituted heteroaryl, optionally substituted aralkyl or optionally substituted heteroaralkyl, or $R_3$ and $R_4$ taken together with the nitrogen to which $R_3$ and $R_4$ are attached form an optionally substituted 4 to 7 membered heterocyclyl;

$X_1$ and $X_{1a}$ are independently selected from H, optionally substituted alkyl, optionally substituted aryl, optionally substituted aralkyl, optionally substituted heteroaryl or optionally substituted heteroaralkyl, or $X_1$ and $X_{1a}$ taken together form oxo;

$X_2$ and $X_{2a}$ are H, or taken together form oxo;

$X_3$ is H, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1a}$ taken together form a 4 to 7 membered cycloalkyl;

$X_4$ is H, optionally substituted alkyl, optionally substituted aralkyl, or hydroxyalkyl;

$X_5$, $X_{5a}$ and $X_{5b}$ are independently selected from H, $R_5R_6N-$, (hydroxy, alkoxy or amino)HN—, $R_7O-$, $R_5R_6NCO-$, $R_5R_6NSO_2-$, $R_7CO-$, halo, cyano, nitro or $R_8(O)C(CH_2)_q-$, and one of $X_5$, $X_{5a}$ and $X_{5b}$ is H, hydroxy or (H, optionally substituted lower alkyl, hydroxy, alkoxy or amino)HN— that substitutes the distal ring of

at a position alpha to a nitrogen thereof;

$Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl;

$R_5$ and $R_6$ are independently H or optionally substituted lower alkyl, or one of $R_5$ and $R_6$ is H and the other of $R_5$ and $R_6$ is $R_8(O)CCH_2-$ or lower acyl;

$R_7$ is H, optionally substituted lower alkyl, lower acyl or $R_8(O)CCH_2-$;

$R_8$ is H, optionally substituted lower alkyl, alkoxy or hydroxy;

m is 0, 1, 2 or 3;

p is 1 or 2;

q is 0 or 1, and x is 1, 2, 3, 4, or 5, or a pharmaceutically acceptable salt thereof, an N-oxide thereof, a hydrate thereof or a solvate thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, hydroxy, alkoxy, amino, acylamino, aroylamino, carboxy, alkoxycarbonyl, aralkyloxycarbonyl, heteroaralkyloxycarbonyl or $R_9R_{10}NCO-$, wherein $R_9$ and $R_{10}$ are independently hydrogen, optionally substituted alkyl, optionally substituted aryl, optionally substituted aralkyl or optionally substituted heteroaralkyl, or $Y^1$ and $Y^2$ taken together with the N through which $R_9$ and $R_{10}$ are linked form a 4 to 7 membered heterocyclyl. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, pyridylmethyloxycarbonylmethyl.

"Alkenyl" means an aliphatic hydrocarbon group containing a carbon-carbon double bond and which may be straight or branched having about 2 to about 15 carbon atoms in the chain. Preferred alkenyl groups have about 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo or cycloalkyl group. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Cycloalkyl" means a non-aromatic mono- or multicyclic ring system of about 3 to about 10 carbon atoms. Exemplary monocyclic cycloalkyl rings include cyclopentyl, fluorocyclopentyl, cyclohexyl and cycloheptyl. The cycloalkyl group is optionally partially unsaturated or optionally substituted by one or more halo, methylene ($H_2C=$), alkyl, fused aryl or fused heteroaryl. Exemplary multicyclic cycloalkyl rings include 1-decalin, adamant-(1- or 2-)yl and norbornyl.

"Heterocyclyl" means a non-aromatic monocyclic or multicyclic ring system of about 3 to about 10 ring atoms. Preferred rings include about 5 to about 6 ring atoms wherein one of the ring atoms is oxygen, nitrogen or sulfur. The heterocyclyl is optionally partially unsaturated or optionally substituted by one or more alkyl, halo, aryl, heteroaryl, fused aryl or fused heteroaryl. Exemplary monocyclic rings include pyrrolidyl, piperidyl, tetrahydrofuranyl, tetrahydrothienyl and tetrahydrothiopyranyl. The thio or nitrogen moiety of the heterocyclyl may also be optionally oxidized to the corresponding N-oxide, S-oxide or S,S-dioxide.

"Aryl" means 6 to 10 membered aromatic monocyclic or multicyclic hydrocarbon ring system. Exemplary aryl include phenyl or naphthyl, or phenyl substituted or naphthyl substituted with one or more aryl group substituents which may be the same or different, where "aryl group substituent" includes hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfonyl, alkylthio, alkylthio, heteroarylthio, aralkylthio, heteroaralkylthio, fused cycloalkyl, fused heterocyclyl, arylazo, heteroarylazo, $R_9R_{10}N-$, $R_9R_{10}NCO-$ or $R_9R_{10}NSO_2-$, wherein $R_9$ and $R_{10}$ are independently hydrogen, optionally substituted alkyl, optionally substituted aryl, optionally substituted aralkyl or optionally substituted heteroaralkyl, or $R_9$ and $R_{10}$ taken together with the N through which $R_9$ and $R_{10}$ are linked form a 4 to 7 membered heterocyclyl. The aryl group substituents are as defined herein. Preferred aryl groups are optionally substituted phenyl or optionally substituted naphthyl. Preferred aryl group substituents include hydrogen, alkyl, hydroxy, acyl, aryl aroyl, aryloxy, halo, nitro, alkoxy, cyano, alkoxycarbonyl, acylamino, alkylthio, $R_9R_{10}N-$, $R_9R_{10}NCO-$ or $R_9R_{10}NSO_2-$, where $R_9$ and $R_{10}$ are independently optionally substituted alkyl, aryl, aralkyl or heteroaralkyl; preferred phenyl group substituents are hydroxy, halogen, alkyl, amino.

"Heteroaryl" means about a 5- to about a 10-membered aromatic monocyclic or multicyclic hydrocarbon ring system in which one or more of the carbon atoms in the ring system is/are element(s) other than carbon, for example nitrogen, oxygen or sulfur. Where the heteroaryl is a multicyclic hydrocarbon ring system then one of said ring systems is optionally partially or fully saturated. The "heteroaryl" may also be substituted by one or more of the above-mentioned "aryl group substituents". Exemplary heteroaryl groups include pyrazinyl, furanyl, thienyl, pyridyl, pyrimidinyl, isoxazolyl, isothiazolyl, oxazolyl, thiazolyl, pyrazolyl, furazanyl, pyrrolyl, imidazo[2,1-b]thiazolyl, benzofurazanyl, indolyl, azaindolyl, benzimidazolyl, benzothienyl, quinolinyl, imidazolyl, thieniopyridyl, quinazolinyl, thienopyrimidyl, pyrrolopyridyl, imidazopyridyl, isoquiniolinyl and 1,2,3,4-tetrahydroisoquinolinyl. Where the heteroaryl is a multicyclic hydrocarbon ring system then it may be bonded through any of the ring systems. Preferred heteroaryl groups in the $R_1$ substituent include benzothienyl, thienyl, thienopyridyl, isoquinolinyl and quinolinyl all of which may be optionally substituted. Preferred

bicyclic heteroaryl groups include isoquinolinyl, quinolinyl, thienopyridyl, quinazolinyl, thienopyrimidyl, pyrrolopyridyl, (1,2- or 2,3-) benzodiazinyl and imidazopyridyl.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthlenemethyl.

"Heteroaralkyl" means a heteroaryl-alkyl- group in which the heteroaryl and alkyl are as previously described. Preferred heteroaralkyls contain a lower alkyl moiety. Exemplary heteroaralkyl groups may contain thienyl, pyridyl, imidazolyl and pyrazinyl.

"Aralkenyl" means an aryl-alkenyl- group in which the aryl and alkenyl are as previously described. Preferred aralkenyls contain a lower alkenyl moiety. An exemplary aralkenyl group is 2-phenethenyl.

"Heteroaralkenyl" means a heteroaryl-alkenlyl- group in which the heteroaryl and alkenyl are as previously described. Preferred heteroaralkenyls contain a lower alkenyl moiety. Exemplary heteroaralkenyl groups may contain thienyl, pyridyl, imidazolyl and pyrazinyl.

"Hydroxyalkyl" means a HO-alkyl- group in which alkyl is as previously defined. Preferred hydroxyalkyls contain lower alkyl, Exemplary hydroxyalkyl groups include hydroxymethyl and 1-hydroxymethyl.

"Acyl" means an H—CO— or alkyl-CO— group in which the alkyl group is as previously described. Preferred acyls contain a lower alkyl, Exemplary acyl groups include formyl, acetyl, propanoyl, 2-methylpropanoyl, butanoyl and palmitoyl.

"Aroyl" means an aryl-CO— group in which the aryl group is as previously described. Exemplary groups include benzoyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy, heptoxy and t-butoxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Exemplary aralkyloxy groups include benzyloxy and 1- or 2-naphthylmethoxy.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"$R_9R_{10}N$—" means a substituted or unsubstituted amino group, wherein $R_9$ and $R_{10}$ are as previously described. Exemplary groups include amino ($H_2N$—), methylamino, ethylmethylamino, dimethylamino, diethylamino, pyrrolidino and piperidino.

"Alkoxycarbonyl" means an alkyl-O—CO— group. Exemplary alkoxycarbonyl groups include (methoxy-, ethoxy- and t-butoxy)carbonyl.

"Aryloxycarbonyl" means an aryl-O—CO— group. Exemplary aryloxycarbonyl groups include phenoxy- and naphthoxycarbonyl.

"Aralkoxycarbonyl" means an aralkyl-O—CO— group. An exemplary aralkoxycarbonyl group is benzyloxycarbonyl.

"$R_9R_{10}NCO$—" means a substituted or unsubstituted carbamoyl group, wherein $R_9$ and $R_{10}$ are as previously described. Exemplary groups are carbamoyl ($H_2NCO$—) and dimethylcarbamoyl ($Me_2NCO$—).

"$R_9R_{10}NSO_2$—" means a substituted or unsubstituted sulfamoyl group, wherein $R_9$ and $R_{10}$ are as previously described. Exemplary groups are sulfamoyl ($H_2NSO_2$—) and dimethylsulfamoyl ($Me_2NSO_2$—).

"Acylamino" is an acyl—NH— group wherein acyl is as defined herein.

"Aroylamino" is an aroyl—NH— group wherein aroyl is as defined herein.

"Alkylsulfonyl" means an alkyl-$SO_2$— group. Preferred groups are those in which the alkyl group is lower alkyl.

"Arylsulfonyl" means an aryl-$SO_2$— group.

"Alkylenyl" means a methylenyl, ethylenyl or propylenyl group.

"Halo" means fluoro, chloro, bromo, or iodo. Preferred are fluoro, chloro or bromo, and more preferred are fluoro or chloro.

Preferred Embodiments

A preferred embodiment of the invention is a method for treating a patient suffering from a physiological disorder capable of being modulated by inhibiting an activity of Factor Xa by administering a therapeutically effective amount of a compound of formula I.

Another preferred compound aspect of the invention is the compound of formula I wherein $R_1$ is H, optionally substituted heteroaralkyl, optionally substituted aralkyl or optionally substituted alkyl.

Another preferred compound aspect of the invention is the compound of formula I wherein $R_2$ is $R_3S(O)_p$—, and more preferred is $R_3S(O)_p$— wherein p is 2.

Another preferred compound aspect of the invention is the compound of formula I wherein $R_3$ is optionally substituted phenyl, optionally substituted naphthyl, optionally substituted thienyl, optionally substituted benzothienyl, optionally substituted thienopyridyl, optionally substituted quinolinyl, or optionally substituted isoquinolinyl; more preferred $R_3$ is optionally substituted naphthyl, optionally substituted thienyl, optionally substituted benzothienyl and optionally substituted thienopyridyl.

Another preferred compound aspect of the invention is the compound of formula I wherein $R_3$ is

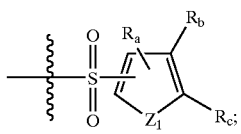

$R_a$ is hydrogen, alkyl, hydroxy, alkoxy, $Y^1Y^2N—$, halogen, $—CO_2R_d$, $—C(O)NY^1Y^2$, $—(CH_2)_xOR_d$, $—(CH_2)_xNY^1Y^2$, or $—CN$;

$R_b$ and $R_c$ are independently selected from hydrogen, hydroxy, alkoxy, $Y^1Y^2N—$, halogen, $—CO_2R_d$, $—C(O)NY^1Y^2$, $—(CH_2)_xOR_d$, $—(CH_2)_xNY^1Y^2$, $—CN$, optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or $R_b$ and $R_c$ taken together with the carbon atoms through which they are linked form an optionally substituted 5 to 7 membered fused cycloalkyl, optionally substituted 5 to 7 membered fused heterocyclyl ring or an optionally substituted 6 membered fused aryl, or an optionally substituted 5 to 6 membered fused heteroaryl ring;

$R_d$ is hydrogen, optionally substituted alkyl, optionally substituted aralkyl or optionally substituted heteroaralkyl;

$Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl;

$Z_1$ is S or $—CH═CH—$; and x is 1, 2, 3, 4, or 5.

Another preferred compound aspect of the invention is the compound of formula I wherein $R_3$ is optionally substituted aralkenyl or optionally substituted heteroaralkenyl; more preferably optionally substituted heteroaralkenyl.

Another preferred compound aspect of the invention is the compound of formula I where when $R_3$ is optionally substituted aralkenyl or optionally substituted heteroaralkenyl then the alkenyl moiety thereof is of the form

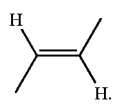

Another preferred compound aspect of the invention is the compound of formula I where when $R_3$ is optionally substituted aralkenyl or optionally substituted heteroaralkenyl then the alkenyl moiety thereof is of the formula

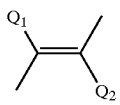

wherein one of $Q_1$ and $Q_2$ is hydrogen, lower alkyl (more preferably methyl), or halo (more preferably fluoro or chloro) and the other of $Q_1$ and $Q_2$ is lower alkyl (more preferably methyl), or halo (more preferably fluoro or chloro).

Another preferred compound aspect of the invention is the compound of formula I where when $R_3$ is optionally substituted aralkenyl then the aryl moiety thereof is halo substituted phenyl; more chloro substituted phenyl.

Another preferred compound aspect of the invention is the compound of formula I where when $R_3$ is optionally substituted heteroaralkenyl then the heteroaryl moiety thereof is halo substituted thienyl; more preferably 2-chlorothien-5-yl.

Another preferred compound aspect of the invention is the compound of formula I wherein $Z_1$ is $—CH═CH—$; and $R_b$ and $R_c$ taken together with the carbon atoms through which $R_b$ and $R_c$ are linked form an optionally substituted 5 or 6 membered heteroaryl ring, preferably containing at least one hetero atom which is N, or an optionally substituted 6 membered aryl ring, and wherein said substituents are preferably chloro, hydroxy or amino.

Another preferred compound aspect of the invention is the compound of formula I wherein $Z_1$ is $—CH═CH—$; $R_b$ is hydrogen; and $R_c$ is an optionally substituted heteroaryl ring, preferably 5 or 6 membered heteroaryl ring, preferably containing at least one hetero atom which is N or S, or an optionally substituted 6 membered aryl ring, and wherein said substituents are preferably chloro, hydroxy or amino.

Another preferred compound aspect of the invention is the compound of formula I wherein $Z_1$ is S (sulfur).

Another preferred compound aspect of the invention is the compound of formula I wherein $Z_1$ is S (sulfur); and $R_b$ and $R_c$ taken together with the carbon atoms through which $R_b$ and $R_c$ are linked form an optionally substituted 5 or 6 membered heteroaryl ring, preferably containing at least one hetero atom which is N, or an optionally substituted 6 membered aryl ring, and wherein said substituents are preferably chloro, hydroxy or amino.

Another preferred compound aspect of the invention is the compound of formula I wherein $Z_1$ is S (sulfur); $R_b$ is hydrogen; and $R_c$ is an optionally substituted heteroaryl ring, preferably 5 or 6 membered heteroaryl ring, preferably containing at least one hetero atom which is N or S, or an optionally substituted 6 membered aryl ring, and wherein said substituents are preferably chloro, hydroxy or amino.

Another preferred compound aspect of the invention is the compound of formula I wherein Z is methylenyl, and m is 1.

Another preferred compound aspect of the invention is the compound of formula I wherein $X_2$ and $X_{2a}$ taken together are oxo.

Another preferred compound aspect of the invention is the compound of formula I wherein $X_1$, $X_{1a}$, $X_3$ and $X_4$ are H.

Another preferred compound aspect of the invention is the compound of formula I wherein

is an optionally substituted isoquinolinyl; more preferred the isoquinolinyl is attached to Z at the 7-position thereof.

Another preferred compound aspect of the invention is the compound of formula I wherein

is an optionally substituted quinolinyl; more preferred the quinolinyl is attached to Z at the 7-position thereof.

Another preferred compound aspect of the invention is the compound of formula I wherein

is an optionally substituted quinazolinyl; more preferred the quinazolinyl is attached to Z at the 7-position thereof.

Another preferred compound aspect of the invention is the compound of formula I wherein

is an optionally substituted moiety of formula

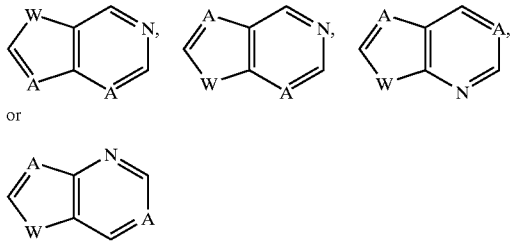

and W is S, O or $NR_{11}$, wherein $R_{11}$ is H, alkyl, aralkyl, heteroaralkyl, or $R_8(O)C(CH_2)_q$—, and A is independently CH or N; more preferably the moiety is bonded to Z through the ring containing W, and further preferred the moiety is bonded to Z through the ring containing W at the 2-position thereof.

Another preferred compound aspect of the invention is the compound of formula I wherein one of $X_5$, $X_{5a}$ and $X_{5b}$ is H, hydroxy or amino that is substituted on the proximal ring of

at a position that is adjacent to the position of the proximal ring to which Z is attached; more preferred one of $X_5$, $X_{5a}$ and $X_{5b}$ on the proximal ring as noted is hydroxy or amino.

Another preferred compound aspect of the invention is the compound of formula I wherein one of $X_5$, $X_{5a}$ and $X_{5b}$ that substitutes the distal ring of

at the position alpha to a nitrogen thereof is H or (H, optionally substituted loweralkyl, hydroxy or amino)HN—.

Species according to the invention are selected from the group consisting of:

7-Methoxynaphthalene-2-sulfonic acid [1-(1-aminoisoquinolin-7-yl-methyl)-2-oxopyrrolidin-3-(R,S)-yl]amide trifluoroacetate;

7-Methoxynaphthalene-2-sulfonic acid [1-(1-aminoisoquinolin-7-yl-methyl)-2-oxopyrrolidin-3-(S)-yl]amide hydrochloride;

7-Methoxynaphthalene-2-sulfonic acid [1-(1-aminoisoquinolin-7-yl-methyl)-2-oxopyrrolidin-3-(S)-yl]amide trifluoroacetate;

7-Methoxynaphthalene-2-sulfonic acid [1-(1-aminoisoquinolin-7-yl-methyl)-2-oxopyrrolidin-3-(R)-yl]amide trifluoroacetate;

7-Methoxynaphthalene-2-sulfonic acid [1-(1-hydroxyisoquinolin-7ylmethyl)-2-oxopyrrolidin-3-(R,S)-yl]amide;

7-Methoxynaphthalene-2-sulfonic acid [1-(1-aminoisoquinolin-7-ylmethyl)-2-oxopyrrolidin-3-(R,S)-yl]methylamide trifluoroacetate;

7-Methoxynaphthalene-2-sulfonic acid [1-(1-aminoisoquinolin-7-ylmethyl)-2-oxopyrrolidin-3-(S)-yl] methyl amide trifluoroacetate;

Benzo[b]thiophene-2-sulfonic acid [1-(1-aminoisoquinolin-7-ylmethyl)-2-oxopyrrolidin-3-(S)-yl]amide trifluoroacetate;

6-Chloro-Benzo[b]thiophene-2-sulfonic acid [1-(1-aminoisoquinolin-7-ylmethyl)-2-oxopyrrolidin-3-(S)-yl] amide trifluoroacetate;

7-Methoxynaphthalene-2-sulfonic acid [1-(1-amino-6-methoxyisoquinolin-7-ylmethyl)-2-oxopyrrolidin-3-(S)-yl]amide hydrochloride;

7-Methoxynaphthalene-2-sulfonic acid [1-(6-methoxyisoquinolin-7-ylmethyl)-2-oxo pyrrolidin-3-(S)-yl]amide trifluoroacetate;

4-(2-Chloro-6-nitrophenoxy)benzene sulfonic acid [1-(1-amino-6-methoxyisoquinolin-7-ylmethyl)-2-oxopyrrolidin-3-(S)-yl]amide trifluoroacetate;

7-Methoxynaphthalene-2-sulfonic acid [1-(1,6-diaminoisoquinolin-7-yl-methyl)-2-oxopyrrolidin-3-(S)-yl]amide trifluoroacetate;

6-Chloro-benzo[b]thiophene-2-sulfonic acid [1-(1,6-diaminoisoquinolin-7-yl-methyl)-2-oxo pyrrolidin-3-(S)-yl]amide trifluoroacetate;

7-Methoxynaphthalene-2-sulfonic acid [1-(2-aminoquinolin-7-ylmethyl)-2-oxopyrrolidin-3-(S)yl] amide trifluoroacetate;

6-Chloro-benzo[b]thiophene-2-sulfonic acid [1-(2-aminoquinolin-7-ylmethyl)-2-oxopyrrolidin-3-(S)-yl] amide trifluoroacetate;

Benzo[b]thiophene-2-sulfonic acid [1-(2-aminoquinolin-7-ylmethyl)-2-oxopyrrolidin-3-(S)-yl]amide trifluoroacetate;

7-Methoxynaphthalene-2-sulfonic acid [1-(2-aminoquinolin-7-ylmethyl)-2-oxopyrrolidin-3-(S)-yl] methyl amide trifluoroacetate;

7-Methoxynaphthalene-2-sulfonic acid [1-(2-hydroxyquinolin-7-ylmethyl)-2-oxopyrrolidin-3-(S)-yl] methyl amide;

7-Methoxynaphthalene-2-sulfonic acid [1-(2-aminoquinolin-5-ylmethyl)-2-oxopyrrolidin-3-(S)-yl] amide trifluoroacetate;

7-Methoxynaphthalene-2-sulfonic acid [1-(2-aminoquinolin-5-ylmethyl)-2-oxopyrrolidin-3-(S)-yl] methyl amide trifluoroacetate;

7-Methoxynaphthalene-2-sulfonic acid [1-(2-hydroxyquinolin-5-ylmethyl)-2-oxopyrrolidin-3-(S)-yl] methylamide;

7-Methoxynaphthalene-2-sulfonic acid [1-(2-aminoquinolin-6-ylmethyl)-2-oxopyrrolidin-3-(S)-yl] amide;

7-Methoxynaphthalene-2-sulfonic acid [1-(2-hydroxyquinolin-6-ylmethyl)-2-oxopyrrolidin-3-(S)-yl] amide;

7-Methoxynaphthalene-2-sulfonic acid [1-(1H-benzimidazol-5-ylmethyl)-2-oxopyrrolidin-3-(S)-yl] amide trifluoroacetate;

7-Methoxynaphthalene-2-sulfonic acid [2-(1H-benzimnidazol-5-ylmethyl)-2-oxopyrrolidin-3-(S)-yl] amide trifluoroacetate;

7-Methoxynaphthalene-2-sulfonic acid [1-(4-aminoquinazolin-6-ylmethyl)-2-oxopyrrolidin-3-(S)-yl] methylamide trifluoroacetate;

7-Methoxynaphthalene-2-sulfonic acid [1-(4-aminothieno[2,3-d]pyrimidin-6-yl-methyl)-2-oxopyrrolidin-3-(S)-yl] amide trifluoroacetate;

7-Methoxynaphthalene-2-sulfonic acid [2-(6-aminothieno[2,3-d]pyrimidin-6-yl-methyl)-2-oxopyrrolidin-3-(S)-yl] amide trifluoroacetate;

7-Methoxynaphthalene-2-sulfonic acid [1-(7-aminothieno[2,3-c]pyridin-3-yl-methyl)-2-oxopyrrolidin-3-(S)-yl] amide trifluoroacetate;

7-Methoxynaphthalene-2-sulfonic acid [1-(7-hydroxythieno[2,3-c]pyridin-3-yl-methyl)-2-oxopyrrolidin-3-(S)-yl] amide trifluoroacetate;

7-Methoxynaphthalene-2-sulfonic acid [1-(4-aminothieno[3,2-c]pyridin-3-yl-methyl)-2-oxopyrrolidin-3-(R,S)-yl] amide trifluoroacetate;

7-Methoxynaphthalene-2-sulfonic acid [1-(4-hydroxythieno[3,2-c]pyridin-3-yl-methyl)-2-oxopyrrolidin-3-(R,S)-yl] amide trifluoroacetate;

Benzo[b]thiophene-2-sulfonic acid [1-(4-aminothieno[3,2-c]pyridin-3-yl-methyl)-2-oxopyrrolidin-3-(R,S)-yl]amide trifluoroacetate;

Thieno[3,2-b]pyridine-2-sulfonic acid [1-(1-amino-isoquinolin-7-ylmethyl)-2-oxo-pyrrolidin-3-(S)-yl] amide;

Thieno[2,3-b]pyridine-2-sulfonic acid [1-(1-amino-isoquinolin-7-ylmethyl)-2-oxo-pyrrolidin-3-(S)-yl]-amide;

4-Pyridin-3-yl-thiophene-2-sulfonic acid [1-(1-amino-isoquinolin-7-ylmethyl)-2-oxo-pyrrolidin-3-(S)-yl]-amide;

5'Chloro-[2,2']bithiophenyl-5-sulfonic acid [2-oxo-1-(1H-pyrrolo[3,2-c]pyridin-2-ylmethyl)-pyrrolidin-3(S)-yl]-amide;

2-(5-Chloro-thiophen-2-yl)-ethenesulfonic acid [2-oxo-1-(1H-pyrrolo[3,2-c]pyridin-2-ylmethyl)-pyrrolidin-3-(S)-yl]-amide;

5'-Chloro-[2,2']bithiophenyl-5-sulfonic acid [1-(1-amino-isoquinolin-7-ylmethyl)-2-oxo-pyrrolidin-3-(S)-yl]-amide;

2-(5-Chloro-thiophen-2-yl)-ethenesulfonic acid [1-(1-amino-isoquinolin-7-ylmethyl)-2-oxo-pyrrolidin-3-(S)-yl]-amide;

6-Chloro-benzo[b]thiophene-2-sulfonic acid [1-(4-aminoquinazolin-6-yl-methyl)-2-oxopyrrolidin-3-(S)-yl]amide trifluoroacetate;

6-Chloro-benzo[b]thiophene-2-sulfonic acid [1-(4-aminothieno[2,3-d]pyrimidin-6-yl-methyl)-2-oxopyrrolidin-3-(S)-yl]amide trifluoroacetate;

6-Chloro-benzo[b]thiophene-2-sulfonic acid [1-(4-aminothieno[3,2-d]pyrimidin-7-yl-methyl)-2-oxopyrrolidin-3-(S)-yl]amide trifluoroacetate; and 5'-Chloro-[2,2']bithiophenyl-5-2-sulfonic acid [1-(4-aminothieno[3,2-d]pyrimidin-7-yl-methyl)-2-oxopyrrolidin-3-(S)-yl]amide trifluoroacetate.

More preferred species according to the invention are selected from the group consisting of 7-Methoxynaphthalene-2-sulfonic acid [1-(1-aminoisoquinolin-7-ylmethyl)-2-oxopyrrolidin-3-(S)-yl] amide trifluoroacetate;

7-Methoxynaphthalene-2-sulfonic acid [1-(1-aminoisoquinolin-7-ylmethyl)-2-oxopyrrolidin-3-(R)-yl] amide trifluoroacetate;

7-Methoxynaphthalene-2-sulfonic acid-[1-(1-aminoisoquinolin-7-ylmethyl)-2-oxopyrrolidin-3-(S)-yl] methylamide trifluoroacetate;

Benzo[b]thiophene-2-sulfonic acid [1-(1-aminoisoquinolin-7-ylmethyl)-2-oxopyrrolidin-3-(S)-yl]amide trifluoroacetate;

6-Chloro-benzo[b]thiophene-2-sulfonic acid [1-(1-aminoisoquinolin-7-ylmethyl)-2-oxopyrrolidin-3-(S)-yl] amide trifluoroacetate;

7-Methoxynaphthalene-2-sulfonic acid-[1-(1,6-diaminoisoquinolin-7-ylmethyl)-2-oxopyrrolidin-3-(S)-yl]amide trifluoroacetate;

6-Chloro-benzo[b]thiophene-2-sulfonic acid[1-(1,6-diaminoisoquinolin-7-yl-methyl)-2-oxopyrrolidin-3-(S)-yl]amide trifluoroacetate;

7-Methoxynaphthalene-2-sulfonic acid [1-(2-aminoquinolin-7-ylmethyl)-2-oxopyrrolidin-3-(S)-yl] amide trifluoroacetate;

6-Chloro-benzo[b]thiophene-2-sulfonic acid [1-(2-aminoquinolin-7-ylmethyl)-2-oxopyrrolidin-3-(S)-yl]-amide trifluoroacetate;

Benzo[b]thiophene-2-sulfonic acid [1-(2-aminoquinolin-7-ylmethyl)-2-oxopyrrolidin-3-(S)-yl]amide trifluoroacetate;

7-Methoxynaphthalene-2-sulfonic acid [1-(4-aminothieno[3,2-c]pyridin-2-ylmethyl)-2-oxo-3-yl]amide trifluoroacetate;

Benzo[b]thiophene-2-sulfonic acid [1-(4-aminothieno[3,2-c]pyridin-2-ylmethyl)-2-oxo-3-yl]-amide trifluoroacetate;

5-Pyridin-4-yl-thiophene-2-sulfonic acid-[1-(1-aminoisoquinolin-7-ylmethyl)-2-oxopyrrolidin-3-(S)-yl]-amide trifluoroacetate;

5-Pyridin-3-yl-thiophene-2-sulfonic acid-[1-(1-aminoisoquinolin-7-ylmethyl)-2-oxopyrrolidin-3-(S)-yl]-amide trifluoroacetate;

Benzothiophene-2-sulfonic acid [1-(4-aminoquinolin-6-ylmethyl)-2-oxopyrrolidin-3-(S)-yl]-amide trifluoroacetate;

6-Chloro-benzo[b]thiophene-2-sulfonic acid [2-oxo-1-(1H-pyrrolo[3,2-c]pyridin-2-ylmethyl)-pyrrolidin-3-(S)-yl]-amide;

7-Methoxynaphthalene-2-sulfonic acid [2-oxo-1-(1H-pyrrolo[3,2-b]pyridin-2-ylmethyl)-pyrrolidin-3-(S)-yl]-amide trifluoroacetate;

6-Chloro-benzo[b]thiophene-2-sulfonic acid [2-oxo-1-(1H-pyrrolo[3,2-b]pyridin-2-ylmethyl)-pyrrolidin-3-(S)-yl]-amide trifluoroacetate;

6-Chloro-benzo[b]thiophene-2-sulfonic acid [2-oxo-1-(1H-pyrrolo[2,3-c]pyridin-2-ylmethyl)-pyrrolidin-3-(S)-yl]-amide trifluoroacetate;

Thieno[3,2-b]pyridine-2-sulfonic acid [2-oxo-1-(1H-pyrrolo[2,3-c]pyridin-2-ylmethyl)-pyrrolidin-3-(S)-yl]-amide ditrifluoroacetate;

Thieno[3,2-b]pyridine-2-sulfonic acid [1-(1-amino-isoquinolin-7-ylmethyl)-2-oxo-pyrrolidin-3-(S)yl]-amide;

5'Chloro-[2,2']bithiophenyl-5-sulfonic acid [2-oxo-1-(1H-pyrrolo[3,2-c]pyridin-2-ylmethyl)-pyrrolidin-3(S)-yl]-amide;

2-(5-Chloro-thiophen-2-yl)-ethenesulfonic acid [2-oxo-1-(1H-pyrrolo[3,2-c]pyridin-2-ylmethyl)-pyrrolidin-3-(S)-yl]-amide;

6-Chloro-benzo[b]thiophene-2-sulfonic acid [1-(4-amino-thieno[2,3-d]pyrimidin-6-yl-methyl)-2-oxopyrrolidin-3-(S)-yl]amide trifluoroacetate;

6-Chloro-benzo[b]thiophene-2-sulfonic acid [1-(4-amino-thieno[3,2-d]pyrimidin-7-yl-methyl)-2-oxopyrrolidin-3-(S)-yl]amide trifluoroacetate; and 5'-Chloro-[2,2']bithiophenyl-5-2-sulfonic acid [1-(4-amino-thieno[3,2-d]pyrimidin-7-yl-methyl)-2-oxopyrrolidin-3-(S)-yl]amide trifluoroacetate.

This invention also encompasses all combinations of preferred aspects of the invention noted herein.

A compound of formula I may be prepared by the application or adaptation of known methods, by which is meant methods used heretofore or described in the literature.

A preparative embodiment according to the invention for preparing a compound of formula I wherein $Ar_1$, $R_1$, $R_2$, $X_3$, $X_4$, $X_5$, $X_{5a}$, $X_{5b}$, Z and m are as defined above, $X_1$ and $X_{1a}$ are H and $X_2$ and $X_{2a}$, taken together form oxo, may be prepared by coupling a compound of formula II

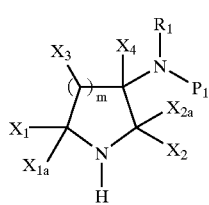

(II)

wherein $X_3$, $X_4$ and m are as defined above, $X_1$ and $X_{1a}$ are H, $X_2$ and $X_{2a}$ taken together form oxo, and $P_1$ is an (alkyl, aralkyl or aryl) carbamate with a compound of formula III

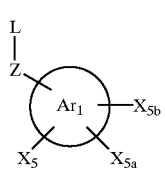

(III)

wherein $Ar_1$, $X_5$, $X_{5a}$ $X_{5b}$ and Z are as defined above, and one of $X_5$, $X_{5a}$, $X_{5b}$ is H, chloro, bromo or aryloxy at the position alpha to the nitrogen of the distal ring of $Ar_1$, and L is a leaving group such as chloro, bromo, iodo, or optionally substituted lower alkylsulfonyloxy or arylsulfonyloxy, to give a compound of formula IV

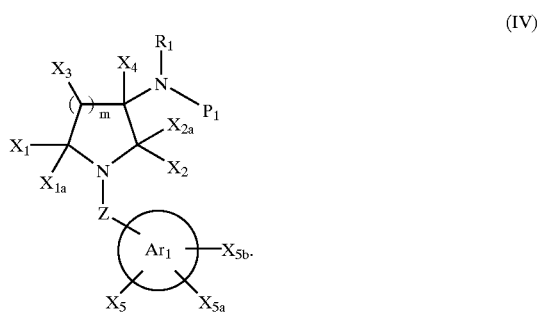

(IV)

A compound of formula IV is converted to a compound of formula I by the methods herein described.

A compound of formula III may be prepared by reacting a compound of formula V, wherein $X_{5c}$ is H, $R_5R_6N$—, $R_7O$—,

(V)

$R_5R_6NCO$—, $R_5R_6NSO_2$—, $R_7CO$—, halo, cyano, nitro or $R_8(O)C(CH_2)_q$—, and wherein an amino or hydroxy group thereof are suitably protected by an amino or hydroxy protecting group, n is 0 to 2, and $Ar_2$ is a monocyclic aryl or heteroaryl ring, with an appropriate malonic acid in a polar solvent such as pyridine or ethanol and a base such as piperidine or pyridine at reflux to give a compound of formula VI wherein $R_{12}$ is H,

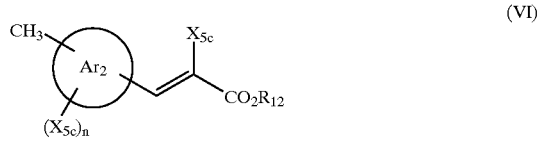

(VI)

$X_{5c}$ attached to the carboxymethylidene moiety is H, $X_{5c}$ attached to

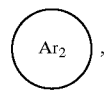, n and

are as described above. Alternatively, a compound of formula VI may be reacted with a suitable Wittig reagent in an inert solvent such as THF to give a compound of formula VI wherein $R_{12}$ is lower alkyl,

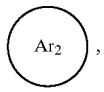

n and

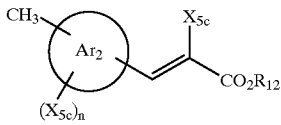
(VI)

$X_{5c}$ attached to the carboxymethylidene moiety or

are as described above. When $R_{12}$ is lower alkyl, the ester is hydrolyzed to the corresponding carboxylic acid, $R_{12}$ is H, by an appropriate strong acid or alkali base. The corresponding acid is converted to the acid chloride using standard methods such as thionyl chloride or is converted to the mixed anhydride in a polar solvent such as acetone or THF to form an activated acyl compound. The activated acyl compound is then treated with a solution of $NaN_3$ in water at about $-10°$ C. to about $25°$ C. to yield the corresponding acyl azide. The acyl azide compound is then heated slowly in an inert solvent such as benzene or toluene at about $60°$ C. to about $110°$ C. then concentrated in vacuo and heated in a higher boiling inert solvent such as 1,2-dichlorobenzene or phenyl ether at about $180°$ C. to about $240°$ C. with a catalyst such as iodine or tributylamine to obtain a compound of formula VII, wherein $X_{5c}$ is H, $R_5R_6N$—.

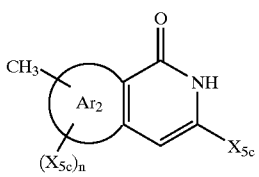
(VII)

$R_7O$—, $R_5R_6NCO$—, $R_5R_6NSO_2$—, $R_7CO$—, halo, cyano, nitro or $R_8(O)C(CH_2)_q$—, and wherein an amino or hydroxy group thereof are suitably protected by an amino or hydroxy protecting group, n is 0 to 2, and $Ar_2$ is a monocyclic aryl or heteroaryl ring. Alternatively the acyl azide compound can be added directly to a high boiling inert solvent such as phenyl ether at about $190°$ C. to about $240°$ C. with a catalyst such as iodine or tributylamine to obtain the compound of formula VII.

A compound of formula VIII, prepared as described in Syn., 739 (1975)

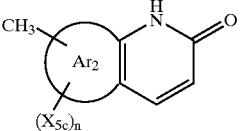
(VIII)

wherein $X_{5c}$ is H, $R_5R_6N$—, $R_7O$—, $R_5R_6NCO$—, $R_5R_6NSO_2$—, $R_7CO$—, halo, cyano, nitro or $R_8(O)C(CH_2)_q$—, and wherein an amino or hydroxy group thereof are suitably protected by an amino or hydroxy protecting group, n is 0 to 2, and $Ar_2$ is a monocyclic aryl or heteroaryl ring, or formula VII above, or those formulae wherein the amino or hydroxy moieties thereof are suitably protected by an amino or hydroxy protecting group, may be chlorinated using standard methods such as $POCl_3$ or $POCl_3/PCl_5$ to obtain the following corresponding chlorinated intermediates (IX) and (X), wherein $X_{5c}$, n and $Ar_2$ are as defined

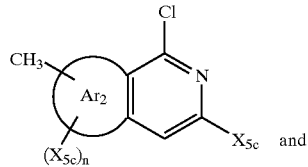
(IX)

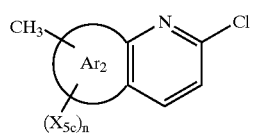
(X)

above.

Furthermore, a compound of formula IX and formula X wherein $X_{5c}$ is a protected amino moiety wherein the protection is effected with an acid labile group such as acyl or dibenzylidene can be deprotected using standard methods such as a strong acid in an alcoholic solvent such as ethanol or a polar solvent such as ethyl acetate to yield the free amine which can then be chlorinated as above. Alternatively the free amine may be liberated by the action of the $POCl_3$, but in either case the free amine may be reprotected with a suitable protecting group such as dibenzylidene.

A compound of formula XI, such as compounds of formulae IX and X, wherein $Ar_1$, $X_5$, $X_{5a}$ and $X_{5b}$ are as defined

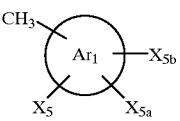
(XI)

above, and one of $X_5$, $X_{5a}$ and $X_{5b}$ is chloro at the position alpha to the nitrogen of the distal ring of $Ar_1$, and the methyl moiety is attached to the proximal ring of $Ar_1$, may be treated with NaBr or an arylhydroxy such as phenol and potassium hydroxide to afford a compound of formula XI wherein the chloro at the position alpha to the nitrogen of the distal ring of $Ar_1$ is replaced by bromo or aryloxy at that position.

The methyl moiety of a compound of formula XI, wherein $Ar_1$, $X_5$, $X_{5a}$ and $X_{5b}$ are as defined above, provided that wherein $X_5$, $X_{5a}$ and $X_{5b}$ is hydroxy or amino bearing a hydrogen then the hydroxy and amino are protected by appropriate hydroxy and/or amino protecting groups, may be halogenated using standard conditions such as N-halosuccinimide and benzoyl peroxide in an inert solvent such as carbon tetrachloride to give the corresponding halomethyl compound of formula III wherein L is bromo, chloro, or iodo, and one of $X_5$, $X_{5a}$ and $X_{5b}$ is chloro, bromo or aryloxy at the position alpha to the nitrogen of the distal ring of $Ar_1$.

Alternatively, a compound of formula III wherein is

is

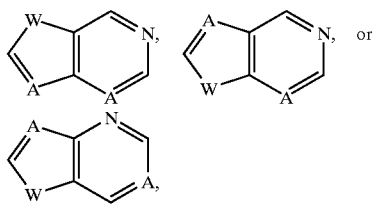

A is CH, W is NH and Z is methylenyl, L is halo, one of $X_5$, $X_{5a}$ and $X_{5b}$ is on the 5-member ring of

and is a substituent as defined above or one wherein amino or hydroxy moieties thereof are suitably protected, another of $X_5$, $X_{5a}$ and $X_{5b}$ is on the 6-member ring of

and is a substituent as defined above or one wherein amino or hydroxy moieties thereof are suitably protected, and the other of $X_5$, $X_{5a}$ and $X_{5b}$ is hydrogen, chloro, bromo or aryloxy and is substituted alpha to the nitrogen in the 6-member ring of

, may be prepared by reacting a compound of formula XII, formula XIII or XIIIa (prepared as

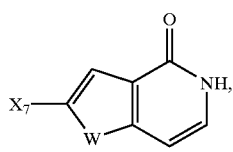 (XII)

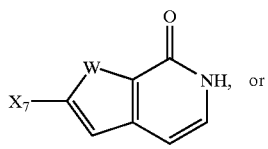 (XIII)

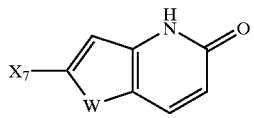 (XIIIa)

described in J. Het. Chem., 29, 359 (1992); Bull. Soc. Chim. Belg. 301 (1970); and J. Med. Chem. 33, 2087 (1990) wherein W is NH and $X_6$ is H, with $POCl_3$ or $POCl_3/PCl_5$ as described above to obtain the corresponding chloro compound. A compound of formula XII or formula XIII wherein W is NH and $X_6$ is H can be protected using standard methods such as with benzenesulfonyl chloride using a strong base such as sodium hydroxide in an halogenated solvent such as dichloromethane in the presence of a phase transfer catalyst such as tetrabutylammonium chloride to yield a compound of formula XII or I formula XIII wherein W is N—$SO_2Ph$ and $X_6$ is H. These are treated with a strong base such as sodium hydride, lithium hexamethyldisilylazide, or lithium diisopropyl amine in an inert organic solvent such as tetrahydrofuran or dimethylformamide at about −78° C. to about 25° C., followed by the addition of ethyl chloroformate to yield a compound of formula XII or formula XIII wherein W is N—$SO_2Ph$ and $X_6$ is —$CO_2$lower alkyl, which in turn can be converted to a compound of formula XII or formula XIII wherein W is N—$SO_2Ph$ and $X_6$ is —$CH_2OH$ using standard hydride reducing agents such as lithium aluminum hydride in an appropriate organic solvent such as diethyl ether at about −10° C. to about 25° C. Then a compound of formula XII or formula XIII wherein W is N—$SO_2Ph$ and $X_6$ is —$CH_2OH$ may be halogenated using standard conditions such as $PBr_3$ in an organic solvent such as diethyl ether to give a compound of formula III as defined above.

Alternatively, a compound of formula III may be prepared by condensing an appropriate beta-aryl or beta-heteroaryl amino acid of formulae XIV and XV, wherein W and $X_7$ are as defined

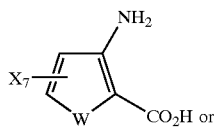 (XIV)

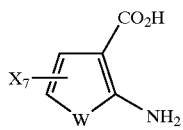 (XV)

herein, with Gold's reagent under basic conditions using sodium hydride or another equally strong base followed by an acidic work-up. The resulting compound is then processed as described above to yield a compound of formula III.

A compound of formula II as defined above is treated with a strong base such as sodium hydride, lithium hexamethyldisilylazide, or lithium diisopropyl amine in an inert organic solvent such as tetrahydrofuran or dimethylformamide at about −78° C. to about 25° C. followed by the addition of a compound of formula III above wherein one $X_5$, $X_{5a}$ and $X_{5b}$ is substituted alpha to a nitrogen of the distal ring of

and is hydrogen, chloro, bromo or aryloxy, and L is a good leaving group such as chloro, bromo, or iodo, to give a compound of formula IV above.

Alternatively a compound of formula IV wherein

is

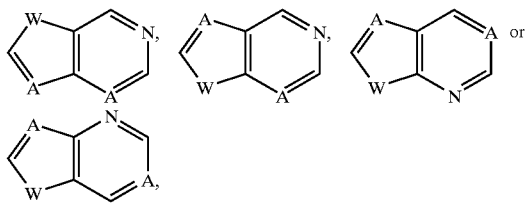

A is CH, W is NH and Z is methylenyl, L is halo, one of $X_5$, $X_{5a}$ and $X_{5b}$ is on the 5-member ring of

and is a substituent as defined above or one wherein amino or hydroxy moieties thereof are suitably protected, another of $X_5$, $X_{5a}$ and $X_{5b}$ is on the 6-member ring of

and is a substituent as defined above or one wherein amino or hydroxy moieties thereof are suitably protected, and the other of $X_5$, $X_{5a}$ and $X_{5b}$ is hydrogen, chloro, bromo or aryloxy and is substituted alpha to the nitrogen in the 6-member ring of

, may be prepared by alkylation of a (2-oxopyrrolidin-3-(S)-yl)-carbamic acid alkyl or aralkyl ester with propargyl bromide in the presence of a base such as sodium hydride. An alkyne that is obtained is heated (100–120° C.) with a halopyridine optionally substituted with hydroxy, alkoxycarbonylamino, or sulfhydryl, a catalyst such as $Pd(PPh_3)_2Cl_2$, copper iodide and triethylamine in a suitable solvent such as acetonitrile in a sealed vessel or in DMF for 2–20 hours. When the pyridine is substituted with a hydroxyl moiety furopyridines are isolated directly if the pyridine is substituted with an alkoxycarbonylamino moiety, additional treatment with DBU at about 60° C. in DMF yields pyrrolopyridines. Subsequent deprotection yields the desired 2-(3-(S)-amino-2-oxopyrrolidin-1-ylmethyl)-furopyridines or pyrrolopyridine-1-carboxylic acid alkyl esters. These compounds are sulfonylated in the normal manner (arene sulfonyl chlorides and base such as triethylamine) and in the case of furopyridines purified (HPLC) to obtain arenesulfonic acid [2-oxo-1-(furopyridinyl-methyl)pyrrolidine-3-(S)-yl]-amides generally as the TFA salts. In the case of pyrrolopyridines an additional deprotection step (such as acid for BOC protecting groups) yields arenesulfonic acid [2-oxo-1-(pyrrolopyridinyl-methyl)-pyrrolidin-3-(S)-yl]-amides.

The $P_1$ moiety of the compound of formula IV is then removed by the appropriate deprotecting procedures known for carbamates such as strong acid, strong base or catalytic hydrogenation to give a compound of formula XVI, wherein $Ar_1$, $X_5$, $X_{5a}$, $X_{5b}$, Z and in are as defined above. The amine of

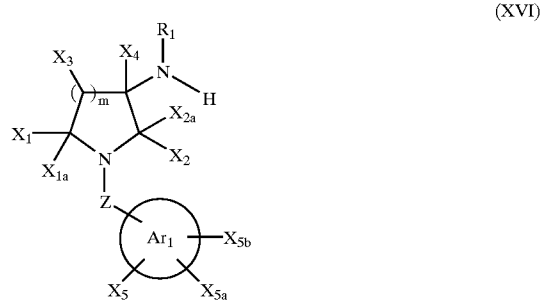

(XVI)

the compound of formula XVI liberated by the removal of $P_1$ is then coupled to a compound of formulae XVIII or XVIII

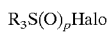

$R_3S(O)_p$Halo    (XVIII)

or

$R_3R_4NS(O)_p$Halo;    (XVIII)

where $R_3$, $R_4$, and p are as defined above, and Halo is a halogen atom such as chloro, using a base such as a trialkylamine in an inert solvent such as dichloromethane, tetrahydrofuran, ether or acetonitrile at about 0° C. to about 100° C. in the presence or absence of an activating agent such as dimethyl aminopyridine (DMAP) to give a compound of formula XIX wherein $Ar_1$, $R_1$, $R_3$,

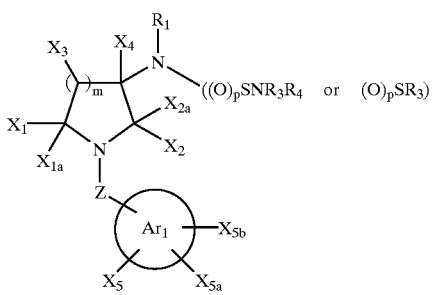
(XIX)

$R_4$, $X_1$, $X_{1a}$, $X_2$, $X_{2a}$, $X_3$, $X_4$, $X_5$, $X_{5a}$, $X_{5b}$, Z and m are as defined above.

Compounds represented by formula XIX wherein one $X_5$, $X_{5a}$, and $X_{5b}$ is substituted alpha to a nitrogen of the distal ring of

and is bromo or chloro may be converted to the corresponding aryloxide by the use of an arylhydroxy such as phenol and a strong alkali base such as potassium hydroxide at 70° C. to about 120° C. The aryloxide intermediate (Y=ArO—) is then treated with an ammonium salt such as ammonium acetate at about 90° C. to 180° C. to give a compound of formula I wherein $Ar_1$, $R_1$, $R_3$, $R_4$, $X_1$, $X_{1a}$, $X_2$, $X_{2a}$, $X_3$, $X_4$, $X_5$, $X_{5a}$, $X_{5b}$, Z and m are as defined above, and wherein one $X_5$, $X_{5a}$ and $X_{5b}$ is substituted alpha to a nitrogen of the distal ring of

and is $NH_2$.

Alternatively, a compound of formula XIX wherein one $X_5$, $X_{5a}$ and $X_{5b}$ is substituted alpha to a nitrogen of the distal ring of

and is bromo or chloro may be treated with an arylhydroxy such as phenol and an ammonium salt such as ammonium acetate at about 90° C. to 180° C. to give compounds represented by formula I wherein $Ar_1$, $R_1$, $R_3$, $R_4$, $X_1$, $X_{1a}$, $X_{2a}$, $X_{2a}$, $X_3$, $X_4$, $X_5$, $X_{5a}$, $X_{5b}$, Z and m are as defined above, and wherein one $X_5$, $X_{5a}$ and $X_{5b}$ is substituted alpha to a nitrogen of the distal ring of

and is $NH_2$,

Alternatively, a compound of formula I may be prepared starting with a compound of formula XX.

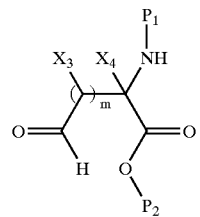
(XX)

wherein $X_3$, $X_4$, $P_1$ and m are as defined above, and $P_2$ is alkyl, aralkyl or aryl, by reductive amination using a (heteroaryl)alkylamine of formula XXI

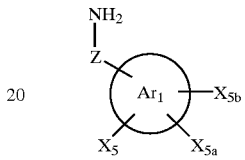
(XXI)

wherein $Ar_1$, $X_5$, $X_{5a}$, $X_{5b}$ and Z are as defined above, in an alcholic solvent such as methanol and an imine reducing reagent such as sodium cyanoborohydride or sodium triacetoxyborohydride at about 0° C. to about 100° C. to give the cyclic structure represented by formula IV which is then converted to a compound of formula I as described above.

A compound of formula XXI used in the reductive amination described above may be prepared by treatment of a compound of formula III wherein one of $X_5$, $X_{5a}$, $X_{5b}$ is H or aryloxy at the position alpha to the nitrogen of the distal ring of $Ar_1$, and L is a leaving group such as chloro, bromo, iodo or other good leaving group with sodium azide followed by reduction using standard reducing methods such as triphenylphosphine in solvents such as water/tetrahydrofuran or catalytic reduction.

A compound of formula I in which $R_1$ is other than H may be prepared starting with a compound of formula I wherein $R_1$ is H by dissolving it in an inert organic solvent such as tetrahydrofuran, dioxane, or dimethyl formamide at about 0° C. to about 100° C. To the resulting solution is added a base such as sodium hydride or potassium carbonate and a compound of formula XXII.

$R_1$—Halo    XXII wherein $R_1$ is as defined above except for H and Halo is a halogen such as bromo or chloro.

A compound of formula I including an heteroaryl group containing one or more nitrogen ring atoms. preferably imine (=N—), may be converted to the corresponding compound wherein one or more nitrogen ring atom of the heteroaryl moiety is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on the activity of Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethenesulfonic acid, benzenesulfonic acid, p-toluenesulfonic acid, cyclohexylsulfamic acid, quinic acid, and the like. The corresponding acid addition salts comprise the following: hydrohalides, e.g. hydroclhloride and hydrobromide, sulfate, phosphate, nitrate, sulfamate, acetate, citrate, lactate, tartarate, malonate, oxalate, salicylate, propionate, succiinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be regenerated from the acid addition salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on the activity of Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydride. hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Salt forms according to invention also include compounds having a quaternarized nitrogen. The quarternarized salts are formed by methods such as by alkylation of a $sp^3$ or $sp^2$ hybridized nitrogen in the compounds.

As will be self-evident to those skilled in the art, some of the compounds of this invention do not form stable salts. However, acid addition salts are most likely to be formed by compounds of this invention having a nitrogen-containing heteroaryl group and/or possessing an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds of the present invention may contain asymmetric centers. These asymmetric centers may independently be in either the (R) or (S) configuration. It will also be apparent to those skilled in the art that certain compounds of formula I may exhibit geometrical isomerism. Geometrical isomers include the cis and trans forms of compounds of the invention having an alkenyl moiety. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents.

The present invention is further exemplified but not limited by the following examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad, bs=broad singlet, q=quartet, AB=AB pattern.

EXAMPLE 1

7-Methoxynaphthalene-2-sulfonic Acid-[1-(1-aminoisoquinolin-7-yl-methyl)-2-oxopyrrolidin-3(R,S)-yl]-amide Trifluoroacetate A. 3-p-Tolyl-acryloyl Chloride.

Thionyl chloride (9.44 mL, 129.5 mmol) is added dropwise to a solution of 3-p-tolyl-acrylic acid (20 g, 123.3 mmol) in benzene (50 mL) at 0° C. The resulting solution is allowed to warm to room temperature then heated to reflux for 2 hours. The mixture is concentrated to dryness on the rotovap to give the crude product (22.3 g, 123.3 mmol) which is taken onto the next step.

$^1$H NMR (CDCl$_3$, 300 MHz) δ 7.80 (d, 1H), 7.50 (d, 2H), 7.26 (d, 2H), 6.58 (d, 1H), 2.40 (s, 3H).

B. 3-p-Tolyl-acryloyl Azide.

3-p-Tolyl-acryloyl chloride (22.3 g, 123.3 mmol) in dioxane (50 mL) is slowly added to an ice cooled solution of sodium azide (16 g, 246.6 mmol) in water/dioxane (50 mL, 1/1, v/v) so as to maintain the temperature between 5–10° C. The mixture was stirred for 1.5 hours then poured over 300 g of ice. The resulting white solid was filtered and washed with additional water. The solid (20.72 g, 110.7 mmol) was dried over P$_2$O$_5$ under vacuum overnight and used in the next step without further purification.

$^1$H NMR (CDCl$_3$, 300 MHz) δ 7.73 (d, 1H), 7.45 (d, 2H), 7.21 (d, 2H), 6.38 (d, 1H), 2.38 (s, 3H). EI MS, [M]$^+$=187.

C. 1-(2-Isocyanato-vinyl)-4-methyl-benzene.

3-p-Tolyl-acryloyl azide (20.72 g, 110.7 mmol) in benzene (100 mL) is heated slowly to 75° C. for 3.5 hours then concentrated to give a brown oil (ca. 20 g). This material was taken onto the next step without further purification.

$^1$H NMR (CDCl$_3$, 300 MHz) δ 7.18 (d, 2H), 7.12 (d, 2H), 6.53 (d, 1H), 6.40 (d, 1H), 2.32 (s, 3H). EI MS, [M]$^+$=159.

D. 7-Methyl-2H-isoquinolin-1-one.

Iodine (0.63 g, 2.51 mmol) is added to a solution of 1-(2-isocyanato-vinyl)-4-methyl-benzene (ca. 20 g, 125.6 mmol) in o-dichlorobenzene (125 mL), then is heated to reflux (180° C.) overnight. The mixture is cooled to room temperature then concentrated to dryness. The residue is purified by column chromatography eluting with 40% EtOAc/hexanes. The product (6.23 g, 39.1 mmol) is obtained as a tan solid.

$^1$H NMR (CDCl$_3$, 300 MHz) δ 12.25 (bs, 1H), 8.21 (s, 1H), 7.42 (bs, 2H), 7.14 (d, 1H), 6.50 (d, 1H), 2.46 (s, 3H). EI MS, [M]$^+$=159.

E. 1-Chloro-7-methylisoquinoline.

7-Methyl-2H-isoquinolin-1-one (2.1 g, 13.2 mmol) in phosphorus oxychloride (30 mL) is heated to reflux for 13 hours. The mixture is cooled to room temperature, then concentrated to a smaller volume. The residue is diluted with ice water and the pH is adjusted to ca. 8 by slow addition of 10 N NaOH. The aqueous solution is extracted with methylenie chloride (4×20 mL) and the combined organic layers are washed with brine, dried over MgSO$_4$, filtered and concentrated. The resulting dark oil is purified by column chromatography eluting with 25% EtOAc/hexanes to give the product (1.6 g, 9 mmol) as a light yellow solid.

$^1$H NMR (CDCl$_3$, 300 MHz) δ 8.18 (d, 1H), 8.05 (d, 1H), 7.71 (d, 1H), 7.55 (m, 2H), 7.55 (s, 3H). EI MS, [M]$^+$=177, 179, Cl pattern.

F. 7-Bromomethyl-1-chloro-isoquinoline.

N-Bromosuccinimide (1.10 g, 6.19 mmol) and benzoyl peroxide (0.39 g, 1.13 mmol) are added to a solution of 1-chloro-7-methylisoquinoline (1 g, 5.63 mmol) in carbon tetrachloride (70 mL). The resulting mixture is heated to reflux for 6 hours then cooled to room temperature and diluted with methylene chloride. The organic layer is washed with 1N NaOH and brine, then dried over MgSO$_4$, filtered and concentrated. The residue is purified by column chromatography eluting with a gradient of 10% EtOAc/hexanes to 25% EtOAc/hexanes to give the product (1.4 g, 5.46 mmol) as a white solid.

$^1$H NMR (CDCl$_3$, 300 MHz) δ 8.31 (s, 1H), 8.28 (d, 1H), 7.86 (d, 1H), 7.77 (dd, 1H), 7.58 (d, 1H), 4.69 (s, 2H). EI MS, [M]$^+$=255, 257, Cl, Br pattern.

G. (2-Oxopyrrolidin-3-(S)-yl)-carbamic Acid tert-Butyl Ester.

(S)-Boc-Diaminobutyric acid (25 g, 115 mmol), triethylamine (35 g, 344 mmol), and hydroxybenzotriazole (19.3 g, 143 mmol) are dissolved in THF (300 mL). 1-(3-Dimethylaminopropyl)-3-ethylcarbodiimide hydrochloride (27.4 g, 143 mmol) is added to the solution. The solution is heated to 60° C. over 15 minutes. A white precipitate forms and the solution is kept at 60° C. for 4 hours. After this time, the solution is filtered and the collected liquid is concentrated. The crude product is purified by column chromatography in a gradient of 1% MeOH/CH$_2$Cl$_2$ to 3% MeOH/CH$_2$Cl$_2$ to afford the title compound (19.6 g, 98 mmol) as a white solid.

$^1$H NMR (CDCl$_3$, 300 MHz) δ 6.17 (bs, 1H), 5.08 (bs, 1H), 4.12 (m, 1H), 3.33 (m, 2H), 2.65 (m, 1H), 2.00 (m, 1H), 1.42 (s, 9H).

H. [1-(1-Chloro-isoquinolin-7-ylmethyl)-2-oxopyrrolidin-3(S)-yl-carbamic Acid tert-Butyl Ester.

Sodium hydride (0.24 g, 6.05 mmol, 60% mineral oil dispersion) is added to a solution of [2-oxopyrrolidin-3(S)-yl]-carbamic acid tert-butyl ester (1.18 g, 5.89 mmol) in THF/DMF (62 mL, 9/1, v/v) at 0° C. The mixture is stirred for 2 minutes, then a solution of 7-bromomethyl-1-chloro-isoquinoline (1.4 g, 5.46 mmol) in THF (10 mL) is added dropwise via a cannula. The resulting yellow solution is stirred for 1 hour at 0° C. then at room temperature for 3 hours. The reaction mixture is quenched with saturated ammonium chloride solution, then diluted with EtOAc. The organic layer is washed with water and brine, then dried over MgSO$_4$, filtered and concentrated. The residue is purified by column chromatography eluting with a gradient of 50% EtOAc/hexanes to 70% EtOAc/hexanes to give the product (1.67 g, 4.44 mmol) as a foamy white solid.

$^1$H NMR (CDCl$_3$, 300 MHz) δ 8.25 (d, 1H), 8.12 (s, 1H), 7.83 (d, 1H), 7.68 (dd, 1H), 7.58 (d, 1H), 5.55 (bs, 1H), 4.71 (AB, 2H), 4.30 (m, 1H), 3.26 (m, 2H), 2.60 (m, 1H), 1.98 (m, 1H), 1.46 (s, 9H). EI MS, [M+H]$^+$=376, 378, Cl pattern.

I. 3-(S)-Amino-]-(1-Chloro-isoquinolin-7-ylmethyl)-pyrrolidin-2-one Hydrochloride.

To a solution of [1-(1-chloro-isoquinolin-7-ylmethyl)-2-oxopyrrolidin-3(S)-yl]-carbamic acid tert-butyl ester (2.1 g, 5.6 mmol) in EtOAc (170 mL) at 0° C. is bubbled HCl gas for 5 minutes. The solution is stirred at 0° C. for 15 minutes, then the ice bath is removed and the solution allowed to warm to room temperature. After 4 hours at room temperature, the solution is concentrated and the remaining solid is washed with ether to give the title compound (1.74 g, 5.6 mmol) as a pale yellow solid.

$^1$H NMR (DMSO-d$_6$, 300 MHz) δ 8.64 (d, 3H), 8.31 (d, 1H), 8.18 (s, 1H), 8.10 (d, 1H), 7.90 (d, 1H), 7.80 (d, 1H), 4.71 (AB, 2H), 4.10 (m, 1H), 3.30 (m, 2H), 2.41 (m, 1H), 1.98 (m, 1H). FAB MS, [M+H]$^+$=276.

J. 7-Methoxynaphthalene-2-sulfonyl Chloride.

To a suspension of 7-hydroxynaphthalene-2-sulfonic acid, sodium salt (15 g, 60.9 mmol) in $H_2O$/ethanol (150 mL, 2:1) is added solid NaOH (2.68 g, 67 mmol) at room temperature. The mixture is stirred until a homogenous solution forms and dimethyl sulfate (6.34 mL, 67 mmol) is then added. A precipitate slowly forms and the mixture is stirred over a period of 16 hours. The crude mixture is concentrated in vacuo and the residue is stirred in absolute EtOH (100 mL) as a slurry for 2 hours. The precipitate is filtered and dried. The solid is heated at reflux in 95% EtOH (100 mL) for 2 h, allowed to cool to room temperature, filtered and dried to give 12.6 g of crude 7-methoxynaphthalene-2-sulfonic acid, sodium salt. A mixture of the sulfonic acid, sodium salt (12.6 g, 48.6 mmol) in phosphorous oxychloride (20 mL) and phosphorous pentachloride (13.2 g, 63.2 mmol) is heated slowly to 60° C. until a homogenous solution forms and then is heated at 120° C. for 4 hours. The resulting mixture is cooled in an ice bath and a mixture of ice/ice water is added slowly with stirring. The mixture is diluted with water and extracted with $CHCl_3$ (2×100 mL). The combined organic layers are washed successively with water, saturated $NaHCO_3$ solution and saturated NaCl. The organic phase is dried over anhydrous $MgSO_4$, filtered and concentrated to give 10 g of a crude oil. The crude product is purified by column chromatography in a gradient of 5% EtOAc/hexanes to 30% EtOAc/hexanes to afford the title compound (3.8 g, 14.8 mmol) as a white crystalline solid.

$^1$H NMR ($CDCl_3$, 300 MHz) δ 8.49 (d, 1H), 7.96 (d, 1H), 7.85 (d, 2H), 7.39 (dd, 1H), 7.29 (d, 1H), 3.99 (s, 3H). EI MS, $[M]^+$=256.

K. 7-Methoxynaphthalene-2-sulfonic Acid [1-(1-Chloro-isoquinolin-7-ylmethyl)-2-oxopyrrolidin-3-(S)-yl-amide.

3-(S)-Amino-1-(1-chloro-isoquinolin-7-ylmethyl)-pyrrolidin-2-one hydrochloride (1.74 g, 5.6 mmol) is suspended in $CH_3CN$ (120 mL). To this solution is added triethylamine (2.35 mL, 16.9 mmol) followed by 7-methoxynaphthalene-2-sulfonyl chloride (1.52 g, 5.93 mmol). The mixture is stirred overnight, then concentrated to dryness. The crude product is purified by column chromatography eluting with a gradient of 2% $MeOH/CH_2Cl_2$ to 5% $MeOH/CH_2Cl_2$ to give the title compound (2.7 g, 5.4 mmol) as a light yellow solid.

$^1$H NMR ($CDCl_3$, 300 MHz) δ 8.35 (d, 1H), 8.27 (d, 1H), 8.08 (s, 1H), 7.91 (d, 1H), 7.80 (d, 1H), 7.78 (s, 1H), 7.74 (dd, 1H), 7.56 (s, 1H), 7.51 (d, 1H), 7.30 (dd, 1H), 7.24 (d, 1H), 5.42 (d, 1H), 4.63 (AB, 2H), 3.95 (s, 3H), 3.78 (m, 1H), 3.25 (m, 2H), 2.60 (m, 1H), 2.08 (m, 1H). FAB MS, $[M+H]^+$=496, 498, Cl pattern.

L. 7-Methoxynaphthalene-2-sulfonic Acid [1-(1-Phenoxy-isoquinolin-7-ylmethyl)-2-oxopyrrolidin-3-(R,S)-yl]-amide.

Phenol (6.81 g, 72.4 mmol) and potassium hydroxide (0.41 g, 7.31 mmol) are added to 7-methoxynaphthalene-2-sulfonic acid [1-(1-chloro-isoquinolin-7-ylmethyl)-2-oxopyrrolidin-3-(S)-yl]amide (1.8 g, 3.6 mmol) and heated to 90° C. until a homogeneous mixture is obtained. The mixture is stirred overnight at 90° C., then cooled to room temperature and diluted with methylene chloride (100 mL) and water. The aqueous layer is neutralized to pH 7 using 1 N HCl, then the two layers are separated and the aqueous layer is extracted with additional methylenechloride. The combined organic layers are washed with brine, dried over $MgSO_4$, filtered and concentrated. The residue is purified by column chromatography eluting with a gradient of 30% EtOAc/hexanes to 60% EtOAc/hexanes to give the product (1.66 g, 3 mmol) as a white solid.

$^1$H NMR ($CDCl_3$, 300 MHz) δ 8.40 (s, 1H), 8.20 (s, 1H), 7.94 (d, 1H), 7.82 (d, 1H), 7.74 (d, 1H), 7.70 (d, 1H), 7.51 (dd, 1H), 7.40 (m, 2H), 7.15–7.30 (m, 7H), 5.80 (bs, 1H), 4.60 (AB, 2H), 3.98 (s, 3H), 3.82 (m, 1H), 3.20 (m, 2H), 2.52 (m, 1H), 2.04 (m, 1H). FAB MS, $[M+H]^+$=554.

M. 7-Methoxynaphthalene-2-sulfonic Acid [1-(1-Aminoisoquinolin-7-yl-methyl)-2-oxopyrrolidin-3-(R,S)-yl]-amide Trifluoroacetate.

In a round-bottomed flask fitted with a water condenser, 7-methoxynaphthalene-2-sulfonic acid [1-(1-phenoxy-isoquinolin-7-ylmethyl)-2-oxopyrrolidin-3-(S)-yl]-amide (0.318 g; 0.574 mmol) and ammonium acetate (5 g, 65 mmol) is heated to 160° C. After ca. 6 hours, the homogeneous mixture is cooled to room temperature and the mixture is purified by RP-HPLC eluting with a gradient of 10% $CH_3CN/H_2O$ (0.1% TFA) to 100% $CH_3CN$. The appropriate fractions are lyophilized to give the title racemic compound (0.157 g, 0.266 mmol) as a white solid.

$^1$H NMR (DMSO-$d_6$, 300 MHz) δ 8.95 (bs, 2H), 8.39 (s, 1H), 8.23–8.29 (m, 2H), 8.02 (d, 1H), 7.95 (d, 1H), 7.93 (d, 1H), 7.77 (d, 1H), 7.74 (dd, 1H), 7.65 (d, 1H), 7.58 (d, 1H), 7.35 (dd, 1H), 7.24 (d, 1H), 4.56 (AB, 2H), 4.20 (m, 1H), 3.89 (s, 3H), 3.15 (m, 2H), 2.05 (m, 1H), 1.60 (m, 1H). FAB MS, $[M+H]^+$=477.

EXAMPLE 2

7-Methoxynaphthalene-2-sulfonic Acid [1-(1-Aminoisoquinolin-7-yl-methyl)-2-oxopyrrolidin-3-(S)-yl]-amide Hydrochloride In a round-bottomed flask fitted with a cold finger condenser, phenol (0.569 g, 6 mmol) and 7-methoxy-naphthalene-2-sulfonic acid [1-(1-chloro-isoquinolin-7-ylmethyl)-2-oxopyrrolidin-3-(S)-yl]-amide (0.2 g, 0.4 mmol) is melted at 70° C. The mixture is stirred for 5 minutes, then ammonium acetate (0.462 g, 6 mmol) is added and heated at 115° C. for 2 hours. After this time, additional ammonium acetate (0.462 g, 6 mmol) is added. After 2 hours the reaction mixture is cooled to room temperature then partitioned between EtOAc and 0.5N NaOH, The organic layer is separated and washed with water and brine, then dried over $Na_2SO_4$, filtered and concentrated. The resulting residue is partially purified by RP-HPLC eluting with a gradient of 10% $CH_3CN/H_2O$ (0.1% TFA) to 100% $CH_3CN$. The appropriate fractions are concentrated in vacuo. The solid which precipitates out from the solution is then filtered, dried and purified again by column chromatography eluting with 5% $MeOH/CH_2Cl_2$. This product is then triturated with cold MeOH and the collected solid is suspended in MeOH and cooled to 0° C. HCl(g) is bubbled through the slurry for a few minutes during which time all the solid dissolves into the solution. The solvent is removed in vacuo and the title product (0.11 g, 0.214 mmol) is washed with ether and dried.

$^1$H NMR (DMSO-$d_6$, 300 MHz) δ 13.30 (bs, 1H), 9.18 (bs, 2H), 8.32 (s, 1H), 8.25 (d, 1H), 7.99 (d, 1H), 7.85–7.91 (m, 2H), 7.60–7.80 (m, 3H), 7.50 (s, 1H), 7.25 (dd, 1H), 7.18 (d, 1H), 4.51 (AB, 2H), 4.23 (m, 1H), 3.85 (s, 3H), 3.12 (m, 2H), 1.95 (m, 1H), 1.65 (m, 1H). FAB MS, $[M+H]^+$=477. Melting point: 187–192° C.

The enantiomeric purity is 88% ee as determined by analytical Chiralpak AD reverse phase HPLC.

EXAMPLE 3

7-Methoxynaphthalene-2-sulfonic Acid [1-(1-Aminoisoquinolin-7-yl-methyl)-2-oxopyrrolidin-3-(S)-yl-amide Trifluoroacetate The title compound is prepared by resolution of the racemic compound described in EXAMPLE 1, Part M using a Chiralpak AD HPLC column (55% EtOH/Heptane(0.1% TFA)).

$^1$H NMR (DMSO-$d_6$, 300 MHz) δ 8.95 (bs, 2H), 8.39 (d, 1H), 8.30 (s, 1H), 8.23 (d, 1H), 8.04 (d, 1H), 7.95 (d, 1H), 7.93 (d, 1H), 7.77 (d, 1H), 7.74 (dd, 1H), 7.65 (d, 1H), 7.58 (d, 1H), 7.35 (dd, 1H), 7.24 (d, 1H), 4.56 (AB, 2H), 4.20 (m, 1H), 3.89 (s, 3H), 3.15 (m, 2H), 2.05 (m, 1H), 1.60 (m, 1H). FAB MS, [M+H]$^+$=477.

The enantiomeric purity is 96.3% ee as determined by analytical Chiralpak AD reverse phase HPLC. [a]$_D$+3.16° (MeOH).

EXAMPLE 4

7-Methoxynaphthalene-2-sulfonic Acid [1-(1-Aminoisoquinolin-7-yl-methyl)-2-oxopyrrolidin-3-(R)-yl]-amide Trifluoroacetate The title compound is prepared by resolution of the racemic compound described in EXAMPLE 1, Part M using a Chiralpak AD HPLC column (55% EtOH/Heptane (0.1% TFA)).

$^1$H NMR (DMSO-$d_6$, 300 MHz) δ 8.95 (bs, 2H), 8.39 (d, 1H), 8.30 (s, 1H), 8.23 (d, 1H), 8.04 (d, 1H), 7.95 (d, 1H), 7.93 (d, 1H), 7.77 (d, 1H), 7.74 (dd, 1H), 7.65 (d, 1H), 7.58 (d, 1H), 7.35 (dd, 1H), 7.24 (d, 1H), 4.56 (AB, 2H), 4.20 (m, 1H), 3.89 (s, 3H), 3.15 (m, 2H), 2.05 (m, 1H), 1.60 (m, 1H). FAB MS, [M+H]$^+$=477.

The enantiomeric purity is 90.7% ee as determined by analytical Chiralpak AD reverse phase HPLC. [a]$_D$–3.89° (MeOH).

EXAMPLE 5

7-Methoxynaphthalene-2-sulfonic Acid [1-(1-Hydroxyisoquinolin-7ylmethyl)-2-oxopyrrolidin-3 (R,S)-yl]-amide 7-Methoxynaphthalene-2-sulfonic acid [1-(1-chloro-isoquinolin-7-ylmethyl)-2-oxopyrrolidin-3-(S)-yl]amide (0.07 g, 0.14 mmol), prepared as described in EXAMPLE 1, Part K, is treated with dioxane (1 mL) and 10% aq. NaOH (3 mL) and heated to reflux for 48 hours. The reaction was cooled, acidified with 1 N HCl and extracted with CH$_2$Cl$_2$. The organic layer is separated, dried and concentrated. The residue is purified by column chromatography eluting with 2.5% MeOH/CH$_2$Cl$_2$.
The product fractions are collected, concentrated and precipitated with dilute HCl/ether to yield the title compound (0.041 g, 0.086 mmol).

$^1$H NMR (CD$_3$OD, 300 MHz) δ 8.41 (s, 1H), 8.25 (d, 1H), 8.06 (bs, 1H), 7.93 (d, 1H), 7.85 (d, 1H), 7.76 (d, 1H), 7.58 (AB, 2H), 7.39 (s, 1H), 7.24 (dd, 1H), 7.17 (d, 1H), 6.66 (bs, 1H), ), 4.55 (AB, 2H), 4.20 (m, 1H), 3.92 (s, 3H), 3.19 (m, 2H), 2.20 (m, 1H), 1.59 (m, 1H), 1.70 (m, 1H). FAB MS, [M+H]$^+$=478. Elemental analysis calculated with 1.6 mole of H$_2$O: C=58.42%, H=4.71%, N=8.18%; found C=59.30%, H=5.04%, N=7.96%.

EXAMPLE 6

7-Methoxynaphthalene-2-sulfonic Acid-[1-(1-Amino-isoquinolin-7-ylmethyl)-2-oxopyrrolidin-3-(R,S)-yl]-methylamide Trifluoroacetate A. 7-Methoxynaphthalene-2-sulfonic Acid [1-(1-Chloro-isoquinolin-7-ylmethyl)-2-oxopyrrolidin-3-(S)-yl]-methyl-amide.

To a solution of 7-methoxynaphthalene-2-sulfonic acid [1(1-chloro-isoquinolin-7-ylmethyl)-2-oxopyrrolidin-3-(S)-yl]-amide (0.151 g, 0.304 mmol) in acetone (20 mL) is added potassium carbonate (0.084 g, 0.608 mmol) followed by methyl iodide (0.12 mL, 1.93 mmol). The resulting mixture is heated to reflux overnight, then cooled to room temperature and diluted with methylene chloride. The solution is washed with saturated NaHCO$_3$ solution, water and brine. The organic layer is dried over MgSO$_4$, filtered and concentrated. The residue is purified by column chromatography eluting with 5% MeOH/CH$_2$Cl$_2$ to give the product (0.093 mg, 0.18 mmol) as an oil.

$^1$H NMR (CDCl$_3$, 300 MHz) δ 8.41 (s, 1H), 8.04 (s, 1H), 8.23–8.26 (m, 2H), 8.07 (s, 1H), 7.90 (d, 1H), 7.90 (d, 1H), 7.77 (s, 1H), 7.75 (s, 1H), 7.58 (dd, 1H), 7.28 (m, 1H), 5.02 (m, 1H), 4.63 (AB, 2H), 3.92 (s, 3H), 3.24 (m, 2H), 2.82 (s, 3H), 2.32 (m, 1H), 2.05 (m, 1H).

B. 7-Methoxynaphthalene-2-sulfonic Acid [1-(1-Phenoxy-isoquinolin-7-ylmethyl)-2-oxopyrrolidin-3-(R,S)-yl]-methylamide.

The title compound is prepared as described in EXAMPLE 1, Part L using 7-methoxynaphthalene-2-sulfonic acid [1-(1-chloro-isoquinolin-7-ylmethyl)-2-oxopyrrolidin-3-(S)-yl]-methylamide in place of 7-methoxynaphthalene-2-sulfonic acid [1-(1-chloro-isoquinolin-7-ylmethyl)-2-oxopyrrolidin-3-(S)-yl]-amide.

$^1$H NMR (CDCl$_3$, 300 MHz) δ 8.45 (s, 1H), 8.20 (s, 1H), 7.90 (d, 1H), 7.81 (d, 1H), 7.74 (d, 1H), 7.70 (d, 1H), 7.54 (dd, 1H), 7.38–7.45 (m, 3H), 7.14–7.30 (m, 6H), 5.00 (m, 1H), 4.62 (AB, 2H), 3.88 (s, 3H), 3.25 (m, 2H), 2.81 (s, 3H), 2.30 (m, 1H), 2.01 (m, 1H).

C. 7-Methoxynaphthalene-2-sulfonic Acid-[1-(1-Amino-isoquinolin-7-ylmethyl)-2-oxopyrrolidin-3-(R,S)-yl]-methylamide Trifluoroacetate.

The title compound is prepared as described in EXAMPLE 1, Part M using 7-methoxynaphthalene-2-sulfonic acid [1-(1-phenoxy-isoquinolin-7-ylmethyl)-2-oxopyrrolidin-3-(R,S)-yl]-methyl-amide in place of 7-methoxynaphthalene-2-sulfonic acid [1-(1-phenoxy-isoquinolin-7-ylmethyl)-2-oxopyrrolidin-3-(R,S)-yl]-amide.

$^1$H NMR (DMSO-$d_6$, 300 MHz) δ 9.00 (bs, 2H), 8.40 (s, 1H), 8.26 (s, 1H), 8.04 (d, 1H), 7.90–7.95 (m, 2H), 7.79 (d, 1H), 7.71 (dd, 1H), 7.65 (d, 1H) 7.56 (d, 1H), 7.32 (d, 1H), 7.21 (d, 1H), 4.95 (m, 1H), 4.54 (AB, 2H), 3.86 (s, 3H), 3.20 (m, 2H), 2.65 (s, 3H), 2.00 (m, 1H), 1.75 (m, 1H). FAB MS, [M+H]$^+$=491. Elemental analysis calculated with 1.5 mole of H$_2$O: C=53.25%, H=4.79%, N=8.87%, found C=53.43%, H=4.50%, N=8.58%.

EXAMPLE 7

7-Methoxynaphthalene-2-sulfonic Acid-[1-(1-Amino-isoquinolin-7-ylmethyl)-2-oxopyrrolidin-3-(S)-yl-methylamide Trifluoroacetate The title compound is prepared by resolution of the racemic compound described in EXAMPLE 6, Part C using a Chiralpak AD reverse phase HPLC column (55% EtOH/Heptane(0.1% TFA)).

$^1$H NMR (DMSO-$d_6$, 300 MHz) δ 13.5 (bs, 1H), 9.20 (bs, 2H), 8.40 (s, 1H), 8.26 (s, 1H), 8.04 (d, 1H), 7.90–8.00 (m,

2H), 7.79 (d, 1H), 7.71 (dd, 1H), 7.65 (d, 1H), 7.58 (d, 1H), 7.34 (dd, 1H), 7.23 (d, 1H), 4.98 (m, 1H), 4.54 (AB, 2H), 3.86 (s, 3H), 3.20 (m, 2H), 2.68 (s, 3H), 2.05 (m, 1H), 1.80 (m, 1H). FAB MS, [M+H]$^+$=491. The enantiomeric purity is 92.6% ee as determined by analytical Chiralpak AD reverse phase HPLC.

EXAMPLE 8

Benzo[b]thiophene-2-sulfonic Acid [1-(1-Amino-isoquinolin-7-ylmethyl)-2-oxopyrrolidin-3-(S)-yl] amide Trifluoroacetate A. Benzo[b]thiophene-2-sulfonyl Chloride.

To a solution of thianaphthalene (11.8 g, 88.1 mmol), in THF (400 mL) at −78° C. is added n-BuLi (55 mL of a 1.6 M solution in hexanes, 88.1 mmol). After 15 minutes. the solution is added by cannula to a precooled (−78° C.) solution of $SO_2$ (200 g) in THF (100 mL). After addition, the solution is allowed to warm to ambient temperatures. After 0.5 h, the solution is concentrated. The residue is suspended in hexanes (400 mL) and is cooled to 0° C. To the solution is added $SO_2Cl_2$ (12.5 g, 92.5 mmol). After stirring for 15 minutes, the solution is concentrated. The residue is dissolved in EtOAc. The organic solution is washed with satuated $NH_4Cl$ (aq.), $H_2O$ and saturated NaCl (aq.). The organic layer is dried over $MgSO_4$, filtered and concentrated. The crude product is dissolved in $CH_2Cl_2$ and filtered through a plug of silica gel. The organic solution is then concentrated. The resulting solid is triturated with hexane to give the title compound (12.1 g, 38 mmol).

$^1$H NMR (CDCl$_3$, 300 MHz) δ 8.16 (s, 1H), 7.97 (m, 2H), 7.57 (m, 2H).

B. Benzo[b]thiophene-2-sulfonic Acid [1-(1-Chloro-isoquinolin-7-ylmethyl)-2-oxopyrrolidin-3-(S)-yl]amide.

The title compound is prepared as described in EXAMPLE 1, Part K using benzo[b]thiophene-2-sulfonyl chloride in place of 7-methoxynaphthalene-2-sulfonyl chloride.

$^1$H NMR (CDCl$_3$, 300 MHz) δ 8.29 (d, 1H), 8.12 (s, 1H), 7.93 (s, 1H), 7.84–7.92 (m, 2H), 7.82 (d, 1H), 7.54–7.62 (m, 2H), 7.46–7.52 (m, 2H), 5.50 (d, 1H), 4.66 (AB, 2H), 3.95 (m, 1H), 3.25 (m, 2H), 2.65 (m, 1H), 2.15(m, 1H). FAB MS, [M+H]$^+$=472, 474, Cl pattern.

C. Benzo[b]thiophene-2-sulfonic Acid [1-(1-Amino-isoquinolin-7-ylmethyl)-2-oxopyrrolidin-3-(S)-yl]-amide Trifluoroacetate.

The title compound was prepared as described in EXAMPLE 2 using benzo[b]thiophene-2-sulfonic acid [1-(1-chloro-isoquinolin-7-ylmethyl)-2-oxopyrrolidin-3-(S)-yl]-amide as the starting material. No extractive work up is performed. The crude product is purified by RP-HPLC eluting with a gradient of 10% $CH_3CN/H_2O$ (0.1% TFA) to 100% $CH_3CN$. The appropriate fractions are lyophilized to provide the title compound as a white solid.

$^1$H NMR (DMSO-d$_6$, 300 MHz) δ 9.00 (bs, 2H), 8.65 (d, 1H), 8.30 (s, 1H), 8.07–8.15 (m, 3H), 8.05 (d, 1H), 7.94 (d, 1H), 7.80 (d, 1H), 7.68 (d, 1H), 7.45–7.58 (m, 2H), 7.22 (d, 1H), 4.55 (AB, 2H), 4.31 (m, 1H), 3.25 (m, 2H), 2.20 (m, 1H), 1.73 (m, 1H). FAB MS, [M+H]$^+$=453.

EXAMPLE 9

6-Chloro-benzo[b]thiophene-2-sulfonic Acid [1-(1-Amino-isoquinolin-7-ylmethyl)-2-oxopyrrolidin-3-(S)-yl]-amide Trifluoroacetate A. 1-Chloro-3-(2,2-dimethoxy-ethyl-sulfanyl)-benzene.

To a solution of 3-chlorothiophenol (2.4 g, 16.6 mmol) in THF (200 mL) at 0° C. is added bromoacetaldehyde dimethyl acetal (2.8 g, 16.6 mmol). To the solution is added sodium hydride (0.70 g, 17.4 mmol, 60% mineral oil dispersion). The reaction is stirred for 16 hours, then quenched by the addition of saturated $NH_4Cl$ (aq.). The solution is diluted with EtOAc. The organic layer is washed with saturated NaCl (aq.). The organic layer is dried over $MgSO_4$, filtered and concentrated. The crude product is purified by column chromatography eluting with hexanes. The title compound (3.7 g, 15.9 mmol) is obtained as an oil.

$^1$H NMR (CDCl$_3$, 300 MHz) δ 7.32 (m, 1H), 7.25 (m, 1H), 7.12 (m, 1H), 4.47 (m, 1H), 3.07 (s, 3H), 3.02 (s, 3H).

B. 4-Chloro-benzo[b]-thiophene and 6-Chloro-benzo[b]-thiophene.

A solution containing polyphosphoric acid (8 g) and chlorobenzene (50 mL) is heated to reflux. A solution containing 1-chloro-3-(2,2-dimethoxy-ethyl-sulfanyl)-benzene (2.7 g, 11.6 mmol) in chlorobenzene (5 mL) is added dropwise to the refluxing polyphosphoric acid solution. After 6 hours, the solution is cooled to ambient temperatures. The solution is diluted with $CH_2Cl_2$ and washed with water and saturated NaCl (aq.). The organic layer is dried over $MgSO_4$, filtered and concentrated. The crude product is purified by column chromatography eluting with hexanes to yield the title compounds (2.4 g, 9 mmol) as a 1:1 isomeric mixture.

$^1$H NMR (CDCl$_3$, 300 MHz) δ 7.88 (m, 1H), 7.75 (m, 2H), 7.42 (m, 2H). EI MS, [M]$^+$=168, 170, Cl pattern.

C. 6-Chloro-benzo[b]thiophene-2-sulfonyl Chloride

The title compound is prepared as described in EXAMPLE 8, Part A substituting the 4-chloro-benzo[b]-thiophene and 6-Chloro-benzo[b]-thiophene mixture for thianaphthalene. The crude product is purified by column chromatography eluting with hexanes to yield the title compound as well as 4-chlorobenzo[b]thiophene-2-sulfonyl chloride as white solids.

6-Chloro-benzo[b]thiophene-2-sulfonyl Chloride $^1$H NMR (CDCl$_3$, 300 MHz) δ 8.11 (s, 1H), 7.88 (m, 2H), 7.50 (m, 1H).

4-Chlorobenzo[b]thiophene-2-sulfonyl Chloride $^1$H NMR (CDCl$_3$, 300 MHz) δ 8.32 (m, 1H), 7.81 (m, 1H), 7.53 (m, 2H).

D. 6-Chloro-benzo[b]thiophene-2-sulfonic Acid [1-(1-Chloro-isoquinolin-7-ylmethyl)-2-oxopyrrolidin-3-(S)-yl]-amide.

The title compound is prepared as in EXAMPLE 1, Part K using 6-chloro-benzo[b]thiophene-2-sulfonyl chloride in place of 7-methoxynaphthalene-2-sulfonyl chloride.

$^1$H NMR (CDCl$_3$, 300 MHz) δ 8.29 (d, 1H), 8.12 (s, 1H), 7.91 (s, 1H), 7.87 (m, 1H), 7.83 (d, 1H), 7.80 (d, 1H), 7.60 (d, 1H), 7.58 (dd, 1H), 7.42 (dd, 1H), 5.50 (d, 1H), 4.65 (AB, 2H), 3.95 (m, 1H), 3.25 (m, 2H), 2.65 (m, 1H), 2.15 (m, 1H). FAB MS, [M+H]$^+$=506, 508, Cl pattern.

E. 6-Chloro-benzo[b]thiophene-2-sulfonic Acid [1-(1-Amino-isoquinolin-7-ylmethyl)-2-oxopyrrolidin-3-(S)-yl]-amide Trifluoroacetate The title compound is prepared as described in EXAMPLE 2 using 6-Chloro-benzo[b]thiophene-2-sulfonic acid [1-(1-chloro-isoquinolin-7-ylmethyl)-2-oxopyrrolidin-3-(S)-yl]-amide as the starting material. No extractive work up is performed. The crude product is purified by RP-HPLC eluting with a gradient of 10% $CH_3CN/H_2O$ (0.1% TFA) to 100% $CH_3CN$. The appropriate fractions are lyophilized to provide the title compound as a solid.

$^1$H NMR (DMSO-d$_6$, 300 MHz) δ 9.00 (bs, 2H), 8.71 (d, 1H), 8.29 (bs, 2H), 8.05 (s, 1H), 8.01 (d, 1H), 7.94 (d, 1H), 7.80 (d, 1H), 7.65 (d, 1H), 7.55 (dd, 1H), 7.21 (d, 1H), 4.58 (AB, 2H), 4.30 (m, 1H), 3.20 (m, 2H), 2.20 (m, 1H), 1.75 (m, 1H). FAB MS, [M+H]$^+$=487,489. Cl pattern.

EXAMPLE 10

7-Methoxynaphthalene-2-sulfonic Acid [1-(1-Amino-6-methoxylisoquinolin-7ylmethyl)-2-oxopyrrolidin-3-(S)-yl]amide Hydrochloride A. 6-Methoxy-7-methyl-2H-isoquinolin-1-one 3-(3-Methoxy-4-methylphenyl)propenoic acid (5.33 g, 27.7 mmol) (prepared according to the procedure described in J. Med. Chem. 1991, 34, 1662–1668) is suspended in benzene (30 mL) and treated dropwise with thionyl chloride (2.22 mL, 30.5 mmol) at 0° C. The reaction is heated to reflux and it is maintained for 1 hour. The volatiles are removed in vacuo and the resulting solid is dissolved in dioxane and added dropwise to a mixture of sodium azide (3.6 g, 55.4 mmol) in water/dioxane (30 mL, 1:5) at 0° C. After stirring 1 hours, the solution is poured over ice-water, the precipitate is collected and washed with water. The solid is dried under vacuum over $P_2O_5$(24 hours), dissolved in benzene (30 mL) and heated to reflux slowly over about 4 hours. The benzene is removed to give 2-(3-methoxy-4-methyl-phenyl)vinylisocyanate as a brown oil. The oil is taken tip in o-dichlorobenzene, treated with iodine and heated to reflux for 3.5 hours. The volatiles are removed and the residue is mixed with 2.5% $MeOH/CH_2Cl_2$ (10 mL), then allowed to stand overnight at room temperature. The resulting solid is collected washed with hexane and ether, and dried to give the title compound (2.67 g, 14.1 mmol).

$^1$H NMR (CDCl$_3$, 300 MHz) δ 11.80 (bs, 1H), 8.18 (s, 1H), 7.16 (d, 1H), 6.86 (s, 1H), 6.51 (d, 1H), 3.94 (s, 3H), 2.35 (s, 3H). EI MS, [M]$^+$=189.

B. 1-Chloro-6-methoxyisoquinolin-7ylmethyl Bromide

6-Methoxy-7-methyl-2H-isoquinolin-1-one (2.6 g, 13.7 mmol) is converted to 6-methoxy-7-methyl-2-chloroisoquinoline (2.45 g, 11.8) by the method described in EXAMPLE 1, Part E. A portion of this material (1.20 g, 5.8 mmol) is converted to 7-bromomethyl-1-chloro-6-methoxy-isoquinoline (0.8 g, 2.8 mmol) by the method described in EXAMPLE 1, Part F.

$^1$H NMR (CDCl$_3$, 300 MHz) δ 8.30 (s, 1H), 8.22 (d, 1H), 7.49 (d, 1H), 7.10 (s, 1H), 4.70 (s, 2H), 4.06 (s, 3H). EI MS, [M]$^+$=285, 287, Cl pattern.

C. [1-(1-Chloro-6-methoxyisoquinolin-7ylmethyl)-2-oxopyrrolidin-3-(S)-yl]carbamic Acid tert-Butyl ester.

Sodium hydride (0.057 g, 1.4 mmol, 60% mineral oil dispersion) is suspended in anhydrous THF (5 mL) and treated with a solution of (2-oxopyrrolidin-3-(S)-yl)-carbamic acid tert-butyl ester (0.223 g, 1.1 mmol) and 7-bromomethyl-1-chloro-6-methoxy-isoquinoline (0.32 g, 1.1 mmol) in THF/DMF (10 mL, 6:1) at 0° C. The reaction mixture is warmed to ambient temperature, stirred for 3 hours, quenched by the addition of saturated NH$_4$Cl and diluted with EtOAc. The layers are separated. The organic layer is washed with saturated NaCl dried over Na$_2$SO$_4$, filtered, and concentrated to give a white solid. The solid is collected, washed with a small amount of EtOAc and copious amounts of Et$_2$O to yield the title compound (0.18 g, 0.47 mmol).

$^1$H NMR (CDCl$_3$, 300 MHz) δ 8.22 (d, 1H), 8.06 (s, 1H), 7.51 (d, 1H), 7.11 (s, 1H), 5.20 (bs, 1H), 4.68 (AB, 2H), 4.23 (m, 1H), 3.98 (s, 3H), 3.21 (m, 2H), 2.65 (m, 1H), 1.90 (m, 1H), 1.46 (s, 9H). FAB MS, [M+H]$^+$=387.

D. 7-Methoxynaphthalene-2-sulfonic Acid [1-(1-Chloro-6-methoxyisoquinolin-7ylmethyl)-2-oxopyrrolidin-3-(S)-yl]-amide

[1-(1-Chloro-6-methoxyisoquinolin-7ylmethyl)-2-oxopyrrolidin-3-(S)-yl]-carbamic acid tert-butyl ester (0.15 g, 0.37 mmol) is converted to 7-methoxynaphthalene-2-sulfonic acid [1-(1-chloro-6-methoxyisoquinolin-7-ylmethyl)-2-oxopyrrolidin-3-(S)-yl]-amide (0.08 g, 0.15 mmol) by the method described in EXAMPLE 1, Parts I and K.

$^1$H NMR (CDCl$_3$/CD$_3$OD, 300 MHz) δ 8.40 (s, 1H), 8.14 (d, 1H), 7.99 (s, 1H), 7.95 (d, 1H), 7.83 (d, 1H), 7.78 (d, 1H), 7.55 (d, 1H), 7.28 (s, 1H), 7.13 (s, 1H), 4.62 (s, 2H), 4.0 (s, 3H), 3.97 (s, 3H), 3.89 (dd, 1H), 3.2–3.4 (m, 2H), 2.52 (m, 1H), 2.07 (m, 1H). FAB MS, [M+H]$^+$=526.

E. 7-Methoxynaphthalene-2-sulfonic Acid [1-(1-Amino-6-methoxyisoquinolin-7ylmethyl)-2-oxopyrrolidin-3-(S)-yl]-amide Hydrochloride.

7-Methoxynaphthalene-2-sulfonic acid [1-(1-chloro-6-methoxyisoquinolin-7ylmethyl)-2-oxopyrrolidin-3-(S)-yl]-amide (0.080 g, 0.15 mmol) and phenol (0.430 g, 4.6 mmol) are melted together with stirring at 70° C. for 5 minutes. Ammonium acetate (0.354 g, 4.6 mmol) is added and the reaction mixture is heated to 115° C. for about 5 hours. Additional ammonium acetate (0.177 g, 2.3 mmol) is added and the reaction is heated for a further 3 hours. The reaction is cooled and partitioned between 0.5 N NaOH and CH$_2$Cl$_2$. The organic layer is dried over Na$_2$SO$_4$ and concentrated. The residue is purified by column chromatography eluting with 5% MeOH/CH$_2$Cl$_2$. The product fractions are collected and concentrated to a small volume, then the residue is acidified with 1N HCl/ether to give a beige solid (0.046 g, 0.095 mmol).

$^1$H NMR (CD$_3$OD, 300 MHz) δ 8.38 (s, 1H), 8.05 (s, 1H), 7.88 (d, 1H), 7.80 (d, 1H), 7.73 (dd, 1H), 7.44 (d, 1H), 7.32 (d, 1H), 7.30 (s, 1H), 7.23 (dd, 1H), 7.07 (d, 1H), 4.53 (AB, 2H), 4.23 (t, 1H), 3.98 (s, 3H), 3.89 (s, 3H), 3.30 (m, 2H), 2.22 (m, 1H), 1.89 (m, 1H). FAB MS, [M+H]$^+$=478. Elemental analysis calculated with 1.4 mole of H$_2$O: C=54.96%, H=5.29%, N=9.86%; found C=54.81%, H=5.12%, N=9.71%.

EXAMPLE 11

7-Methoxynaphthalene-2-sulfonic Acid [1-(6-Methoxyisoquinolin-7-ylmethyl)-2-oxopyrrolidin-3-(S)-yl]amide Trifluoroacetate A suspension of 7-methoxynaphthalene-2-sulfonic acid [1-(1-chloro-6-methoxyisoquinolin-7-ylmethyl)-2-oxopyrrolidin-3-(S)-yl]-amide in methanol/CH$_2$Cl$_2$ (35 mL, 6:1) is treated with THF (5 mL), AcOH (5 mL) and 10% Pd on carbon (0.04 g). The suspension is stirred under an atmosphere of hydrogen for 7 hours. The suspension is filtered, then the filtrate is concentrated and the residue is purified by RP-HPLC eluting in a gradient of 10% CH$_3$CN/H$_2$O (0.1% TFA) to 90% CH$_3$CN/H$_2$O (0.1% TFA). The appropriate product fractions are lyophilized to provide the title compound as a white solid (0.325 g, 0.66 mmol)

$^1$H NMR (CD$_3$OD, 300 MHz) δ 9.37 (s, 1H), 8.40 (d, 1H), 8.38 (d, 1H), 8.23 (d, 1H), 8.15 (s, 1H), 7.93 (d, 1H), 7.85 (d, 1H), 7.77 (dd, 1H), 7.66 (s, 1H), 7.35 (s, 1H), 7.27 (dd, 1H), 4.66 (AB, 2H), 4.28 (t, 1H), 4.12 (s, 3H), 3.92 (s, 3H), 3.40 (m, 2H), 2.35 (m, 1H), 1.92 (m, 1H). FAB MS, [M+H]$^+$=492. Elemental analysis calculated with 1.2 mole of H$_2$O: C=53.66%, H=4.57%, N=6.70%; found C=53.62%, H=4.38%, N=6.67%.

EXAMPLE 12

4-(2-Chloro-6-nitrophenoxy)benzene Sulfonic Acid [1-(1-Amino-6-methoxyisoquinolin-7-ylmethyl)-2-oxopyrrolidin-3-(S)-yl]-amide Trifluoroacetate

[1-(1-Chloro-6-methoxyisoquiniolin-7-ylmethyl)-2-oxopyrrolidin-3-(S)-yl]-carbamic acid tert-butyl ester (0.845 g, 2 mmol) is converted to [1-(1-amino-6-methoxyisoquinolin-7-ylmethyl)-2-oxopyrrolidin-3-(S)-yl]-carbamic acid tert-butyl ester (0.314 g, 0.081 mmol) by the method described in EXAMPLE 10, Part E. A portion of this material (0.285 g, 0.7 mmol) is deprotected as described in EXAMPLE 1, Part I to yield [1-(1-amino-6-methoxyisoquinolin-7-ylmethyl)-2-oxopyrrolidin-3-(S)-yl]-amine dihydrochloride (0.28 g, 0.78 mmol) and coupled with 4-(2-chloro-6-nitophelnoxy)benzene sulfonyl chloride (0.35 g, 1 mmol) as described in EXAMPLE 1, Part K. The material obtained upon extractive workup and column chromatography is further purified by RP HPLC to give the title compound (0.04 g, 0.067 mmol).

$^1$H NMR (CD$_3$OD, 300 MHz) δ 8.14 (s, 1H), 8.07 (d, 1H), 7.92–7.98 (m, 3H), 7.53–7.60 (m, 2H), 7.40 (s, 1H), 7.18 (d, 1H), 7.05 (d, 2H), 4.63 (AB, 2H), 4.18 (t, 1H), 4.06 (s, 3H), 3.36 (m, 2H), 2.32 (m, 1H), 1.87 (m, 1H). FAB MS, [M+H]$^+$=598, 600, Cl pattern. Elemental analysis calculated with 1.5 mole of H$_2$O: C=47.13%, H=3.82%, N=9.48%; found C=47.07%, H=3.66%, N=9.24%.

EXAMPLE 13

7-Methoxynaphthalene-2-sulfonic Acid-[1-(1,6-Diamino-isoquinolin-7-yl-methyl)-2-oxopyrrolidin-3-(S)-yl-amide Trifluoroacetate A. 3-(3-Acetamido-4-methylphenyl)propenoic Acid.

To a solution of 3-acetamido-4-methylbenzaldehyde (14 g, 79 mmol) in pyridine (210 mL) is added piperidine (3.9 mL, 39.4 mmol) and malonic acid (15.26 g, 146.6 mmol). The mixture is heated to 100° C. for 4 hours, then stirred at room temperature overnight. The solution is concentrated in vacuo, then diluted with water. Cold 1 N HCl is added to the slurry until pH is ca. 4. The solid product (16.178 g, 73.8 mmol) is collected and washed generously with water. The title compound (16.178 g, 73.8 mmol) is then dried over P$_2$O$_5$ under vacuum overnight to yield a white solid.

$^1$H NMR (DMSO-d$_6$, 300 MHz) δ 12.30 (bs, 1H), 9.30 (bs, 1H), 7.65 (s, 1H), 7.51 (d, 1H), 7.42 (d, 1H), 7.25 (d, 1H), 6.42 (d, 1H), 2.25 (s, 3H), 2.09 (s, 3H). EI MS [M+H]$^+$=220.

B. 3-(3-Acetylamino-4-methyl-phenyl)-acryloyl Azide.

To a slurry of 3-(3-acetamido-4-methylphenyl)propenoic acid (20.11 g, 91.7 mmol) in acetone (450 mL) at 0° C. is added triethylamine (12.8 mL, 91.8 mmol) followed by dropwise addition of ethyl chloroformate (11.8 mL, 123 mmol) over a 10 minutes period. The resulting yellow slurry is stirred using a mechanical stirrer for 1.5 hours, then a solution of sodium azide (8.94 g, 138 mmol) in water (25 mL) is added slowly so as to maintain the temperature below 5° C. The thick mixture is stirred at 0° C. for 1 hours, then the ice bath is removed and the reaction mixture allowed to warm to room temperature. The suspension is poured over water (800 mL) then filtered. The remaining solid is washed generously with water and dried under vacumn over P$_2$O$_5$ overnight to give the product as a pale yellow solid (21.40 g, 87.6 mmol).

$^1$H NMR (CDCl$_3$, 300 MHz) δ 8.10 (s, 1H), 6.71 (d, 1H), 7.22 (m, 2H), 6.95 (bs, 1H), 6.38 (d, 1H), 2.29 (s, 3H), 2.21 (s, 3H). EI MS [M]$^+$=244.

C. N-(7-Methyl-1-oxo-1,2-dihydro-isoquinolin-6-yl)-acetamide.

To a solution of diphenyl ether (250 mL) and tributylamine (11.9 mL, 49.9 mmol) at 220–240° C. is added a slurry of 3-(3-acetylamino-4-methyl-phenyl)-acryloyl azide (12.2 g, 49.9 mmol) in diphenyl ether. After 2 hours, the yellow solution is cooled to room temperature and poured over hexane (800 mL). A brown solid precipitates out and the title product (3.56 g, 16.5 mmol) is obtained as a light yellow solid by recrystallization from DMF/MeOH.

$^1$H NMR (DMSO-d$_6$, 300 MHz) δ 11.0 (bs, 1H), 9.35 (s, 1H), 7.98 (s, 1H), 7.89 (s, 1H), 7.05 (m, 1H), 6.45 (d, 1H), 2.32 (s, 3H), 2.12 (s, 3H). EI MS [M ]$^+$=216.

D. 6-Amino-7-methyl-2H-isoquinolin-1-one.

N-(7-Methyl-1-oxo-1,2-dihydro-isoquinolin-6-yl)-acetamide (0.366 g, 1.69 mmol) and conc. HCl (0.5 mL) is heated to reflux in EtOH (0.84 mL). After 6 hours, the mixture is concentrated to dryness, then diluted with water and basified using 1 N NaOH until pH is ca. 10. The aqueous solution is extracted with methylene chloride (4×50 mL) and the organic layers are combined and washed with brine, dried over MgSO$_4$, filtered and concentrated. The crude product is purified by column chromatography eluting with a gradient of 3% MeOH/CH$_2$Cl$_2$ to 5% MeOH/CH$_2$Cl$_2$ to give the title product (0.200 g, 1.15 mmol) as a white solid.

$^1$H NMR (CDCl$_3$, 300 MHz) δ 8.90 (bs, 1H), 8.06 (s, 1H), 6.90 (m, 1H), 6.65 (s, 1H), 6.28 (d, 1H), 4.05 (bs, 2H), 2.20 (s, 3H). EI MS [M]$^+$=174.

E. 1-Chloro-7-methyl-isoquinolin-6-ylamine.

The title compound is prepared as described in EXAMPLE 1, Part E using 6-amino-7-methyl-2H-isoquinolin-1-one as the starting material. The crude product is purified by column chromatography eluting with a gradient of 5% MeOH/CH$_2$Cl$_2$ to 10% MeOH/CH$_2$Cl$_2$ to afford the title compound as a yellow solid.

$^1$H NMR (CDCl$_3$, 300 MHz) δ 8.05 (d, 1H), 8.00 (s, 1H), 7.30 (d, 1H), 6.90 (s, 1H), 4.25 (bs, 2H), 2.40 (s, 3H). EI MS [M]$^+$=192, 194, Cl pattern.

F. Benzhydrylidene-(1-chloro-7-methyl-isoquinolin-6-yl)-amine.

To a solution of 1-chloro-7-methyl-isoquinolin-6-ylamine (0.1 g, 0.52 mmol) in MeOH (5 mL) at 0° C. is bubbled HCl gas for 1 minute, then the solvent is removed in vacuo. The remaining white solid is diluted with 1,2 dichloroethane and benzophenone imine (0.15 mL, 0.89 mmol) is added. The resulting suspension is heated to reflux for 48 hours, then cooled to room temperature and concentrated to dryness. The crude material is diluted with CH$_2$Cl$_2$ and washed with saturated NaHCO$_3$ solution and brine. The organic layer is dried over MgSO$_4$, filtered and concentrated. The crude product is purified by column chromatography using 10% EtOAc/hexanes as the eluent to afford the title compound (0.159g, 0.45 mmol) as a yellow oil.

$^1$H NMR (CDCl$_3$, 300 MHz) δ 8.05 (m, 2H), 7.80 (m, 2H), 7.45–7.55 (m, 4H), 7.20–7.30(m, 3H), 7.10 (m, 2H), 6.75 (s, 1H), 2.50 (s, 3H). FAB MS, [M+H]$^+$=357, 359, Cl pattern.

G. Benzhydrylidene-(7-bromomethyl-1-chloro-isoquinolin-6-yl)-amine.

The title compound is prepared as described in EXAMPLE 1, Part F using benzhydrylidene-(1-chloro-7-methyl-isoquinolin-6-yl)-amine as the starting material. The title compound is obtained as an oil.

$^1$H NMR (CDCl$_3$, 300 MHz) δ 8.33 (s, 1H), 8.06 (d, 1H), 7.84 (m, 2H), 7.41 (m, 4H), 7.32 (m, 4H), 7.20 (d, 1H), 6.66 (s, 1H), 4.79 (s, 2H). FAB MS, [M+H]$^+$=435, 437, Cl, Br pattern.

H. {1-[6-(Benzhydrylidene-amino)-1-chloro-isoquinolin-7-ylmethyl]-2-oxopyrrolidin-3-(S)-yl}-carbamic Acid tert-Butyl Ester.

The title compound is prepared as described in EXAMPLE 1, Part H using benzhydrylidene-(7-bromomethyl-1-chloro-isoquinolin-6-yl)-amine in place of 7-bromomethyl-1-chloroisoquinoline. The crude product is purified by column chromatography eluting with a gradient of 10% EtOAc/hexanes to 30% EtOAc/hexanes to give the product as a foamy yellow solid.

$^1$H NMR (CDCl$_3$, 300 MHz) δ 8.09 (d, 1H), 8.01 (s, 1H), 7.80 (m, 2H), 7.20–7.45 (m, 9H), 6.70 (s, 1H), 5.30 (d, 1H), 4.65 (AB, 2H), 4.21 (m, 1H), 3.32 (m, 2H), 2.70 (m, 1H), 1.95 (m, 1H), 1.46 (s, 9H). FAB MS, [M+H]$^+$=555, 557, Cl pattern.

I. 7-Methoxynaphthalene-2-sulfonic Acid [1-(6-Amino-1-chloro-isoquinolin-7-ylmethyl)-2-oxopyrrolidin-3-(S)-yl]-amide.

{1-[6-(Benzhydrylidene-amino)-1-chloro-isoquinolin-7-ylmethyl]-2-oxopyrrolidin-3-(S)-yl}-carbamic acid tert-butyl ester is deprotected as described in EXAMPLE 1, Part I to yield 3-(S)-amino-1-(6-amino-1-chloro-isoquinolin-7-ylmethyl)-pyrrolidin-2-one hydrochloride and coupled with 7-methoxynaphthalene-2-sulfonyl chloride as described in EXAMPLE 1, Part K. The material obtained upon extractive workup is purified by column chromatography eluting with a gradient of 30% EtOAc/hexanes to 60% EtOAc/hexanes to give the product.

$^1$H NMR (CDCl$_3$, 300 MHz) δ 8.34 (s, 1H), 8.02 (d, 1H), 7.93 (s, 1H), 7.87 (d, 1H), 7.79 (d, 1H), 7.72 (dd, 1H), 7.29 (dd, 1H), 7.26 (d, 1H), 7.25 (s, 1H), 6.77 (s, 1H), 5.61 (bs, 1H), 4.93 (bs, 2H), 4.49 (AB, 2H), 3.92 (s, 3H), 3.85 (m, 1H), 3.20 (m, 2H), 2.52 (m, 1H), 2.05 (m, 1H). Ion spray MS, [M+H]$^+$=511, 513, Cl pattern.

J. 7-Methoxynaphthalene-2-sulfonic Acid [1-(1,6-Diamino-isoquinolin-7-ylmethyl)-2-oxopyrrolidin-3-(S)-yl]-amide Trifluoroacetate.

The title compound is prepared as described in EXAMPLE 2 using 7-methoxynaphthalene-2-sulfonic acid [1-(6-amino-1-chloro-isoquinolin-7-ylmethyl)-2-oxopyrrolidin-3-(S)-yl]-amide as the starting material. No extractive work up is performed. The crude product is purified by RP-HPLC eluting with a gradient of 10% CH$_3$CN/H$_2$O (0.1% TFA) to 100% CH$_3$CN. The appropriate fractions are lyophilized to provide the title compound as a white solid.

$^1$H NMR (DMSO-d$_6$, 300 MHz) δ 12.25 (bs, 1H), 8.34–8.38 (d, 2H), 8.24 (d, 1H), 7.95 (d, 1H), 7.90–7.93 (d, 2H), 7.68 (dd, 1H), 7.53 (d, 1H), 7.38 (d, 1H), 7.30 (dd, 1H), 6.83 (d, 1H), 6.78 (s, 1H), 6.49 (bs, 1H), 4.26 (AB, 2H), 4.20 (m, 1H), 3.90 (s, 3H), 3.06 (m, 2H), 2.00 (m, 1H), 1.60 (m, 1H). FAB MS, [M+H]$^+$=492.

EXAMPLE 14

6-Chloro-benzo[b]thiophene-2-sulfonic Acid [1-(1,6-Diamino-isoquinolin-7-yl-methyl)-2-oxopyrrolidin-3-(S)-yl]amide Trifluoroacetate A. 6-Chloro-benzo[b]thiophene-2-sulfonic Acid [1-(6-Amino-1-chloro-isoquinolin-7-ylmethyl)-2-oxopyrrolidin-3-(S)-yl]-amide.

{1-[6-(Benzhydrylidene-amino)-1-chloro-isoquinolin-7-ylmethyl]-2-oxopyrrolidin-3-(S)-yl}-carbamic acid tert-butyl ester is deprotected as described in EXAMPLE 1, Part I to yield 3-(S)-amino-1-(6-amino-1-chloro-isoquinolin-7-ylmethyl)-pyrrolidin-2-one hydrochloride and coupled with 6-chloro-benzo[b]thiophene-2-sulfonyl chloride as described in EXAMPLE 1, Part K. The material obtained upon extractive workup is purified by column chromatography eluting with a gradient of 20% EtOAc/hexanes to 60% EtOAc/hexanes to give the product.

$^1$H NMR (CDCl$_3$, 300 MHz) δ 8.05 (d, 1H), 8.02 (s, 1H), 7.98 (s, 1H), 7.89 (s, 1H), 7.86 (d, 1H), 7.81 (d, 1H), 7.44 (dd, 1H), 6.82 (s, 1H), 5.40 (d, 1H), 4.90 (bs, 2H), 5.42 (AB, 2H), 3.95 (m, 1H), 3.30 (m, 2H), 2.65 (m, 1H), 2.05 (m, 1H). Ion spray MS, [M+H]$^+$=521, 523, Cl pattern.

B. 6-Chloro-benzo[b]thiophene-2-sulfonic Acid [1-(1,6-Diamino-isoquinolin-7-ylmethyl)-2-oxopyrrolidin-3-(S)-yl-amide Trifluoroacetate.

The title compound is prepared as described in EXAMPLE 2 using 6-chloro-benzo[b]thiophene-2-sulfonic acid[1-(6-amino-1-chloro-isoquinolin-7-ylmethyl)-2-oxopyrrolidin-3-(S)-yl]-amide as the starting material. No extractive work up is performed. The crude product is purified by RP-HPLC eluting with a gradient of 10% CH$_3$CN/H$_2$O (0.1% TFA) to 100% CH$_3$CN/H$_2$O. The appropriate fractions are lyophilized to provide the title compound as a tan solid.

$^1$H NMR (DMSO-d$_6$, 300 MHz) δ 12.05 (bs, 1H), 8.70 (d, 1H), 8.35 (bs, 2H), 8.20 (s, 1H), 8.00–8.05 (m, 2H), 7.94 (s, 1H), 7.51 (d, 1H), 7.38 (m, 1H), 6.71–6.80 (m, 2H), 6.51 (bs, 2H), 4.30 (m, 3H), 3.20 (m, 2H), 2.15 (m, 1H), 1.71 (m, 1H). Ion spray MS, [M+H]$^+$=502, 504, Cl pattern.

EXAMPLE 15

7-Methoxynaphthalene-2-sulfonic Acid [1-(2-Aminoquinolin7-ylmethyl)-2-oxopyrrolidin-3-(S)-yl]-amide Trifluoroacetate A. 7-Methyl-1H-quinolin-2-one and 5-methyl-1H-quinolin-2-one.

The title compounds are prepared from m-toluidine and cinnamoyl chloride according to the procedure described in *Synthesis* 1975, 739. The crude solid residue obtained is triturated in Et$_2$O/hexanes and filtered to give a mixture of product isomers in a ratio of 1.5:1 of 7-methyl-1H-quinolin-2-one to 5-methyl-1H-quinolin-2-one as a beige solid. Several attempts at purification through fractional crystallization in methanol gave only an enriched 2:1 mixture of isomers which is used in the subsequent step.

$^1$H NMR (DMSO-d$_6$, 300 MHz) δ 7.85 (d, 1H), 7.53 (d, 1H), 7.09 (s, 1H), 7.01 (d, 1H), 6.42 (d, 1H), 2.38 (s, 3H) for major isomer (7-methyl); and δ 8.03 (d, 1H), 7.38 (dd, 1H), 7.17 (s, 1H), 7.01 (d, 1H), 6.51 (d, 1H), 2.50 (s, 3H) for minor isomer (5-methyl).

B. 2-Chloro-7-methyl-quinoline and 2-Chloro-5-methyl-quinoline.

The title compounds are prepared as described in EXAMPLE 1, Part E using a 2:1 mixture of 7-methyl-1H-quinolin-2-one and 5-methyl-1H-quinolin-2-one in place of 7-methyl-2H-isoquinolin-1-one. The crude product is purified by column chromatography eluting with a gradient of 5% EtOAc/CH$_2$Cl$_2$ to 10% EtOAc/CH$_2$Cl$_2$ to afford a 2:1 mixture of 2-chloro-7-methyl-quinoline to 2-chloro-5-methyl-quinoline as a beige solid.

$^1$H NMR (CDCl$_3$, 300 MHz) δ 8.02 (d, 1H), 7.78 (s, 1H), 7.68 (d, 1H), 7.39 (m, 1H), 7.30 (d, 1H), 2.56 (s, 3H) for major isomer (7-methyl); and δ 8.25 (d, 1H), 7.86 (d, 1H), 7.60 (dd, 1H), 7.39 (m, 2H), 2.65 (s, 3H) for minor isomer (5-methyl).

C. 7-Bromomethyl-2-chloro-quinoline and 5-Bromomethyl-2-chloro-quinoline.

The title compounds are prepared as described in EXAMPLE 1, Part F using a 2:1 mixture of 2-chloro-7-methyl-quinoline and 2-chloro-5-methyl-quinoline in place of 1-chloro-7-methyl-isoquinoline. The crude mixture of isomers obtained is partially purified by trituration in EtOAc/hexanes to yield the 7-bromomethyl-2-chloro-quinoline as a beige solid (7.4 g, 38%).

$^1$H NMR (CDCl$_3$, 300 MHz) δ 8.10 (d, 1H), 8.00 (s, 1H), 7.82 (d, 1H), 7.60 (d, 1H), 4.67 (s, 2H).

An enriched 2:1 mixture of 5-bromomethyl-2-chloro-quinoline to 7-bromomethyl-2-chloro-quinoline is isolated as a beige solid (6.8 g) from the concentrated filtrate by fractional recrystallization in Et$_2$O/hexanes/EtOAc.

¹H NMR (CDCl₃, 300 MHz) δ 8.43 (d, 1H), 8.09 (dd, 1H), 8.03 (m, 1H), 7.68 (m, 1H), 7.50 (d, 1H), 4.88 (s, 2H) for major isomer (5-bromomethyl).

D. [1-(2-Chloro-quinolin-7-ylmethyl)-2-oxopyrrolidin-3-(S)-1-carbamic Acid tert-Butyl Ester.

The title compound is prepared from (2-oxopyrrolidin-3-(S)-yl)-carbamic acid tert-butyl ester as described in EXAMPLE 1, Part H using 7-bromomethyl-2-chloro-quinoline in place of 7-bromomethyl-1-chloro-isoquinoline. The crude product is triturated in 20% EtOAc/hexanes and filtered to afford the title compound as a beige solid.

¹H NMR (CDCl₃, 300 MHz) δ 8.10 (d, 1H), 7.83 (s, 1H), 7.80 (d, 1H), 7.46 (d, 1H), 7.40 (d, 1H), 5.17 (bs, 1H), 4.68 (AB, 2H), 4.25 (m, 1H), 3.26 (m, 2H), 2.64 (m, 1H), 1.88 (m, 1H), 1.46 (s, 9H).

E. 7-(3-(S)-Amino-2-oxopyrrolidin-1-ylmethyl)-2-chloro-quinoline Hydrochloride.

The title compound is prepared as described in EXAMPLE 1, Part I using [1-(2-chloro-quinolin-7-ylmethyl)-2-oxopyrrolidin-3-(S)-yl]-carbamic acid tert-butyl ester as the starting material. The title compound is obtained as a white solid.

¹H NMR (DMSO-d₆, 300 MHz) δ 8.75 (bs, 2H), 8.47 (d, 1H), 8.06 (d, 1H), 7.86 (s, 1H), 7.61 (d, 1H), 7.58 (d, 1H), 4.69 (AB, 2H), 4.15 (m, 1H), 3.35 (m, 2H), 2.43 (m, 1H), 2.04 (m, 1H).

F. 7-Methoxynaphthalene-2-sulfonic Acid [1-(2-Chloro-quinolin-7-ylmethyl)-2-oxopyrrolidin-3-(S)-yl]-amide.

The title compound is prepared in CH₂Cl₂ instead of CH₃CN as described in EXAMPLE 1, Part K using 7-(3-(S)-amino-2-oxopyrrolidin-1-ylmethyl)-2-chloro-quinoline hydrochloride in place of 7-(3-(S)-amino-2-oxopyrrolidin-1-ylmethyl)-1-chloro-isoquinoline hydrochloride and 7-methoxynaphthalene-2-sulfonyl chloride as prepared in EXAMPLE 1, Part J. The crude product is triturated in 20% EtOAc/hexanes and filtered to afford the title compound as a white solid.

¹H NMR (CDCl₃, 300 MHz) δ 8.38 (s, 1H), 8.08 (d, 1H), 7.92 (d, 1H), 7.81 (d, 1H), 7.76 (m, 3H), 7.38 (d, 1H), 7.36 (dd, 1H), 7.30 (dd, 1H), 7.25 (m, 1H), 5.44 (s, 1H), 4.61 (s, 2H), 3.96 (s, 3H), 3.78 (m, 1H), 3.23 (m, 2H), 2.60 (m, 1H), 2.10 (m, 1H). FAB MS, [M+H]⁺=496, 498, Cl pattern. Elemental analysis calculated C=60.54%, H=4.47%, N=8.47%, Cl=7.15%, found C=60.44%, H=4.18%, N=8.45%, Cl=7.19%.

G. 7-Methoxynaphthalene-2-sulfonic Acid [1-(2-Aminoquinolin7-ylmethyl)-2-oxopyrrolidin-3-(S)-yl-amide Trifluoroacetate.

7-Methoxynaphthalene-2-sulfonic acid [1-(2-chloro-quinolin-7-ylmethyl)-2-oxopyrrolidin-3-(S)-yl]-amide is converted to the title compound when heated at 125° C. as described in EXAMPLE 2. The crude product is partially purified by RP-HPLC eluting in a gradient of 10% CH₃CN/H₂O (0.1% TFA) to 60% CH₃CN/H₂O (0.1% TFA) and the appropriate product fractions are concentrated in vacuo, filtered and triturated with MeOH as previously described to provide the title compound as a white solid.

¹H NMR (DMSO-d₆, 300 MHz) δ 8.62 (bs, 2H), 8.38 (s, 1H), 8.31 (d, 1H), 8.25 (d, 1H), 8.03 (d, 1H), 7.94 (d, 1H), 7.86 (d, 1H), 7.72 (d, 1H), 7.55 (s, 1H), 7.43 (s, 1H), 7.32 (dd, 1H), 7.27 (d, 1H), 7.01 (d, 1H), 4.50 (AB, 2H), 4.11 (m, 1H), 3.88 (s, 3H), 3.09 (m, 2H), 2.00 (m, 1H), 1.58 (m, 1H). Ion spray MS, [M+H]⁺=477. Elemental analysis calculated C=54.93%, H=4.27%, N=9.49%, found C=54.69%, H=4.24%, N=9.30%. The enantiomeric purity is 81.9% ee as determined by analytical Chiralpak AS RP-HPLC.

EXAMPLE 16

6-Chloro-benzo[b]thiophene-2-sulfonic Acid [1-(2-Aminoquinolin7-ylmethyl)-2-oxopyrrolidin-3-(S)-yl] amide Trifluoroacetate A. 6-Chloro-benzo[b]thiophene-2-sulfonic Acid [1-(2-Chloro-quinolin-7-ylmethyl)-2-oxopyrrolidin-3-(S)-yl]-amide.

The title compound is prepared in CH₂Cl₂ instead of CH₃CN from 7-(3-(S)-amino-2-oxopyrrolidin-1-ylmethyl)-2-chloro-quinoline hydrochloride as described in EXAMPLE 1, Part K using 6-chloro-benzo[b]thiophene-2-sulfonyl chloride as prepared in EXAMPLE 9, Parts A, B and C in place of 7-methoxynaphthalene-2-sulfonyl chloride. The crude product is triturated from EtOAc/hexanes to afford the title compound as a beige solid.

¹H NMR (DMSO-d₆, 300 MHz) δ 8.77 (d, 1H), 8.42 (d, 1H), 8.27 (s, 1H), 8.07 (s, 1H), 8.04 (d, 1H), 8.02 (d, 1H), 7.75 (s, 1H), 7.58 (d, 1H), 7.52 (dd, 1H), 7.48 (d, 1H), 4.55 (AB, 2H), 4.28 (m, 1H), 3.18 (m, 2H), 2.18 (m, 1H), 1.71 (m, 1H). Ion spray MS, [M+H]⁺=506, 508, Cl pattern.

B. 6-Chloro-benzo[b]thiophene-2-sulfonic Acid [1-(2-Aminoquinolin7-ylmethyl)-2-oxopyrrolidin-3-(S)-yl]-amide Trifluoroacetate.

6-Chloro-benzo[b]thiophene-2-sulfonic acid [1-(2-Chloro-quinolin-7-ylmethyl)-2-oxopyrrolidin-3-(S)-yl]-amide is converted to the title compound when heated at 120° C. as described in EXAMPLE 2. The crude product is purified by RP-HPLC eluting in a gradient of 10% CH₃CN/H₂O (0.1% TFA) to 80% CH₃CN/H₂O (0.1% TFA) and the appropriate product fractions are lyophilized to provide the title compound as a tan solid.

¹H NMR (DMSO-d₆, 500 MHz) δ 8.73 (d, 1H), 8.34 (d, 1H), 8.29 (s, 1H), 8.07 (s, 1H), 8.03 (d, 1H), 7.89 (d, 1H), 7.54 (dd, 1H), 7.52 (d, 1H), 7.47 (s, 1H), 7.31 (d, 1H), 7.04 (d, 1H), 6.94 (d, 1H), 6.42 (d, 1H), 4.53 (AB, 2H), 4.22 (m, 1H), 3.18 (m, 2H), 2.18 (m, 1H), 1.72 (m, 1H). FAB MS, [M+H]⁺=487.

EXAMPLE 17

Benzo[b]thiophene-2-sulfonic Acid [1-(2-Aminoquinolin7-ylmethyl)-2-oxopyrrolidin-3-(S)-yl] amide Trifluoroacetate A. Benzo[b]thiophene-2-sulfonic Acid [1-(2-Chloro-quinolin-7-ylmethyl)-2-oxopyrrolidin-3-(S)-yl]-amide.

The title compound is prepared in CHCl₃ instead of CH₃CN from 7-(3-(S)-amino-2-oxopyrrolidin-1-ylmethyl)-2-chloro-quinoline hydrochloride as described in EXAMPLE 1, Part K using benzo[b]thiophene-2-sulfonyl chloride as prepared in EXAMPLE 8, Part A in place of 7-methoxynaphthalene-2-sulfonyl chloride. The crude product is triturated from CH₂Cl₂ to afford the title compound as a beige solid.

¹H NMR (CDCl₃, 300 MHz) δ 8.08 (d, 1H), 7.95 (d, 1H), 7.88 (m, 2H), 7.99 (d, 1H), 7.76 (s, 1H), 7.49 (m, 2H), 7.39 (m, 2H), 5.62 (s, 1H), 4.64 (s, 2H), 3.95 (m, 1H), 3.27 (m, 2H), 2.65 (m, 1H), 2.16 (m, 1H).

B. Benzo[b]thiophene-2-sulfonic Acid [1-(2-Aminoquinolin7-ylmethyl)-2-oxopyrrolidin-3-(S)-yl-amide Trifluoroacetate.

Benzo[b]thiophene-2-sulfonic acid [1-(2-chloro-quinolin-7-ylmethyl)-2-oxopyrrolidin-3-(S)-yl]-amide is converted to the title compound when heated at 130° C. as described in EXAMPLE 2. The crude product is purified by RP-HPLC eluting in a gradient of 10% CH₃CN/H₂O (0.1% TFA) to 60% CH₃CN/H₂O (0.1% TFA) and the appropriate product fractions are lyophilized to provide the title compound as a tan solid.

¹H NMR (DMSO-d₆, 500 MHz) δ 8.68 (d, 1H), 8.35 (d, 1H), 8.09 (dd, 1H), 8.06 (s, 1H), 8.02 (dd, 1H), 7.90 (d, 1H), 7.52 (m, 2H), 7.45 (s, 1H), 7.32 (d, 1H), 7.04 (d, 1H), 4.53 (AB, 2H), 4.22 (m, 1H), 3.17 (m, 2H), 2.18 (m, 1H), 1.72 (m, 1H). Ion spray MS, [M+H]⁺=453.

EXAMPLES 18 AND 19

7-Methoxynaphthalene-2-sulfonic Acid [1-(2-Aminoquinolin7-ylmethyl)-2-oxopyrrolidin-3-(S)-yl] methyl amide Trifluoroacetate and 7-methoxynaphthalene-2-sulfonic Acid Methyl-2-oxo-1-(2-oxo-1,2-dihydro-quinolin-7-ylmethyl)-pyrrolidin-3-(S)-yl]-amide A. 7-Methoxynaphthalene-2-sulfonic Acid [1-(2-Chloro-quinolin-7-ylmethyl)-2-oxopyrrolidin-3-(S)-yl]-methyl amide.

7-Methoxynaphthalene-2-sulfonic acid [1-(2-chloro-quinolin-7-ylmethyl)-2-oxopyrrolidin-3-(S)-yl]-amide (0.4 g, 0.81 mmol), prepared as in EXAMPLE 15, Part F, is dissolved in DMF (20 mL) and cooled to 0° C. To the solution is added methyliodide (0.28 g, 2.01 mmol) and sodium hydride (34 mg, 0.85 mmol, 60% mineral oil dispersion). The ice water bath is removed and the mixture is stirred at room temperature for 3 hours. The resulting solution is poured into a separatory funnel and diluted with EtOAc (100 mL). The organic layer is washed with 1N HCl, H₂O and saturated NaCl. The organic phase is then dried over MgSO₄, filtered and concentrated. The crude residue is purified by column chromatography eluting with 10% EtOAc/CH₂Cl₂ to give the title compound (0.36 g, 0.71 mmol) as a solid.

¹H NMR (CDCl₃, 300 MHz) δ 8.44 (s, 1H), 8.09 (d, 1H), 7.92 (d, 1H), 7.82 (dd, 1H), 7.78 (m, 3H), 7.42 (dd, 1H), 7.40 (d, 1H), 7.28 (dd, 1H), 7.26 (s, 1H), 5.00 (m, 1H), 4.62 (AB, 2H), 3.94 (s, 3H), 3.23 (m, 2H), 2.84 (s, 3H), 2.33 (m, 1H), 2.03 (m, 1H).

B. 7-Methoxynaphthalene-2-sulfonic Acid [1-(2-Aminoquinolin7-ylmethyl)-2-oxopyrrolidin-3-(S)-yl]-methyl Amide Trifluoroacetate and 7-methoxynaphthalene-2-sulfonic Acid Methyl-[2-oxo-1-(2-oxo-1,2-dihydro-quinolin-7-ylmethyl)-pyrrolidin-3-(S)-yl]-amide.

7-Methoxynaphthalene-2-sulfonic acid [1-(2-chloro-quinolin-7-ylmethyl)-2-oxopyrrolidin-3-(S)-yl]-methyl amide is converted to the title compounds when heated at 125° C. as described in EXAMPLE 2. The crude mixture of products is purified by RP-HPLC eluting in a gradient of 10% CH₃CN/H₂O (0.1% TFA) to 80% CH₃CN/H₂O (0.1% TFA) and the appropriate product fractions are lyophilized to provide 7-methoxynaphthalene-2-sulfonic acid [1-(2-aminoquinolin7-ylmethyl)-2-oxopyrrolidin-3-(S)-yl]methyl amide trifluoroacetate as a white solid.

¹H NMR (DMSO-d₆, 300 MHz) δ 8.42 (s, 1H), 8.33 (d, 1H), 8.04 (d, 1H), 7.96 (d, 1H), 7.87 (d, 1H), 7.70 (dd, 1H), 7.58 (s, 1H), 7.42 (s, 1H), 7.35 (dd, 1H), 7.31 (d, 1H), 7.02 (d, 1H), 4.93 (m, 1H), 4.51 (AB, 2H), 3.89 (s, 3H), 3.18 (m, 2H), 2.70 (s, 3H), 2.02 (m, 1H), 1.78 (m, 1H). Ion spray MS, [M+H]⁺=491. Elemental analysis calculated with 1.8 mol of H₂O cal. C=52.79%, H=4.84%, N=8.80%, found C=52.80%, H=4.35%, N=8.55%.

7-Methoxynaphthalene-2-sulfonic acid methyl-[2-oxo-1-(2-oxo-1,2-dihydro-quinolin-7-ylmethyl)-pyrrolidin-3-(S)-yl]-amide is also isolated from the reaction mixture as a by-product.

¹H NMR (DMSO-d₆, 300 MHz) δ 8.42 (s, 1H), 8.04 (d, 1H), 7.97 (d, 1H), 7.85 (d, 1H), 7.70 (d, 1H), 7.60 (d, 1H), 7.58 (s, 1H), 7.35 (dd, 1H), 7.04 (s, 1H), 6.98 (d, 1H), 6.45 (d, 1H), 4.90 (m, 1H), 4.40 (AB, 2H), 3.89 (s, 3H), 3.15 (m, 2H), 2.71 (s, 3H), 2.01 (m, 1H), 1.76 (m, 1H). Ion spray MS, [M+H]⁺=492.

EXAMPLE 20

7-Methoxynaphthalene-2-sulfonic Acid [1-(2-Aminoquinolin5-ylmethyl)-2-oxopyrrolidin-3-(S)-yl]-amide Trifluoroacetate A. [1-(2-Chloro-quinolin-5-ylmethyl)-2-oxopyrrolidin-3-(S)-yl-carbamic Acid tert-Butyl Ester.

The title compound is prepared from (2-oxopyrrolidin-3-(S)-yl)-carbamic acid tert-butyl ester as described in EXAMPLE 1, Part H using a 2:1 mixture of 5-bromomethyl-2-chloro-quinoline to 7-bromomethyl-2-chloro-quinoline, as prepared in EXAMPLE 15, Part C, in place of 7-bromomethyl-1-chloro-isoquinoline. The crude product mixture is purified by column chromatography eluting with 1% MeOH in 25% EtOAc/CH₂Cl₂ to afford as the major product the title compound as a beige solid.

¹H NMR (CDCl₃, 300 MHz) δ 8.53 (d, 1H), 7.98 (d, 1H), 7.69 (dd, 1H), 7.50 (d, 1H), 7.41 (d, 1H), 5.59 (d, 1H), 4.89 (AB, 2H), 4.22 (m, 1H), 3.19 (m, 1H), 3.12 (m, 1H), 2.51 (m, 1H), 1.86 (m, 1H), 1.45 (s, 9H).

B. 5-(3-(S)-Amino-2-oxopyrrolidin-1-ylmethyl)-2-chloro-quinoline Hydrochloride.

The title compound is prepared as described in EXAMPLE 1, Part I using [1-(2-chloro-quinolin-5-ylmethyl)-2-oxopyrrolidin-3-(S)-yl]-carbamic acid tert-butyl ester as the starting material. The title compound is obtained as a white solid.

¹H NMR (DMSO-d₆, 300 MHz) δ 8.63 (d, 1H), 8.59 (bs, 3H), 7.94 (d, 1H), 7.81 (m, 1H), 7.65 (m, 2H), 4.89 (s, 2H), 4.08 (m, 1H), 3.24 (m, 2H), 2.34 (m, 1H), 1.94 (m, 1H).

C. 7-Methoxynaphthalene-2-sulfonic Acid [1-(2-Chloro-quinolin-5-ylmethyl)-2-oxopyrrolidin-3-(S)-yl]-amide.

The title compound is prepared in CH₂Cl₂ instead of CH₃CN as described in EXAMPLE 1, Part K using 5-(3-(S)-amino-2-oxopyrrolidin-1-ylmethyl)-2-chloro-quinoline hydrochloride in place of 7-(3-(S)-amino-2-oxopyrrolidin-1-ylmethyl)-1-chloro-isoquinoline hydrochloride and 7-methoxynaphthalene-2-sulfonyl chloride as prepared in EXAMPLE 1, Part J. The crude product is purified by column chromatography eluting with 25% EtOAc/CH₂Cl₂ to provide the title compound as a light yellow solid.

¹H NMR (CDCl₃, 300 MHz) δ 8.36 (d, 1H), 8.33 (s, 1H), 7.98 (d, 1H), 7.91 (d, 1H), 7.82 (d, 1H), 7.73 (d, 1H), 7.66 (m, 1H), 7.42 (d, 1H), 7.35 (d, 1H), 7.30 (dd, 1H), 7.25 (dd, 1H), 5.40 (s, 1H), 4.82 (AB, 2H), 3.94 (s, 3H), 3.71 (m, 1H), 3.12 (m, 1H), 3.02 (m, 1H), 2.50 (m, 1H), 1.98 (m, 1H). EI MS, [M]⁺=495, 497, Cl pattern. Elemental analysis calculated C=60.54%, H=4.47%, N=8.47%, Cl=7.15%, found C=59.79%, H=4.70%, N=7.88, Cl=7.21%.

D. 7-Methoxynaphthalene-2-sulfonic Acid [1-(2-Aminoquinolin5-ylmethyl)-2-oxopyrrolidin-3-(S)-yl]-amide Trifluoroacetate.

7-Methoxynaphthalene-2-sulfonic acid [1-(2-chloro-quinolin-5-ylmethyl)-2-oxopyrrolidin-3-(S)-yl]-amide is converted to the title compound when heated at 125° C. as described in EXAMPLE 2. The crude product is partially purified by RP-HPLC eluting in a gradient of 10% CH₃CN/H₂O (0.1% TFA) to 80% CH₃CN/H₂O (0.1% TFA) and the appropriate product fractions are concentrated in vacuo, filtered, triturated with MeOH and then purified further by column chromatography eluting with a gradient of 1% MeOH/CH₂Cl₂ to 3% MeOH/CH₂Cl₂ to yield the title compound as a pale yellow solid.

¹H NMR (DMSO-d₆, 300 MHz) δ 8.48 (d, 1H), 8.37 (s, 1H), 8.23 (d, 1H), 8.03 (d, 1H), 7.93 (d, 1H), 7.72 (m, 1H), 7.69 (d, 1H), 7.60 (d, 1H), 7.55 (s, 1H), 7.33 (m, 2H), 7.07 (d, 1H), 4.71 (AB, 2H), 4.11 (m, 1H), 3.88 (s, 3H), 3.00 (m, 2H), 1.94 (m, 1H), 1.48 (m, 1H). FAB MS, [M+H]⁺=477.

Elemental analysis calculated with 2.5 mol of H₂O cal. C=50.98%, H=4.14%, N=8.38%, found C=50.96%, H=4.14%, N=8.38%. The enantiomeric purity is 84.5% ee as determined by analytical Chiralpak AS RP-HPLC.

EXAMPLES 21 AND 22

7-Methoxynaphthalene-2-sulfonic Acid [1-(2-Aminoquinolin5-ylmethyl)-2-oxopyrrolidin-3-(S)-yl]-methyl Amide Trifluoroacetate and 7-methoxynaphthalene-2-sulfonic Acid Methyl-[2-oxo-1-(2-oxo-1,2-dihydro-quinolin-5-ylmethyl)-pyrrolidin-3-(S)-yl]-amide A. 7-Methoxynaphthalene-2-sulfonic Acid [1-(2-chloro-quinolin-5-ylmethyl)-2-oxopyrrolidin-3-(S)-yl]methyl Amide.

The title compound is prepared as in EXAMPLES 18 AND 19, Part A using 7-methoxynaphthalene-2-sulfonic acid [1-(2-chloro-quinolin-5-ylmethyl)-2-oxopyrrolidin-3-(S)-yl]-amide as the starting material. The crude product is purified by column chromatography eluting with 50% EtOAc/hexanes to afford the title compound as a white solid.

$^1$H NMR (CDCl₃, 300 MHz) δ 8.42 (s, 1H), 8.38 (s, 1H), 7.97 (d, 1H), 7.91 (d, 1H), 7.78 (m, 2H), 7.66 (dd, 1H), 7.43 (d, 1H), 7.30 (d, 1H), 7.25 (m, 2H), 4.92 (m, 1H), 4.80 (AB, 2H), 3.92 (s, 3H), 3.08 (m, 2H), 2.74 (s, 3H), 2.22 (m, 1H), 1.80 (m, 1H).

B. 7-Methoxynaphthalene-2-sulfonic Acid [1-(2-Aminoquinolin5-ylmethyl)-2-oxopyrrolidin-3-(S)-yl]-5methyl Amide Trifluoroacetate and 7-Methoxynaphthalene-2-sulfonic Acid Methyl-[2-oxo-1-(2-oxo-1,2-dihydro-quinolin-5-ylmethyl)-pyrrolidin-3-(S)-yl]-amide.

7-Methoxynaphthalene-2-sulfonic acid [1-(2-chloro-quinolin-5-ylmethyl)-2-oxopyrrolidin-3-(S)-yl]-methyl amide is converted to the title compounds when heated at 120° C. as described in EXAMPLE 2. The crude product is purified by RP-HPLC eluting in a gradient of 10% CH₃CN/H₂O (0.1% TFA) to 80% CH₃CN/H₂O (0.1% TFA) and the appropriate product fractions are lyophilized to provide 7-methoxynaphthalene-2-sulfonic acid [1-(2-aminoquinolin5-ylmethyl)-2-oxopyrrolidin-3-(S)-yl]-methyl amide trifluoroacetate as a white solid.

$^1$H NMR (DMSO-d₆, 300 MHz) δ 8.46 (d, 1H), 8.39 (s, 1H), 8.03 (d, 1H), 7.96 (d, 1H), 7.70 (m, 2H), 7.60 (d, 1H), 7.58 (s, 1H), 7.36 (dd, 1H), 7.34 (d, 1H), 7.06 (d, 1H), 4.90 (m, 1H), 4.71 (AB, 2H), 3.89 (s, 3H), 3.11 (m, 1H), 3.00 (m, 1H), 2.63 (s, 3H), 1.95 (m, 1H), 1.68 (m, 1H). FAB MS, [M+H]⁺=491. 7-Methoxynaphthalene-2-sulfonic acid methyl-[2-oxo-1-(2-oxo-1,2-dihydro-quinolin-5-ylmethyl)-pyrrolidin-3-(S)-yl]-amide is also isolated from the reaction mixture as a by-product.

$^1$H NMR (DMSO-d₆, 300 MHz) δ 8.39 (s, 1H), 8.04 (d, 1H), 7.98 (d, 1H), 7.94 (d, 1H), 7.68 (d, 1H), 7.57 (s, 1H), 7.42 (m, 1H), 7.34 (dd, 1H), 7.25 (d, 1H), 7.05 (d, 1H), 6.46 (d, 1H), 4.88 (m, 1H), 4.60 (AB, 2H), 3.89 (s, 3H), 3.08 (m, 1H), 2.97 (m, 1H), 2.63 (s, 3H), 1.96 (m, 1H), 1.65 (m, 1H). FAB MS, [M+H]⁺=492.

EXAMPLES 23 AND 24

7-Methoxynaphthalene-2-sulfonic Acid [1-(2-Aminoquinolin6-ylmethyl)-2-oxopyrrolidin-3-(S)-yl]-amide and 7-methoxynaphthalene-2-sulfonic Acid [2-oxo-1-(2-oxo-1,2-Dihydro-quinolin-6-ylmethyl)-pyrrolidin-3-(S)-yl]-amide A. 6-Methyl-1H-quinolin-2-one.

The title compound is prepared from p-toluidine and cinnamoyl chloride according to the procedure described in *Synthesis* 1975, 739. The crude product obtained is triturated in Et₂O/hexanes and filtered to give the title compound as a beige solid which is used in the subsequent step.

$^1$H NMR (DMSO-d₆, 300 MHz) δ 11.60 (bs, 1H), 7.82 (d, 1H), 7.41 (s, 1H), 7.30 (d, 1H), 7.18 (d, 1H), 6.45 (d, 1H), 2.30 (s, 3H).

B. 2-Chloro-6-methyl-quinoline.

The title compound is prepared as described in EXAMPLE 1, Part E using 6-methyl-1H-quinolin-2-one in place of 7-methyl-2H-isoquinolin-1-one. The crude product precipitated out during neutralization of the aqueous workup and the solid is filtered and dried. The crude product is recrystallized in MeOH to afford the title compound as a beige solid.

$^1$H NMR (CDCl₃, 300 MHz) δ 8.02 (d, 1H), 7.92 (d, 1H), 7.60 (s, 1H), 7.58 (d, 1H), 7.33 (d, 1H), 2.53 (s, 3H).

C. 6-Bromomethyl-2-chloro-quinoline.

The title compound is prepared as described in EXAMPLE 1, Part F using 2-chloro-6-methyl-quinoline in place of 1-chloro-7-methyl-isoquinoline. The crude residue obtained is recrystallized from 50% EtOAc/hexanes to yield 7.4 g (38%) of the 6-bromomethyl-2-chloro-quinoline as a beige solid.

$^1$H NMR (CDCl₃, 300 MHz) δ 8.08 (d, 1H), 8.02 (d, 1H), 7.83 (s, 1H), 7.77 (dd, 1H), 7.40 (d, 1H), 4.65 (s, 2H). EI MS, [M]⁺=256, 258, Cl pattern.

D. [1-(2-Chloro-quinolin-6-ylmethyl)-2-oxopyrrolidin-3-(S)-yl]carbamic Acid tert-Butyl Ester.

The title compound is prepared from (2-oxopyrrolidin-3-(S)-yl)-carbamic acid tert-butyl ester as described in EXAMPLE 1, Part H using 6-bromomethyl-2-chloro-quinoline in place of 7-bromomethyl-1-chloro-isoquinoline. The crude product is purified by column chromatography eluting with a gradient of 2% MeOH/CH₂Cl₂ to 4% MeOH/CH₂Cl₂ to afford the title compound as a beige solid.

$^1$H NMR (CDCl₃, 300 MHz) δ 8.08 (d, 1H), 8.00 (d, 1H), 7.69 (s, 1H), 7.61 (dd, 1H), 7.40 (d, 1H), 5.23 (bs, 1H), 4.67 (AB, 2H), 4.25 (m, 1H), 3.26 (m, 2H), 2.63 (m, 1H), 1.90 (m, 1H), 1.46 (s, 9H).

E. 6-(3-(S)-Amino-2-oxopyrrolidin-1-ylmethyl)-2-chloro-quinoline Hydrochloride.

The title compound is prepared as described in EXAMPLE 1, Part I using [1-(2-chloro-quinolin-6-ylmethyl)-2-oxopyrrolidin-3-(S)-yl]-carbamic acid tert-butyl ester as the starting material. The title compound is obtained as a white solid.

$^1$H NMR (DMSO-d₆, 300 MHz) δ 8.74 (bs, 3H), 8.48 (d, 1H), 8.00 (s, 1H), 7.95 (d, 1H), 7.71 (d, 1H), 7.60 (d, 1H), 4.64 (AB, 2H), 4.11 (m, 1H), 3.35 (m, 2H), 2.42 (m, 1H), 2.09 (m, 1H).

F. 7-Methoxynaphthalene-2-sulfonic Acid [1-(2-Chloro-quinolin-6-ylmethyl)-2-oxopyrrolidin-3-(S)-yl]-amide.

The title compound is prepared in CH₂Cl₂ instead of CH₃CN as described in EXAMPLE 1, Part K using 6-(3-(S)-amino-2-oxopyrrolidin-1-ylmethyl)-2-chloro-quinoline hydrochloride as the starting material and 7-methoxynaphthalene-2-sulfonyl chloride. The crude product is triturated in CH₂Cl₂ and filtered to provide the title compound as a white solid.

$^1$H NMR (CDCl₃, 300 MHz) δ 8.36 (s, 1H), 8.03 (d, 1H), 7.97 (d, 1H), 7.91 (d, 1H), 7.80 (d, 1H), 7.75 (dd, 1H), 7.60 (s, 1H), 7.51 (dd, 1H), 7.37 (d, 1H), 7.29 (dd, 1H), 7.25 (dd, 1H), 5.43 (s, 1H), 4.58 (AB, 2H), 3.94 (s, 3H), 3.76 (m, 1H), 3.22 (m, 2H), 2.59 (m, 1H), 2.09 (m, 1H). FAB MS, [M+H]⁺=496, 498, Cl pattern. Elemental analysis calculated C=60.54%, H=4.47%, N=8.47%, Cl=7.15%, found C=60.43%, H=4.17%, N=8.37, Cl=7.06%.

G. 7-Methoxynaphthalene-2-sulfonic Acid [1-(2-Aminoquinolin6-ylmethyl)-2-oxopyrrolidin-3-(S)-yl]-amide and 7-Methoxynaphthalene-2-sulfonic Acid [2-oxo-1-(2-oxo-1,2-Dihydro-quinolin-6-ylmethyl)-pyrrolidin-3-(S)-yl-amide.

7-Methoxynaphthalene-2-sulfonic acid [1-(2-chloro-quinolin-6-ylmethyl)-2-oxopyrrolidin-3-(S)-yl]-methyl amide is converted to the title compounds when heated at 130° C. as described in EXAMPLE 2. The crude mixture of products is purified by RP-HPLC eluting in a gradient of 10% $CH_3CN/H_2O$ (0.1% TFA) to 60% $CH_3CN/H_2O$ (0.1% TFA) and the appropriate product fractions are concentrated in vacuo and then purified further by column chromatography eluting with 5% $MeOH/CH_2Cl_2$ to yield 7-methoxynaphthalene-2-sulfonic acid [1-(2-aminoquinolin6-ylmethyl)-2-oxopyrrolidin-3-(S)-yl]-amide as a tan solid.

$^1$H NMR (DMSO-$d_6$, 300 MHz) δ 8.38 (s, 1H), 8.23 (d, 1H), 8.03 (d, 1H), 7.93 (d, 1H), 7.80 (d, 1H), 7.72 (d, 1H), 7.55 (s, 1H), 7.41 (s, 1H), 7.38 (d, 1H), 7.32 (dd, 1H), 7.25 (d, 1H), 6.73 (d, 1H), 6.43 (bs, 2H), 4.37 (AB, 2H), 4.10 (m, 1H), 3.88 (s, 3H), 3.04 (m, 2H), 1.96 (m, 1H), 1.51 (m, 1H). FAB MS, [M+H]$^+$=477. Elemental analysis calculated with 0.6 mol of $H_2O$ cal. C=61.58%, H=5.22%, N=11.49%, found C=61.59%, H=5.08%, N=11.14%. The enantiomeric purity is 87.0% ee as determined by analytical Chiralpak AS RP-HPLC.

7-Methoxynaphthalene-2-sulfonic acid [2-oxo-1-(2-oxo-1,2-dihydro-quinolin-6-ylmethyl)-pyrrolidin-3-(S)-yl]-amide is also isolated from the reaction mixture as a minor by-product.

$^1$H NMR (DMSO-$d_6$, 300 MHz) δ 11.70 (bs, 1H), 8.37 (s, 1H), 8.21 (d, 1H), 8.01 (d, 1H), 7.93 (d, 1H), 7.82 (d, 1H), 7.69 (d, 1H), 7.56 (s, 1H), 7.45 (s, 1H), 7.32 (m, 2H), 7.25 (m, 1H), 6.47 (d, 1H), 4.35 (s, 2H), 4.12 (m, 1H), 3.89 (s, 3H), 3.06 (m, 2H), 1.97 (m, 1H), 1.53 (m, 1H). FAB MS, [M+H]$^+$=478.

EXAMPLE 25

7-Methoxynaphthalene-2-sulfonic Acid [1-(1H-Benzoimidazol-5-ylmethyl)-2-oxopyrrolidin-3-(S)-yl]-amide Trifluoroacetate A. [1-(4-Nitrobenzyl)-2-oxopyrrolidin-3-(S)-yl]-carbamic Acid tert-Butyl Ester.

The title compound is prepared from (2-oxopyrrolidin-3-(S)-yl)-carbamic acid tert-butyl ester as described in EXAMPLE 1, Part H using 4-nitrobenzyl bromide in place of 7-bromomethyl-1-chloro-isoquinoline. The crude product is purified by column chromatography eluting with a gradient of 10% $EtOAc/CH_2Cl_2$ to 25% $EtOAc/CH_2Cl_2$ to afford the title compound as a yellow solid.

$^1$H NMR (CDCl$_3$, 300 MHz) δ 8.20 (d, 2H), 7.43 (d, 2H), 5.18 (bs, 1H), 4.58 (AB, 2H), 4.22 (m, 1H), 3.26 (m, 2H), 2.65 (m, 1H), 1.93 (m, 1H), 1.46 (s, 9H).

B. 3-(S)-Amino-1-(4-nitrobenzyl)-pyrrolidin-2-one Hydrochloride.

The title compound is prepared as described in EXAMPLE 1, Part I using [1-(4-nitrobenzyl)-2-oxopyrrolidin-3-(S)-yl]-carbamic acid tert-butyl ester as the starting material. The title compound is obtained as a white solid.

$^1$H NMR (DMSO-$d_6$, 300 MHz) δ 8.65 (bs, 3H), 8.22 (d, 2H), 7.57 (d, 2H), 4.59 (AB, 2H), 4.10 (m, 1H), 3.32 (m, 2H), 2.40 (m, 1H), 2.03 (m, 1H).

C. 2,2,2-Trifluoro-N-[1-(4-nitrobenzyl)-2-oxopyrrolidin-3-(S)-yl]-acetamide.

The title compound is prepared in $CH_2Cl_2$ instead of $CH_3CN$ as described in EXAMPLE 1, Part K using 3-(S)-amino-1-(4-nitrobenzyl)-pyrrolidin-2-one hydroclhloride as the starting material and trifluoroacetic anhydride in place of 7-methoxynaphthalene-2-sulfonyl chloride. The crude product is concentrated in vacuo and used as is in the subsequent step.

$^1$H NMR (CDCl$_3$, 300 MHz) δ 8.24 (d, 2H), 7.43 (d, 2H), 7.25 (bs, 1H), 4.60 (AB, 2H), 4.44 (m, 1H), 3.35 (m, 2H), 2.80 (m, 1H), 2.01 (m, 1H).

D. N-[1-(4-Acetylamino-3-nitrobenzyl)-2-oxopyrrolidin-3-(S)-yl]-2,2,2-trifluoroacetamide.

To a solution of 2,2,2-trifluoro-N-[1-(4-nitrobenzyl)-2-oxopyrrolidin-3-(S)-yl]-acetamide (0.75 g, 2.27 mmol) in AcOH (12 mL) is added acetic anhydride (1 mL) and a catalytic amount of 10% palladium on activated carbon. The heterogenous mixture is hydrogenated at room temperature on a Parr apparatus under 70 p.s.i. of $H_2$. After 4.5 h, the reaction mixture is filtered through a pad of Celite, washed with $CH_2Cl_2$ and then MeOH. The crude product is concentrated in vacuo to yield 1.2 g of crude N-[1-(4-acetylamino-benzyl)-2-oxopyrrolidin-3-(S)-yl]-2,2,2-trifluoroacetamide as a residue (wet with HOAc). A solution of the crude N-[1-(4-acetylamino-benzyl)-2-oxopyrrolidin-3-(S)-yl]-2,2,2-trifluoroacetamide (1.2 g, wet with AcOH) in AcOH (12 mL) is cooled at 0° C. and acetic anhydride (1 mL) is added. The resulting mixture is treated with a catalytic amount of $NaNO_2$, followed by the dropwise addition of fuming $HNO_3$ (3.8 mL). The reaction mixture is stirred at 0° C. for 1.5 hours, then at room temperature for 1.5 hours. Upon re-cooling to 0° C., a mixture of ice/ice water is added slowly with stirring. The mixture is diluted further with water and extracted with EtOAc (3×50 mL). The combined organic layers are washed twice with water. The organic phase is dried over anhydrous $MgSO_4$, filtered and concentrated. The crude product is purified by column chromatography eluting with a gradient of 25% $EtOAc/CH_2Cl_2$ to 50% $EtOAc/CH_2Cl_2$ to provide the title compound (0.65 g, 1.67 mmol) as a beige solid.

$^1$H NMR (CDCl$_3$, 300 MHz) δ 10.27 (s, 1H), 8.77 (d, 1H), 8.08 (s, 1H), 7.54 (m, 1H), 7.40 (bs, 1H), 4.51 (AB, 2H), 4.46 (m, 1H), 3.34 (m, 2H), 2.78 (m, 1H), 2.31 (s, 3H), 1.98 (m, 1H) for the major component of a mixture of rotamers.

E. 3-(S)-Amino-1-(4-amino-3-nitrobenzyl)-pyrrolidin-2-one.

To a solution of N-[1-(4-acetylamino-3-nitrobenzyl)-2-oxopyrrolidin-3-(S)-yl]-2,2,2-trifluoroacetamide (0.65 g, 1.67 mmol) in EtOH (4 mL) is added 1 N NaOH (6 mL) solution. The yellow mixture is heated at 50° C. for 3 hours as a brown solution resulted. The reaction mixture is allowed to cool and then concentrated in vacuo. The crude residue is diluted with water and 1 N NaOH 10 mL) and the aqueous phase is extracted with CHCl$_3$ (4×50 mL). The combined organic layers are dried over anhydrous $Na_2SO_4$, filtered and concentrated to give the title compound (0.22 g, 0.88 mmol) as a yellow solid which is used as is in the subsequent step.

$^1$H NMR (CDCl$_3$, 300 MHz) δ 7.98 (s, 1H), 7.30 (dd, 1H), 6.79 (d, 1H), 6.12 (bs, 2H), 4.36 (AB, 2H), 3.67 (m, 1H), 3.19 (m, 2H), 2.43 (m, 1H), 1.71 (m, 1H).

F. 7-Methoxynaphthalene-2-sulfonic Acid [1-(4-Amino-3-nitrobenzyl)-2-oxopyrrolidin-3-(S)-yl]-amide.

The title compound is prepared in $CH_2Cl_2$ instead of $CH_3CN$ as described in EXAMPLE 1, Part K using 3-(S)-amino-1-(4-amino-3-nitrobenzyl)-pyrrolidin-2-one in place of 7-(3-(S)-amino-2-oxopyrrolidin-1-ylmethyl)-1-chloro-isoquinoline hydrochloride and 7-methoxynaphthalene-2-sulfonyl chloride as prepared in EXAMPLE 1, Part J. The crude product is purified by column chromatography eluting with a gradient of 20% $EtOAc/CH_2Cl_2$ to 50% $EtOAc/CH_2Cl_2$ to afford the title compound as a pale yellow solid.

¹H NMR (CDCl₃, 300 MHz) δ 8.37 (s, 1H), 7.94 (s, 1H), 7.92 (d, 1H), 7.82 (d, 1H), 7.75 (dd, 1H), 7.30 (dd, 1H), 7.25 (dd, 1H), 7.19 (dd, 1H), 6.77 (d, 1H), 6.12 (bs, 2H), 5.38 (bs, 1H), 4.30 (AB, 2H), 3.94 (s, 3H), 3.73 (m, 1H), 3.18 (m, 2H), 2.58 (m, 1H), 2.05 (m, 1H).

G. 7-Methoxynaphthalene-2-sulfonic Acid [1-(1H-Benzoimidazol-5-ylmethyl)-2-oxopyrrolidin-3-(S)-yl]-amide Trifluoroacetate.

To a solution of 7-methoxynaphthalene-2-sulfonic acid [1-(4-amino-3-nitrobenzyl)-2-oxopyrrolidin-3-(S)-yl]-amide (0.38 g, 0.82 mmol) in 88% HCO₂H (15 mL) is added a catalytic amount of 10% palladium on activated carbon. The heterogenous mixture is hydrogenated at room temperature on a Parr apparatus under 70 p.s.i. of H₂ for 1 hour. The reaction mixture is filtered through a pad of Celite. washed with EtOAc and MeOH, and the filtrate is concentrated in vacuo. The crude product is purified by RP-HPLC eluting in a gradient of 10% CH₃CN/H₂O (0.1% TFA) to 80% CH₃CN/H₂O (0.1% TFA) and the appropriate product fractions are lyophilized to provide the title compound (0.17 g, 0.30 mmol) as a white solid.

¹H NMR (DMSO-d₆, 300 MHz) δ 9.38 (bs, 1H), 8.38 (s, 1H), 8.25 (d, 1H), 8.03 (d, 1H), 7.95 (d, 1H), 7.78 (d, 1H), 7.72 (dd, 1H), 7.66 (bs, 1H), 7.56 (s, 1H), 7.35 (d, 1H), 7.32 (dd, 1H), 4.48 (AB, 2H), 4.09 (m, 1H), 3.88 (s, 3H), 3.06 (m, 2H), 1.96 (m, 1H), 1.53 (m, 1H). FAB MS, [M+H]⁺=451. Elemental analysis calculated with 1.2 mol H₂O cal. C=51.19%, H=4.37%, N=9.55%, found C=51.19%, H=3.95%, N=9.36%.

EXAMPLE 26

7-Methoxynaphthalene-2-sulfonic Acid [2-(1H-Benzoimidazol-5-ylmethyl)-2-oxopyrrolidin-3-(S)-yl]-amide Trifluoroacetate A. Boc-L-Asp(H)-OBn.

Boc-L-Asp-OBn (15 g, 46.4 mmol) is dissolved in THF (50 mL) and cooled to −10° C. The solution is treated with N-methylmorpholine (4.9 g, 48.7 mmol) and stirred for 5 minutes. To the solution is added dropwise isobutyl chloroformate (6.3 g, 46.4 mmol). After the addition is completed, the mixture is stirred for 1 minute and then filtered through a pad of Celite. The filtrate is cooled to −10° C. To the solution is added sodium borohydride (2.63 g, 70 mmol) which is predissolved in water (50 mL). The resulting solution is stirred for 2 minutes. The solution is poured into a separatory funnel and diluted with EtOAc (800 mL). The organic layer is washed with water and saturated NaCl. The organic layer is dried over MgSO₄, filtered and concentrated in in vacuo. The residue is added to a solution of oxalyl chloride (30 mL, 60 mmol, 2M solution in CH₂Cl₂), and methyl sulfoxide (7.25 g, 92.8 mmol) in CH₂Cl₂ (250 mL) at −78° C. The mixture is stirred at −78° C. for 40 minutes, then triethylamine (14 g, 140 mmol) is added. The reaction mixture is stirred at −78° C. for 1 hour and then is stirred at room temperature for 30 minutes. The solution is poured into a 20% citric acid/water (200 mL) solution. The resulting mixture is poured into a separatory funnel and the layers are separated. The organic layer is washed with water and saturated NaCl. The organic phase is dried over MgSO₄, filtered and concentrated. The crude residue is purified by column chromatography eluting with a gradient of 10% EtOAc/hexanes to 30% EtOAc/hexanes to give the title compound (12.0 g, 39 mmol) as an oil.

¹H NMR (CDCl₃, 300 MHz) δ 9.68 (s, 1H), 7.32 (m, 4H), 5.42 (bs, 1H), 5.16 (s, 2H), 4.62 (m, 1H), 3.05 (ddd, 2H), 1.40 (s, 9H).

B. {1-[2-(4-Nitrophenyl)-ethyl]-2-oxopyrrolidin-3-(S)-yl}-carbamic Acid tert-Butyl Ester.

To a solution of Boc-L-Asp(H)-OBn (3.3 g, 10.7 mmol) dissolved in methanol (50 mL) is added 4Å molecular sieves, 4-nitrophenethylamine hydrochloride (4.35 g, 21.5 mmol) and triethylamine (2,25 g, 22.2 mmol). The solution is stirred at room temperature for 45 minutes and then the mixture is treated with sodium cyanoborohydride (0.72 g, 11.5 mmol). The reaction mixture is stirred at room temperature for 16 hours. After this time, 1 N NaOH (10 mL) followed by water (25 mL) is added. The resulting mixture is stirred for 30 minutes and then concentrated in vacuo to a smaller volume. The solution is diluted with EtOAc (250 mL), filtered through a pad of Celite and washed with water and EtOAc. The solution is poured into a separatory funnel and the layers are separated. The aqueous layer is extracted with EtOAc. The combined organic layers are washed with 1N HCl, H₂O, saturated NaHCO₃ solution and saturated NaCl. The organic phase is dried over MgSO₄, filtered and concentrated. The crude residue is purified by column chromatography eluting with 50% EtOAc/CH₂Cl₂ to afford the title compound (1.46 g, 4.18 mmol) as a pale yellow solid.

¹H NMR (CDCl₃, 300 MHz) δ 8.17 (d, 2H), 7.39 (d, 2H), 5.12 (bs, 1H), 4.09 (m, 1H), 3.63 (m, 2H), 3.25 (m, 2H), 2.99 (t, 2H), 2.62 (m, 1H), 1.83 (m, 1H), 1.44 (s, 9H).

C. 3-(S)-Amino-1-[2-(4-nitrophenyl)-ethyl]-pyrrolidin-2-one Hydrochloride.

The title compound is prepared as described in EXAMPLE 1, Part I using {1-[2-(4-nitrophenyl)-ethyl]-2-oxopyrrolidin-3-(S)-yl}-carbamic acid tert-butyl ester as the starting material. The title compound is obtained as a beige solid.

¹H NMR (CDCl₃/CD₃OD, 300 MHz) δ 8.77 (bs, 1H), 8.72 (bs, 1H), 8.16 (d, 2H), 7.45 (d, 2H), 4.15 (m, 1H), 3.59 (t, 2H), 3.38 (m, 2H), 2.98 (t, 2H), 2.58 (m, 1H), 2.37 (m, 1H).

D. 2,2,2-Trifluoro-N-{1-[2-(4-nitrophenyl)-ethyl]-2-oxopyrrolidin-3-(S)-yl}-acetamide.

The title compound is prepared in CH₂Cl₂ instead of CH₃CN as described in EXAMPLE 1, Part K using 3-(S)-amino-1-[2-(4-nitrophenyl)-ethyl]-pyrrolidin-2-one hydrochloride as the starting material and trifluoroacetic anhydride in place of 7-methoxynaphthalene-2-sulfonyl chloride. The crude product is concentrated in vacuo and used as is in the subsequent step.

¹H NMR (CDCl₃, 300 MHz) δ 8.17 (d, 2H), 8.15 (bs, 1H), 7.39 (d, 2H), 4.40 (m, 1H), 3.70 (m, 1H), 3.55 (m, 1H), 3.34 (m, 2H), 2.99 (t, 2H), 2.68 (m, 1H), 1.96 (m, 1H).

E. N-{1-[2-(4-Acetylamino-3-nitrophenyl)-ethyl]-2-oxopyrrolidin-3-(S)-yl]-2,2,2-trifluoroacetamide.

The title compound is prepared as described in EXAMPLE 25, Part D using 2,2,2-trifluoro-N-{1-[2-(4-nitrophenyl)-ethyl]-2-oxopyrrolidin-3-(S)-yl}-acetamide as the starting material. The crude intermediate is concentrated in vacuo to yield N-{1-[2-(4-acetylamino-phenyl)-ethyl]-2-oxopyrrolidin-3-(S)-yl]-2,2,2-trifluoroacetamide as a residue (wet with HOAc) which is also used directly in the nitration step. The nitric acid reaction mixture is allowed to warm to room temperature and stirred for 18 hours. The crude product is purified by column chromatography eluting with a gradient of 25% EtOAc/CH₂Cl₂ to 50% EtOAc/CH₂Cl₂ to provide the title compound as a solid.

¹H NMR (CDCl₃, 300 MHz) δ 10.24 (s, 1H), 8.70 (d, 1H), 7.98 (bs, 1H), 7.40 (d, 1H), 7.26 (bs, 1H), 4.43 (m, 1H), 3.58 (m, 2H), 3.38 (m, 2H), 2.94 (m, 2H), 2.66 (m, 1H), 2.06 (s, 3H), 1.98 (m, 1H) for the major component of a mixture of rotamers.

F. 3-(S)-Amino-1-[2-(4-amino-3-nitrophenyl)-ethyl]-pyrrolidin-2-one.

The title compound is prepared as described in EXAMPLE 25, Part F using N-{1-[2-(4-acetylamino-3-nitrophenyl)-ethyl]-2-oxopyrrolidin-3-(S)-yl]-2,2,2-trifluoroacetamide as the starting material. The reaction mixture is stirred at room temperature for 18 hours. After similar workup, the organic phase is concentrated in vacuo to give the title compound as a yellow solid which is used as is in the subsequent step.

$^1$H NMR (CDCl$_3$, 300 MHz) δ 7.90 (s, 1H), 7.25 (d, 1H), 6.80 (d, 1H), 6.24 (bs, 1H), 3.48 (m, 3H), 3.26 (m, 2H), 2.77 (t, 2H), 2.40 (m, 1H), 2,25 (bs, 3H), 1.69 (m, 1H).

G. 7-Methoxynaphthalene-2-sulfonic Acid {1-[2-(4-Amino-3-nitrophenyl)-ethyl]-2-oxopyrrolidin-3-(S)-yl}-amide.

The title compound is prepared in CH$_2$Cl$_2$ instead of CH$_3$CN as described in EXAMPLE 1, Part K using 3-(S)-amino-1-[2-(4-amino-3-nitrophenyl)-ethyl]-pyrrolidin-2-one in place of 7-(3-(S)amino-2-oxopyrrolidin-1-ylmethyl)-1-chloro-isoquinoline hydrochloride and 7-methoxynaphthalene-2-sulfonyl chloride as prepared in EXAMPLE 1, Part J. After similar workup, the organic phase is concentrated in vacuo to afford the title compound as a pale yellow solid which is used as is in the subsequent step.

$^1$H NMR (CDCl$_3$, 300 MHz) δ 8.36 (s, 1H), 7.87 (d, 1H), 7.83 (s, 1H), 7.77 (d, 1H), 7.72 (dd, 1H), 7.27 (dd, 1H), 7.22 (s, 1H), 7.13 (dd, 1H), 6.68 (d, 1H), 6.04 (bs, 2H), 5.33 (bs, 1H), 3.93 (s, 3H), 3.68 (m, 1H), 3.44 (m, 2H), 3.20 (m, 2H), 2.68 (t, 2H), 2.49 (m, 1H), 1.98 (m, 1H).

H. 7-Methoxynaphthalene-2-sulfonic Acid {1-[2-(1H-Benzoimidazol-5-yl)-ethyl]-2-oxopyrrolidin-3-(S)-yl]-amide Trifluoroacetate.

7-Methoxynaphthalene-2-sulfonic acid {1-[2-(4-amino-3-nitrophenyl)-ethyl]-2-oxopyrrolidin-3-(S)-yl}-amide is converted to the title compound as described in EXAMPLE 25, Part H. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ 9.38 (bs, 1H), 8.35 (s, 1H), 8.13 (d, 1H), 8.02 (d, 1H), 7.93 (d, 1H), 7.73 (d, 1H), 7.69 (s, 1H), 7.65 (d, 1H), 7.55 (s, 1H), 7.38 (d, 1H), 7.32 (dd, 1H), 3.90 (m, 1H), 3.88 (s, 3H), 3.39 (m, 2H), 3.11 (m, 2H), 2.88 (t, 2H), 1.94 (m, 1H), 1.47 (m, 1H). FAB MS, [M+H]$^+$=465. Elemental analysis calculated with 1.4 mol H$_2$O cal. C=51.68%, H=4.65%, N=9.27%, found C=51.68%, H=4.25%, N=8.93%.

EXAMPLE 27

7-Methoxynaphthalene-2-sulfonic Acid Acetyl-[2-oxo-1-(2-Pyrrolo[3,2-b]pyridin-1-ylmethyl)-pyrrolidin-3-(S)-yl]-amide Trifluoroacetate A. 1H-Pyrrolo[3,2-c]pyridine.

The title compound is prepared from 3-picoline-N-oxide according to the procedure described in Tetrahedron 1993, 2885. The crude product obtained is dissolved in EtOH and decolorizing carbon is added. The mixture is filtered through a large column of SiO$_2$ gel eluting with EtOH to provide the title compound as a beige solid.

$^1$H NMR (CDCl$_3$, 300 MHz) δ 10.92 (bs, 1H), 8.98 (s, 1H), 8.31 (d, 1H), 7.36 (d, 1H), 7.32 (d, 1H), 6.66 (d, 1H).

B. Pyrrolo[3,2-c]pyridin-1-yl-acetic Acid tert-Butyl Ester.

The title compound is prepared from 1H-pyrrolo[3,2-c]pyridine as described in EXAMPLES 18 and 19, Part A using tert-butyl bromoacetate in place of methyl iodide. The crude product is purified by column chromatography eluting with a gradient of 3% MeOH/CH$_2$Cl$_2$ to 6% MeOH/CH$_2$Cl$_2$ to give the title compound as an oil.

$^1$H NMR (CDCl$_3$, 300 MHz) δ 8.93 (s, 1H), 8.34 (d, 1H), 7.18 (d, 1H), 7.12 (d, 1H), 6.65 (d, 1H), 4.75 (s, 2H), 1.45 (s, 9H).

C. Pyrrolo[3,2-c]pyridin-1-yl-acetic Acid.

To a solution of pyrrolo[3,2-c]pyridin-1-yl-acetic acid tert-butyl ester (0.44 g, 1.89 mmol) in CH$_2$Cl$_2$ (10 mL) at 0° C. is added trifluoroacetic acid (1 mL). After 15 minutes, the solution is allowed to warm to room temperature and stirred for 18 hours. The reaction mixture is concentrated in in vacuo and then azeotroped with toluene to give 0.5 g of the title compound as a residue (wet with excess TFA) which is used as is in the subsequent step $^1$H NMR (CDCl$_3$+CD$_3$OD, 300 MHz) δ 9.09 (s, 1H), 8.34 (d, 1H), 7.91 (d, 1H), 7.71 (d, 1H), 7.08 (d, 1H), 5.18 (s, 2H).

D. 2-(S)-Benzyloxycarbonylamino-4-(2-pyrrolo[3,2-c]pyridin-1-yl-acetylamino)-butyric Acid Methyl Ester.

Pyrrolo[3,2-c]pyridin-1-yl-acetic acid (0.50 g, 1.89 mmol), 2-(S)-benzyloxycarbonylamino-4-amino-butyric acid methyl ester trifluoroacetate (0.93 g, 2.45 mmol), 4-methylmorpholine (0.75 g, 7.41 mmol), and 1-hydroxybenzoiriazole hydrate (0.36 g, 2.65 mmol) are dissolved in DMF (11 mL) and the resulting mixture is cooled to 0° C. 1-(3-Dimethylaminopropyl)-3-ethylcarbodiimide hydrochloride (0.80 g, 4.17 mmol) is added to the solution. The ice bath is removed and the reaction mixture is stirred at room temperature. After 18 hours, the solution is diluted with a saturated solution of NH$_4$Cl and extracted twice with EtOAc. The combined organic layers are washed with H$_2$O, saturated NaHCO$_3$ and saturated NaCl. The organic phase is dried over MgSO$_4$, filtered and concentrated in vacuo. The crude product is purified by column chromatography in a gradient of 3% MeOH/CH$_2$Cl$_2$ to 10% MeOH/CH$_2$Cl$_2$ to afford the title compound (0.33 g, 0.78 mmol) as a solid.

$^1$H NMR (CDCl$_3$, 300 MHz) δ 8.95 (s, 1H), 8.35 (d, 1H), 7.34 (m, 3H), 7.27 (m, 3H), 7.17 (d, 1H), 6.73 (d, 1H), 6.44 (bs, 1H), 5.45 (d, 1H), 4.93 (s, 2H), 4.78 (s, 2H), 4.08 (m, 1H), 3.69 (s, 3H), 3.67 m, 1H), 2.90 (m, 1H), 2.03 (m, 1H), 1.58 (m, 1H).

E. 7-Methoxynaphthalene-2-sulfonic Acid Acetyl-[2-oxo-1-(2-pyrrolo[3,2-b]pyridin-1-ylmethyl)-pyrrolidin-3-(S)-yl]-amide Trifluoroacetate.

To a solution of 2-(S)-benzyloxycarbonylamino-4-(2-pyrrolo[3,2-c]pyridin-1-yl-acetylamino)-butyric acid methyl ester (0.51 g, 1.20 mmol) in THF (5 mL) is added diborane (5 mL, 0.500 mmol, 1 M solution in THF). The resulting mixture is stirred at room temperature for 4 hours and then concentrated in vacuo. The residue is suspended in EtOAc (10 mL), treated with 10 drops of H$_2$O, 5 drops of 1 N NaOH and further quenched with saturated NH$_4$Cl solution. The mixture is concentrated in vacuo to about 1/2 volume, partitioned between EtOAc and 10% Na$_2$CO$_3$ solution and the layers are separated. The aqueous layer is extracted with EtOAc. The combined organic phases are washed with saturated NaCl, dried over MgSO$_4$, filtered and concentrated in in vacuo. The crude product obtained is partially purified by column chromatography in a gradient of 2% MeOH/CH$_2$Cl$_2$ to 10% MeOH/CH$_2$Cl$_2$ to afford [2-oxo-1-(2-pyrrolo[3,2-c]pyridin-1-yl-ethyl)-pyrrolidin-3-(S)-yl]-carbamic acid benzyl ester. FAB MS, [M+H]$^+$=379. To a solution of this crude [2-oxo-1-(2-pyrrolo[3,2-c]pyridin-1-yl-ethyl)-pyrrolidin-3-(S)-yl]-carbamic acid benzyl ester in MeOH (10 mL) and AcOH (3 mL) is added a catalytic amount of 10% palladium on activated carbon. The heterogenous mixture is stirred at room temperature under a balloon of $H_2$ for 18 hours. The reaction mixture is filtered through a pad of Celite and washed with MeOH (3x). The crude product is concentrated in vacuo and then azeotroped with toluene to give 3-(S)-amino-1-(2-pyrrolo[3,2-c] pyridin-1-yl-ethyl)-pyrrolidin-2-one acetate as a residue (wet with excess HOAc). FAB MS, [M+H]$^+$=245. The title compound is prepared in $CH_2Cl_2$ instead of $CH_3CN$ as described in EXAMPLE 1, Part K using the above 3-(S)-amino-1-(2-pyrrolo[3,2-c]pyridin-1-yl-ethyl)-pyrrolidin-2-one acetate in place of 7-(3-(S)-amino-2-oxopyrrolidin-1-ylmethyl)-1-chloro-isoquinoline hydrochloride and 7-methoxynaphthalene-2-sulfonyl chloride as prepared in EXAMPLE 1. Part J. The crude product is partially purified by column chromatography eluting in a gradient of 3% MeOH/$CH_2Cl_2$ to 5% MeOH/$CH_2Cl_2$. The residue obtained is further purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 9.24 (s, 1H), 8.58 (s, 1H), 8.48 (d, 1H), 8.20 (d, 1H), 8.08 (d, 1H), 8.00 (d, 1H), 7.98 (s, 1H), 7.75 (dd, 1H), 7.61 (s, 1H), 7.42 (dd, 1H), 7.03 (d, 1H), 4.87 (m, 1H), 4.56 (m, 2H), 3.90 (s, 3H), 3.63 (m, 2H), 3.30 (m, 2H), 2,27 (m, 1H), 2.15 (s, 3H), 2.04 (m, 1H). FAB MS, [M+H]$^+$=507.

EXAMPLE 28

7-Methoxynaphthalene-2-sulfonic Acid [1-1-(4-Amino-quinazolin-6-yl-methyl)-2-oxopyrrolidin-3-(S)-yl]-methylamide Trifluoroacetate A. 6-Methyl-3H-quinazolin-4-one.

Sodium hydride (2.6 g, 65 mmol, 60% mineral oil dispersion) is added to dioxane (100 mL) at 0° C. To the solution is added 2-amino-5-methyl benzoic acid (7.6 g, 50 mmol) followed by [3-(dimethylamino)-2-azoprop-2-en-1-ylidene] dimethyl ammonium chloride (9.9 g, 60 mmol). After addition, the solution is heated to reflux. Refluxing is continued for 16 hours. The reaction mixture is cooled to ambient temperature and methanol (3 mL) is added followed by AcOH (10 mL). The solution is then refluxed for 3 hours. The solution is cooled to ambient temperatures. The solution is concentrated. The resulting solid is diluted with water (60 mL). The pH of the resulting solution is adjusted to 7. The solution is filtered. The resulting solid is dried under vacuum to give the title compound (6.0 g, 38 mmol).

$^1$H NMR (CDCl$_3$, 300 MHz) δ 8.03 (s, 1H), 7.89 (s, 1H), 7.57 (m, 2H), 2.41 (s, 3H). EI MS, [M+H]$^+$=507.

B. 4-Chloro-6-methyl-quinazoline.

6-Methyl-3H-quinazolin-4-one (1.1 g, 6.9 mmol) is dissolved in toluene (70 mL). To the solution is added triethyl amine (1.82 g, 18 mmol) and P(O)Cl$_3$ (1.06 g, 6.9 mmol). The solution is heated to reflux. After 3 h, the solution is poured into water (100 mL). The solution is diluted with EtOAc (200 mL). The layers are separated. The organic layer is washed with water, saturated NaHCO$_3$ (aq.) and saturated NaCl (aq.). The organic layer is dried over MgSO$_4$, filtered and concentrated. The title compound is obtained as an oil (0.75 g, 4.2 mmol).

$^1$H NMR (CDCl$_3$, 300 MHz) δ 8.98 (s, 1H), 8.04 (s, 1H), 7.98 (d, 1H), 7.82 (d, 1H), 2.62 (s, 3H).

C. 6-Bromomethyl-4-chloro-quinazoline.

The title compound is prepared as described in EXAMPLE 1, Part F substituting 4-chloro-6-methyl-quinazoline for 1-chloro-7-methylisoquinoline. The crude product is purified by column chromatography eluting with a gradient of 5% EtOAc/hexanes to 10% EtOAc/hexanes to give the title compound as a white solid.

$^1$H NMR (CDCl$_3$, 300 MHz) δ 9.08 (s, 1H), 8.23 (s, 1H), 8.00 (dd, 2H), 4.68 (s, 2H).

D. 7-Methoxynaphthalene-2-sulfonic Acid (2-Oxopyrrolidin-3-(S)-yl)-amide.

To a solution of trifluoroacetic acid/$CH_2Cl_2$ (20 mL) at 0° C. is added (2-oxopyrrolidin-3-(S)-yl)-carbamic acid tert-butyl ester (0.4 g, 2 mmol), prepared as described in EXAMPLE 1, Part G. The resulting solution is allowed to warm to ambient temperatures and is stirred for 12 hours. The solution is then concentrated. The resulting oil is reconcentrated from toluene. The oil is then dissolved in $CH_3CN$ (6 mL). To the solution is added $CH_2Cl_2$(6 mL). The resulting solution is cooled to 0° C. and triethyl amine (0.67 g, 6.6 mmol) followed by 7-methoxynaphthalene sulfonyl chloride (0.64 g, 2.5 mmol), prepared as described in EXAMPLE 1, Part J, are added. The solution is stirred for 6 hours. After this time, the solution is concentrated. The resulting crude solid is triturated with EtOAc. The crude solid is then further purified by column chromatography eluting with a gradient of 2.5% MeOH/$CH_2Cl_2$ to 5% MeOH/$CH_2Cl_2$ to give the title compound (0.40 g, 1.25 mmol) as a white foam.

$^1$H NMR (CDCl$_3$, 300 MHz) δ 8.35 (s, 1H), 7.88 (d, 1H), 7.78 (d, 1H), 7.28 (m, 2H), 5.65 (bs, 1H), 5.34 (bs, 1H), 3.94 (s, 3H), 3.67 (m, 1H), 3.32 (m, 2H), 2.62 (m, 1H), 2.21 (m, 1H).

E. 7-Methoxynaphthalene-2-sulfonic Acid Methyl-(2-oxopyrrolidin-3-(S)-yl)-amide.

The title compound is prepared as described in EXAMPLE 6, Part A substituting 7-methoxynaphthalene-2-sulfonic acid (2-oxopyrrolidin-3-(S)-yl)-amide for 7-methoxynaphthalene-2-sulfonic acid [1-(1-chloro-isoquinolin-7-ylmethyl)-2-oxopyrrolidin-3-(S)-yl]-amide. The crude product is purified by column chromatography eluting with a gradient of 40% EtOAc/$CH_2Cl_2$ to 60% EtOAc/$CH_2Cl_2$ to give the title compound as a white solid.

$^1$H NMR (CDCl$_3$, 300 MHz) δ 8.39 (s, 1H), 7.90 (d, 1H), 7.76 (m, 2H), 7.28 (m, 2H), 6.42 (bs, 1H), 4.82 (m, 1H), 3.92 (s, 3H), 3.32 (m, 2H), 2.80 (s, 3H), 2.31 (m, 1H), 2.05 (m, 1H).

F. 7-Methoxynaphthalene-2-sulfonic Acid [1-(4-Chloro-quinazolin-6-ylmethyl)-2-oxopyrrolidin-3-(S)-yl-methyl Amide.

To a solution of 7-methoxynaphthalene-2-sulfonic acid methyl-(2-oxopyrrolidin-3-(S)-yl)-amide (0.35 g, 1.04 mmol) in THF (7 mL) at 0° C. is added is added LiN(SiMe$_3$)$_2$ (1 mL, 1 mmol, 1 M solution in THF). The solution is stirred at 0° C. for 40 minutes. After this time, 6-bromomethyl-4-chloro-quinazoline (0.24 g, 0.94 mmol) is added. The resulting solution is stirred for 4 hours. The reaction is quenched by the addition of a saturated NH$_4$Cl solution. The solution is diluted with EtOAc and water. The layers are separated. The organic layer is washed with water and brine. The organic layer is dried over MgSO$_4$, filtered and concentrated. The crude product is purified by column chromatography eluting with a gradient of 20% EtOAc/$CH_2Cl_2$ to 40% EtOAc/$CH_2Cl_2$ to give the title compound (0.25 g, 0.49 mmol) as a white solid.

$^1$H NMR (CDCl$_3$, 300 MHz) δ 9.03 (s, 1H), 8.40 (s, 1H), 8.03 (m, 2H), 7.89 (d, 1H), 7.81 (m, 3H), 7.28 (m, 2H), 5.00 (m, 1H), 4.75 (AB, 1H), 4.50 (AB, 1H), 3.92 (s, 3H), 3.22 (m, 2H), 2.87 (s, 3H), 2.38 (m, 1H), 2.03 (m, 1H). FAB MS, [M+H]$^+$=511.

G. 7-Methoxynaphthalene-2-sulfonic Acid [1-(4-Amino-quinazolin-6-yl-methyl)-2-oxopyrrolidin-3-(S)-yl]-methylamide Trifluoroacetate.

To 7-methoxynaphthalene-2-sulfonic acid [1-(4-chloro-quinazolin-6-ylmethyl)-2-oxopyrrolidin-3-(S)-yl]-methyl amide (0.05 g, 0.1 mmol) suspended in EtOH (10 mL) is added triethylamine (0.02 g, 0.2 mmol) and ammonium acetate (0.08 g, 1 mmol). The reaction is heated to 80° C. The solution is concentrated. The residue is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound (0.03 g, 0.05 mmol) as a white solid.

$^1$H NMR (DMSO-$d_6$, 300 MHz) δ 9.78 (bs, 2H), 8.78 (s, 1H), 8.36 (s, 1H), 8.11 (s, 1H), 8.02 (d, 1H), 7.92 (d, 1H), 7.83 (d, 1H), 7.68 (m, 2H), 7.56 (s, 1H), 7.49 (s, 1H), 7.32 (dd, 1H), 4.93 (m, 1H), 4.50 (AB, 2H), 3.82 (s, 3H), 3.15 (m, 2H), 2.62 (s, 3H), 2.02 (m, 1H), 1.78 (m, 1H). FAB MS, $[M+H]^+=492$.

EXAMPLE 29

7-Methoxynaphthalene-2-sulfonic Acid [1-(4-Amino-thieno[2,3-d]pyrimidin-6-yl-methyl)-2-oxopyrrolidin-3-(S)-yl]amide Trifluoroacetate A. 2-Amino-5-methylthiophene-3-carboxylic Acid Methyl Ester.

To a solution of methyl cyanoacetate (19.8 g, 200 mmol) in DMF (25 mL) is added triethyl amine (10.9 g, 108 mmol). To the solution is added sulfur (6.4 g, 200 mmol). The solution is heated to 60° C. Over a 20 minutes period, propionaldehyde (11.6 g, 200 mmol) is added dropwise. After addition, the solution is allowed to cool to ambient temperatures over 1 hour. The solution is stirred for 16 hours. The reaction is poured into water (300 mL). The resulting solution is extracted with $Et_2O$ (2×200 ml ). The combined $Et_2O$ extracts are washed with water and saturated NaCl (aq.). The organic layer is dried over $MgSO_4$, filtered and concentrated. The resulting crude product is recrystallized from $MeOH/CH_2Cl_2$ to give the title compound (13.7 g, 80 mmol) as a yellow solid.

$^1$H NMR (CDCl$_3$, 300 MHz) δ 6.58 (s, 1H), 5.78 (bs, 2H), 3.78 (s, 3H), 2.28 (s, 3H).

B. 2-Amino-5-methylthiophene-3-carboxylic Acid.

To a solution of 2-amino-5-methylthiophene-3-carboxylic acid methyl ester (13.7 g, 80 mmol) in $MeOH/H_2O/THF$ (400 mL, 1:1:1) is added LiOH $H_2O$ (16 g, 400 mmol). The solution is heated to 50° C. After 4 hours, the solution is concentrated. The resulting residue is dissolved in water. The pH of the solution is adjusted to between 5–6 using 1 N HCl. The precipitate is collected by filtration, washed with a small amount of water and is dried under vacuum. The title compound (12 g, 76 mmol) is obtained as a yellow solid. EI MS, $[M]^+=157$.

C. 6-Methyl-thieno[2,3-d]pyrimidin-4-ol.

The title compound is prepared as described in EXAMPLE 28, Part A substituting 2-amino-5-methylthiophene-3-carboxylic acid for 2-amino-5-methyl benzoic acid. The crude product is purified by column chromatography eluting with a gradient of 2% $MeOH/CH_2Cl_2$ to 6% $MeOH/CH_2Cl_2$ to give the title compound as a solid. EI MS, $[M]^+=165$.

D. 4-Chloro-6-methyl-thieno[2,3-d]pyrimidine.

The title compound is prepared as described in EXAMPLE 28, Part B substituting 6-methyl-thieno[2,3-d]pyrimidin-4-ol for 6-methyl-3H-quinazolin-4-one. The crude product is purified by column chromatography eluting with a gradient of $CH_2Cl_2$ to 5% EtOAc/$CH_2Cl_2$ to give the title compound as a solid.

$^1$H NMR (CDCl$_3$, 300 MHz) δ 8.84 (s, 1H), 7.42 (s, 1H), 2.68 (s, 3H).

E. 6-Bromomethyl-4-chloro-thieno[2,3-d]pyrimidine.

The title compound is prepared as described in EXAMPLE 1, Part F substituting 4-chloro-6-methyl-thieno [2,3-d]pyrimidine for 1-chloro-7-methylisoquinoline. The crude product is purified by column chromatography eluting with a gradient of 70% $CH_2Cl_2$/hexanes to 100% $CH_2Cl_2$ to give the title compound as a white solid.

$^1$H NMR (CDCl$_3$, 300 MHz) δ 8.84 (s, 1H), 7.42 (s, 1H), 4.72 (s, 2H).

F. [1-(4-Chloro-thieno[2,3-d]pyrimidin-6-ylmethyl)-2-oxopyrrolidin-3-(S)-yl]-carbamic Acid tert-Butyl Ester.

The title compound is prepared as described in EXAMPLE 1, Part H substituting 6-bromomethyl-4-chloro-thieno[2,3-d]pyrimidine for 7-bromomethyl-1-chloroisoquinoline. The crude product is purified by column chromatography eluting with a gradient of 20% EtOAc/$CH_2Cl_2$ to 30% EtOAc/$CH_2Cl_2$ to give the title compound as a white foam.

$^1$H NMR (CDCl$_3$, 300 MHz) δ 8.80 (s, 1H), 7.31 (s, 1H), 5.15 (bs, 1H), 4.75 (AB, 2H), 4.18 (m, 1H), 3.36 (m, 2H), 2.62 (m, 1H), 1.96 (m, 1H), 1.42 (s, 9H).

G. 7-Methoxynaphthalene-2-sulfonic Acid [1-(4-chloro-thieno[2,3-d]pyrimidin-6-yl-methyl)-2-oxopyrrolidin-3-(S)-yl]amide.

The title compound is prepared as described in EXAMPLE 1, Part I substituting [1-(4-chloro-thieno[2,3-d] pyrimidin-6-ylmethyl)-2-oxopyrrolidin-3-(S)-yl]-carbamic acid tert-butyl ester for [1-(1-chloro-isoquinolin-7-ylmethyl)-2-oxopyrrolidin-3-(S)-yl]-carbamic acid tert-butyl ester. The resulting product is then taken directly on as described in EXAMPLE 1, Part K. The crude product is purified by column chromatography eluting with a gradient of 30% EtOAc/$CH_2Cl_2$ to 40% EtOAc/$CH_2Cl_2$ to give the title compound as a white solid.

$^1$H NMR (CDCl$_3$, 300 MHz) δ 8.80 (s, 1H), 8.32 (s, 1H), 7.92 (d, 1H), 7.76 (m, 2H), 7.24 (m, 3H), 5.51 (bs, 1H), 4.68 (s, 2H), 3.93 (s, 3H), 3.78 (m, 1H), 3.32 (m, 2H), 2.62 (m, 1H), 2.12 (m, 1H).

H. 7-Methoxynaphthalene-2-sulfonic Acid [1-(4-Amino-thieno[2,3-d]pyrimidin-6-yl-methyl)-2-oxopyrrolidin-3-(S)-yl]amide Trifluoroacetate.

The title compound is prepared as described in EXAMPLE 28, Part G substituting 7-methoxynaphthalene-2-sulfonic acid [1-(4-chloro-thieno[2,3-d]pyrimidin-6-yl-methyl)-2-oxopyrrolidin-3-(S)-yl]amide for 7-methoxynaphthalene-2-sulfonic acid [1-(4-chloro-quinazolin-6-ylmethyl)-2-oxopyrrolidin-3-(S)-yl]-methyl amide. The residue is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 8.33 (m, 2H), 8.21 (d, 1H), 8.02 (m, 2H), 7.91 (d, 1H), 7.70 (dd, 1H), 7.52 (s, 1H), 7.43 (s, 1H), 7.30 (dd, 1H), 4.58 (AB, 2H), 4.05 (m, 2H), 3.93 (s, 3H), 3.17 (m, 2H), 1.98 (m, 1H), 1.55 (m, 1H). FAB MS, $[M+H]^+=484$.

EXAMPLE 30

7-Methoxynaphthalene-2-sulfonic Acid [2-(6-Amino-thieno[2,3-d]pyrimidin-6-yl-methyl)-2-oxopyrrolidin-3-(S)-yl]amide Trifluoroacetate

A. 4-Chloro-7-methyl-thieno[3,2-d]pyrimidine.

The title compound is prepared as described in EXAMPLE 28, Part B substituting 7-methyl-thieno[2,3-d]pyrimidin-4-ol for 6-methyl-3H-quinazolin-4-one. The crude product is purified by column chromatography eluting with a gradient of $CH_2Cl_2$ to 10% $EtOAc/CH_2Cl_2$ to give the title compound as a solid.

$^1$H NMR (CDCl$_3$, 300 MHz) δ 9.02 (s, 1H), 7.68 (s, 1H), 2.51 (s, 3H).

B. 7-Bromomethyl-4-chloro-thieno[3,2-d]pyrimidine.

The title compound is prepared as described in EXAMPLE 1, Part F substituting 4-chloro-7-methyl-thieno[3,2-d]pyrimidine for 1-chloro-7-methylisoquinoline. The crude product is purified by column chromatography eluting with a gradient of 5% EtOAc/hexanes to 10% EtOAc/hexanes to give the title compound as a white solid.

$^1$H NMR (CDCl$_3$, 300 MHz) δ 9.04 (s, 1H), 8.08 (s, 1H), 4.77 (s, 2H).

C. [1-(4-Chloro-thieno[3,2-d]pyrimidin-7-ylmethyl)-2-oxopyrrolidin-3-(S)-yl]-carbamic Acid tert-Butyl Ester.

The title compound is prepared as described in EXAMPLE 1, Part H substituting 7-bromomethyl-4-chloro-thieno[3,2-d]pyrimidine for 7-bromomethyl-1-chloroisoquinoline. The crude product is purified by column chromatography eluting with a gradient of 20% $EtOAc/CH_2Cl_2$ to 30% $EtOAc/CH_2Cl_2$ to give the title compound as a white foam.

$^1$H NMR (CDCl$_3$, 300 MHz) δ 8.95 (s, 1H), 8.06 (s, 1H), 5.18 (bs, 1H), 4.76 (AB, 2H), 4.13 (m, 1H), 3.44 (m, 1H), 3.37 (m, 1H), 2.64 (m, 1H), 1.92 (m, 1H), 1.42 (s, 9H).

D. 7-Methoxylnaphthalene-2-sulfonic Acid [1-(4-Chloro-thieno[3,2-d]pyrimidin-7-ylmethyl)-2-oxopyrrolidin-3-(S)-yl]amide.

The title compound is prepared as described in EXAMPLE 1, Part I substituting [1-(4-chloro-thieno[3,2-d]pyrimidin-7-ylmethyl)-2-oxopyrrolidin-3-(S)-yl]-carbamic acid tert-butyl ester for [1-(1-chloro-isoquinolin-7-ylmethyl)-2-oxopyrrolidin-3-(S)-yl]-carbamic acid tert-butyl ester. The resulting product is then taken directly on as described in EXAMPLE 1, Part K. The crude product is purified by column chromatography eluting with a gradient of 30% $EtOAc/CH_2Cl_2$ to 40% $EtOAc/CH_2Cl_2$ to give the title compound as a white solid.

$^1$H NMR (CDCl$_3$, 300 MHz) δ 8.92 (s, 1H), 8.32 (s, 1H), 7.96 (s, 1H), 7.86 (d, 1H), 7.74 (m, 2H), 7.28 (d, 1H), 7.19 (d, 1H), 5.64 (bs, 1H), 4.71 (AB, 2H), 3.93 (s, 3H), 3.72 (m, 1H), 3.44 (m, 1H), 3.32 (m, 1H), 2.52 (m, 1H), 2.05 (m, 1H).

E. 7-Methoxynaphthalene-2-sulfonic Acid [2-(4-Amino-thieno[3,2-d]pyrimidin-7-yl-methyl)-2-oxopyrrolidin-3-(S)-yl]amide Trifluoroacetate.

The title compound is prepared as described in EXAMPLE 28, Part G substituting 7-methoxynaphthalene-2-sulfonic acid [1-(4-chloro-thieno[3,2-d]pyrimidin-7-ylmethyl)-2-oxopyrrolidin-3-(S)-yl]amide for 7-methoxynaphthalene-2-sulfonic acid [1-(4-chloro-quinazolin-6-ylmethyl)-2-oxopyrrolidin-3-(S)-yl]-methyl amide. The residue is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-d$_6$, 300 MHz) δ 8.55 (s, 1H), 8.35 (bs, 3H), 8.14 (d, 1H), 8.00 (m, 2H), 7.93 (d, 1H), 7.68 (d, 1H), 7.52 (s, 1H), 7.32 (dd, 1H), 4.49 (AB, 2H), 4.09 (m, 1H), 3.90 (s, 3H), 3.18 (m, 2H), 1.96 (m, 1H), 1.54 (m, 1H). FAB MS, [M+H]$^+$=483. Elemental analysis calculated with 1.5 mol $H_2O$ and 1.5 mol trifluoroacetate cal. C=44.75%, H=3.83%, N=10.44%, found C=44.75%, H=3.77%, N=11.12%.

EXAMPLE 31

7-Methoxynaphthalene-2-sulfonic Acid [1-(7-Amino-thieno[2,3-c]pyridin-3-yl-methyl)-2-oxopyrrolidin-3-(S)-yl]amide Trifluoroacetate

A. 3-Bromomethyl-7-chloro-thieno[2,3-c]pyridine.

The title compound is prepared as described in EXAMPLE 1, Part F substituting 7-chloro-3-methyl-thieno[2,3-c]pyrimidine for 1-chloro-7-methylisoquinoline. The crude product is purified by column chromatography eluting with a gradient of 5% EtOAc/hexanes to 10% EtOAc/hexanes to give the title compound as a white solid.

$^1$H NMR (CDCl$_3$, 300 MHz) δ 8.38 (d, 1H), 7.73 (s, 1H), 7.71 (d, 1H), 4.72 (s, 2H).

B. [1-(7-Chloro-thieno[2,3-c]pyridin-3-ylmethyl)-2-oxopyrrolidin-3-(S)-yl]-carbamic Acid tert-Butyl Ester.

The title compound is prepared as described in EXAMPLE 1, Part H substituting 3-bromomethyl-7-chloro-thieno[2,3-c]pyridine for 7-bromomethyl-1-chloroisoquinoline. The crude product is purified by column chromatography eluting with a gradient of 20% $EtOAc/CH_2Cl_2$ to 40% $EtOAc/CH_2Cl_2$ to give the title compound as a white foam.

$^1$H NMR (CDCl$_3$, 300 MHz) δ 8.28 (d, 1H), 7.74 (d, 1H), 7.64 (s, 1H), 5.18 (bs, 1H), 4.68 (AB, 2H), 4.17 (m, 1H), 3.18 (m, 2H), 2.54 (m, 1H), 1.86 (m, 1H), 1.42 (s, 9H).

C. 7-Methoxynaphthalene-2-sulfonic Acid [1-(7-Chloro-thieno[2,3-c]pyridin-3-yl-methyl)-2-oxopyrrolidin-3-(S)-yl] amide.

The title compound is prepared as described in EXAMPLE 1, Part I substituting [1-(7-chloro-thieno[2,3-c]pyridin-3-ylmethyl)-2-oxopyrrolidin-3-(S)-yl]-carbamic acid tert-butyl ester for [1-(1-chloro-isoquinolin-7-ylmethyl)-2-oxopyrrolidin-3-(S)-y]-carbamic acid tert-butyl ester. The resulting product is then taken directly on as described in EXAMPLE 1, Part K. The crude product is purified by column chromatography eluting with a gradient of 30% $EtOAc/CH_2Cl_2$ to 40% $EtOAc/CH_2Cl_2$ to give the title compound as a white solid.

$^1$H NMR (DMSO-d$_6$, 300 MHz) δ 8.33 (s, 1H), 8.30 (d, 1H), 8.16 (d, 1H), 8.07 (s, 1H), 7.99 (d, 1H), 7.92 (d, 1H), 7.78 (d, 1H), 7.67 (d, 1H), 7.51 (d, 1H), 7.28 (dd, 1H), 4.58 (AB, 2H), 4.08 (m, 1H), 3.88 (s, 2H), 1.89 (m, 1H), 1.48 (m, 1H).

D. 7-Methoxynaphthalene-2-sulfonic Acid [1-(7-Amino-thieno[2,3-c]pyridin-3-yl-methyl)-2-oxopyrrolidin-3-(S)-yl] amide Trifluoroacetate.

The title compound is prepared as described in EXAMPLE 28, Part G substituting 7-methoxynaphthalene-2-sulfonic acid [1-(7-chloro-thieno[2,3-c]pyridin-3-yl-methyl)-2-oxopyrrolidin-3-(S)-yl]amide for 7-methoxynaphthalene-2-sulfonic acid [1-(4-chloro-quinazolin-6-ylmethyl)-2-oxopyrrolidin-3-(S)-yl]-methyl amide. The residue is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-d$_6$, 300 MHz) δ 8.90 (bs, 3H), 8.34 (s, 1H), 8.16 (d, 1H), 7.90 (d, 1H), 7.82 (d, 1H), 7.68 (d, 1H), 7.62 (d, 1H), 7.34 (m, 3H), 7.23 (dd, 1H), 4.64 (AB, 2H), 4.08 (m, 1H), 3.88 (s, 3H), 3.09 (m, 2H), 2.11 (m, 1H), 1.60 (m, 1H). FAB MS, [M+H]$^+$=483.

EXAMPLE 32

7-Methoxynaphthalene-2-sulfonic Acid [1-(7-Hydroxy-thieno[2,3-c]pyridin-3-yl-methyl)-2-oxopyrrolidin-3-(S)-yl]amide Trifluoroacetate

A. 7-Methoxynaphthalene-2-sulfonic Acid [1-(7-Hydroxy-thieno[2,3-c]pyridin-3-yl-methyl)-2-oxopyrrolidin-3-(S)-yl] amide Trifluoroacetate.

The title compound is prepared as described in EXAMPLE 28, Part G substituting 7-methoxynaphthalene-2-sulfonic acid [1-(7-chloro-thieno[2,3-c]pyridin-3-yl-methyl)-2-oxopyrrolidin-3-(S)-yl]amide for 7-methoxynaphthalene-2-sulfonic acid [1-(4-chloro-quinazolin-6-ylmethyl)-2-oxopyrrolidin-3-(S)-yl]-methyl amide. The residue is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 8.36 (s, 1H), 8.18 (d, 1H), 8.01 (d, 1H), 7.92 (d, 1H), 7.86 (s, 1H), 7.68 (d, 1H), 7.52 (s, 1H), 7.28 (m, 3H), 6.62 (d, 1H), 4.42 (AB, 2H), 4.00 (m, 1H), 3.88 (s, 3H), 3.04 (m, 2H), 1.89 (m, 1H), 1.44 (m, 1H). FAB MS, [M+H]$^+$=484.

EXAMPLE 33

7-Methoxynaphthalene-2-sulfonic Acid [1-(4-Amino-thieno[3,2-c]pyridin-3-yl-methyl)-2-oxopyrrolidin-3-(S)-yl]amide Trifluoroacetate

A. 3-(5-Methyl-thiophene-2-yl)-acrylic Acid Methyl Ester.

To 5-methyl-thiophene-2-carboxaldelhyde (5 g, 40 mmol) in $CH_2Cl_2$ (100 mL) is added methyl (triphenylphosphoranylidene) acetate (13.3 g, 40 mmol). The solution is stirred for 72 hours. After this time, the solution is concentrated. The residue is slurried in $Et_2O$. The solution is filtered through a bed of Celite. The collected liquid is concentrated. The residue is purified by column chromatography eluting with a gradient of 50% EtOAc/hexanes to 60% EtOAc/hexanes to give the title compound (4.5 g, 25 mmol) as an oil.

$^1$H NMR (CDCl$_3$, 300 MHz) δ 7.69 (d, 1H), 7.04 (d, 1H), 6.71 (d, 1H), 6.11 (d, 1H), 3.79 (s, 3H), 2.49 (s, 3H).

B. 3-(5-Methyl-thiophene-2-yl)-acrylic Acid.

The title compound is prepared as described in EXAMPLE 29, Part B substituting 3-(5-methyl-thiophene-2-yl)-acrylic acid methyl ester for 2-amino-5-methylthiophene-3-carboxylic acid methyl ester. The title compound is obtained by filtration as a white solid.

$^1$H NMR (CDCl$_3$, 300 MHz) δ 7.58 (d, 1H), 7.24 (d, 1H), 7.82 (d, 1H), 5.98 (d, 1H), 2.46 (s, 3H).

C. 2-Methyl-5H-thieno[3,2-c]pyridin-4-one.

The title compound is prepared as described in EXAMPLE 1, Part A, substituting 3-(5-methyl-thiophene-2-yl)-acrylic acid for 3-p-tolyl-acrylic acid. The product is then treated as described in EXAMPLE 1, Part B, C, and D. The crude product is purified by column chromatography eluting with 1% MeOH/$CH_2Cl_2$ to 5% MeOH/$CH_2Cl_2$ to give the title compound as a white solid.

$^1$H NMR (CDCl$_3$, 300 MHz) δ 11.72 (bs, 1H), 7.31 (s, 1H), 7.18 (d, 1H), 6.68 (d, 1H), 2.58 (s, 3H). EI MS, [M]$^+$=165.

D. 4-Chloro-2-methyl-thieno[3,2-c]pyridine.

The title compound is prepared as described in EXAMPLE 1, Part E, substituting 2-methyl-5H-thieno[3,2-c]pyridin-4-one for 7-methyl-2H-isoquinolin-1-one. The crude product is purified by column chromatography eluting with a gradient of 70% $CH_2Cl_2$/hexanes to 100% $CH_2Cl_2$ to give the title compound as a white solid.

$^1$H NMR (CDCl$_3$, 300 MHz) δ 8.13 (d, 1H), 7.58 (d, 1H), 7.16 (d, 1H), 2.61 (s, 3H).

E. 2-Bromomethyl-4-chloro-thieno[3,2-c]pyridine.

The title compound is prepared as described in EXAMPLE 1, Part F substituting 4-chloro-2-methyl-thieno[3,2-c]pyridine for 1-chloro-7-methylisoquinoline. The crude product is purified by column chromatography eluting with a gradient of 5% EtOAc/hexanes to 10% EtOAc/hexanes to give the title compound as a white solid.

$^1$H NMR (CDCl$_3$, 300 MHz) δ 8.21 (d, 1H), 7.63 (d, 1H), 7.49 (s, 1H), 4.80 (s, 2H).

F. 1-(4-Chloro-thieno[3,2-c]pyridin-2-ylmethyl)-2-oxopyrrolidin-3-(S)-yl]carbamic Acid tert-Butyl Ester.

The title compound is prepared as described in EXAMPLE 1, Part H substituting 2-bromomethyl-4-chloro-thieno[3,2-c]pyridine for 7-bromomethyl-1-chloroisoquinoline. The crude product is purified by column chromatography eluting with a gradient of 20% EtOAc/$CH_2Cl_2$ to 30% EtOAc/$CH_2Cl_2$ to give the title compound as a white foam.

$^1$H NMR (CDCl$_3$, 300 MHz) δ 8.22 (d, 1H), 7.63 (d, 1H), 7.39 (s, 1H), 5.13 (bs, 1H), 4.78 (AB, 2H), 4.21 (m, 1H), 3.33 (m, 2H), 2.62 (m, 1H), 1.90 (m, 1H), 1.42 (s, 9H).

G. 3-(S)-Amino-1-(4-chloro-thieno[3,2-c]pyridin-2-ylmethyl)-pyrrolidin-2-one Hydrochloride.

The title compound is prepared as described in EXAMPLE 1, Part I substituting 1-(4-chloro-thieno[3,2-c]pyridin-2-ylmethyl)-2-oxopyrrolidin-3-(S)-yl]carbamic acid tert-butyl ester for [1-(1-chloro-isoquinolin-7-ylmethyl)-2-oxopyrrolidin-3-(S)-yl]-carbamic acid tert-butyl ester. The title compound is obtained asia white solid.

$^1$H NMR (DMSO-$d_6$, 300 MHz) δ 8.50 (bs, 3H), 8.22 (d, 1H), 8.06 (d, 1H), 7.51 (s, 1H), 4.81 (AB, 2H), 4.04 (m, 2H), 3.32 (m, 2H), 2,31 (m, 1H), 1.96 (m, 1H).

H. 7-Methoxynaphthalene-2-sulfonic Acid [1-(4-Chloro-thieno[3,2-c]pyridin-3-yl-methyl)-2-oxopyrrolidin-3-(S)-yl] amide.

The title compound is prepared as described in EXAMPLE 1, Part K substituting 3-amino-1-(4-chloro-thieno[3,2-c]pyridin-2-ylmethyl)-pyrrolidin-2-one for 3-(S)-amino-1-(1-chloro-isoquinolin-7-ylmethyl)-pyrrolidin-2-one hydrochloride. The title compound is obtained as a white solid.

$^1$H NMR (DMSO-$d_6$, 300 MHz) δ 8.36 (s, 1H), 8.28 (d, 1H), 8.18 (d, 1H), 8.02 (m, 2H), 7.91 (d, 1H), 7.69 (d, 1H), 7.56 (d, 1H), 7.42 (s, 1H), 7.29 (dd, 1H), 4.66 (AB, 2H), 4.10 (m, 1H), 3.88 (s, 3H), 3.14 (m, 2H), 1.97 (m, 1H), 1.58 (m, 1H).

I. 7-Methoxynaphthalene-2-sulfonic Acid [1-(4-Amino-thieno[3,2-c]pyridin-3-yl-methyl)-2-oxopyrrolidin-3-(S)-yl] amide Trifluoroacetate.

The title compound is prepared as described in EXAMPLE 1, Part L substituting 7-methoxynaphthalene-2-sulfonic acid [1-(4-chloro-thieno[3,2-c]pyridin-3-yl-methyl)-2-oxopyrrolidin-3-(S)-yl]amide for 7-methoxynaphthalene-2-sulfonic acid [1-(1-chloro-isoquinolin-7-ylmethyl)-2-oxopyrrolidin-3-(S)-yl]-amide. The resulting product is then treated as described in EXAMPLE 1, Part M. The residue is purified by RP-HPLC eluting with a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 8.58 (bs, 3H), 8.32 (s, 1H), 8.26 (d, 1H), 8.02 (d, 1H), 7.92 (d, 1H), 7.78 (s, 1H), 7.69 (m, 2H), 7.49 (dd, 1H), 7.28 (dd, 1H), 4.62 (AB, 2H), 4.02 (m, 1H), 3.88 (s, 3H), 3.13 (m, 2H), 1.96 (m, 1H), 1.58 (m, 1H). FAB MS, [M+H]$^+$=483.

EXAMPLE 34

7-Methoxynaphthalene-2-sulfonic Acid [1-(4-Hydroxy-thieno[3,2-c]pyridin-3-yl-methyl)-2-oxopyrrolidin-3-(S)-yl]amide Trifluoroacetate A. 7-Methoxynaphthalene-2-sulfonic Acid [1-(4-Hydroxy-thieno[3,2-c]pyridin-3-yl-methyl)-2-oxopyrrolidin-3-(S)-yl] amide Trifluoroacetate.

The title compound is prepared as described in EXAMPLE 1, Part L substituting 7-methoxynaphthalene-2-sulfonic acid [1-(4-chloro-thieno[3,2-c]pyridin-3-yl-methyl)-2-oxopyrrolidin-3-(S)-yl]amide for 7-methoxynaphthalene-2-sulfonic acid [1-(1-chloro-isoquinolin-7-ylmethyl)-2-oxopyrrolidin-3-(S)-yl]-amide. The resulting product is then treated as described in EXAMPLE 1, Part M. The residue is purified by RP-HPLC eluting with a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 11.32 (bs, 1H), 8.33 (s, 1H), 8.20 (d, 1H), 8.02 (d, 1H), 7.92 (d, 1H), 7.69 (d, 1H), 7.52 (d, 1H), 7.46 (s, 1H), 7.30 (m, 2H), 7.19 (m, 1H), 6.71 (d, 1H), 4.52 (AB, 2H), 4.06 (m, 1H), 3.88 (s, 3H), 3.10 (m, 2H), 1.90 (m, 1H), 1.50 (m, 1H). FAB MS, [M+H]$^+$=484.

EXAMPLE 35

Benzo[b]thiophene-2-sulfonic Acid [1-(4-Amino-thieno[3,2-c]pyridin-3-yl-methyl)-2-oxopyrrolidin-3-(S)-yl]amide Trifluoroacetate A. Benzo[b]thiophene-2-sulfonic Acid [1-(4-Chloro-thieno[3,2-c]pyridin-3-yl-methyl)-2-oxopyrrolidin-3-(S)-yl] amide.

The title compound is prepared as described in EXAMPLE 1, Part K substituting 3-amino-1-(4-chloro-thieno[3,2-c]pyridin-2-ylmethyl)-pyrrolidin-2-one for 3-(S)-amino-1-(1-chloro-isoquinolin-7-ylmethyl)-pyrrolidin-2-one hydrochloride and benzo[b]thiophene-2-sulfonyl chloride for 7-methoxynaphthalene-2-sulfonyl chloride. The title compound is obtained as a white solid.

$^1$H NMR (CDCl$_3$, 300 MHz) δ 8.21 (d, 1H), 7.96 (s, 1H), 7.90 (m, 2H), 7.64 (d, 1H), 7.49 (m, 2H), 7.39 (s, 1H), 5.58 (bs, 1H), 4.76 (s, 2H), 3.97 (m, 1H), 3.38 (m, 2H), 2.68 (m, 1H), 2.18 (m, 1H).

C. Benzo[b]thiophene-2-sulfonic Acid [1-(4-Amino-thieno[3,2-c]pyridin-3-yl-methyl)-2-oxopyrrolidin-3-(S)-yl]amide Trifluoroacetate.

The title compound is prepared as described in EXAMPLE 1, Part L substituting benzo[b]thiophene-2-sulfonic acid [1-(4-chloro-thieno[3,2-c]pyridin-3-yl-methyl)-2-oxopyrrolidin-3-(S)-yl]amide for 7-methoxynaphthalene-2-sulfonic acid [1-(1-chloro-isoquinolin-7-ylmethyl)-2-oxopyrrolidin-3-(S)-yl]-amide. The resulting product is then treated as described in EXAMPLE 1, Part M. The residue is purified by RP-HPLC eluting with a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 8.70 (d, 1H), 8.55 (bs, 2H), 8.07 (m, 3H), 7.78 (s, 1H), 7.70 (d, 1H), 7.49 (m, 3H), 4.66 (AB, 2H), 4.16 (m, 1H), 3.24 (m, 2H), 2.12 (m, 1H), 1.72 (m, 1H). FAB MS, [M+]$^+$=459.

EXAMPLE 36

5-Pyridin-4-yl-thiophene-2-sulfonic Acid-[1-(1-Aminoisoquinolin-7-ylmethyl)-2-oxopyrrolidin-3-(S)-yl]-amide Trifluoroacetate A. 4-Thiophene-2-yl-pyridine.

2-Bromothiophene (7.6 mL, 78.5 mmol) is added dropwise to a flame and vacuum dried three-necked round-bottomed flask fitted with a condenser, stopper and magnesium (2 g, 82.3 mmol) in diethyl ether (70 mL). The resulting grey solution is stirred at reflux for 1.5 hours. Meanwhile 4-bromopyridine hydrochloride is converted to the free base in the following manner: 4-Bromopyridine hydrochloride (15.3 g, 78.7 mmol) is dissolved in water (100 mL), and cooled in an ice bath. One equivalent of 1 N NaOH (ca. 100 mL) is added dropwise until pH is ~5.6. The ice-cooled aqueous solution is extracted with hexane (3×150 mL) and the combined organic layers are dried over MgSO$_4$ and filtered. Hexane is removed under vacuum (11 mm Hg) while cooling in an ice-bath to a volume of ca. 30 mL. The resulting colorless clear solution is diluted with THF (150 mL) under N$_2$. The Grignard reagent is then cooled to room temperature and added via cannula to the solution of NiCl$_2$dppp (0.54 g, 1 mmol) and 4-bromopyridine in THF. The resulting dark solution is refluxed overnight. The reaction mixture is then poured over saturated NH$_4$Cl solution and extracted with diethyl ether (3×200 mL). The combined ethereal layers are acidified with 2 N HCl (300 mL) and the aqueous layer is washed with diethyl ether. The aqueous layer is then cooled in an ice-bath and neutralized with sodium bicarbonate. The aqueous layer is extracted with ethyl acetate (3×200 mL) and the combined organic layers are dried over MgSO$_4$, filtered and concentrated to give a brown solid. The crude solid is taken up in hot hexanes and the yellow solution is separated from the insoluble black solid. The hexane solution is concentrated and the above procedure is repeated. Upon cooling the hexane solution. yellow solid precipitates form. The yellow solid is collected to give the title compound (8.99 g, 55.8 mmol).

$^1$H NMR (CDCl$_3$, 300 MHz) δ 8.60 (d, 2H), 7.51 (m, 1H), 7.49 (d, 2H), 7.42 (dd, 1H), 7.14 (dd, 1H). EI MS, [M]$^+$=161.

B. 5-Pyridin-4-yl-thiophene-2-sulfonyl Chloride.

To a solution of 4-thiophene-2-yl-pyridine (3.33 g, 20.7 mmol) in THF (137 mL) at −78° C. is added n-BuLi (8.7 mL of a 2.5 M solution in hexanes, 21.7 mmol). After stirring for 15 minutes, SO2 gas is bubbled through the solution for 30 minutes. The solution is then allowed to warm to room temperature and stirred overnight. The solution is concentrated to dryness and the resulting solid is suspended in hexane (100 mL). To the ice-cooled solution is added sulfuryl chloride (1.7 mL, 21.7 mmol). The ice bath is removed and the suspension is stirred for 2 hours. The mixture is then concentrated to dryness and diluted with ethyl acetate and washed with saturated NaHCO$_3$ (aq), water and brine. The organic layer is dried over MgSO$_4$, filtered and concentrated to give a yellow solid as the title product (3.39 g, 13.1 mmol) which is used in the subsequent step without further purification.

$^1$H NMR (CDCl$_3$, 300 MHz) δ 8.75(d, 2H), 8.60 (d, 1H), 7.90 (d, 1H), 7.51 (d, 2H). EI, [M]$^+$=259, 261, Cl pattern.

C. 5-Pyridin-4-yl-thiophene-2-sulfonic Acid-[1-(1-Chloro-isoquinolin-7-ylmethyl)-2-oxopyrrolidin-3-(S)-yl]-amide.

5-Pyridin-4-yl-thiophene-2-sulfonyl chloride is added to a solution of 3-(S)-amino-1-(1-chloro-isoquinolin-7-ylmethyl)-pyrrolidin-2-one hydrochloride (0.12 g, 0.38 mmol) in pyridine (2 mL). The resulting mixture is stirred overnight then concentrated to dryness. The residue is diluted with methylene chloride and washed with saturated NaHCO$_3$ solution and brine. The organic layer is dried over MgSO$_4$, filtered and concentrated to give 105 mg of a crude solid. The crude product is purified by column chromatography eluting with 5% MeOH/CH$_2$Cl$_2$ to afford the title product (0.026 g, 0.052 mmol) as a white solid.

$^1$H NMR (CDCl$_3$, 300 MHz) δ 8.67 (d, 2H), 8.30 (d, 1H), 8.14 (s, 1H), 7.83 (d, 1H), 7.70 (d, 1H), 7.57–7.61 (m, 2H), 7.48–7.46 (m, 3H), 5.60 (bs, 1H), 4.67 (AB, 2H), 3.98 (m, 1H), 3.29 (m, 2H), 2.68 (m, 1H), 2.15 (m, 1H). APCI MS, [M+H]$^+$=499, 501. Cl pattern.

D. 5-Pyridin-4-yl-thiophene-2-sulfonic Acid-[-(1-Aminoisoquinolin-7-ylmethyl)-2-oxopyrrolidin-3-(S)-yl]-amide Trifluoroacetate.

Ammonium acetate (0.12 g, 1.56 mmol), pheniol (0.049 g, 0.52 mmol), and 5-pyridin-4-yl-thiophene-2-sulfonic acid-[1-(1-chloro-isoquinolin-7-ylmethyl)-2-oxopyrrolidin-3-(S)-yl]-amide (0.026 g, 0.052 mmol) is heated to 90° C. for 6 hours then cooled to room temperature. The product is purified by RP-HPLC eluting with a gradient of 10% CH$_3$CN/H$_2$O (0.1% TFA) to 80% CH$_3$CN/H$_2$O (0.1% TFA) and the appropriate product fractions are lyophilized to give the title compound (0.005 g, 0.007 mmol) as a white solid.

$^1$H NMR (DMSO-d$_6$, 300 MHz) δ 13.0 (bs, 1H), 9.0 (bs, 1H), 8.60–8.70 (m, 3H), 8.29 (s, 1H), 7.91 (d, 1H), 7.89 (d, 1H), 7.71–7.80 (m, 4H), 7.66 (d, 1H), 7.23 (d, 1H). FAB MS, [M+H]$^+$=480.

EXAMPLE 37

5-Pyridin-3-yl-thiophene-2-sulfonic Acid-[1-(1-aminoisoquinolin-7-ylmethyl)-2-oxopyrrolidin-3-(S)-yl]-amide Trifluoroacetate A. 3-Thiophene-2-yl-pyridine.

The title compound is prepared as described in EXAMPLE 36, Part A using 3-bromopyridine in place of 4-bromopyridine hydrochloride.

$^1$H NMR (CDCl$_3$, 300 MHz) δ 8.89 (dd, 1H), 8.52 (dd, 1H), 7.87 (ddd, 1H), 7.38 (s, 1H), 7.36 (d, 1H), 7.31 ((m, 1H), 7.12 (dd, 1H). EI, [M]$^+$=161.

B. 5-Pyridin-3-yl-thiophene-2-sulfonyl Chloride.

The title compound is prepared as described in EXAMPLE 36, Part B using 3-thiophene-2-yl-pyridine in place of 4-thiophene-2-yl-pyridine.

$^1$H NMR (CDCl$_3$, 300 MHz) δ 8.95 (bs, 1H), 8.70 (bs, 1H), 7.95 (d, 1H), 7.90 (d, 1H), 7.45 (bs, 1H), 7.44 (d, 1H). EI, [M]$^+$=259, 261, Cl pattern.

C. 5-Pyridin-3-yl-thiophene-2-sulfonic Acid-[1-(1-Chloro-isoquinolin-7-ylmethyl)-2-oxopyrrolidin-3-(S)-yl]-amide.

Triethylamine (0.35 mL, 2.5 mmol) is added dropwise to a solution of 5-pyridin-3-yl-thiophene-2-sulfonyl chloride (0.22 g, 0.85 mmol) and 3-(S)-amino-1-(1-chloro-isoquinolin-7-ylmethyl)-pyrrolidin-2-one hydrochloride (0.22 g, 0.71 mmol) in CH$_3$CN (5 ml). The suspension is stirred at room temperature overnight then concentrated to dryness. The residue is diluted with methylene chloride and washed with saturated NaHCO$_3$ solution and brine. The organic layer is dried over MgSO$_4$, filtered, concentrated, and then purified by column chromatography eluting with a gradient of 1% MeOH/CH$_2$Cl$_2$ to 5% MeOH/CH$_2$Cl$_2$ to give the product (0.23 g, 0.45 mmol) as a white solid.

$^1$H NMR (CDCl$_3$, 300 MHz) δ 8.89 (d, 1H), 8.63 (dd, 1H), 8.30 (d, 1H), 8.13 (d, 1H), 7.82–7.89 (m, 2H), 7.70 (d, 1H), 7.57–7.68 (m, 2H), 7.33–7.40 (m, 2H), 5.45 (d, 1H), 4.67 (AB, 2H), 3.95 (m, 1H), 3.28 (m, 2H), 2.75 (m, 1H), 2.10 (m, 1H). Ion spray MS, [M+H]$^+$=499, 501, Cl pattern.

D. 5-Pyridin-3-yl-thiophene-2-sulfonic Acid-[1-(1-Aminoisoquinolin-7-ylmethyl)-2-oxopyrrolidin-3-(S)-yl]-amide Trifluoroacetate.

The title compound is prepared as described in EXAMPLE 36, Part D using 5-pyridin-3-yl-thiophene-2-sulfonic acid-[1-(1-chloro-isoquinolin-7-ylmethyl)-2-oxopyrrolidin-3-(S)-yl]-amide in place of 5-pyridin-4-yl-thiophene-2-sulfonic acid-[1-(1-chloro-isoquinolin-7-ylmethyl)-2-oxopyrrolidin-3-(S)-yl]-amide and heating at 100° C. overnight. The crude product is purified by RP-HPLC eluting with a gradient of 10% CH$_3$CN/H$_2$O (0.1% TFA) to 100% CH$_3$CN. The appropriate product fractions are lyophilized to give the title compound as a white solid.

$^1$H NMR (DMSO-d$_6$, 300 MHz) δ 12.95 (bs, 1H), 8.90–9.05 (m, 2H), 8.55–8.65 (m, 2H), 8.31 (s, 1H), 8.17 (m, 1H), 8.96 (d, 1H), 8.82 (d, 1H), 7.70–7.72 (m, 2H), 7.65 (d, 1H), 7.53 (dd, 1H), 7.21 (d, 1H), 4.60 (AB, 2H), 4.30 (m, 1H), 3.25 (m, 2H), 2.29 (m, 1H), 1.78 (m, 1H). FAB MS, [M+H]$^+$=480.

EXAMPLE 38

Benzothiophene-2-sulfonic Acid [1-(4-Aminoquinolin-6-ylmethyl)-2-oxopyrrolidin-3-(S)-yl]-amide Trifluoroacetate A. 4-Chloro-6-methylquinoline 6-Methyl-(1H)-quinolin-4-one (1.57 g, 9.7 mmol) in 20 mL phosphorus oxychloride is heated to 110° C. for 4 hours. The mixture is cooled to room temperature then diluted with ice water (~200 mL) and the pH is adjusted to ca. 10 by the slow addition of 10 N NaOH. The aqueous solution is extracted with methylene chloride (4×250 mL) and the combined organic layers washed with brine, dried over Na$_2$SO$_4$, filtered and concentrated. The crude residue is filtered through silica gel with 33% EtOAc/hexanes to give the product (1.05 g, 5.9 mmol) as a yellow solid.

$^1$H NMR (CDCl$_3$, 300 MHz) δ 8.69 (d, 1H), 8.0 (m, 2H), 7.58 (dd, 1H), 7.44 (d, 1H), 2.58 (s, 3H). EI MS, [M ]$^+$=177, 179, Cl pattern.

B. 6-Bromomethyl-4-chloroquinoline.

N-Bromosuccinimide (1.1 g, 6.19 mmol) and 70% benzoyl peroxide (0.215 g, 0.62 mmol) are added to a solution of 4-chloro-6-methylquinoline (1.05 g, 5.93 mmol) in 35 mL, carbon tetrachloride. The resulting mixture is heated to reflux overnight then cooled to room temperature and diluted with methylene chloride. The organic layer is washed with 1 N NaOH, dried over Na$_2$SO$_4$, filtered and concentrated. The residue is purified by column chromatography eluting with 33% EtOAc/hexanes to give the product (0.915 g 3.57 mmol) as a white solid.

$^1$H NMR (CDCl$_3$, 300 MHz) δ 8.73 (d, 1H), 8.13 (d, 1H), 8.07 (d, 1H), 7.74 (dd, 1H), 7.42 (d, 1H), 4.67 (s, 2H). Ion Spray, [M+H ]$^+$=256, 258, 260 Cl, Br pattern.

C. 3-(S)-Amino-1-(4-Chloroquinolin-6-ylmethyl)-pyrrolidin-2-one Hydrochloride

Sodium hydride (0.096 g, 2.4 mmol, 60% by weight) is added to a solution of [2-oxopyrrolidin-3-(S)-yl]-carbamic acid tert-butyl ester (0.4 g, 2 mmol) in 15 mL, of THF at 0° C. The mixture is stirred for 30 minutes then a solution of 6-bromomethyl-4-chloroquinoline (0.513 g, 2 mmol) in 15 mL THF is added slowly. The resulting solution is warmed to room temperature over 4 hours. The reaction mixture is quenched with saturated ammonium chloride solution then diluted with EtOAc. The organic layer is separated, washed with brine, dried over Na$_2$SO$_4$, filtered and concentrated. The residue is dissolved in ethyl acetate (50 mL), and saturated with HCl gas at 0° C. The solution is stirred at 0° C. for 15 minutes, then the solution is warmed to room temperature. After four hours at room temperature, the solid that precipitates is collected, and washed with ether to give the title compound (0.445 g, 1.43 mmol) as a pale yellow solid.

¹H NMR (DMSO-d₆, 300 MHz) δ 9.05 (d, 1H), 8.78 (bs, 3H), 8.27 (d, 1H), 8.23 (s, 1H), 8.02 (d, 1H), 7.96 (d, 1H), 4.67 (AB, 2H), 4.12 (m, 1H), 3.35 (m, 2H), 2.43 (m, 1H), 2.09 (m, 1H). Ion Spray MS, [M+H]⁺=276, 278.

D. Benzothiophene-2-sulfonic Acid [1-(4-Chloroquinolin-6-ylmethyl)-2-oxopyrrolidin-3-(S)-yl]-amide.

3-(S)-Amino-1-(4-chloroquinolin-6-ylmethyl)-pyrrolidin-2-one hydrochloride (0.12g, 0.38 mmol) is suspended in 15 mL CH₃CN. To this solution is added triethylamine (110 mL, 0.79 mmol) followed by benzothiophene-2-sulfonyl chloride (0.094 g, 0.40 mmol). The mixture is stirred overnight at room temperature, subjected to aqueous work up then concentrated to dryness. The crude product is purified by column chromatography eluting with 2–10% MeOH/CH₂Cl₂ to give the title compound (0.11 g, 0.23 mmol) as an off-white solid.

¹H NMR (CDCl₃, 300 MHz) δ 8.77 (d, 1H), 8.08 (d, 1H), 8.04 (s, 1H), 7.97 (s, 1H), 7.88 (m, 2H), 7.58 (dd, 1H), 7.49 (m, 3H), 6.01 (bs, 1H), 4.67 (AB, 2H), 4.03 (t, 1H), 3.27 (m, 2H), 2.65 (m, 1H), 2.16 (m, 1H). FAB MS, [M+H]⁺=472, 474, Cl pattern.

E. Benzothiophene-2-sulfonic Acid [1-(4-Aminoquinolin-6-ylmethyl)-2-oxopyrrolidin-3-(S)-yl]-amide Trifluoroacetate.

Benzothiophene-2-sulfonic acid [1-(4-chloroquinolin-6-ylmethyl)-2-oxopyrrolidin-3-(S)-yl]-amide (0.11 g, 0.23 mmol) is treated with phenol (1 g) and ammonium acetate (0.22 g, 2.8 mmol) at 110° C. as previously described. After five hours the mixture is cooled to room temperature and diluted with 100 ml methylene chloride. The organic solution is washed with 1 N NaOH (2×) and saline, dried over Na₂SO₄, filtered and concentrated. The residue is purified by HPLC eluting with a gradient of 10 to 100% CH₃CN/0.1% TFA in water over 30 minutes. Fractions containing pure product are lyophilized to give the title compound as a white solid (0.02 g, 0.044 mmol).

¹ NMR (CD₃OD, 300 MHz) δ 8.25 (d, 1H), 8.13 (s, 1H), 7.97 (s, 1H), 7.85 (m, 2H), 7.80 (AB, 2H), 7.48 (m, 2H), 6.80 (d, 1H), 4.64 (s, 2H), 4.35 (t, 1H), 3.31 (m, 2H), 2.48 (m, 1H), 1.89 (m, 1H). Ion Spray MS, [M+H]⁺=453.

EXAMPLE 39

6-Chloro-benzo[b]thiophene-2-sulfonic Acid [1-(1-Amino-isoquinolin-6-ylmethyl)-2-oxopyrrolidin-3-(S)-yl]-amide Trifluoroacetate A. 1-Phenoxy-6-bromomethyl-isoquinoline.

To 1-chloro-6-methyl-isoquinoline (2.28 g, 13.3 mmol), which is prepared as described in EXAMPLE 1, Part E, substituting 6-methyl-2H-isoquinolin-1-one for 7-methyl-2H-isoquinolin-1-one, is added 20 g of phenol. The solution is heated to 80° C. and KOH (3.73 g, 66.4 mmol) is added. After the addition, the solution is stirred and heated to 140° C. After 24 hours, the solution is cooled to ambient temperatures, and dissolved in CH₂Cl₂. The organic solution is washed with H₂O. The organic layer is washed with 1 N NaOH and saturated NaCl. The organic layer is dried over MgSO₄, filtered and concentrated. The resulting residue is dissolved in 50 mL of CCL₄, to the resulting solution is added NBS (2.01 g, 11.27 mmol) and benzoyl peroxide (0.6 g, 1.73 mmol). The solution is heated to reflux. After 16 hours, the solution is diluted with CH₂Cl₂. The organic layer is washed with 10% Na₂CO₃ and saturated NaCl. The organic layer is dried over MgSO₄, filtered and concentrated. The residue is purified by column chromatography eluting with 5% EtOAc/hexanes and 10%EtOAc/hexanes. MS, [M]⁺=313, 315, Br pattern.

B. [1-(1-Chloro-isoquinolin-6-ylmethyl)-2-oxopyrrolidin-3-(S)-yl]-carbamic Acid Benzyl Ester.

To a solution of (2-oxopyrrolidin-3-(S)-yl)-carbamic acid benzyl ester (0.15 g, 0.64 mmol) in 6 mL of 10:1 THF:DMF at 0° C. is added a 60% NaH dispersion (0.03 g, 0.71 mmol) followed by 1-phenoxy-6-bromomethyl-isoquinoline (0.2 g, 0.64 mmol). After 16 hours, the solution is treated with 10 mL of saturated NH₄Cl. The solution is diluted with CH₂Cl₂. The organic layer is washed with H₂O and saturated NaCl. The resulting product is suspended in 5 g of NH₄OAc and heated to 120° C. After 36 hours, the solution is cooled to ambient temperatures. The solution is diluted with H₂O and CH₂Cl₂. The organic layer is washed with H₂O and saturated NaCl. The organic layer is dried over MgSO₄, filtered and concentrated. The residue is purified by column chromatography eluting with 5% MeOH/CH₂Cl₂ to 10% MeOH/CH₂Cl₂ to give the product as a white solid (0.043 g, 0.11 mmol).

¹H NMR (CDCl₃, 300 MHz) δ 8.41 (d, 1H), 7.98 (d, 1H), 7.63 (s, 1H), 7.42 (m, 3H), 7.32 (m, 4H), 7.22 (m, 5H), 5.40 (bs, 1H), 5.14 (s, 2H), 4.64 (AB, 2H), 4.30 (m, 1H), 3.24 (m, 2H), 2.66 (m, 1H), 1.92 (m, 1H). FAB MS, [M+H]⁺=391.

C. 6-Chloro-benzo[b]thiophene-2-sulfonic Acid [1-(1-Amino-isoquinolin-6-ylmethyl)-2-oxopyrrolidin-3-(S)-yl]-amide Trifluoroacetate.

To a solution of [1-(1-chloro-isoquinolin-6-ylmethyl)-2-oxopyrrolidin-3(S)-yl]-carbamic acid benzyl ester (0.043 g, 0.11 mmol) in 4 mL of MeOH, is added 10% by weight Pd/C (0.02 g). The atmosphere above the reaction is replaced by hydrogen. After 16 hours, the solution is filtered through Celite and the Celite is washed with MeOH. The collected solution is concentrated. The resulting residue is dissolved in 3 mL of CH₂Cl₂:EtOH (2:1). To the solution is added Et₃N (0.01 g, 0.11 mmol) and 6-Chloro-benzo[b]thiophene sulfonyl chloride (0.03 g, 0.11 mmol). After 4 hours, the solution is concentrated. The residue is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 8.95 (bs, 3H), 8.71 (d, 1H), 8.46 (d, 1H), 8.24 (s, 1H), 8.04 (m, 2H), 7.71 (s, 1H), 7.63 (d, 1H), 7.52 (m, 2H), 7.12 (d, 1H), 4.52 (AB, 2H), 4.28 (m, 1H), 3.17 (m, 2H), 2.12 (m, 1H), 1.67 (m, 1H). FAB MS, [M+H]⁺=487, 489, Cl pattern.

EXAMPLE 40

6-Chloro-benzo[b]thiophene-2-sulfonic Acid [2-oxo-1-(1,2,3,4-Tetrahydro-isoquinolin-7-ylmethyl)-pyrrolidin-3-(S)-yl]-amide Trifluoroacetate A. [1-(1-(1,2,3,4-Tetrahydro-isoquinolin-7-ylmethyl)-2-oxopyrrolidin-3(S)-yl]carbamic Acid tert-Butyl Ester.

To a solution of [1-(1-chloro-isoquinoline-7-ylmethyl)-2-oxopyrrolidin-3(S)-yl]carbamic acid tert-butyl ester (0.48 g, 1.28 mmol) in 50 mL of AcOH:MeOH (1:1) is added 5% by weight PtO₂/C (0.1 g). The atmosphere over the reaction is replaced by hydrogen. After 16 hours, the solution is filtered through Celite and the Celite is washed with MeOH. The organic solution is concentrated to give the product as a white foam. MS, [M+H]⁺=346.

B. 7-(3-tert-Butoxycarbonylamino-2-oxopyrrolidin-1-ylmethyl)-3,4-dihydro-1H-isoquinoline-2-carboxylic Acid Benzyl Ester.

To a solution of [1-(1-(1,2,3,4-tetrahydro-isoquinolin-7-ylmethyl)-2-oxopyrrolidin-3(S)-yl]carbamic acid tert-butyl ester (0.54 g, 1.58 mmol) in 50 mL of CH₂Cl₂ is added triethyl amine (0.66 mL, 4.73 mmol) and benzyl chloroformate (0.39 mL, 1.89 mmol). The solution is stirred for 16 hours. After this time, the solution is diluted with CH₂Cl₂.

The organic solution is washed with H₂O and saturated NaCl. The residue is purified by column chromatography eluting with 20% EtOAc/CH₂Cl₂.

¹H NMR (CDCl₃, 300 MHz) δ 7.35 (m, 5H), 7.08 (d, 1H), 7.02 (d, 1H), 6.95 (s, 1H), 5.14 (s, 2H), 5.10 (m, 1H), 4.58 (s, 2H), 4.38 (m, 2H), 4.16 (m, 1H), 3.68 (m, 2H), 3.18 (dd, 2H), 2.78 (m, 2H), 2.59 (m, 1H), 1.81 (m, 1H), 1.42 (s, 9H). FAB MS, [M+H]⁺=480.

C. 7-[3-(6-Chloro-benzo[b]thiophene-2-sulfonylamino)-2-oxopyrrolidin-1-ylmethyl]-3,4-dihydro-1H-isoquinoline-2-carboxylic Acid Benzyl Ester.

To a solution of 7-(3-tert-butoxycarbonylamino-2-oxopyrrolidin-1-ylmethyl)-3,4-dihydro-1H-isoquinoline-2-carboxylic acid benzyl ester (0.347 g, 0.72 mmol) is in 8 mL of CH₂Cl₂ is added 2 mL of TFA. After 4 hours, the solution is concentrated. The residue is dissolve in CH₂Cl₂ and Et₃N (0.30 mL, 2.17 mmol) and 6-chloro benzo[b]thiophene sulfonyl chloride (0.23 g, 0.87 mmol) are added. After 16 hours, the solution is concentrated. The residue is purified by column chromatography eluting with 10% EtOAc/CH₂Cl₂. The product (0.25 g, 0.51 mmol) was obtained as a white solid.

¹H NMR (CDCl₃, 300 MHz) δ 7.91 (s, 1H), 7.80 (m, 2H), 7.42 (d, 1H), 7.34 (m, 5H), 7.08 (d, 1H), 6.96 (d, 1H), 6.88 (s, 1H), 5.10 (s, 2H), 4.58 (s, 2H), 4.34 (s, 2H), 3.88 (m, 1H), 3.68 (m, 2H), 3.18 (m, 2H), 2.77 (m, 2H), 2.59 (m, 1H), 2.08 (m, 1H).

D. 6-Chloro-benzo[b]thiophene-2-sulfonic Acid [2-oxo-1-(1,2,3,4-Tetrahydro-isoquinolin-7-ylmethyl)-pyrrolidin-3-(S)-yl]-amide Trifluoroacetate.

7-[3-(6-Chloro-benzo[b]thiophene-2-sulfonylamino)-2-oxopyrrolidin-1-ylmethyl]-3,4-dihydro-1H-isoquinoline-2-carboxylic acid benzyl ester (0.25 g, 0.51 mmol) is added to 5 mL of 30% HBr/AcOH at 0° C. The solution is stirred for 30 minutes. After this time, 30 mL of Et₂O is added. The resulting solid is collected by filtration. The crude solid is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆,₃₀₀ MHz) δ 8.95 (bs, 2H), 868 (d, 1H), 8.24 (s, 1H), 8.00 (m, 2H), 7.51 (dd, 1H), 7.16 (d, 1H), 7.06 (m, 1H), 6.96 (s, 1H) 4.27 (s, 2H), 4.16 (m, 3 H), 3.30 (m, 2H), 3.05 (m, 2H), 2.92 (m, 2H), 2.08 (m, 1H), 1.60 (m, 1H). FAB MS, [M+H]⁺=476, 478, chlorine pattern.

EXAMPLE 41

6-Chloro-benzo[b]thiophene-2-sulfonic Acid [1-(4-Chloro-1H-pyrrolo[3,2-c]pyridin-2-ylmethyl)-2-oxopyrrolidin-3-(S)-yl]-amide A. 1-Benzenesulfonyl-4-chloro-1H-pyrrolo[3,2-c]pyridine.

Benzenesulfonyl chloride (3 mL, 23.5 mmol) is added dropwise to a solution of tetrabutylammonium hydrogen sulfate (.0.53 g, 1.56 mmol), sodium hydroxide (1.56 g, 38.9 mmol) and 4-chloro-1H-pyrrolo[3,2-c]pyridine (2.38 g, 15.6 mmol) (prepared according to Rasmussen. M. *J. Het. Chem*, 1992, 29, 359) in CH₂Cl₂. The mixture is stirred at room temperature for 4 hours the diluted with CH₂Cl₂ and washed with saturated NH₄Cl solution and brine. The organic layer is dried over MgSO₄, filtered and concentrated. The crude product is purified by column chromatography eluting with 1% MeOH/CH₂Cl₂ to 2% MeOH/CH₂Cl₂ to afford the title product (3.21 g, 11 mmol) as a white solid.

¹H NMR (CDCl₃, 300 MHz) δ 8.25 (d, 1H), 7.92 (m, 1H), 7.90 (d, 1H), 7.83 (dd, 1H), 7.60–7.66 (m, 2H), 7.51 (m, 2H), 6.80 (dd, 1H). EI MS, [M]⁺=292, 294, Cl pattern.

B. 1-Benzenesulfonyl-4-chloro-1H-pyrrolo[3,2-c]pyridine-2-carboxylic Acid Ethyl Ester.

Lithium diisopropylamide (3.2 ml. of a 1.5 M solution in THF, 4.80 mmol) is added to a solution of tetramethylethylenediamimine (0.71 mL, 4.75 mmol) and 1-benzenesulfonyl-4-chloro-1H-pyrrolo[3,2-c]pyridine (1 g, 3.42 mmol) in THF (13 mL). The resulting yellow solution is stirred at −78° C. for 1 hour, and then ethyl chloroformate (0.78 mL, 8.16 mmol) is added dropwise. The mixture is slowly brought to room temperature over a 3.5 hour period. The reaction is quenched with saturated NH₄Cl solution and then diluted with ethyl acetate. The organic layer is washed with brine, dried over MgSO₄, filtered and concentrated to give a light brown solid (1.46 g) as the product which is used in the subsequent step without further purification.

¹H NMR (CDCl₃, 300 MHz) δ 8.30 (d, 1H), 8.12 (d, 2H), 8.03 (d, 1H), 7.70 (m, 1H), 7.55 (m, 2H), 7.30 (s, 1H), 4.45 (q, 2H), 1.46 (t, 3H). FAB MS, [M+H]⁺=365, 367, Cl pattern.

C. 1-Benzenesulfonyl-4-chloro-1H-pyrrolo[3,2-c]pyridin-2-yl)-methanol.

Lithium aluminum hydride (3.4 mL of a 1 M solution in THF) is added dropwise to a solution of the 1-benzenesulfonyl-4-chloro-1H-pyrrolo[3,2-c]pyridine-2-carboxylic acid ethyl ester (1.46 g, 3.42 mmol) in THF (27 mL) at 0° C. After stirring for 1.5 hours at 0° C., the reaction is quenched with H₂O then diluted with ethyl acetate. The organic layer is washed with saturated NH₄Cl solution and brine then dried over MgSO₄, filtered and concentrated. The crude product is purified by column chromatography eluting with a gradient of 1% MeOH/CH₂Cl₂ to 3% MeOH/CH₂Cl₂ to afford the title product (0.78 g, 2.42 mmol) as a white solid.

¹H NMR (CDCl₃, 300 MHz) δ 8.25 (d, 1H), 8.85–8.95 (m, 3H), 7.64 (m, 1H), 7.51 (m, 2H), 6.80 (s, 1H), 4.97 (d, 2H), 2.85 (t, 1H). EI MS, [M]⁺=322, 324, Cl pattern.

D. 1-Benzenesulfonyl-2-bromomethyl-4-chloro-1H-pyrrolo[3,2-c]pyridine.

Carbon tetrabromide (0.939 g, 2.83 mmol) is added to a solution of triphenylphosphine (1.485 g, 5.66 mmol) and 1-benzenesulfonyl-4-chloro-1H-pyrrolo[3,2-c]pyridin-2-yl)-methanol (0.914 g, 2.83 mmol) in CH₂Cl₂ (12 mL) at 0° C. The resulting yellow solution is stirred for 1 hour at 0° C. then warmed to room temperature over a 1 hour period. The reaction mixture is concentrated then purified by column chromatography eluting with 1% MeOH/CH₂Cl₂ to afford the title product (0.760 g, 1.97 mmol) as a white solid.

¹H NMR (CDCl₃, 300 MHz) δ 8.27 (d, 1H), 7.91–8.00 (m, 3H), 7.67 (m, 1H), 7.51 (m, 2H), 6.95 (s, 1H), 4.94 (s, 2H). FAB MS, [M+H]³⁰ =385, 387, 389, Br, Cl pattern.

E. [1-(1-Benzenesulfonyl-4-chloro-1H-pyrrolo[3,2-c]pyridin-2-ylmethyl)-2-oxopyrrolid-3-(S)-yl]-carbamic Acid tert-Butyl Ester.

Sodium hydride (0.081 g, 2.02 mmol, 60% mineral oil dispersion) is added to a solution of [2-oxopyrrolidin-3-(S)-yl]-carbamic acid tert-butyl ester (0.404 g, 2.02 mmol) in DMF (5 mL) at 0° C. The mixture is stirred for 10 minutes, then cannulated dropwise to a solution of 1-benzenesulfonyl-2-bromomethyl-4-chloro-1H-pyrrolo[3,2-c]pyridine (0.74 g, 1.92 mmol) in DMF (10 mL) at 0° C. The resulting yellow solution is stirred for 1 hour at 0° C. then quenched with saturated ammonium chloride solution and diluted with EtOAc. The organic layer is washed with water and brine, then dried over MgSO₄, filtered and concentrated. The solid product (0.94 g, 1.86 mmol) is used in the subsequent step without further purification.

¹H NMR (CDCl₃, 300 MHz) δ 8.25 (d, 1H), 7.98 (m, 2H), 7.83 (d, 1H), 7.68 (m, 1H), 7.50 (m, 2H), 6.70 (s, 1H), 4.95 (AB, 2H), 4.20 (m, 1H), 3.55 (m, 2H), 2.65 (m, 1H), 2.03 (m, 1H), 1.45 (s, 9H). FAB MS, [M+H]⁺=505, 507, Cl pattern.

F. 3-(S)-Amino-1-(1-benzenesulfonyl-4-chloro-1H-pyrrolo [3,2-c]pyridin-2-ylmethyl)-pyrrolidin-2-one Hydrochloride.

The title compound is prepared as described in EXAMPLE 1, Part I using [1-(1-benzenesulfonyl-4-chloro-1H-pyrrolo[3,2-c]pyridin-2-ylmethyl)-2-oxopyrrolid-3-(S)-yl]-carbamic acid tert-butyl ester in place of [1-(1-chloroisoquinolin-7-ylmethyl)-2-oxopyrrolidin-3(S)-yl]-carbamic acid tert-butyl ester and stirring for 2 hours at 0° C. without warming to room temperature.

$^1$H NMR (CDCl$_3$, 300 MHz) δ 8.50 (d, 1H), 8.28 (d, 1H), 8.04 (m, 2H), 7.82 (m, 1H), 7.65 (m, 2H), 6.83 (s, 1H), 4.93 (s, 2H), 4.20 (m, 1H), 3.51 (m, 2H), 2.41 (m, 1H), 2.01 (m, 1H). FAB MS, [M+H]$^+$=405, 407, Cl pattern.

G. 6-Chloro-benzo[b]thiophene-2-sulfonic Acid [1-(1-Benzenesulfonyl-4-chloro-1H-pyrrolo[3,2-c]pyridin-2-ylmethyl)-2-oxopyrrolidin-3-(S)-yl]-amide.

The title compound is prepared as described in EXAMPLE 1, Part K using 6-chloro-benzo[b]thiophene-2-sulfonyl chloride and 3-amino-1-(1-benzenesulfonyl-4-chloro-1H-pyrrolo[3,2-c]pyridin-2-ylmethyl)-pyrrolidin-2-one hydrochloride as the starting material. The crude product is purified by column chromatography eluting with a gradient of 1% MeOH/CH$_2$Cl$_2$ to 3% MeOH/CH$_2$Cl$_2$ to give the product as a white solid.

$^1$H NMR (CDCl$_3$, 300 MHz) δ 8.23 (d, 1H), 7.96 (d, 1H), 7.90 (s, 1H), 7.70–7.88 (m, 3H), 7.55–7.61 (m, 2H), 7.40–7.50 (m, 3H), 6.51 (s, 1H), 5.45 (bs, 1H), 4.86 (s, 2H), 3.98 (m, 1H), 3.41 (m, 2H), 2.70 (m, 1H), 2.18 (m, 1H). FAB MS, [M+H]$^+$=635, 637, Cl pattern.

H. 6-Chloro-benzo[b]thiophene-2-sulfonic Acid [1-(4-Chloro-1H-pyrrolo[3,2-c]pyridin-2-ylmethyl)-2-oxopyrrolidin-3-(S)-yl]-amide.

Ammonia gas is bubbled for 5 minutes into a solution of 6-chloro-benzo[b]thiophene-2-sulfonic acid[1-(1-benzenesulfonyl-4-chloro-1H-pyrrolo[3,2-c]pyridin-2-ylmethyl)-2-oxopyrrolidin-3-(S)-yl]-amide (0.14 g, 0.22 mmol) in MeOH (10 mL). The solution is refluxed overnight then concentrated to dryness. The crude product is purified by column chromatography eluting with 5% MeOH/CH$_2$Cl$_2$ to give the product (0.065 g, 0.13 mmol) as a white solid.

$^1$H NMR (DMSO-d$_6$, 300 MHz) δ 11.95 (bs, 1H), 8.71 (d, 1H), 8.30 (s, 1H), 8.05 (m, 1H), 7.91 (d, 1H), 7.50 (d, 1H), 7.35 (d, 1H), 6.40 (s, 1H), 4.50 (AB, 2H), 4.23 (m, 1H), 3.23m, 2H), 2.41 (M, 1H), 1.78 (m, 1H). Ion spray MS, [M+H]$^{30}$ =495, 497, Cl pattern.

EXAMPLE 42

6-Chloro-benzo[b]thiophene-2-sulfonic Acid [2-oxo-1-(1H-Pyrrolo[3,2-c]pyridin-2-ylmethyl)-pyrrolidin-3-(S)-yl]-amide Palladium on carbon (0.01 g) is added to a solution of 6-chloro-benzo[b]thiophene-2-sulfonic acid [1-(4-chloro-1H-pyrrolo[3,2-c]pyridin-2-ylmethyl)-2-oxopyrrolidin-3-(S)-yl]-amide in 95% ethanol (5 mL) and charged with H$_2$ gas. The mixture is heated at 65° C. overnight then cooled to room temperature and filtered through Celite. The solvent is removed and the crude product is purified by RP-HPLC eluting with a gradient of 10% CH$_3$CN/H$_2$O (0.1% TFA) to 100% CH$_3$CN. The appropriate product fractions are lyophilized to give the title compound as a white solid.

$^1$H NMR (DMSO-d$_6$, 300 MHz) δ 14.60 (bs, 1H), 12.70 (bs, 1H), 9.15 (s, 1H), 8.71 (d, 1H), 8.38 (d, 1H), 8.29 (s, 1H), 8.08 (s, 1H), 8.00 (d, 1H), 7.85 (d, 1H), 7.52 (dd, 1H), 6.88 (s, 1H), 4.63 (AB, 2H), 4.21 (m, 1H), 3.25 (m, 2H), 2.10 (m, 1H), 1.75 (m, 1H). Ion spray MS, [M+H]$^+$=461, 463. Cl pattern.

EXAMPLE 43

7-Methoxynaphthalene-2-sulfonic Acid [2-oxo-1-(1H-Pyrrolo[3,2-b]pyridin-2-ylmethyl)-pyrrolidin-3-(S)-yl]-amide Trifluoroacetate A. 5-Chloro-1H-pyrrolo[3,2-b]pyridine.

A mixture of pyrrolo[3,2-b]pyrid-5-one (prepared according to the procedure described in *J. Med. Chem.* 1990, 33, 2087) (1.33 g, 9.91 mmol) and 20 mL of phosphorous oxychloride is heated in a sealed Parr high pressure stainless steel vessel at 180° C. for 2.5 hours. After cooling, excess phosphorous oxychloride is removed in vacuo. The residue is cooled in an ice bath and quenched with ice water. The resulting mixture is neutralized by addition of saturated NaHCO$_3$ solution and extracted with EtOAc (3x). The combined organic layers are dried over MgSO$_4$, filtered and concentrated in vacuo. The crude product (1.07 g, 7.01 mmol) is used in the subsequent step without further purification.

$^1$H NMR (CDCl$_3$+CD$_3$OD, 300 MHz) δ 7.71 (d, 1H), 7.49 (d, 1H), 7.10 (d, 1H), 6.59 (d, 1H). EI MS, [M]$^+$=152, 154, Cl pattern.

B. 1-Benzenesulfonyl-5-chloro-1H-pyrrolo[3,2-b]pyridine.

The title compound is prepared from 5-chloro-1H-pyrrolo [3,2-b]pyridine as described in EXAMPLE 41, Part A. The crude product is purified by column chromatography eluting with a gradient of 10% EtOAc/hexanes to 20% EtOAc/hexanes to give the title compound as a solid.

$^1$H NMR (CDCl$_3$, 300 MHz) δ 8.23 (d, 1H), 7.87 (d, 2H), 7.81 (d, 1H), 7.62 (m, 1H), 7.49 (m, 2H), 7.26 (d, 1H), 6.81 (d, 1H).

C. 1-Benzenesulfonyl-5-chloro-1H-pyrrolo[3,2-b]pyridine-2-carboxylic Acid Ethyl Ester.

The title compound is prepared from 1-benzenesulfonyl-5-chloro-1H-pyrrolo[3,2-b]pyridine as described in EXAMPLE 41, Part B. The crude product is purified by column chromatography eluting with a gradient of 10% EtOAc/hexanes to 33% EtOAc/hexanes to yield the title compound as a solid.

$^1$H NMR (CDCl$_3$, 300 MHz) δ 8.41 (d, 1H), 8.04 (d, 2H), 7.66 (m, 1H), 7.55 (m, 2H), 7.37 (d, 1H), 7.21 (s, 1H), 4.41 (q, 2H), 1.40 (t, 3H). EI MS, [M]$^+$=364 366, Cl pattern.

D. (1-Benzenesulfonyl-5-chloro-1H-pyrrolo[3,2-b]pyridin-2-yl)-methanol.

The title compound is prepared from 1-benzenesulfonyl-5-chloro-1H-pyrrolo[3,2-b]pyridine-2-carboxylic acid ethyl ester as described in EXAMPLE 41, Part C. The crude product is purified by column chromatography eluting with a gradient of 20% EtOAc/hexanes to 50% EtOAc/hexanes to afford the title compound as a solid.

$^1$H NMR (CDCl$_3$, 300 MHz) δ 8.30 (d, 1H), 7.81 (d, 2H), 7.63 (m, 1H), 7.50 (m, 2H), 7.25 (d, 1H), 6.80 (s, 1H), 4.97 (s, 2H), 2.99 (bs, 1H). EI MS, [M]$^+$=322, 324, Cl pattern.

E. 1-Benzenesulfonyl-2-bromomethyl-5-chloro-1H-pyrrolo[3,2-b]pyridine.

To a solution of (1-benzenesulfonyl-5-chloro-1H-pyrrolo [3,2-b]pyridin-2-yl)-methanol (0.16 g, 0.50 mmol) in 4 mL, Et$_2$O/CH$_2$Cl$_2$ (1:1) at 0° C. is added phosphorous tribromide (0.023 mL, 0.25 mmol) dropwise. The reaction vessel is kept in the dark and stirred at 0° C. for 1 hour, then at room temperature for 2 hours. The mixture is diluted with water and EtOAc and the layers are separated. The aqueous layer is extracted with EtOAc. The combined organic layers are washed with water, saturated NaHCO$_3$ solution and saturated NaCl solution, then dried over MgSO$_4$, filtered and concentrated. The crude product (0.16 g, 0.41 mmol) is used in the subsequent step without further purification.

$^1$H NMR (CDCl$_3$, 300 MHz) δ 8.33 (d, 1H), 7.87 (d, 2H), 7.64 (m, 1H), 7.50 (m, 2H), 7.28 (d, 1H), 6.93 (s, 1H), 4.96 (s, 2H).

F. [1-(1-Benzenesulfonyl-5-chloro-1H-pyrrolo[3,2-b]pyridin-2-ylmethyl)-2-oxopyrrolidin-3-(S)-yl]-carbamic Acid tert-Butyl Ester.

The title compound is prepared from (2-oxopyrrolidin-3-(S)-yl)-carbamic acid tert-butyl ester as described in EXAMPLE 1, Part H using 1-benzenesulfonyl-2-bromomethyl-5-chloro-1H-pyrrolo[3,2-b]pyridine in place of 7-bromomethyl-1-chloro-isoquinolin. The crude product is purified by column chromatography eluting with a gradient of 15% EtOAc/hexanes to 50% EtOAc/hexanes to give the title compound as a beige solid.

$^1$H NMR (CDCl$_3$, 300 MHz) δ 8.36 (d, 1H), 7.80 (d, 2H), 7.64 (m, 1H), 7.50 (m, 2H), 7.25 (s, 1H), 6.58 (s, 1H), 5.13 (bs, 1H), 4.93 (AB, 2H), 4.22 (m, 1H), 3.39 (m, 2H), 2.66 (m, 1H), 1.95 (m, 1H), 1.46 (s, 9H).

G. 3-(S)-Amino-1-(1-benzenesulfonyl-5-chloro-1H-pyrrolo[3,2-b]pyridin-2-ylmethyl)-pyrrolidin-2-one Hydrochloride.

The title compound is prepared as described in EXAMPLE 1, Part I using [1-(1-benzenesulfonyl-5-chloro-1H-pyrrolo[3,2-b]pyridin-2-ylmethyl)-2-oxopyrrolidin-3-(S)-yl]-carbamic acid tert-butyl ester as the starting material. The title compound is obtained as a white solid. $^1$H NMR (DMSO-d$_6$, 300 MHz) δ 8.51 (bs, 2H), 8.42 (d, 1H), 8.00 (d, 2H), 7.78 (m, 1H), 7.64 (m, 2H), 7.41 (d, 1H), 6.96 (s, 1H), 4.90 (AB, 2H), 4.16 (m, 1H), 3.49 (m, 2H), 2.47 (m, 1H), 2.10 (m, 1H).

H. 7-Methoxynaphthalene-2-sulfonic Acid [1-(1-Benzenesulfonyl-5-chloro-1H-pyrrolo[3,2-b]pyridin-2-ylmethyl)-2-oxopyrrolidin-3-(S)-yl]-amide.

The title compound is prepared as described in EXAMPLE 1, Part K using 7-methoxynaphthalene-2-sulfonyl chloride and 3-(S)-amino-1-(1-benzenesulfonyl-5-chloro-1H-pyrrolo[3,2-b]pyridin-2-ylmethyl)-pyrrolidin-2-one hydrochloride as starting material. The crude product is used in the subsequent step without further purification.

$^1$H NMR (CDCl$_3$, 300 MHz) δ 8.37 (s, 1H), 8.34 (d, 1H), 7.92 (d, 1H), 7.79 (m, 2H), 7.72 (m, 2H), 7.58 (m, 1H), 7.45 (m, 2H), 7.31 (dd, 1H), 7.24 (m, 2H), 6.48 (s, 1H), 5.42 (s, 1H), 4.85 (s, 2H), 3.96 (s, 3H), 3.76 (m, 1H), 3.34 (m, 2H), 2.63 (m, 1H), 2.10 (m, 1H).

I. 7-Methoxynaphthalene-2-sulfonic Acid [1-(5-Chloro-1H-pyrrolo[3,2-b]pyridin-2-ylmethyl)-2-oxopyrrolidin-3-(S)-yl]-amide.

The title compound is prepared from 7-methoxynaphthalene-2-sulfonic acid [1-(1-benzenesulfonyl-5-chloro-1H-pyrrolo[3,2-b]pyridin-2-ylmethyl)-2-oxopyrrolidin-3-(S)-yl]-amide as described in EXAMPLE 41, Part H. The crude product is purified by column chromatography eluting with a gradient of 1% MeOH/CH$_2$Cl$_2$ to 6% MeOH/CH$_2$Cl$_2$ to yield the title compound as a solid.

$^1$H NMR (CDCl$_3$, 300 MHz) δ 9.73 (bs, 1H), 8.35 (s, 1H), 7.70 (m, 3H), 7.49 (d, 1H), 7.30 (dd, 1H), 7.20 (m, 1H), 6.99 (d, 1H), 6.75 (bs, 1H), 6.48 (s, 1H), 4.58 (m, 2H), 3.93 (m, 1H), 3.90 (s, 3H), 3.35 (m, 2H), 2.48 (m, 2H), 2.08 (m, 1H).

J. 7-Methoxynaphthalene-2-sulfonic Acid [2-oxo-1-(1H-Pyrrolo[3,2-b]pyridin-2-ylmethyl)-pyrrolidin-3-(S)-yl]-amide Trifluoroacetate.

The title compound is prepared from 7-methoxynaphthalene-2-sulfonic acid [1-(5-chloro-1H-pyrrolo[3,2-b]pyridin-2-ylmethyl)-2-oxopyrrolidin-3-(S)-yl]-amide as described in EXAMPLE 42 at room temperature using a catalytic amount of KOH in MeOH/benzene (1:1) instead of EtOH solvent. The crude product is purified by RP-HPLC eluting in a gradient of 10% CH$_3$CN/H$_2$O (0.1% TFA) to 70% CH$_3$CN/H$_2$O (0.1% TFA) and the appropriate product fractions are lyophilized to provide the title compound as a white solid.

$^1$H NMR (DMSO-d$_6$, 300 MHz) δ 12.65 (bs, 1H), 8.60 (bs, 1H), 8.43 (d, 1H), 8.39 (s, 1H), 8.26 (d, 1H), 8.03 (d, 1H), 7.94 (d, 1H), 7.71 (dd, 1H), 7.56 (m, 2H), 7.32 (dd, 1H), 6.80 (s, 1H), 4.66 (AB, 2H), 4.17 (m, 1H), 3.88 (s, 3H), 3.20 (m, 2H), 2.00 (m, 1H), 1.60 (m, 1H). FAB MS, [M+H]$^+$=451.

EXAMPLE 44

6-Chloro-benzo[b]thiophene-2-sulfonic Acid (1-Furo[3,2-b]pyridin-2-ylmethyl-2-oxopyrrolidin-3-(S)-yl)-amide A. (2-Oxo-1-prop-2-ynyl-pyrrolidin-3-(S)-yl)-carbamic Acid tert-Butyl Ester.

The title compound is prepared from (2-oxopyrrolidin-3-(S)-yl)-carbamic acid tert-butyl ester as described in EXAMPLE 1, Part H using propargyl bromide in place of 7-bromomethyl-1-chloro-isoquinoline. The crude product is triturated from Et$_2$O/hexanes to give the title compound as a white solid.

$^1$H NMR (CDCl$_3$, 300 MHz) δ 5.09 (bs, 1H), 4.19 (m, 1H), 4.15 (m, 2H), 3.45 (m, 2H), 2.69 (m, 1H), 2.29 (t, 1H), 1.91 (m, 1H), 1.48 (s, 9H).

B. (1-Furo[3,2-b]pyridin-2-ylmethyl-2-oxopyrrolidin-3-(S)-yl)-carbamic Acid tert-Butyl Ester.

A mixture of 2-iodo-3-hydroxy-pyridine (0.44 g, 2 mmol), (2-oxo-1-prop-2-ynyl-pyrrolidin-3-(S)-yl)-carbamic acid tert-butyl ester (0.6 g, 2.5 mmol), bis(triphenylphosphine)-palladium(II) chloride (Pd(PPh$_3$)$_2$Cl$_2$) (50 mg), copper iodide (25 mg) and triethylamine (3 mL) in 3 mL of acetonitrile is heated in a sealed tube at 120° C. for 2 hours. After cooling, the reaction mixture is diluted with water and EtOAc and the layers are separated. The aqueous layer is extracted with EtOAc. The combined organic layers are washed with water and saturated NaCl solution, then dried over MgSO$_4$, filtered and concentrated. The crude product is purified by column chromatography eluting with a gradient of 25% EtOAc/CH$_2$Cl$_2$ to 90% EtOAc/CH$_2$Cl$_2$ to yield the title compound as a white solid.

$^1$H NMR (CDCl$_3$, 300 MHz) δ 8.53 (d, 1H), 7.72 (dd, 1H), 7.21 (dd, 1H), 6.86 (s, 1H), 5.15 (bs, 1H), 4.69 (AB, 2H), 4.23 (m, 1H), 3.38 (m, 2H), 2.66 (m, 1H), 1.91 (m, 1H), 1.45 (s, 9H).

C. 3-(S)-Amino-1-(furo[3,2-b]pyridin-2-ylmethyl)-pyrrolidin-2-one Hydrochloide.

The title compound is prepared as described in EXAMPLE 1, Part I using (1-furo[3,2-b]pyridin-2-ylmethyl-2-oxopyrrolidin-3-(S)-yl)-carbamic acid tert-butyl ester as the starting material. The title compound is obtained as a tan solid.

$^1$H NMR (DMSO-d$_6$, 300 MHz) δ 8.70 (bs, 2H), 8.65 (d, 1H), 8.35 (d, 1H), 7.58 (dd, 1H), 7.28 (s, 1H), 4.77 (s, 2H), 4.10 (m, 1H), 3.47 (m, 2H), 2.41 (m, 1H), 2.09 (m, 1H).

D. 6-Chloro-benzo[b]thiophene-2-sulfonic Acid (1-Furo[3,2-b]pyridin-2-ylmethyl-2-oxopyrrolidin-3-(S)-yl)-amide.

The title compound is prepared as described in EXAMPLE 1, Part K using 6-chloro-benzo[b]thiophene-2-sulfonyl chloride and 3-(S)-amino-1-(furo[3,2-b]pyridin-2-ylmethyl)-pyrrolidin-2-one hydrochloride as starting material. The crude product is purified by column chromatography eluting with a gradient of 25% EtOAc/CH$_2$Cl$_2$ to 90% EtOAc/CH$_2$Cl$_2$ to provide the title compound as a white solid.

$^1$H NMR (CDCl$_3$+CD$_3$OD, 300 MHz) δ 8.49 (bs, 1H), 7.92 (s, 1H), 7.85 (s, 1H), 7.81 (d, 1H), 7.77 (d, 1H), 7.41 (dd, 1H), 7.24 (m, 1H), 6.85 (s, 1H), 4.63 (AB, 2H), 4.03 (m, 1H), 3.41 (m, 2H), 2.63 (m, 1H), 2.16 (m, 1H). FAB MS, [M+H]$^+$=462, 464, Cl pattern.

EXAMPLE 45

6-Chloro-benzo[b]thiophene-2-sulfonic Acid (1-Furo[3,2-b]pyridin-2-ylmethyl-2-oxopyrrolidin-3-(S)-yl)-amide A. 1-Fluoro-3-(2,2-dimethoxy-ethyl1-sulfanyl)-benzene.

The title compound is prepared as described in EXAMPLE 9, Part A substituting 3-fluorothiophenol for 3-chlorothiophenol. The crude product is purified by column chromatography eluting with a gradient of hexanes to 10% EtOAc/hexanes to afford the title compound as an oil.

$^1$H NMR (CDCl$_3$, 300 MHz) δ 7.21 (m, 1H), 7.09 (m, 2H), 6.82 (m, 2H), 4.51 (m, 1H), 3.09 (s, 3H), 3.07 (s, 3H).

B. 6-Fluoro-benzo[b]thiophene.

The title compound is prepared as described in EXAMPLE 9, Part B substituting 1-fluoro-3-(2,2-dimethoxy-ethyl-sulfanyl)-benzene for 1-chloro-3-(2,2-dimethoxy-ethyl-sulfanyl)-benzene. The crude product is purified by column chromatography eluting with hexanes to afford the title compound as a white solid. EI MS, [M]$^+$=152.

C. 6-Fluoro-benzo[b]thiophene-2-sulfonyl Chloride.

The title compound is prepared as described in EXAMPLE 8, Part A substituting 6-fluoro-benzo[b]thiophene for thianaphthalene. The crude product is purified by column chromatography eluting with hexanes to yield the title compound as a white solid.

$^1$H NMR (CDCl$_3$, 300 MHz) δ 8.08 (s, 1H), 7.94 (dd, 1H), 7.58 (dd, 1H), 7.23 (dt, 1H).

D. 6-Fluoro-benzo[b]thiophene-2-sulfonic Acid (1-Furo[3,2-b]pyridin-2-ylmethyl-2-oxopyrrolidin-3-(S)-yl)-amide.

The title compound is prepared as described in EXAMPLE 1, Part K using 6-fluoro-benzo[b]thiophene-2-sulfonyl chloride and 3-(S)-amino-1-(furo[3,2-b]pyridin-2-ylmethyl)-pyrrolidin-2-one hydrochloride as starting material. The crude product is purified by column chromatography eluting with 66% EtOAc/CH$_2$Cl$_2$ to provide the title compound as a white solid.

$^1$H NMR (CDCl$_3$, 300 MHz) δ 8.46 (m, 1H), 7.96 (s, 1H), 7.91 (m, 1H), 7.77 (d, 1H), 7.58 (d, 1H), 7.44 (s, 1H), 7.29 (m, 2H), 6.86 (s, 1H), 4.65 (s, 2H), 4.14 (m, 1H), 3.42 (m, 2H), 2.58 (m, 1H), 2.09 (m, 1H). FAB MS, [M+H]$^+$=446.

EXAMPLE 46

6-Chloro-benzo[b]thiophene-2-sulfonic Acid [2-oxo-1-(1H-Pyrrolo[3,2-b]pyridin-2-ylmethyl)-pyrrolidin-3-(S)-yl]-amide Trifluoroacetate A. 2-Iodo-3-nitro-pyridine.

To a solution of 2-amino-3-nitro-pyridine (8 g, 57.5 mmol) in 60 mL of 6 N HCl cooled to 0° C. is added dropwise a solution of sodium nitrite (6.35 g, 92 mmol) in 40 mL of water. The mixture is stirred at 0° C. for 1.5 hours. Then a solution of potassium iodide (22.9 g, 138 mmol) in 40 mL of water is added dropwise to the yellow solution. The resulting red mixture is stirred at 0° C. for 30 minutes and then heated at 60° C. for 45 minutes. After cooling, the mixture is made basic by the careful addition of 3 N NaOH. The aqueous layer is extracted with CH$_2$Cl$_2$(4×) and the combined organic layers are washed with 1 N HCl, dilute Na$_2$SO$_3$ and water. The organic layer is dried over MgSO$_4$, filtered and concentrated in vacuo. The crude product (2.72 g, 10.9 mmol) is used in the subsequent step without further purification.

$^1$H NMR (CDCl$_3$, 300 MHz) δ 8.65 (d, 1H), 8.25 (dd, 1H), 7.48 (m, 1H). IS MS, [M+H]$^+$=251.

B. 3-Amino-2-iodo-pyridine.

To a solution of 2-iodo-3-nitro-pyridine (2.72 g, 10.9 mmol) in 10 mL of concentrated HCl is added dropwise a solution of tin(II) chloride dihydrate (10.3 g, 45.7 mmol) in 12 mL of concentrated HCl. The mixture is heated at 90° C. for 15 minutes. The resulting red mixture is cooled to 0° C. and stirred for 2 hours as a precipitate forms. The solid is filtered, dissolved in water and made basic by addition of 1N NaOH. The aqueous layer is extracted with CH$_2$Cl$_2$ (4×) and the combined organic layers are dried over MgSO$_4$, filtered and concentrated in vacuo. The crude product (1.5 g, 6.82 mmol) is used in the subsequent step without further purification.

$^1$H NMR (CDCl$_3$, 300 MHz) δ 7.81 (m, 1H), 7.07 (m, 2H), 4.05 (bs, 2H). IS MS, [M+H]$^+$=221.

C. (2-Iodo-pyridin-3-yl)-carbamic Acid Ethyl Ester.

Ethyl chloroformate (0.91 mL, 9.5 mmol) is added to a solution of 3-amino-2-iodo-pyridine (1.4 g, 6.36 mmol) in 15 mL of pyridine cooled at 0° C. The mixture is stirred at 0° C. for 2 hours and allowed to warm slowly to room temperature. At this time, excess pyridine is removed in vacuo. The residue is diluted with EtOAc and washed with water, 1N HCl and saturated NaHCO$_3$. The organic layer is dried over MgSO$_4$, filtered and concentrated in vacuo. The crude product is purified by column chromatography eluting with 30% EtOAc/hexanes to give the title compound (1.2 g, 4.11 mmol) as a beige solid.

$^1$H NMR (CDCl$_3$, 300 MHz) δ 8.51 (d, 1H), 8.07 (dd, 1H), 7.25 (dd, 1H), 7.16 (bs, 1H), 4.28 (q, 2H), 1.38 (t, 3H).

D. 2-(3-(S)-tert-Butoxycarbonylamino-2-oxopyrrolidin-1-ylmethyl)-pyrrolo[3,2-b]pyridine-1-carboxylic Acid Ethyl Ester.

A mixture of (2-iodo-pyridin-3-yl)-carbamic acid ethyl ester (0.6 g, 2.05 mmol), (2-oxo-1-prop-2-ynyl-pyrrolidin-3-(S)-yl)-carbamic acid tert-butyl ester (0.49 g, 2.05 mmol), Pd(PPh$_3$)$_2$Cl$_2$ (72 mg), copper iodide (12 mg) and triethylamine (1.1 mL) in 4 mL of acetonitrile is heated in a sealed tube at 100° C. for 18 hours. After cooling, the reaction mixture is diluted with MeOH and filtered through a Celite pad. The filtrate is concentrated in cacuo. The residue is diluted with EtOAc and washed with water (4×). The combined aqueous layers are extracted with EtOAc (2×). The combined organic layers are washed with water, then dried over MgSO$_4$, filtered and concentrated to yield the crude intermediate coupled acetylene. IS MS, [M+H]$^+$=403. The crude acetylene intermediate is dissolved in 16 mL of DMF and treated with 1,8-diaza-bicyclo[5.4.0]undec-7ene (DBU) (0.58 mL, 4.1 mmol). The mixture is heated at 60° C. for 2 hours. After cooling, the resulting mixture is diluted with water and EtOAc and the layers are separated. The organic layer is washed with water and then dried over MgSO$_4$, filtered and concentrated. The crude product is purified by column chromatography eluting with 90% EtOAc/CH$_2$Cl$_2$ to yield the title compound (0.07 g, 0.22 mmol) as a beige solid.

$^1$H NMR (CDCl$_3$, 300 MHz) δ 8.51 (d, 1H), 8.35 (d, 1H), 7.21 (dd, 1H), 6.60 (s, 1H), 5.34 (bs, 1H), 4.95 (AB, 2H), 4.55 (q, 2H), 4.30 (m, 1H), 3.48 (m, 2H), 2.70 (m, 1H), 2.05 (m, 1H), 1.50 (t, 3H), 1.46 (s, 9H). IS MS, [M+H]$^+$=403.

E. 2-(3-(S)-Amino-2-oxopyrrolidin-1-ylmethyl)-pyrrolo[3,2-b]pyridine-1-carboxylic Acid Ethyl Ester Hydrochloride.

The title compound is prepared as described in EXAMPLE 1, Part I using 2-(3-(S)-tert-butoxycarbonylamino-2-oxopyrrolidin-1-ylmethyl)-pyrrolo[3,2-b]pyridine-1-carboxylic acid ethyl ester as the starting material. The title compound is obtained as a beige solid.

$^1$H NMR (DMSO-d$_6$, 300 MHz) δ 8.70 (m, 1H), 8.58 (m, 4H), 7.50 (m, 1H), 6.91 (s, 1H), 4.91 (m, 2H), 4.51 (q, 2H), 4.01 (m, 1H), 3.50 (m, 2H), 2.48 (m, 1H), 2.10 (m, 1H), 1.43 (t, 3H).

F. 2-[3-(S)-(6-Chloro-benzo[b]thiophene-2-sulfonylamino)-2-oxopyrrolidin-1-ylmethyl]-pyrrolo[3,2-b]pyridine-1-carboxylic Acid Ethyl Ester.

The title compound is prepared as described in EXAMPLE 1, Part K using 6-chloro-benzo[b]thiophene-2-sulfonyl chloride and 2-(3-(S)-amino-2-oxopyrrolidin-1-ylmethyl)-pyrrolo[3,2-b]pyridine-1-carboxylic acid ethyl ester hydrochloride as starting material. The crude product is purified by column chromatography eluting with 60% EtOAc/CH$_2$Cl$_2$ to provide the title compound as a solid.

$^1$H NMR (CDCl$_3$, 300 MHz) δ 8.49 (d, 1H), 8.30 (d, 1H), 7.90 (s, 1H), 7.78 (s, 1H), 7.75 (d, 1H), 7.48 (dd, 1H), 7.20 (dd, 1H), 6.88 (bs, 1H), 6.49 (s, 1H), 4.81 (AB, 2H), 4.49 (q, 2H), 4.13 (m, 1H), 3.39 (m, 2H), 2.61 (m, 1H), 2.13 (m, 1H), 1.45 (t, 3H).

G. 6-Chloro-benzo[b]thiophene-2-sulfonic Acid [2-oxo-1-(1H-Pyrrolo[3,2-b]pyridin-2-ylmethyl)-pyrrolidin-3-(S)-yl]-amide Trifluoroacetate.

To a solution of 2-[3-(S)-(6-chloro-benzo[b]thiophene-2-sulfonylamino)-2-oxopyrrolidin-1-ylmethyl]-pyrrolo[3,2-b]pyridine-1-carboxylic acid ethyl ester (0.03 g, 0.06 mmol) in 3 mL of MeOH is added 4 drops of 10 N NaOH solution. The mixture is stirred at room temperature for 1 hour. The crude mixture is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound (0.015 g, 0.026 mmol) as a white solid.

$^1$H NMR (DMSO-d$_6$, 300 MHz) δ 8.72 (d, 1H), 8.58 (bs, 1H), 8.41 (d, 1H), 8.27 (d, 1H), 8.05 (s, 1H), 8.02 (d, 1H), 7.55 (m, 2H), 6.69 (bs, 1H), 4.68 (AB, 2H), 4.25 (m, 1H), 3.30 (m, 2H), 2.20 (m, 1H), 1.73 (m, 1H). IS MS, [M+H]$^+$=461, 463, Cl pattern. Elemental analysis calculated with 1.6 mol H$_2$O cal. C=43.76%, H=3.54%, N=9.28%, found C=43.76%, H=2.98%, N=8.95%.

EXAMPLE 47

6-Chloro-benzo[b]thiophene-2-sulfonic Acid [2-oxo-1-(1H-pyrrolo[2,3-c]pyridin-2-ylmethyl)-pyrrolidin-3-(S)-yl]-amide Trifluoroacetate A. 3-(S)-Amino-1-prop-2-ynyl-pyrrolidin-2-one Hydrochloride.

The title compound is prepared as described in EXAMPLE 1, Part I using (2-oxo-1-prop-2-ynyl-pyrrolidin-3-(S)-yl)-carbamic acid tert-butyl ester as the starting material. The title compound is obtained as a beige solid.

$^1$H NMR (CDCl$_3$+DMSO-d$_6$, 300 MHz) δ 8.75 (bs, 3H), 4.15 (AB, 2H), 3.90 (m, 1H), 3.53 (m, 2H), 2.76 (t, 1H), 2.59 (m, 1H), 2.19 (m, 1H).

B. 6-Chloro-benzo[b]thiophene-2-sulfonic Acid (2-oxo-1-Prop-2-ynyl-pyrrolidin-3-(S)-yl)-amide.

The title compound is prepared as described in EXAMPLE 1, Part K using 6-chloro-benzo[b]thiophene-2-sulfonyl chloride and 3-(S)-amino-1-prop-2-ynyl-pyrrolidin-2-one hydrochloride as starting material. The crude product is isolated as a beige foam and used in the subsequent step without further purification.

$^1$H NMR (CDCl$_3$, 300 MHz) δ 7.90 (s, 1H), 7.85 (s, 1H), 7.80 (d, 1H), 7.41 (dd, 1H), 5.53 (bs, 1H), 4.11 (AB, 2H), 3.91 (m, 1H), 3.42 (m, 2H), 2.70 (m, 1H), 2.27 (t, 1H), 2.15 (m, 1H).

C. (4-Iodo-pyridin-3-yl)-carbamic Acid tert-Butyl Ester.

To a solution of (pyridin-3-yl)-carbamic acid tert-butyl ester (prepared according to the procedure described in *Tetrahedron Lett*. 1994, 35, 9003) (2.2 g, 11.3 mmol) in 20 mL of THF at −78° C. is added dropwise t-BuLi (15.4 mL of a 1.7 M solution in pentane, 26 mmol). After 15 minutes, the solution is warmed to −10° C. for 3 hours. The mixture is cooled to −78° C. and a solution of iodine (5.7 g, 22.4 mmol) in 20 mL of THF is added via syringe. The resulting mixture is stirred at −78° C. for 1 hour, then allowed to warm to room temperature and quenched with saturated NH$_4$Cl Solution. The aqueous layer is extracted with EtOAc (2×). The combined organic layers are washed with 1 N HCl, water, dilute Na$_2$S$_2$O$_3$, saturated NaHCO$_3$ and saturated NaCl. The organic layer is then dried over MgSO$_4$, filtered and concentrated. The crude product is purified by column chromatography eluting with a gradient of 5% EtOAc/CH$_2$Cl$_2$ to 20% EtOAc/CH$_2$Cl$_2$ to yield the title compound (1.3 g, 4.06 mmol) as a brown solid.

$^1$H NMR (CDCl$_3$, 300 MHz) δ 9.17 (s, 1H), 7.92 (d, 1H), 7.70 (d, 1H), 6.69 (bs, 1H), 1.58 (s, 9H). EI MS, [M]$^+$=320.

D. 2-[3-(S)-(6-Chloro-benzo[b]thiophene-2-sulfonylamino)-2-oxopyrrolidin-1-ylmethyl]-pyrrolo[2,3-c]pyridine-1-carboxylic Acid tert-Butyl Ester.

A mixture of (4-iodo-pyridin-3-yl)-carbamic acid tert-butyl ester (0.85 g, 2.65 mmol), 6-chloro-benzo[b]thiophene-2-sulfonic acid (2-oxo-1-prop-2-ynyl-pyrrolidin-3-(S)-yl)-amide (0.98 g, 2.65 mmol), Pd(PPh$_3$)$_2$Cl$_2$ (95 mg), copper iodide (18 mg) and triethylamine (1.45 mL) in 8 mL of DMF is heated at 100° C. for 1.5 hours. The reaction mixture is cooled to 50° C. and DBU is added. The resulting mixture is heated at 50° C. for 1.5 hours. After cooling, the crude mixture is diluted with EtOAc and washed with saturated NH$_4$Cl solution, water and saturated NaCl. The organic layer is dried over MgSO$_4$, filtered and concentrated. The crude product is purified by column chromatography eluting with a gradient of 1% MeOH/CH$_2$Cl$_2$ to 4% MeOH/CH$_2$Cl$_2$ to afford the title compound (0.73 g, 1.3 mmol) as a tan solid.

$^1$H NMR (CDCl$_3$, 300 MHz) δ 9.28 (s, 1H), 8.38 (d, 1H), 7.88 (m, 2H), 7.68 (d, 1H), 7.46 (m, 3H), 6.31 (s, 1H), 4.93 (AB, 2H), 4.00 (m, 1H), 3.49 (m, 2H), 2.76 (m, 1H), 2.26 (m, 1H), 1.60 (s, 9H). IS MS, [M]$^+$=561, 563, Cl pattern.

E. 6-Chloro-benzo[b]thiophene-2-sulfonic Acid [2-oxo-1-(1H-Pyrrolo[2,3-c]pyridin-2-ylmethyl)-pyrrolidin-3-(S)-yl]-amide Trifluoroacetate.

The title compound is prepared from 2-[3-(S)-(6-chloro-benzo[b]thiophene-2-sulfonylamino)-2-oxopyrrolidin-1-ylmethyl]-pyrrolo[23-c]pyridine-1-carboxylic acid tert-butyl ester as described in EXAMPLE 27, Part C. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ 13.07 (bs, 1H), 9.07 (s, 1H), 8.74 (d, 1H), 8.29 (s, 1H), 8.27 (d, 1H), 8.03 (m, 3H), 7.52 (dd, 1H), 6.79 (s, 1H), 4.71 (AB, 2H), 4.27 (m, 1H), 3.29 (m, 2H), 2.20 (m, 1H), 1.77 (m, 1H). FAB MS, [M+H]$^+$=461, 463, Cl pattern. Elemental analysis calculated with 0.7 mol H$_2$O cal. C=44.94%, H=3.33%, N=9.53%, found C=44.92%, H=2.91% N=8.91%.

EXAMPLE 48

Thieno[3,2-b]pyridine-2-sulfonic Acid [2-oxo-1-(1H-Pyrrolo[2,3-c]pyridin-2-ylmethyl)-pyrrolidin-3-(S)-yl]-amide Ditrifluoroacetate A. Thieno[3,2-b]pyridine-2-sulfonyl Chloride.

The title compound is prepared as described in EXAMPLE 8, Part A using thieno[3,2-b]pyridine (prepared according to the procedure described in *J. Heterocyclic Chem*. 1984, 21, 785) in place of thianaphthalene. The crude product is used in the subsequent step without further purification.

¹H NMR (CDCl₃, 300 MHz) δ 8.93 (dd, 1H), 8.39 (s, 1H), 8.38 (d, 1H), 7.59 (m, 1H). EI MS, [M]⁺=233, 235, Cl pattern.

B. Thieno[3,2-b]pyridine-2-sulfonic Acid (2-oxo-1-Prop-2-ynyl-pyrrolidin-3-(S)-yl)-amide.

The title compound is prepared as described in EXAMPLE 1, Part K using thieno[3,2-b]pyridine-2-sulfonyl chloride and 3-(S)-amino-1-prop-2-ynyl-pyrrolidin-2-one hydrochloride as starting material.

The crude product is isolated as a white solid and used in the subsequent step without further purification.

¹H NMR (CDCl₃, 300 MHz) δ 8.81 (d, 1H), 8.22 (d, 1H), 8.13 (s, 1H), 7.41 (m, 1H), 6.05 (bs, 1H), 4.10 (AB, 2H), 3.98 (m, 1H), 3.48 (m, 2H), 2.70 (m, 1H), 2.27 (t, 1H), 2.17 (m, 1H).

C. Thieno[3,2-b]pyridine-2-sulfonic Acid [2-oxo-1-(1H-pyrrolo[2,3-c]pyridin-2-ylmethyl)-pyrrolidin-3-(S)-yl]-amide Ditrifluoroacetate.

The title compound is prepared from thieno[3,2-b]pyridine-2-sulfonic acid (2-oxo-1-prop-2-ynyl-pyrrolidin-3-(S)-yl)-amide as described in EXAMPLE 47, Part D. The crude mixture is diluted with EtOAc and washed with saturated NH₄Cl solution, water and saturated NaCl. The aqueous layer is concentrated in vacuo to a residue. The mixture of salts is triturated with MeOH and CH₂Cl₂, filtered, washed with CH₂Cl₂/MeOH and the yellow filtrate is concentrated. The crude product is purified by RP-HPLC eluting in a gradient of 10% CH₃CN/H₂O (0.1% TFA) to 50% CH₃CN/H₂O (0.1% TFA) and the appropriate product fractions are lyophilized to provide the title compound as a beige solid.

¹H NMR (DMSO-d₆, 300 MHz) δ 13.00 (bs, 1H), 9.06 (s, 1H), 8.88 (d, 1H), 8.77 (m, 1H), 8.60 (d, 1H), 8.26 (d, 1H), 8.12 (s, 1H), 8.01 (d, 1H), 7.52 (m, 1H), 6.80 (s, 1H), 4.71 (AB, 2H), 4.35 (m, 1H), 3.30 (m, 2H), 2.22 (m, 1H), 1.78 (m, 1H). IS MS, [M+H]⁺=428. Elemental analysis calculated with 1.9 mol H₂O cal. C=40.05%, H=3.33%, N=10.15%, found C=40.06%, H=2.82%, N=9.87%.

EXAMPLE 49

Benzo[b]thiophene-2-sulfonic Acid (2-oxo-1-thieno [3,2-c]pyridin-2-ylmethyl-pyrrolidin-3-(S)-yl)-amide Trifluoroacetate A. 1-(Thieno[3,2-c]pyridin-2-ylmethyl)-2-oxopyrrolidin-3-(S)-yl]carbamic Acid tert-Butyl Ester.

To a solution of 1-(4-chloro-thieno[3,2-c]pyridin-2-ylmethyl)-2-oxopyrrolidin-3-(S)-yl]carbamic acid tert-butyl ester (0.46 g, 1.2 mmol), prepared as described in EXAMPLE 33, Part F, in 20 mL of MeOH is added 10% by weight Pd/C (0.1 g) and KOH (0.13 g, 2.4 mmol). The atmosphere above the reaction is replaced by hydrogen and the solution is heated to 50° C. After 16 hours, the solution is filtered through Celite and the Celite is washed with MeOH. The crude material is purified by column chromatography eluting with a gradient of 30% EtOAc/CH₂Cl₂ to 40% EtOAc/CH₂Cl₂ to give the product as a white solid (0.2 g, 0.7 mmol).

¹H NMR (CDCl₃, 300 MHz) δ 9.00 (s, 1H), 8.44 (d, 1H), 7.70 (s, 1H), 7.31 (s, 1H), 5.12 (bs, 1H), 4.72 (AB, 2H), 4.18 (m, 1H), 3.32 (m, 2H), 2.62 (m, 1H), 1.88 (m, 1H), 1.42 (s, 9H). FAB MS, [M+H]⁺=348.

B. Benzo[b]thiophene-2-sulfonic Acid (2-oxo-1-thieno[3,2-c]pyridin-2-ylmethyl-pyrrolidin-3-(S)-yl)-amide Trifluoroacetate.

To a solution of 1-(thieno[3,2-c]pyridin-2-ylmethyl)-2-oxopyrrolidin-3-(S)-yl]carbamic acid tert-butyl ester (0.1 g, 0.35 mmol) in 4 mL of CH₂Cl₂ is added Et₃N (0.08 g, 0.78 mmol) and benzo[b]thiophene sulfonyl chloride (0.08 g, 0.35 mmol). After 6 hours, the solution is diluted with CH₂Cl₂ and washed with 10% Na₂CO and saturated NaCl. The residue is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 9.25 (bs, 1H), 8.63 (d, 1H), 8.50 (m, 1H), 8.39 (m, 1H), 7.99 (m, 4H), 7.61 (s, 1H), 7.46 (m, 2H), 4.70 (s, 2H), 4.14 (m, 1H), 3.11 (m, 2H), 2.08 (m, 1H), 1.62 (m, 1H). FAB MS, [M+H]⁺=444.

EXAMPLE 50

7-Methoxynaphthalene-2-sulfonic Acid [1-(1H-Imidazo[4,5-c]pyridin-2-ylmethyl)-2-oxopyrrolidin-3-(S)-yl]amide Trifluoroacetate A. [3-(S)-Amino-2-oxo-cyclopentyl]-acetic Acid Benzyl Ester Hydrochloride.

Sodium hydride (0.13 g, 3.3 mmol, 60% by weight) is added to a solution of [2-oxopyrrolidin-3-(S)-yl]-carbamic acid tert-butyl ester (0.6 g, 3 mmol) in THF (30 mL) at 0° C. The mixture is stirred for 30 minutes then benzyl 2-bromo-acetate (0.76 g, 3.3 mmol) is added. The resulting solution is warmed to room temperature and stirred for 1.5 hours. The reaction mixture is quenched with saturated ammonium chloride solution then diluted with methylene chloride. The organic layer is separated, washed with brine, dried over MgSO₄, filtered and concentrated. The residue is purified by flash chromatography (0–3% MeOH/CH₂Cl₂) and the material isolated is treated in ethyl acetate with HCl gas (as described in EXAMPLE 1, Part I) to give the title compound (0.55 g, 1.9 mmol) as a pale yellow solid.

¹H NMR (CD₃OD, 300 MHz) δ6 7.32 (m, 5H), 5.17 (s, 2H), 4.15 (d, 2H), 4.08 (m, 1H), 3.54 (m, 2H), 2.54 (m, 1H), 2.03 (m, 1H). EI MS, [M ]⁺=248.

B. 3-(S)-(7-Methoxy-naphthalene-2-sulfonylamino)-2-oxopyrrolidin-1-yl]-acetic Acid. [3-(S)-Amino-2-oxo-cyclopentyl]-acetic acid benzyl ester hydrochloride (0.34 g, 1.2 mmol) is suspended in CH₃CN (20 mL). To this mixture is added triethylamine (0.36 g, 3.6 mmol) followed by 7-methoxy-naphthalene-2-sulfonyl chloride (0.31 g, 1.2 mmol). The mixture is stirred overnight at room temperature, subjected to aqueous work up then concentrated to dryness. The crude material is purified by flash chromatography (0–5% MeOH/CH₂Cl₂). Subsequent hydrogenolysis in MeOH/CH₂Cl₂ with 5% Pd/C at 25 psi for 1.5 hours gave the title compound (0.40 g, 1 mmol) as a white solid.

¹H NMR (CDCl₃, 300 MHz) δ 8.33 (S, 1H), 7.80 (m, 3H), 7.23 (m, 2H), 5.90 (br, 1H), 3.95 (m, 6H), 3.38 (m, 2H), 2.40 (m, 1H), 2.07 (m, 1H). Ion Spray MS, [M+H]⁺=379.

C. N-(3-Amino-pyridin-4-yl)-2-[3-(S)-(7-methoxy-naphthalene-2-sulfonylamino)-2-oxopyrrolidin-1-yl]-acetamide.

Triethylamine (0.13 g, 1.3 mmol) and isobutyl chloroformate (0.18 g, 1.3 mmol) are added to a solution of [3-(S)-(7-methoxy-naphthalene-2-sulfonylamino)-2-oxopyrrolidin-1-yl]-acetic acid (0.5 g, 1.3 mmol) in THF (15 mL) at −10° C. The mixture is stirred for 20 minutes then treated with a solution of 3.4-diaminopyridine (0.16 g, 1.5 mmol) in DMF (5 mL). The resulting mixture is warmed to room temperature and stirred for 3 hours. The reaction mixture is concentrated in vacuo, then diluted with methylene chloride. The organic layer is washed with brine, dried over MgSO₄, filtered and concentrated. The residue is purified by flash chromatography (5–8% MeOH/CH₂Cl₂), to give the title compound (0.27 g, 0.58 mmol) as a solid.

$^1$H NMR (CDCl$_3$, 300 MHz) δ 8.88 (br, 1H), 8.30 (s, 1H), 8.00 (s, 1H), 7.85 (d, 1H), 7.70 (m, 3H), 7.40 (d, 1H), 7.20 (d, 1H), 7.12 (s, 1H), 5.28 (s, 2H), 4.07 (m, 4H), 3.88 (3, 3H), 3.34 (m, 2H), 2.22 (m, 1H), 1.90 (m, 1H). Ion Spray MS, [M+H]$^+$=470.

D. 7-Methoxy-naphthalene-2-sulfonic Acid [1-(1H-imidazo[4,5-c]pyridin-2-ylmethyl-2-oxopyrrolidin-3-(S)-yl]-amide Trifluoroacetate.

N-(3-Amino-pyridin-4-yl)-2-[3-(7-methoxy-naphthalene-2-sulfonylamino)-2-oxopyrrolidin-1-yl]-acetamide (0.22 g, 0.47 mmol) in acetic acid (15 mL) is heated at 110° C. overnight. The resulting solution is concentrated to dryness. The residue is purified by HPLC eluting with a gradient of 10 to 100% CH$_3$CN/0.1% TFA in water over 30 minutes. Fractions containing pure product are lyophilized to give the title compound as a white solid (0.24 g, 0.42 mmol).

$^1$H NMR (CDCl$_3$, 300 MHz) δ 9.30 (s, 1H), 8.40 (d, 1H), 8.28 (s, 1H), 7.95 (d, 1H), 7.70 (m, 3H), 7.40 (m, 1H), 7.20 (m, 2H), 7.14 (s, 1H), 4.92 (m, 2H), 4.46 (m, 1H), 3.82 (s, 3H), 3.38 (m, 2H), 2.20 (m, 1H), 2.03 (m, 1H). Ion Spray MS, [M+H]$^+$=452.

EXAMPLE 51

7-Methoxynaphthalene-2-sulfonic Acid [1-(2-Amino-3H-benzoimidazol-5-methyl)-2-oxopyrrolidin-3-(S)-yl]-amide Trifluoroacetate A. 7-Methoxynaphthalene-2-sulfonic Acid [1-(3,4-diaminobenzyl)-2-oxopyrrolidin-3-(S)-yl]-amide.

10% Palladium on carbon (0.08 g) is added to a solution of 7-methoxy-naphthalene-2-sulfonic acid[1-(4-amino-3-nitrobenzyl)-2-oxopyrrolidin-3-(S)-yl]-amide (0.22 g, 0.5 mmol) (prepared as described in EXAMPLE 25, Part F) in MeOH (40 mL) and CHCl$_3$ (3 mL) under nitrogen atmosphere. The heterogeneous mixture is hydrogenated at room temperature on a Parr apparatus under 47 p.s.i. of hydrogen for 5 hours. The catalyst is filtered and the filtrate checked by tlc shows no starting material. The filtrate is concentrated in vacuo and used in the subsequent step without further purification.

$^1$H NMR (CD$_3$OD, 300 MHz) δ 8.41 (s, 1H), 7.93 (d, 1H), 7.85 (d, 1H), 7.73 (d, 1H), 7.39 (d, 1H), 7.25 (dd, 1H), 7.02 (d, 1H), 6.89 (s, 1H), 6.79 (dd, 1H), 4.30 (s, 2H), 4.13 (t, 1H), 3.95 (s, 3H), 3.13 (m, 2H), 2.14 (m, 1H), 1.70 (m, 1H). Ion Spray MS, [M+H]$^+$=441.

B. 7-Methoxynaphthalene-2-sulfonic Acid [1-(2-Amino-3H-benzoimidazol-5-methyl)-2-oxopyrrolidin-3-(S)-yl]-amide Trifluoroacetate.

Triethylamine (0.063 mL, 0.45 mmol) is added to a solution of 7-methoxynaphthalene-2-sulfonic acid [1-(3,4-diaminobenzyl)-2-oxopyrrolidin-3-(S)-yl]-amide (0.205 g, 0.47 mmol) in MeOH (8 mL) under nitrogen. Cyanogen bromide (0.19 ml, of a 3 M solution, 0.56 mmol) is added dropwise to the reaction mixture at 0° C. After stirring for 5 minutes at 0° C., the reaction is brought to room temperature and stirred overnight. The clear solution is then concentrated in vacuo and the crude residue purified using column chromatography eluting with a gradient of 9% MeOH/CH$_2$Cl$_2$ to 50% MeOH/CH$_2$Cl$_2$ to provide tile product in 56% yield. The product is lyophilized in acetonitrile/TFA-water to give the title compound as an off-white solid.

$^1$H NMR (CD$_3$OD, 300 MHz) δ 8.40 (d, 1H), 7.90 (d, 1H), 7.81 (d, 1H), 7.75 (d, 1H), 7.6 (d, 1H), 7.25 (dd, 1H), 7.15 (d, 1H), 7.11 (d, 1H), 6.92 (dd, 1H), 4.41 (AB, 2H), 4.15 (t, 1H), 3.91 (s, 3H), 3.10 (m, 2H), 2.10 (m, 1H), 1.64 (m, 1H). Ion Spray MS, [M+H]$^+$=466.

EXAMPLE 52

3-(S)-Amino-1-(1-aminoisoquinolin-7-ylmethyl)-pyrrolidin-2-one Hydrochloride

A. 7-Methyl-1-phenoxyisoquinoline.

The title compound is prepared as described in Example 1, Part L using 1-chloro-7-methylisoquinoline as the starting material. The crude material is purified by column chromatography eluting with 20% EtOAc/hexanes to afford the title product as a pale yellow oil.

$^1$H NMR (CDCl$_3$, 300 MHz) δ 8.22 (s, 1H), 7.90 (d, 1H), 7.68–7.60 (m, 1H), 7.60–7.52 (m, 1H), 7.50–7.40 (m, 2H), 7.30–7.20 (m, 4H), 2.57 (s, 3H).

B. 7-Bromomethyl-1-phenoxyisoquinoline.

The title compound is prepared as described in Example 1, Part F using 7-methyl-1-phenoxyisoquinoline as the starting material. The crude product is purified by column chromatography eluting with 10% EtOAc/hexanes to afford the title product as a clear oil.

$^1$H NMR (CDCl$_3$, 300 MHz) δ 8.40 (s, 1H), 7.95 (d, 1H), 7.80–7.65 (m, 2H), 7.50–7.40 (m, 2H), 7.30–7.20 (m, 4H), 4.65 (s, 2H).

C. [1-(1-Phenoxyisoquinolin-7-ylmethyl)-2-oxopyrrolidin-3-(S)-yl]-carbamic Acid Benzyl Ester.

The title compound is prepared as described in Example 1, Part H using 7-bromomethyl-1-phenoxyisoquinoline and [2-oxopyrrolidin-3-(S)-yl]carbamic acid benzyl ester as the starting materials. The crude product is purified by column chromatography eluting with 70% EtOAc/hexanes to afford the title product as a clear oil.

$^1$H NMR (CDCl$_3$, 300 MHz) δ 8.25 (s, 1H), 7.97 (d, 1H), 7.79 (d, 1H), 7.60 (d, 1H), 7.48–7.40 (m, 2H), 7.38–7.20 (m, 9H), 5.40 (bs, 1H), 5.15 (s, 2H), 4.75 (AB, 2H), 4.30 (m, 1H), 3.30 (m, 2H), 2.67 (m, 1H), 1.90 (m, 1H).

D. [1-(1-aminoisoquinolin-7-ylmethyl)-2-oxopyrrolidin-3-(S)-yl]-carbamic Acid Benzyl Ester.

The title compound is prepared as described in Example 1, Part M using [1-(1-phenoxyisoquinolin-7-ylmethyl)-2-oxopyrrolidin-3-(S)-yl]-carbamic acid benzyl ester as the starting material. The reaction mixture is diluted with methylene chloride and washed with 3 N NaOH and brine. The organic layer is dried over MgSO$_r$, filtered and concentrated in vacuo. The crude product is purified by column chromatography eluting with 10% MeOH/CH$_2$Cl$_2$ to afford the title product as a foamy yellow solid.

$^1$H NMR (CDCl$_3$, 300 MHz) δ 7.95–7.87 (m, 2H), 7.70 (d, 1H), 7.45 (d, 1H), 7.40–7.30 (m, 5H), 7.00 (d, 1H), 5.75–5.55 (m, 3H), 5.20–5.15 (m, 4H), 4.3–4.1 (m, 1H), 3.25 (m, 2H), 2.55 (m, 1H), 2.27 (m, 1H).

E. 3-(S)-Amino-1-(1-aminoisoquinolin-7-ylmethyl)-pyrrolidin-2-one Hydrochloride.

10% Palladium on carbon (0.089 g) is added to a solution of [1-(1-aminoisoquinolin-7-ylmethyl)-2-oxopyrrolidin-3-(S)-yl]-carbamic acid benzyl ester (0.33 g, 0.84 mmol) in ethanol. The heterogeneous mixture is hydrogenated at room temperature on a Parr apparatus under 45 p.s.i. of hydrogen for 3 hours. The reaction mixture is filtered through a pad of Celite, washed with ethanol and the filtrate is concentrated in vacuo to give the product (0.2 g, 0.78 mmol) as a foamy solid. The product is dissolved in diethyl ether and cooled to 0° C. Hydrogen chloride gas is bubbled through the solution to yield the product as a hydrochloride salt.

$^1$H NMR (DMSO-d$_6$, 300 MHz) d 8.95–8.50 (b, 2H), 8.05 (s, 1H), 7.75–7.70 (m, 2H), 7.53 (d, 1H), 7.30–7.10 (b, 2H), 6.93 (d, 1H), 4.57 (AB, 2H), 3.40 (m, 1H), 3.15 (m, 1H), 2.37 (m, 1H), 2.02 (m, 1H). FAB MS: [M+H]$^+$=257.

F. 7-Methoxynaphthalene-2-sulfonic Acid [1-(1-aminoisoquinolin-7-yl-methyl)-2-oxo-pyrrolidin-3-(S)-yl]-amide Trifluoroacetate.

The title compound can be prepared by an alternative route using 3-(S)-amino-1-(1-aminoisoquinolin-7-ylmethyl)-pyrrolidin-2-one hydrochloride and 7-methoxynaphthalene-2-sulfonyl chloride as the starting material and proceeding as described in Example 1, Part K.

EXAMPLE 53

6-Chlorothieno[2,3-b]pyridine-2-sulfonyl Chloride

A. 2-Bromo-6-chlorothieno[2,3-b]pyridine.

The title compound is prepared from 2-bromo-5-acetyl thiophene according to the procedure described in J. Chem. Soc., Perkin Trans. I. 1981, 1531. The crude product is purified by column chromatography eluting with 2% EtOAc/hexanes to afford a white solid.

1H NMR (CDCl3, 300 MHz) δ 7.89 (d, 1H), 7.28 (d, 1H), 7.27 (d, 1H).

B. 6-Chlorothieno[2,3-b]pyridine-2-sulfonyl Chloride.

The title compound is prepared as described in EXAMPLE 1, Part D using 2-bromo-6-chlorothieno[2,3-b]pyridine in place of thianaphthalene. The crude product is obtained as a white solid and is of sufficient purity to be used in the subsequent step.

1H NMR (CDCl3, 300 MHz) δ 8.22 (d, 1H), 8.09 (s, 1H), 7.52 (d, 1H). EI MS [M]+=267, 269, Cl pattern.

EXAMPLE 54

6-Fluorobenzo[b]thiophene-2-sulfonyl Chloride

The title compound is prepared as described in EXAMPLE 9, Parts A-C using 3-fluorothiophenol in place of 3-chlorothiophenol.

EXAMPLE 55

6-Chlorothieno[3,2-b]pyridine-2-sulfonyl Chloride

The title compound is prepared as described in EXAMPLE 48, Part A using 6-chlorothieno[3,2-b]pyridine (prepared according to the procedure described in *J. Heterocyclic Chem.* 1984, 21, 785) in place of thianaphthalene. The crude product is used in the subsequent step without further purification.

Other compounds prepared according to the procedures above include those encompassed by the following formula:

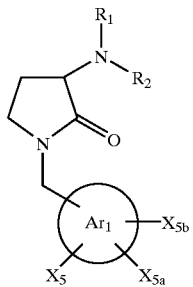

wherein

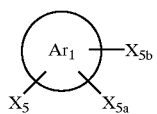

is selected from the group of formulae consisting of

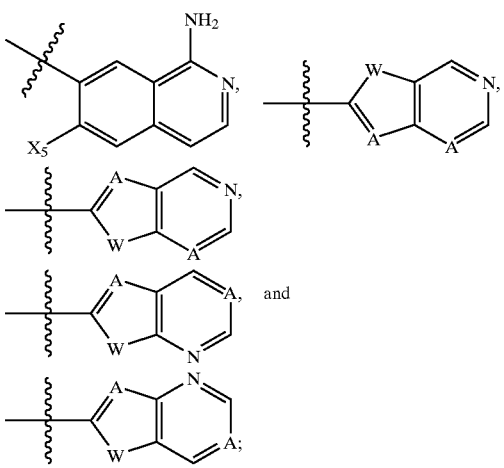

$R_1$, $X_5$, W and A are as defined herein; and $R_2$ is selected from the group of formulae consisting of

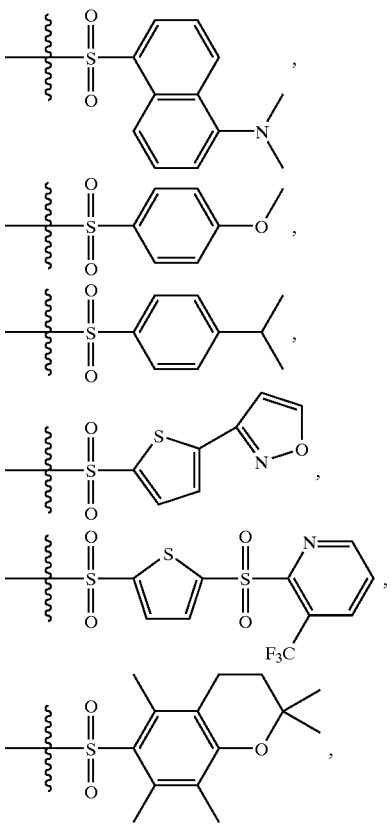

-continued
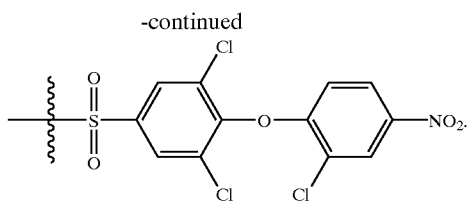,
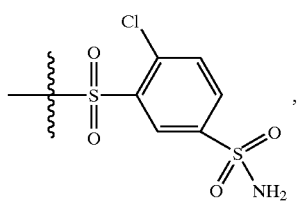,
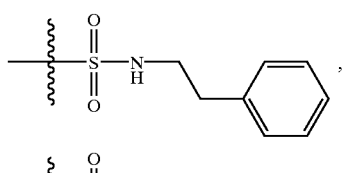,
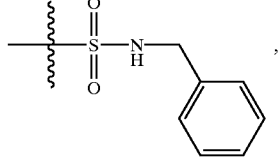,
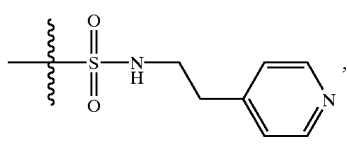,
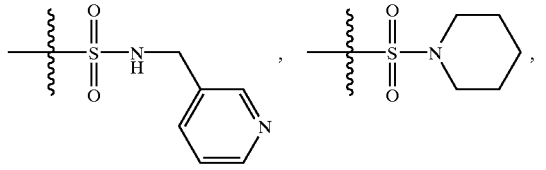,
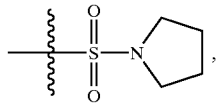,
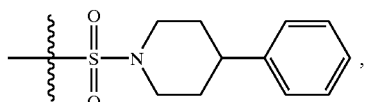,
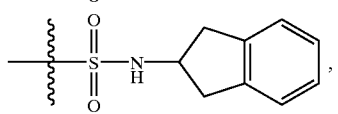,
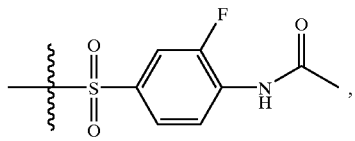,
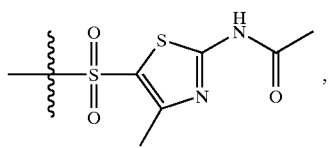,
-continued
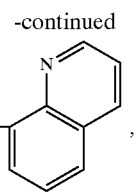,
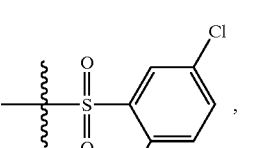,
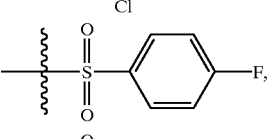,
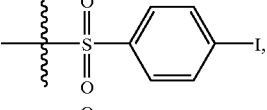,
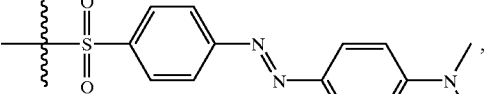,
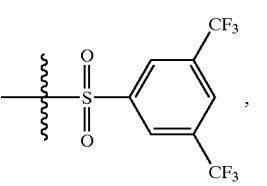,
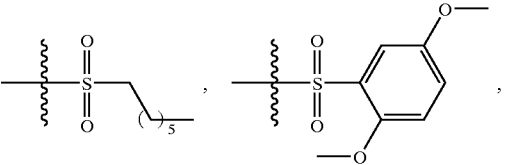,
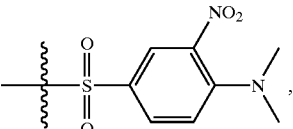,
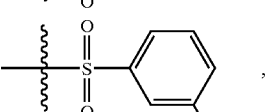,
,
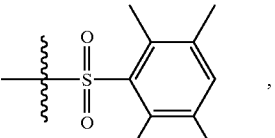,
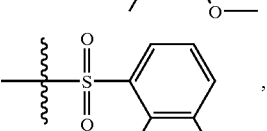,
,

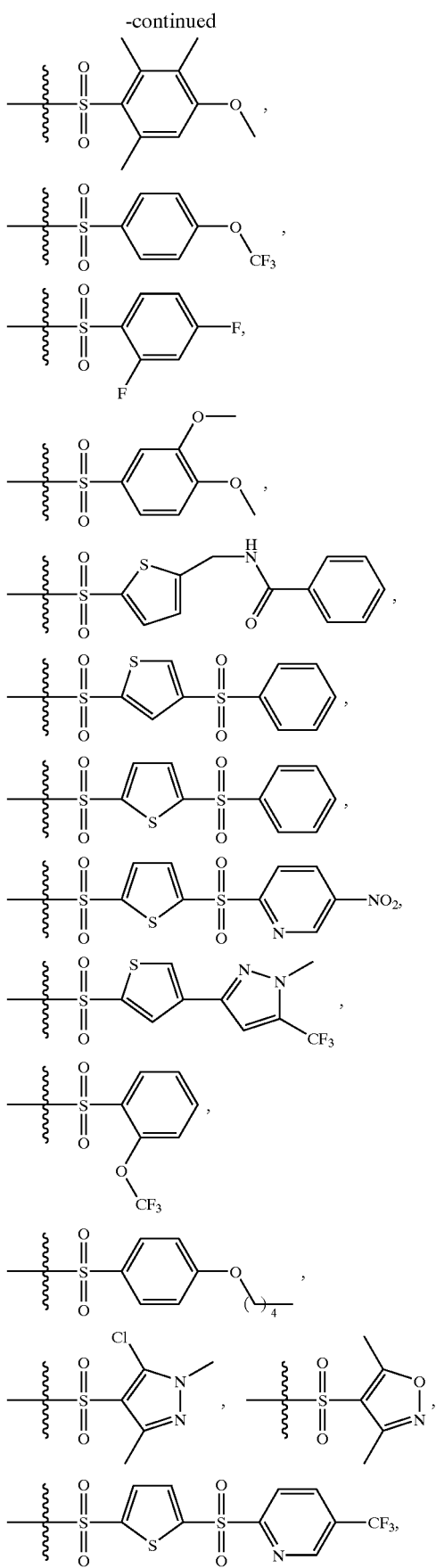
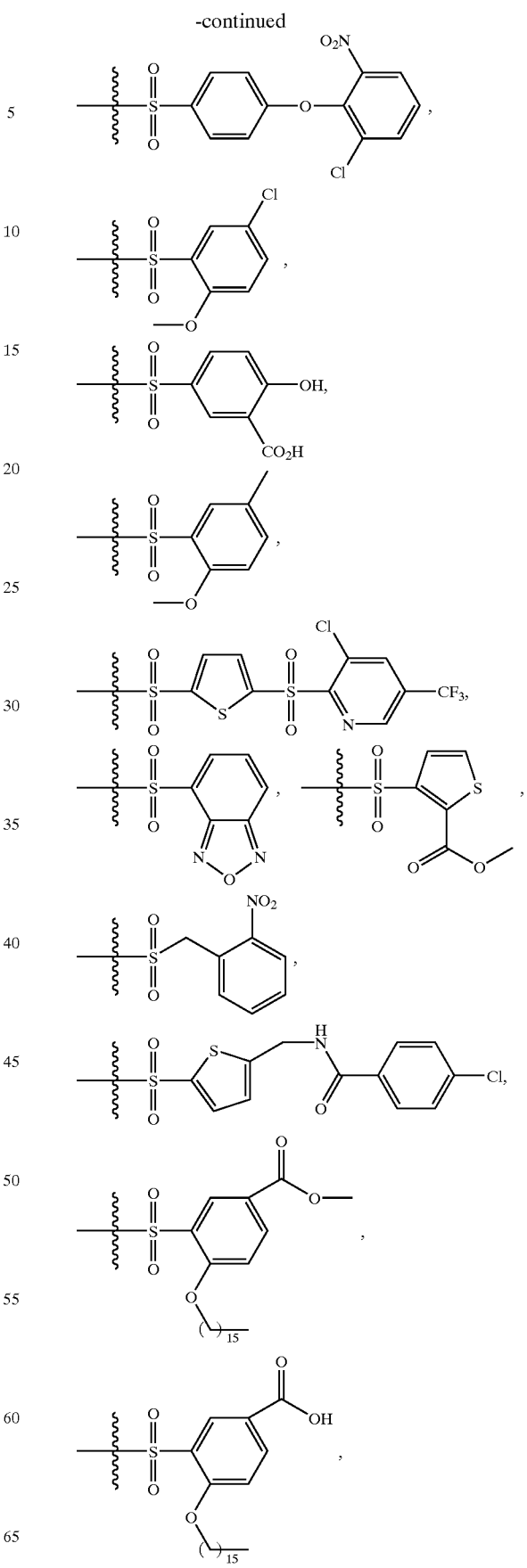

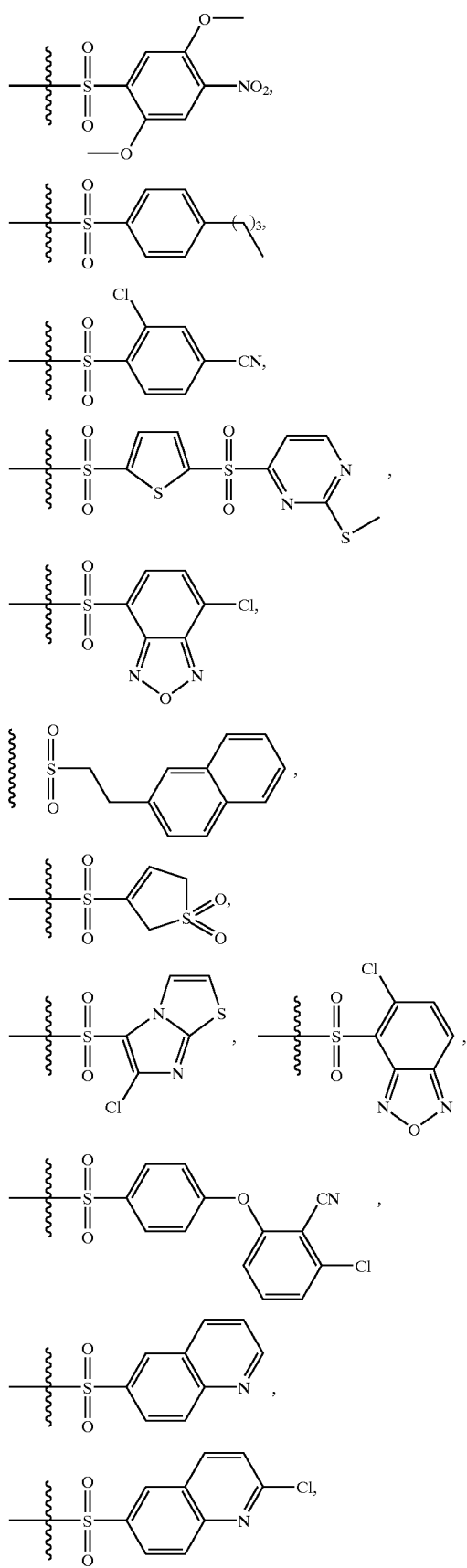
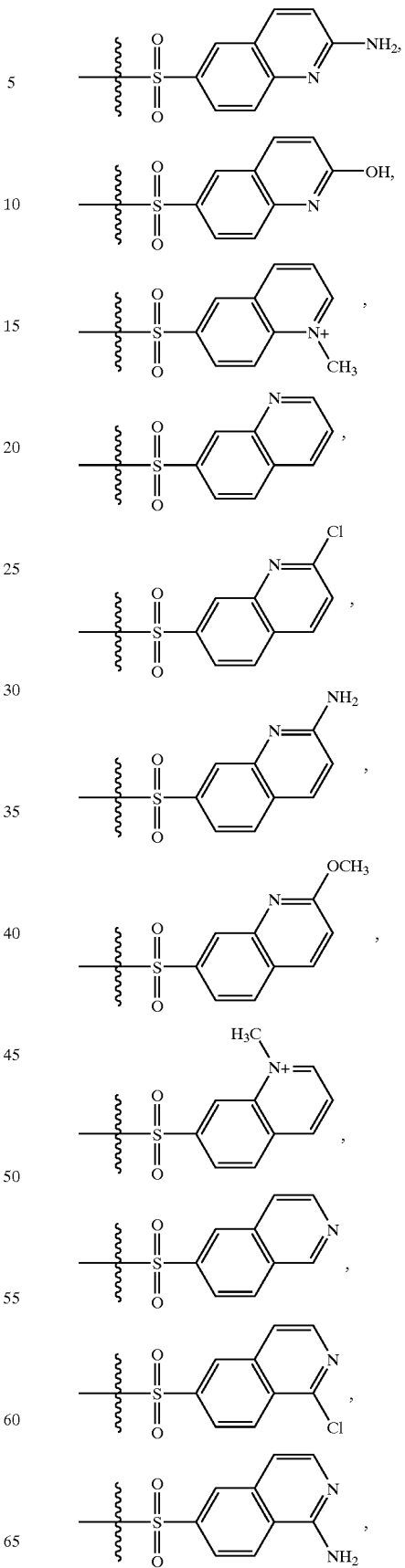

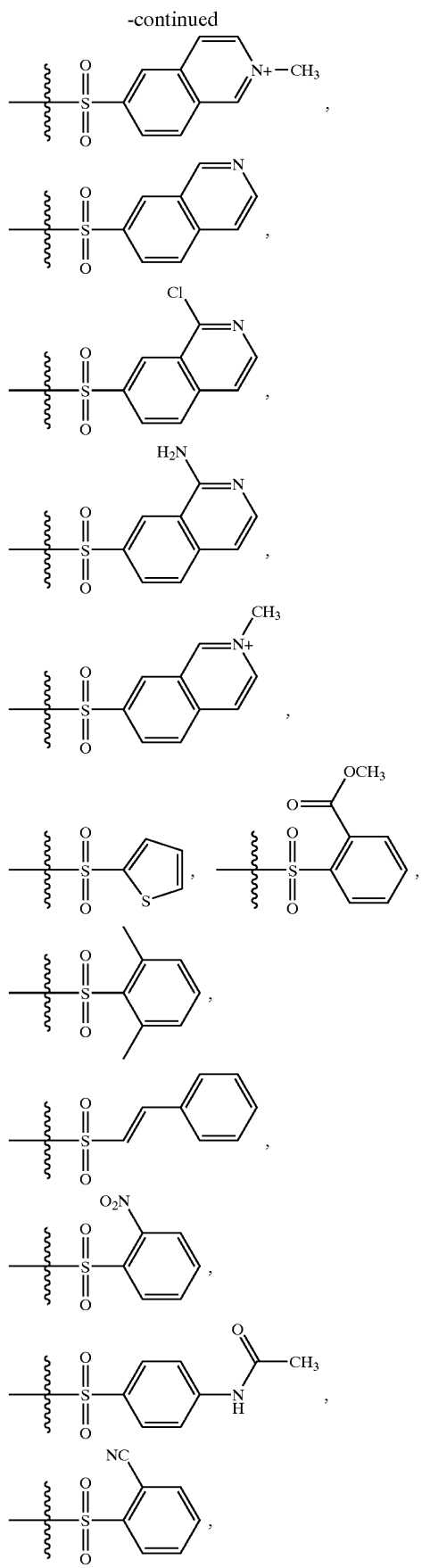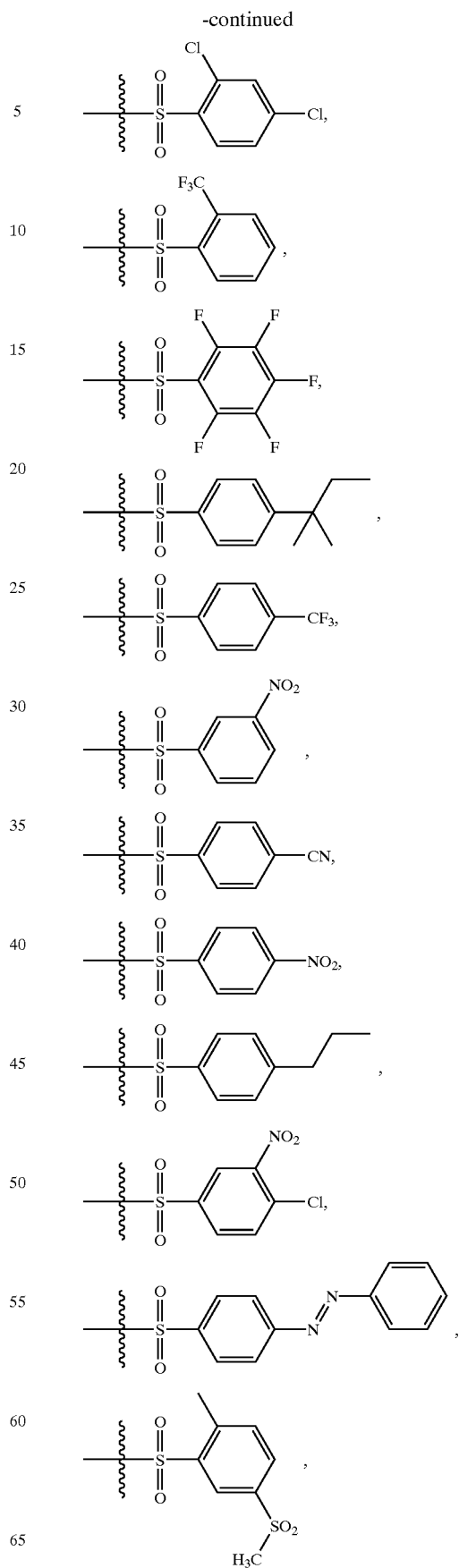

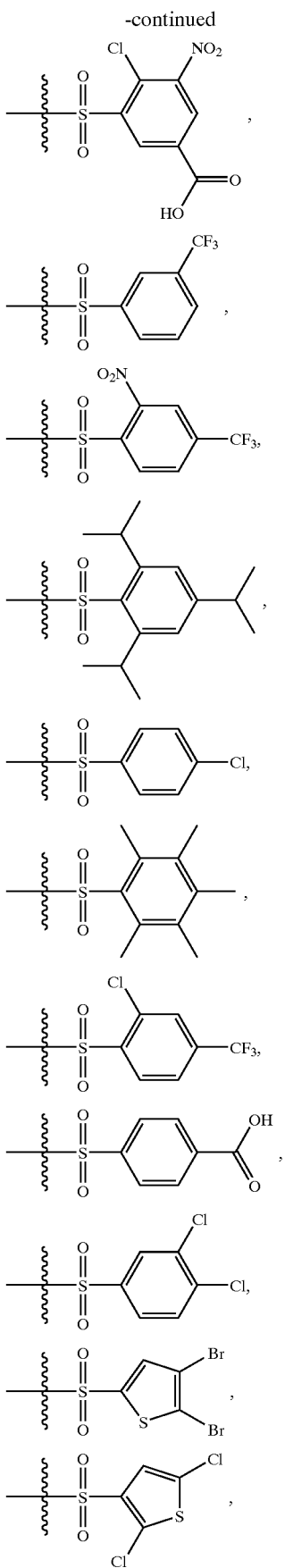
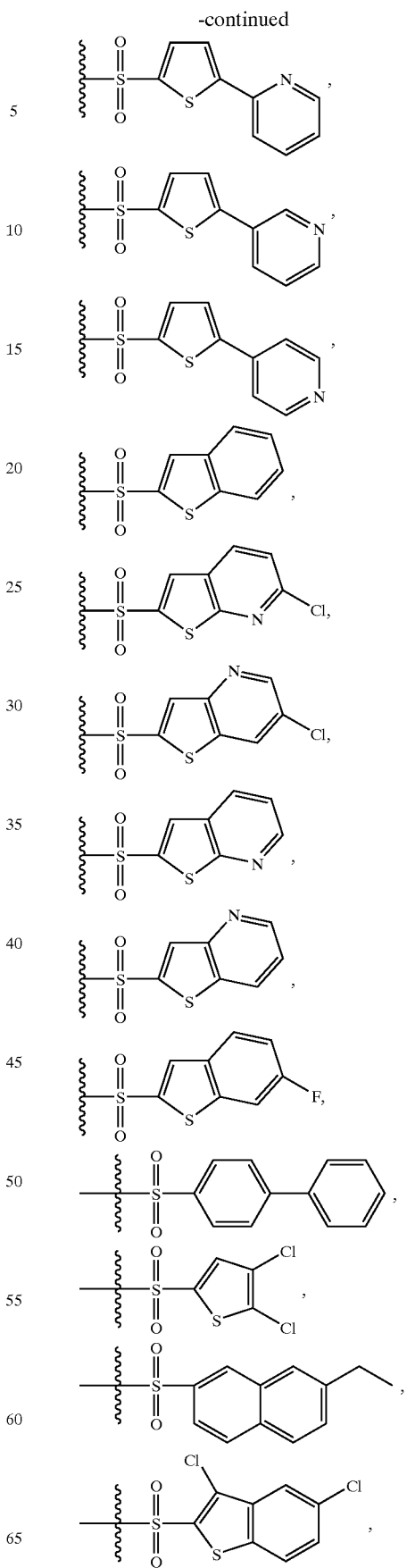

-continued

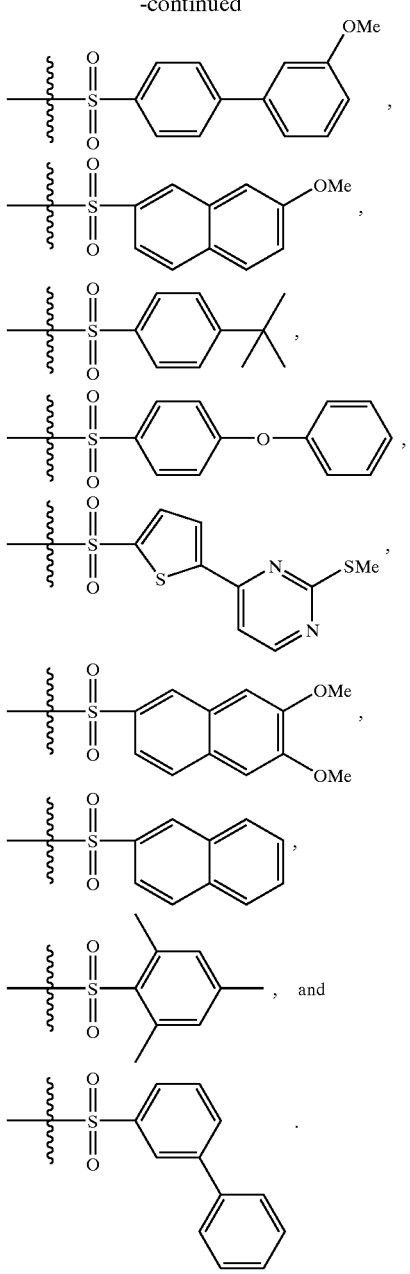

EXAMPLE 56

Thieno[3,2-b]pyridine-2-sulfonic Acid [1-(1-Amino-isoquinolin-7-ylmethyl)-2-oxo-pyrrolidin-3-(S)-yl]-amide A. Thieno[3,2-b]pyridine-2-sulfonic Acid [1-(1-Chloro-isoquinolin-7-ylmethyl)-2-oxopyrrolidin-3-(S)-yl]-amide.

To a solution of 3-(S)-amino-1-(1-chloro-isoquinolin-7-ylmethyl)-pyrrolidin-2-one hydrochloride (0.15 g, 0.48 mmol) suspended in CH₃CN (2.5 mL) is added triethylamine (0.23 mL, 1.6 mmol) followed by thieno[3,2-b]pyridine-2-sulfonyl chloride (0.14 g, 0.55 mmol). The mixture is stirred overnight, then concentrated. The residue is diluted with CH₂Cl₂ and washed with saturated NaHCO₃ and brine. The organic layer is dried over MgSO₄, filtered and concentrated to dryness. The crude product is purified by column chromatography eluting with 5% MeOH/CH₂Cl₂ to give the title compound (0.076 g, 0.16 mmol) as a light yellow solid.

$^1$H NMR (CDCl₃, 300 MHz) δ 8.85 (d, 1H), 8.32 (d, 1H), 8.27 (d, 1H), 8.15 (s, 2H), 7.85 (d, 1H), 7.58–7.65 (m, 2H), 7.45 (dd, 1H), 5.60 (bs, 1H), 4.68 (AB, 2H), 4.00 (m, 1H), 3.31 (m, 2H), 2.72 (m, 1H), 2.20 (m, 1H). EI MS, [M]⁺=472.

B. Thieno[3,2-b]pyridine-2-sulfonic Acid [1-(1-amino-isoquinolin-7-ylmethyl)-2-oxo-pyrrolidin-3-(S)-yl]-amide.

Thieno[3,2-b]pyridine-2-sulfonic acid [1-(1-chloro-isoquinolin-7-ylmethyl)-2-oxopyrrolidin-3-(S)-yl]-amide (1.36 g, 2.88 mmol) and phenol (2.22 g, 23.6 mmol) are melted together with stirring at 70° C. for 5 minutes. Ammonium acetate (2.71 g, 28.8 mmol) is added and the reaction mixture is heated to 90° C. and stirred overnight. Additional ammonium acetate (0.50 g, 5.31 mmol) is added and the reaction is heated for 20 more hours. The reaction is cooled and the residue is purified by RP-HPLC eluting in a gradient of 10% CH₃CN/H₂O (0.1% TFA) to 100% CH₃CN. The appropriate product fractions are lyophilized to provide the title compound as a white solid. The enantiomeric purity is 90.5% ee as determined by analytical Chiralpak AS RP-HPLC.

$^1$H NMR (DMSO-d₆, 300 MHz) δ 12.90 (bs, 1H), 9.00 (bs, 1H), 8.88 (d, 1H), 8.79 (dd, 1H), 8.60 (dd, 1H), 8.30 (s, 1H), 8.13 (s, 1H), 7.95 (d, 1H), 7.79 (dd, 1H), 7.65 (d, 1H), 7.53 (dd, 1H), 7.23 (d, 1H), 4.50 (AB, 2H), 4.38 (m, 1H), 3.21 (m, 2H), 2.20 (m, 1H), 1.81 (m, 1H). Ion Spray, [M+H]⁺=454.

EXAMPLE 57

Thieno[2,3-b]pyridine-2-sulfonic Acid [1-(1-amino-isoquinolin-7-ylmethyl)-2-oxo-pyrrolidin-3-(S)-yl]-amide A. Thieno[2,3-b]pyridine-2-sulfonyl Chloride.

n-Butyl lithium (6.0 mL of a 1.6 M solution in hexanes, 9.6 mmol) is added to a solution of thieno[2,3-b]pyridine (1.18 g, 8.7 mmol) (J. Org. Chem. 1969, 34(2), 347) in THF (30 mL) at −78° C. After 40 min., the solution is added to a precooled (−78° C.) solution of SO₂ (ca. 6 mL) in Et₂O (30 mL) via cannula. After addition, the solution is stirred for 30 min. then allowed to warm to ambient temperatures. After 2 h, the solution is concentrated to give a brown solid. The residue is suspended in hexanes (30 mL) and SO₂Cl₂ (0.6 mL, 7.5 mmol) is added dropwise at room temperature. After stirring for 1 h, the solution is concentrated then diluted with methylene chloride and saturated NaHCO₃ solution. The organic layer is separated and dried over MgSO₄, filtered and concentrated. The crude product is purified by column chromatography eluting with 20% EtOAc/hexanes to give a white solid as the title product.

$^1$H NMR (CDCl₃, 300 MHz) δ 8.81 (dd, 1H), 8.30 (dd, 1H), 8.12 (s, 1H), 7.50 (dd, 1H). EI MS, [M]⁺=233, 235. Cl pattern.

B. Thieno[2,3-b]pyridine-2-sulfonic Acid [1-(1-chloro-isoquinolin-7-ylmethyl)-2-oxo-pyrrolidin-3-(S)-yl]-amide.

The title compound is prepared as described in EXAMPLE 56, Part A using thieno[2,3-b]pyridine-2-sulfonyl chloride and 3-(S)-amino-1-(1-chloro-isoquinolin-7-ylmethyl)-pyrrolidin-2-one hydrochloride as starting material. The crude product is purified by column chromatography eluting with 5% MeOH/CH₂Cl to give the title compound as a white solid.

$^1$H NMR (CDCl₃, 300 MHz) δ 8.72 (dd, 1H), 8.31 (d, 1H), 8.22 (dd, 1H), 8.13 (d, 1H), 7.92 (s, 1H), 7.81 (d, 1H), 7.60 (d, 1H), 7.58 (d, 1H), 7.43 (dd, 1H), 5.89 (d, 1H), 4.70 (AB, 2H), 4.05 (m, 1H), 3.31 (m, 2H), 2.68 (m, 1H), 2.13 (m, 1H). Ion Spray, [M+H]⁺=473,475, Cl pattern.

C. Thieno[2,3-b]pyridine-2-sulfonic Acid [1-(1-Amino-isoquinolin-7-ylmethyl)-2-oxo-pyrrolidin-3-(S)-yl]-amide.

The title compound is prepared as described in EXAMPLE 56, Part B using thieno[2,3-b]pyridine-2-sulfonic acid [1-(1-chloro-isoquinolin-7-ylmethyl)-2-oxo-pyrrolidin-3-(S)-yl]-amide as starting material. The crude product is purified by RP-HPLC eluting with a gradient of 10% $CH_3CN/H_2O$ (0.1% TFA) to 100% $CH_3CN$. The appropriate fractions are lyophilized to provide the title compound as a white solid.

$^1$H NMR (DMSO-$d_6$, 300 MHz) δ 12.90 (bs, 1H), 9.00 (bs, 1H), 8.80 (d, 1H), 8.72 (dd, 1H), 8.42 (dd, 1H), 8.27 (s, 1H), 8.08 (s, 1H), 7.95 (d, 1H), 7.79 (d, 1H), 7.65 (d, 1H), 7.58 (dd, 1H), 7.21 (d, 1H), 4.50 (AB, 2H), 4.35 (m, 1H), 3.25 (m, 2H), 2.21 (m, 1H), 1.80 (m, 1H). Ion Spray, [M+H]$^+$=454.

EXAMPLE 58

4-Pyridin-3-yl-thiophene-2-sulfonic Acid [1-(1-amino-isoquinolin-7-ylmethyl)-2-oxo-pyrrolidin-3-(S)-yl]-amide A. 4-Pyridin-3-yl-thiophene-2-sulfonyl Chloride.

The title compound is prepared as described in EXAMPLE 57, Part A using 2-bromo-4-pyridin-3-yl-thiophene (*J. Hel. Chem.* 1995, 32, 435) in place of thieno[2,3-b]pyridine and performing the reaction at −100° C. rather than at −78° C. The crude product is purified by column chromatography eluting with a gradient of 10% EtOAc/hexanes to 20% EtOAc/hexanes to give a pale yellow solid.

$^1$H NMR (CDCl$_3$, 300 MHz) δ 8.87 (dd, 1H), 8.65 (dd, 1H), 8.3 (d, 1H), 7.98 (d, 1H), 7.90 (m, 1H), 7.42 (m, 1H). EI MS, [M]$^+$=259, 261, Cl pattern.

B. 4-Pyridin-3-yl-thiophene-2-sulfonic Acid [1-(1-Chloro-isoquinolin-7-ylmethyl)-2-oxo-pyrrolidin-3-(S)-yl]-amide.

The title compound is prepared as described in EXAMPLE 56, Part A using 4-pyridin-3-yl-thiophene-2-sulfonyl chloride and 3-(S)-amino-1-(1-chloro-isoquinolin-7-ylmethyl)-pyrrolidin-2-one hydrochloride as starting material. The crude product is purified by column chromatography eluting with a gradient of 2% MeOH/$CH_2Cl_2$ to 4% MeOH/$CH_2Cl_2$ to give the title compound as a white solid.

$^1$H NMR(CDCl$_3$, 300MHz) δ 8.88 (d, 1H), 8.60 (dd, 1H), 8.31 (d, 1H), 8.14 (s, 1H), 7.95 (d, 1H), 7.88 (m, 1H), 7.82 (d, 1H), 7.79 (d, 1H), 7.55–7.60 (m, 2H), 7.38 (m, 1H), 5.45 (d, 1H), 4.63 (AB, 2H), 3.95 (m, 1H), 3.29 (m, 2H), 2.68 (m, 1H), 2.14 (m, 1H), 1.6 (s, 9H). Ion Spray, [M+H]$^+$=499, 501.

C. 4-Pyridin-3-yl-thiophene-2-sulfonic Acid [1-(1-amino-isoquinolin-7-ylmethyl)-2-oxo-pyrrolidin-3-(S)-yl]-amide.

The title compound is prepared as described in EXAMPLE 56, Part B using 4-pyridin-3-yl-thiophene-sulfonic acid [1-(1-chloro-isoquinolin-7-ylmethyl)-2-oxo-pyrrolidin-3-(S)-yl]-amide as starting material. The crude product is purified by RP-HPLC eluting with a gradient of 10% $CH_3CN/H_2O$ (0.1% TFA) to 100% $CH_3CN$. The appropriate fractions are lyophilized to provide the title compound as a white solid.

$^1$H NMR (DMSO-$d_6$, 300 MHz) δ 12.98 (bs, 1H), 9.00 (bs, 2H), 8.48–8.57 (m, 2H), 8.39 (s, 1H), 8.27 (s, 1H), 8.15–8.21 (m, 2H), 7.92 (d, 1H), 7.78 (d, 1H), 7.61 (d, 1H), 7.48 (m, 1H), 7.21 (d, 1H), 4.56 (AB, 2H), 4.39 (m, 1H), 3.20 (m, 2H), 2.20 (m, 1H), 1.73 (m, 1H). Ion Spray, [M+H]$^+$=480.

EXAMPLE 59

5'Chloro-[2,2']bithiophenyl-5-sulfonic Acid [2-oxo-1-(1H-pyrrolo[3,2-c]pyridin-2-ylmethyl)-pyrrolidin-3(S)-yl]-amide A. 4-Amino-3-iodo-pyridine.

A solution of potassium iodide (19.48 g, 117.4 mmol) and iodine (18.37 g, 72.3 mmol) in water (77 mL) is added dropwise via an addition funnel to a refluxing solution of 4-aminopyridine (9.21 g, 97.8 mmol) and sodium carbonate (6.12 g, 57.7 mmol) in water (35 mL). Upon complete addition the mixture is stirred for 2 h at reflux then cooled to room temperature and extracted with ethyl acetate. The combined organic layers are washed with saturated sodium thiosulfate solution (×3) and brine then dried over MgSO$_4$, filtered and concentrated to give the title product (8.37 g, 38.0 mmol) and a trace of the di-iodo compound as an yellow/orange solid. This material was used in the subsequent step without further purification.

$^1$H NMR (CDCl$_3$, 300 MHz) δ 8.70 (s, 1H), 8.10 (d, 1H), 6.55 (d, 1H), 4.60 (bs, 2H).

B. (3-Iodo-pyridin-4-yl)-carbamic Acid tert-Butyl Ester.

Di-tert-butyl dicarbonate (20.7 g, 94.8 mmol) is added to a solution of 4-amino-3-iodo-pyridine (19.0 g, 86.4 mmol) in THF (86 mL). The resulting solution is stirred for 2 h at room temperature then concentrated to dryness. The residue is diluted with ethyl acetate and washed with saturated sodium bicarbonate solution and brine. The organic layer is dried over MgSO$_4$, filtered and concentrated to dryness. The residue is purified by column chromatography eluting with 1% EtOAc/$CH_2Cl_2$ to give the title product and a small amount of the BOC-protected di-iodo compound. Trituration of the mixture with ether/hexane removes the undesired compound leaving the title product in the solution. Filtration of the solid and concentration of the filtrate yields the title product (18.95 g, 59.2 mmol).

$^1$H NMR (CDCl$_3$, 300 MHz) δ 8.75 (s, 1H), 8.35 (d, 1H), 8.1 (d, 1H), 7.0 (bs, 1H), 1.55 (s, 9H).

C. (2-Oxo-1-prop-2-ynyl-pyrrolidin-3-(S)-yl)-carbamic Acid Benzyl Ester.

Sodium hydride (1.11 g, 27.7 mmol, 60% mineral oil dispersion) is added to a solution of [2-oxopyrrolidin-3-(S)-yl]-carbamic acid benzyl ester (6.20 g, 26.4 mmol) in THF/DMF (88 mL, 3/1 v/v) at 0° C. The mixture is stirred for 5 min. then propargyl bromide (4.4 mL, 49.4 mmol) is added dropwise. The resulting solution is stirred for 1 h then brought to room temperature and stirred for 2 h. The reaction is quenched with saturated ammonium chloride solution then diluted with ethyl acetate and washed with water (×4) and brine. The organic layer is dried over MgSO$_4$, filtered and concentrated to dryness. The residue is purified by column chromatography eluting with 5% MeOH/$CH_2Cl_2$ to give the product (7.20 g, 26.4 mmol) as a white solid.

$^1$H NMR (CDCl$_3$, 300 MHz) δ 7.35 (m, 5H), 5.30 (bs, 1H), 5.12 (s, 2H), 4.21 (m, 1H), 4.13 (s, 2H), 3.43 (m, 2H), 2.73 (m, 1H), 2.25 (s, 1H), 1.95 (m, 1H).

D. 2-[3-(S)-Benzyloxycarbonylamino-2-oxo-pyrrolidin-1-ylmethyl)-pyrrolo[3,2-c]pyridine-1-carboxylic Acid tert-Butyl Ester.

Pd(PPh$_3$)$_2$Cl$_2$ (0.49 g, 0.70 mmol), CuI (0.08 g, 0.42 mmol) followed by triethylamine (7.8 mL, 56.0 mmol) is added to a solution of (2-oxo-1-prop-2-ynyl-pyrrolidin-3-(S)-yl)-carbamic acid benzyl ester (3.81 g, 13.9 mmol) and (3-iodo-pyridin-4-yl)-carbamic acid tert-butyl ester (4.48 g, 14.0 mmol) in DMF (50 ml) at room temperature. The mixture is heated to 100° C. and stirred for 1.5 h. The reaction mixture is then cooled to 50° C. and DBU (4.2 mL, 28.1 mmol) is added. After 30 min the solution is cooled to room temperature, diluted with ethyl acetate and washed with saturated ammonium chloride, water and brine. The organic layer is dried over $MgSO_4$, filtered and concentrated to dryness in vacuo. The resulting solid is purified by column chromatography eluting with a gradient of 2% MeOH/ $CH_2Cl_2$ to 5% MeOH/$CH_2Cl_2$ to give the product (4.79 g, 10.3 mmol) as a white solid.

$^1$H NMR (CDCl$_3$, 300 MHz) δ 8.80 (s, 1H), 8.48 (d, 1H), 7.90 (d, 1H), 6.51 (s, 1H), 7.39 (m, 5H), 5.45 (d, 1H), 5.19 (s, 2H), 4.90 (AB, 2H), 4.30 (m, 1H), 3.49 (m, 2H), 2.75 (m, 1H), 2.10 (m, 1H), 1.78 (s, 9H). Ion spray MS, [M+H]$^+$=465.

E. 2-[3-(S)-Amino-2-oxo-pyrrolidin-1-ylmethyl)-pyrrolo[3,2-c]pyridine-1-carboxylic Acid tert-Butyl Ester.

2-[3-(S)-Benzyloxycarbonylamino-2-oxo-pyrrolidin-1-ylmethyl)-pyrrolo[3,2-c]pyridine-1-carboxylic acid tert-butyl ester (2.8 g, 6.0 mmol) in HCO$_2$H/MeOH (30 mL, 4.4% solution) is quickly added via cannula to a solution of palladium black (2.0 g, 18.8 mmol) in water (1 mL). After ca. 40 min the catalyst is filtered through Celite and basified with saturated sodium bicarbonate solution. The filtrate is concentrated in vacuo to remove methanol then the resulting solution is extracted with methylene chloride. The organic layer is washed with brine, dried over $MgSO_4$, filtered and concentrated to dryness. The resulting white solid can be used in the subsequent step without further purification. The title compound was purified in the following manner to prepare a focused sulfonamide library. The crude solid was purified by RP-HPLC eluting with a gradient of 10% CH$_3$CN/H$_2$O (0.1% TFA) to 100% CH$_3$CN. The appropriate fractions are combined and neutralized with saturated sodium bicarbonate solution then concentrated to remove CH$_3$CN. The aqueous layer is extracted with methylene chloride (×4) and the organic layers are washed with brine, dried over $MgSO_4$, filtered and concentrated to give the title compound as a white solid.

$^1$H NMR (CDCl$_3$, 300 MHz) δ 8.80 (s, 1H), 8.43 (d, 1H), 7.90 (d, 1H), 6.41 (s, 1H), 4.88 (AB, 2H), 3.65 (m, 1H), 3.45 (m, 2H), 2.55 (m, 1H), 1.90 (m, 1H), 1.75 (s, 9H). Ion spray MS, [M+H]$^+$=331.

F. 5-Chloro-[2,2']bithiophenyl.

The title compound is prepared from 2-chloro-thiophene according to the procedure described in *Bull. Chem. Soc. Japan.* 1979, 1126. The crude product is purified by column chromatography eluting with a gradient of 5% EtOAc/hexanes to 10% EtOAc/hexanes to afford a white solid.

$^1$H NMR (CDCl$_3$, 300 MHz) δ 7.24 (m, 1H), 7.11 (d, 1H), 7.03 (dd, 1H), 6.94 (d, 1H), 6.83 (d, 1H). EI MS, [M]$^+$=200, 202, Cl pattern.

G. 5'-Chloro-[2,2']bithiophenyl-5-sulfonyl Chloride.

The title compound is prepared as described in EXAMPLE 57, Part A using 5-chloro-[2,2']bithiophenyl in place of thieno[2,3-b]pyridine. The crude product is purified by column chromatography eluting with a gradient of 5% EtOAc/hexanes to 10% EtOAc/hexanes to give a white solid.

$^1$H NMR (CDCl$_3$, 300 MHz) δ 7.76 (d, 1H), 7.14 (d, 1H), 7.09 (d, 1H), 6.92 (d, 1H). EI MS, [M]$^+$=298, 300, Cl pattern.

H. 2-[3-(S)-(5'-Chloro-[2,2']bithiophenyl-5-sulfonylamino)-2-oxo-pyrrolidin-1-ylmethyl]pyrrolo[3,2-c]pyridine-1-carboxylic Acid tert-Butyl Ester.

The title compound is prepared as described in EXAMPLE 56, Part A using 5'-chloro-[2,2']bithiophenyl-5-sulfonyl chloride and 2-[3-(S)-amino-2-oxo-pyrrolidin-1-ylmethyl)-pyrrolo[3,2-c]pyridine-1-carboxylic acid tert-butyl ester as starting material. The crude product can be purified by column chromatography eluting with 5% MeOH/ $CH_2Cl_2$ to give the title compound as a white solid or used in the subsequent step after an aqueous work-up without further purification. Ion spray MS, [M+H]$^+$=593, 595, Cl pattern.

I. 5'-Chloro-[2,2']bithiophenyl-5-sulfonic Acid [2-oxo-1-(1H-pyrrolo[3,2-c]pyridin-2-ylmethyl)-pyrrolidin-3(S)-yl]-amide.

Trifluoroacetic acid (1.0 mL, 13.0 mmol) is added dropwise to a slurry of 2-[3-(S)-(5'-chloro-[2,2']bithiophenyl-5-sulfonylamino)-2-oxo-pyrrolidin-1-ylmethyl]pyrrolo[3,2-c]pyridine-1-carboxylic acid tert-butyl ester (0.13 g, 0.22 mmol) in $CH_2C_2$ (2 mL) at 0° C. After 30 min the ice bath is removed and the solution is stirred at room temperature for 4 h. The reaction mixture is concentrated to dryness and the crude product is purified by RP-HPLC eluting in a gradient of 10% CH$_3$CN/H$_2$O (0.1% TFA) to 100% CH$_3$CN. The appropriate product fractions are lyophilized to provide the title compound as a white solid.

$^1$H NMR (DMSO-d$_6$, 300 MHz) δ 14.60 (bs, 1H), 12.78 (s, 1H), 9.18 (s, 1H), 8.55 (d, 1H), 8.40 (d, 1H), 7.88 (d, 1H), 7.61 (d, 1H), 7.38 (d, 1H), 7.36 (d, 1H), 7.21 (d, 1H), 6.91 (s, 1H), 4.70 (AB, 2H), 4.21 (m, 1H), 3.30 (m, 2H), 2.25 (m, 1H), 1.75 (m, 1H). Ion spray MS, [M+H]$^+$=493.495, Cl pattern.

EXAMPLE 60

2-(5-Chloro-thiophen-2-yl)-ethenesulfonic Acid [2-oxo-1-(1H-pyrrolo[3,2-c]pyridin-2-ylmethyl)-pyrrolidin-3-(S)-yi]-amide A. 2-(5-Chloro-thiophen-2-yl)-ethenesulfonic Acid Ethyl Ester.

n-Butyl lithium (1.6 ml of a 2.5 M solution in hexanes, 4.0 mmol) is added dropwise to a solution of ethyl diethylphosphorylmethianiesulfoniate (1.0 g, 3.8 mmol), prepared as described in *Tetrahedron*, 1987, 43(21), 5125, at −78° C. in THF (15 mL). The mixture is stirred for 20 min. then 5-chloro-2-thiophenecarboxaldehyde (0.45 ml, 4.2 mmol) is slowly added. The yellow mixture is stirred at −78° C. for 1 h then allowed to warm to room temperature overnight. The bulk of the solvents are evaporated and the residue is treated with water (2 mL) and extracted with $CH_2Cl_2$. The organic layer is washed with brine, dried over $MgSO_4$, filtered and concentrated. The crude product is purified by column chromatography eluting with $CH_2Cl_2$ to give the title compound as a yellow solid.

$^1$H NMR(CDCl$_3$, 300 MHz) δ 7.55 (d, 1H), 7.11 (d, 1H), 6.90 (d, 1H), 6.41 (d, 1H), 4.20 (q, 2H), 1.39 (t, 3H). Ion spray MS, [M+H]$^+$=253.

B. 2-(5-Chloro-thiophen-2-yl)-ethene tetra-n-butylammonium Sulfonate.

2-(5-Chloro-thiophen-2-yl)-ethenesulfonic acid ethyl ester (0.92 g, 3.2 mmol) in acetone (16 mL) is treated with tetrabutylammonium iodide (1.3 g, 3.5 mmol) and heated to reflux for 19 h. The mixture is concentrated to dryness then diluted with $CH_2Cl_2$ and washed with water and brine. The organic layer is dried over $MgSO_4$, filtered and concentrated to give an oil/solid which is taken on to the next step without further purification.

$^1$H NMR (CDCl$_3$, 300 MHz) δ 7.28 (d, 1H), 6.81 (d, 1H), 6.77 (d, 1H), 6.73 (d, 1H), 3.29 (t, 8H), 1.65 (m, 8), 1.45 (m, 8H), 1.00 (t, 12H).

C. 2-(5-Chlorothiophen-2-yl)-ethenesulfonyl Chloride.

Sulfuryl chloride (0.61 mL, 7.6 mmol) is added to a solution of triphenylphosphine (1.8 g, 6.9 mmol) in $CH_2Cl_2$ (8.6 mL) at 0° C. The ice bath is removed and 2-(5-chlorothiophen-2-yl)-ethene tetra-n-butylammonium sulfonate (1.6 g, 3.4 mmol) in $CH_2Cl_2$(17 mL) is added to the reaction mixture via cannula. The resulting yellow solution is stirred for 1.5 h then hexane/ether (1:1 v/v, 200 mL) is added until the solution is no longer cloudy and two layers form. The solution is decanted and the lower oily layer is discarded. The solution is concentrated to dryness and the product is purified by column chromatography eluting with $CH_2Cl_2$ to give the title compound as a pale yellow solid.

$^1$H NMR (CDCl$_3$, 300 MHz) δ 7.71 (d, 1H), 7.25 (d, 1H), 7.00 (d, 1H), 6.91 (d, 1H). EI MS, [M]$^+$=242, 244, 246, Cl pattern.

D. 2-{3-(S)-[2-(5-Chloro-thiophene-2-yl)-ethenesulfonylamino]-2-oxo-pyrrolidin-1-ylmethyl}-pyrrolo[3,2-c]pyridine-1-carboxylic Acid tert-Butyl Ester.

The title compound is prepared as described in EXAMPLE 56. Part A using 2-(5-chlorothiophen-2-yl)-ethenesulfonyl chloride and 2-[3-(S)-amino-2-oxo-pyrrolidin-1-ylmethyl)-pyrrolo[3,2-c]pyridine-1-carboxylic acid tert-butyl ester as starting material. The crude product can be purified by column chromatography eluting with 5% MeOH/CH$_2$Cl$_2$ to give the title compound as a white solid or used in the subsequent step after an aqueous work-up without further purification.

$^1$H NMR (CDCl$_3$, 300 MHz) δ 8.75 (s, 1H), 8.46 (d, 1H), 7.85 (d, 1H), 7.48 (d, 1H), 7.05 (d, 1H), 6.85 (d, 1H), 6.67 (d, 1H), 6.40 (s, 1H), 4.90 (AB, 2H), 4.15 (m, 1H), 3.49 (m, 2H), 2.71 (m, 1H), 2.21 (m, 1H), 1.7 (s, 9H). Ion spray MS, [M+H]$^+$=537, 539, Cl pattern.

E. 2-(5-Chloro-thiophen-2-yl)-ethenesulfonic Acid [2-oxo-1-(1H-pyrrolo[3,2-c]pyridin-2-ylmethyl)-pyrrolidin-3-(S)-yl]-amide.

The title compound is prepared as described in EXAMPLE 59, Part I using 2-{3-(S)-[2-(5-chloro-thiophene-2-yl)-ethenesulfonylamino]-2-oxo-pyrrolidin-1-ylmethyl}-pyrrolo[3,2-c]pyridine-1-carboxylic acid tert-butyl ester as starting material. The crude product is purified by RP-HPLC eluting with a gradient of 10% CH$_3$CN/H$_2$O (0.1% TFA) to 100% CH$_3$CN. The appropriate fractions are lyophilized to provide the title compound as a white solid.

$^1$NMR (DMSO-d$_6$, 300 MHz) δ6 9.19 (s, 1H), 8.48 (d, 1H), 7.91 (d, 1H), 7.88 (d, 1H), 7.50 (d, 1H), 7.43 (d, 1H), 7.20 (d, 1H), 7.02 (d, 1H), 6.90 s, 1H), 4.71 (AB, 2H), 4.12 (m, 1H), 3.21 (m, 2H), 2.42 (m, 1H), 1.85 (m, 1H). EI MS, [M]$^+$=436, 438, Cl pattern.

EXAMPLE 61

5'-Chloro-[2,2']bithiophenyl-5-sulfonic Acid [1-(1-Amino-isoquinolin-7-ylmethyl)-2-oxo-pyrrolidin-3-(S)-yl]-amide A. 5'-Chloro-[2,2']bithiophenyl-5-sulfonic Acid [1-(1-chloro-isoquinolin-7-ylmethyl)-2-oxo-pyrrolidin-3-(S)-yl]-amide.

The title compound is prepared as described in EXAMPLE 56, Part A using 5'-chloro-[2,2']bithiophenyl-5-sulfonyl chloride and 3-(S)-amino-1-(1-chloro-isoquinolin-7-ylmethyl)-pyrrolidin-2-one hydrochloride as starting material. The crude product is purified by column chromatography eluting with 5% MeOH/CH$_2$Cl$_2$ to give the title compound as a white solid.

$^1$H NMR (CDCl$_3$, 300 MHz) δ 8.30 (d, 1H), 8.15 (s, 1H), 7.82 (d, 1H), 7.52–7.60 (m, 3H), 7.01–7.09 (m, 2H), 6.88 (d, 1H), 5.41 (s, 1H), 4.68 (AB, 2H), 3.90 (m, 1H), 3.29 (m, 2H), 2.61 (m, 1H), 2.11 (m, 1H). Ion spray MS, [M+H]$^+$= 538,540, Cl pattern.

B. 5'-Chloro-[2,2']bithiophenyl-5-sulfonic Acid [1-(1-Amino-isoquinolin-7-ylmethyl)-2-oxo-pyrrolidin-3-(S)-yl]-amide.

The title compound is prepared as described in EXAMPLE 56, Part B using 5'-chloro-[2,2']bithiophenyl-5-sulfonic acid [1-(1-chloro-isoquinolin-7-ylmethyl)-2-oxo-pyrrolidin-3-(S)-yl]-amide as starting material. The crude product is purified by RP-HPLC eluting with a gradient of 10% CH$_3$CN/H$_2$O (0.1% TFA) to 100% CH$_3$CN. The appropriate fractions are lyophilized to provide the title compound as a white solid.

$^1$H NMR (DMSO-d$_6$, 300 MHz) δ 9.03 (bs, 2H), 8.58 (d, 1H), 8.31 (s, 1H), 7.95 (d, 1H), 7.81 (d, 1H), 7.69 (d, 1H), 7.61 (d, 1H), 7.30–7.41 (m, 2H), 7.29–7.25 (m, 2H), 4.60 (AB, 2H), 4.25 (m, 1H), 3.23 (m, 2H), 2.20 (m, 1H), 1.75 (m, 1H). Ion spray MS, [M+H]$^+$=519, 521, Cl pattern.

EXAMPLE 62

2-(5-Chloro-thiophen-2-yl)-ethenesulfonic Acid [1-(1-Amino-isoquinolin-7-ylmethyl)-2-oxo-pyrrolidin-3-(S)-yl]-amide The title compound is prepared as described in EXAMPLE 56, Part B using 2-(5-chloro-thiophen-2-yl)-ethenesulfonic acid [1-(1-chloro-isoquinolin-7-ylmethyl)-2-oxo-pyrrolidin-3-(S)-yl]-amide as starting material. The crude product product is purified by RP-HPLC eluting with a gradient of 10% CH$_3$CN/H$_2$O (0.1% TFA) to 100% CH$_3$CN. The appropriate fractions are lyophilized to provide the title compound as a pale pink solid.

$^1$H NMR (DMSO-d$_6$, 300 MHz) δ 9.00 (bs, 2H), 8.32 (s, 1H), 7.90–7.98 (m, 2H), 7.80 (d, 1H), 7.63 (d, 1H), 7.50 (d, 1H), 7.48 (d, 1H), 7.25 (d, 1H), 7.18 (d, 1H), 7.00 (d, 1H), 6.73 (d, 1H), 4.52 (AB, 2H), 4.20 (m, 1H), 3.23 (m, 2H), 2.48 (m, 1H), 1.88 (m, 1H). Ion spray MS, [M+H]$^+$=463, 465, Cl pattern.

EXAMPLE 63

6-Chloro-benzo[b]thiophene-2-sulfonic Acid [1-(4-Amino-quinazolin-6-yl-methyl)-2-oxopyrrolidin-3-(S)-yl]amide Trifluoroacetate The title compound is prepared as described in example 28 Parts E, F, G using 6-chloro-benzo[b]thiophene-2-sulfonyl chloride.

$^1$H NMR (DMSO-d$_6$, 300 MHz) δ6 9.83 (bs, 2H), 8.86 (m, 2H), 8.25 (s, 1H), 8.11 (s, 1H), 8.00 (m, 3H). 7.85 (m, 2H), 7.55 (m, 1H), 4.50 (AB, 2H), 4.15 (m, 1H), 3.14 (m, 2H), 2.17 (m, 1H), 1.72 (m, 1H). FAB MS, [M+H]$^+$=488, 490; Cl pattern.

EXAMPLE 64

6-Chloro-benzo[b]thiophene-2-sulfonic Acid [1-(4-Amino-thieno[2,3-d]pyrimidin-6-yl-methyl)-2-oxopyrrolidin-3-(S)-yl]amide Trifluoroacetate The title compound is prepared as described in example 29 Parts F, G and H using 6-chloro-benzo[b]thiophene-2-sulfonyl chloride.

$^1$H NMR (DMSO-d$_6$, 300 MHz) δ 8.78 (m, 2H), 8.28 (m, 2H), 8.04 (m, 2H), 7.82 (m, 2H), 7.51 (d, 1H), 7.40 (s, 1H), 4.58 (AB, 2H), 4.13 (m, 1H), 3.19 (m, 2H), 2.17 (m, 1H), 1.68 (m, 1H). FAB MS, [M+H]$^+$=494, 496; Cl pattern.

EXAMPLE 65

6-Chloro-benzo[b]thiophene-2-sulfonic Acid [1-(4-Amino-thieno[3,2-d]pyrimidin-7-yl-methyl)-2-oxopyrrolidin-3-(S)-yl]amide Trifluoroacetate The title compound is prepared as described in example 30 Parts D, E using 6-chloro-benzo[b]thiophene-2-sulfonyl chloride.

$^1$H NMR (DMSO-d$_6$, 300 MHz) δ 8.52 (m, 2H), 8.20 (m, 1H), 8.11 (s, 1H), 7.91 (m, 2H), 7.71 (s, 1H), 7.42 (m, 1H), 7.30 (m, 2H), 4.58 (AB, 2H), 4.15 (m, 1H), 3.21 (m, 2H), 2.20 (m, 1H), 1.72 (m, 1H). FAB MS, [M+H]$^+$=494, 496; Cl pattern.

EXAMPLE 66

5-Chloro-[2,2']bithiophenyl-5-2-sulfonic Acid [1-(4-Amino-thieno[3,2-d]pyrimidin-7-yl-methyl)-2-oxopyrrolidin-3-(S)-yl]amide Trifluoroacetate The title compound is prepared as described in example 30 Parts D, E using 5'-chloro-[2,2']bithiophenyl-5-sulfonyl chloride.

$^1$H NMR (DMSO-d$_6$, 300 MHz) δ 9.30 (m, 2H), 8.70 (m, 1H), 8.44 (m, 1H), 8.20 (m, 1H), 7.55 (m, 1H), 7.21 (m, 2H), 7.00 (m, 1H), 4.57 (AB, 2H), 4.15 (m, 1H), 3.20 (m, 2H), 2.19 (m, 1H), 1.70 (m, 1H). FAB MS, [M+H]$^+$=526, 528; Cl pattern.

EXAMPLE 67

2-(3-(S)-Amino-2-oxo-pyrrolidin-1-ylmethyl)-pyrrolo[3,2-b]pyridine-1-carboxylic Acid tert-Butyl Ester A. (2-Bromo-pyridin-3-yl)-carbamic Acid tert-Butyl Ester.

To a solution of 3-amino-2-bromopyridine (1.5 g, 8.7 mmol) and di-tert-butyl dicarbonate (2.0 g, 9.2 mmol) in THF (15 ml) is added 1.0) M sodium bis(trimethylsilyl) amide in THF (18 ml, 18 mmol) at 0° C. The mixture is stirred at r.t. for 4 h. and then concentrated, quenched with saturated NH$_4$Cl, diluted with EtOAc, and washed with water. The organic layer is dried over MgSO$_4$, treated with charcoal, filtered and concentrated to dryness. Title compound is obtained as a light yellow solid (2.1 g, 7.7 mmol).

$^1$H NMR (CDCl$_3$, 300 MHz) δ 8.44 (d, 1H), 8.03 (d, 1H), 7.20 (m, 1H), 7.02 (bs, 1H), 1.50 (s, 9H). EI MS [M+H]$^+$=273, 275.

B. 2-(3-(S)-Amino-2-oxo-pyrrolidin-1-ylmethyl)-pyrrolo[3,2-b]pyridine-1-carboxylic Acid tert-Butyl Ester.

The title compound is prepared from (2-bromo-pyridin-3-yl)-carbamic acid tert-butyl ester (1.6 g, 5.9 mmol) and (2-oxo-1-prop-2-ynyl-pyrrolidin-3-(S)-yl carbamic acid benzyl ester (1.6 g, 5.9 mmol) according to the methods described in EXAMPLE 59, Parts C,D and E. The title compound was obtained as a white solid (0.29 g, 0.88 mmol).

$^1$H NMR (CDCl$_3$, 300 MHz) δ 8.45 (d, 1H), 8.27 (d, 1H), 7.18 (dd, 1H), 6.50 (s, 1H), 4.90 (AB, 2H), 3.64 (m, 1H), 3.45 (m, 2H), 2.52 (m, 1H), 1.85 (m, 1H), 1.70 (s, 9H). EI MS [M+H]$^+$=331.

EXAMPLE 68

6-Chloro-1H-benzimidazole-2-sulfonyl Chloride

A mixture of 4-chloro-1,2-phenylenediamine (4.3 g, 30 mmol), potassium hydroxide (1.9 g, 34 mmol), carbon disulfide (2.1 ml, 34 mmol), ethanol (30 ml) and water (4.5 ml) is heated under reflux for 3 h. Norit is added, the mixture is refluxed 10 min, then filtered. The warm filtrate is diluted with water (30 ml, 50–75° C.) followed by aqueous acetic acid (7.5 ml, 3%) with stirring, Brown solid forms, and the mixture is cooled with an ice bath, 6-Chloro-1H-benzimidazole-2-thiol (4.2 g, 2.3 mmol) is collected, washed with water and vacuum dried. :$^1$H NMR (DMSO-d$_6$, 300 MHz) δ 12.6 (d, 2H), 7.1 (s, 3H), EI MS M$^+$=184, 186. A suspension of 6-chloro-1H-benzimidazole-2-thiol (1.0 g, 5.4 mmol) in 20% AcOH (30 ml) is cooled in an ice bath: Cl$_2$ gas is bubbled through the mixture for 40 min. The resulting solid is collected by filtration, washed with H$_2$O and air dried to give the title compound as a light brown solid.

$^1$H NMR (CDCl$_3$, 300 MHz) δ 7.75 (m, 2H), 7.5 (d, 1H).

EXAMPLE 69

Thieno[2,3-b]pyridine-2-sulfonyl Chloride

Thieno[2,3-b]pyridine (1.18 g, 8.7 mmol) is to subjected to the three step sequence described in EXAMPLE 8, Part A, Flash chromatography (20% EtOAc/Hexane) of the crude product gives the title compound (0.59 g, 2.5 mmol): $^1$H NMR (CDCl$_3$, 300 MHz) δ 8.78 (dd, 1H), 8.26 (dd, 1H), 8.10 (s, 1H), 7.47 (dd, 1H), EI MS M$^+$=233,235.

EXAMPLE 70

6-Chloro-thieno[2,3-b]pyridine-2-sulfonyl Chloride

6-Chloro-thieno[2,3-b]pyridine (0.73 g, 4.3 mmol) is to subjected to the three step sequence described in EXAMPLE 8, Part A. Flash chromatography (15% EtOAc/Hexane) of the crude product gives the title compound (0.75 g, 2.8 mmol): $^1$H NMR (CDCl$_3$, 300 MHz) δ 8.19 (d, 1H), 8.07 (s, 1H), 7.47 (d, 1H). EI MS M$^+$=267, 269, 271.

PREPARATION 1

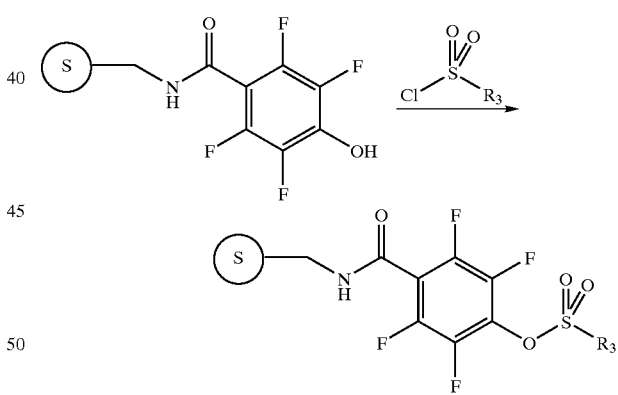

Reaction vessels are charged with 4-hydroxy-2,3,5,6-tetraflurobenzamidomethyl-copoly-(styrene-1%-divinylbenzene)-resin (0.20 g, 0.15 mmol). Each container is treated with methylene chloride (2 mL) for 10 minutes followed by an aromatic sulfonyl chloride (0.45 mmol) and diisopropyethyl amine (0.104 ml, 0.60 mmol). The containers are sealed and agitated for about 16 h. The reaction mixtures are individually filtered and sequentially washed with 20% aqueous DMF (10x), THF (5x) and dichloromethane (5x), then dried in vacuo at ambient temperature overnight. By way of example 6-chlorobenzothiophene-2-sulfonyl)oxy-2,3,5,6-tetrafluro-benzamidomethyl-copoly-(styrene-1%-divinylbenzene)-resin showed: $^{19}$F-NMR d −144.572, −145.608; IR (cm-1) 1684 (C=O stretch), 1391, (asymmetric SO₂ stretch) 1195, 1177 (symmetric SO₂ stretch).

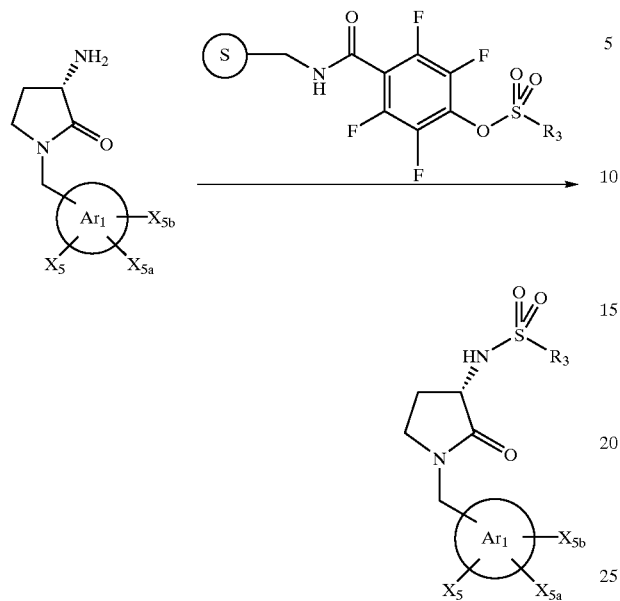

Reaction vessels are changed with arylsulfonyloxy-2,3,5,6-tetrafluro-benzamidomethyl-copoly-(styrene-1%-divinylbenzene)-resins (0.024 g, 0.012 mmol), prepared as described above. The resins are swelled with DMF, then treated with a 0.01 M solution of an amine (1 ml, 0.01 mmol) in DMF. The containers are covered with aluminum foil and agitated for 72 h. The progress of the reaction is monitored by TLC; for sluggish reactions 1,5,7-triazabicyclo[4.4.0]dec-5-ene resin is added. The reaction mixtures are individually filtered and the resins washed with methanol. The filtrates are concentrated with a stream of nitrogen. The residues are redissolved in methanol and reconcentrated twice more. The resulting residues are treated with 20% trifluoroacetic acid in methylene chloride (1 ml) and agitated overnight. The reaction mixture is concentrated by a steam of nitrogen. Methylene choride (1 ml) is added; concentrate with a steam of nitrogen. Methanol (1 ml) is added; concentrate with a stream of nitrogen. The final residues are analyzed by LC/mass spec; evidence of desired product was obtained in each case. By way of example, the product from the reaction of 6-chlorobenzothiophene-2-sulfonyl)oxy-2,3,5,6-tetrafluro-benzamidomethyl-copoly-(styrene-1%-(divinylbenzene)-resin with 2-(3-(S)-amino-2-oxopyrrolidin-1-ylmethyl)-pyrrolo[3,2-b]pyridine-1-carboxylic acid tert-butyl ester and subsequent deprotection with 20% TFA in methylene chloride showed: M+H=461. This material had an $IC_{50}$ against Factor Xa of less than 500 nM.

By the methods described in this preparation 2-(3-(S)-amino-2-oxopyrrolidin-1-ylmethyl)-pyrrolo[3,2-b]pyridine-1-carboxylic acid tert-butyl ester, 2-(3-(S)-amino-2-oxopyrrolidin-1-ylmethyl)-pyrrolo[3,2-c]pyridine-1-carboxylic acid tert-butyl ester and 2-(3-(S)-amino-2-oxopyrrolidin-1-ylmethyl)-pyrrolo[2,3-c]pyridine-1-carboxylic acid tert-butyl ester are reacted with fourteen arylsulfonyloxy-2,3,5,6-tetrafluro-benzamidomethyl-copoly-(styrene-1%-divinylbenzene)-resins to obtain, after deprotection, compounds encompassed by the following formula:

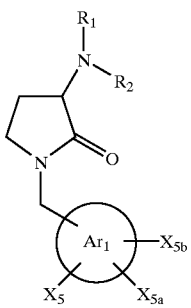

wherein

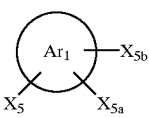

is selected from:

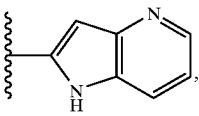

$R_1$ is H; and $R_2$ is selected from the group of formulae consisting of:

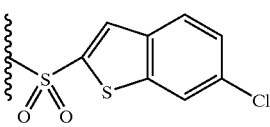 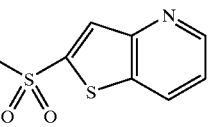

LCMS: M + H = 461    LCMS: M + H = 428

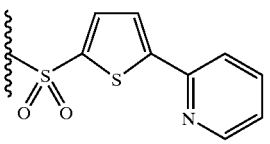

LCMS: M + H = 454

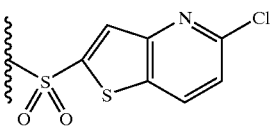 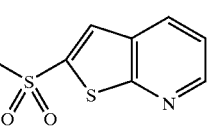

LCMS: M + H = 462    LCMS: M + H = 428

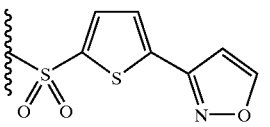

LCMS: M + H = 444

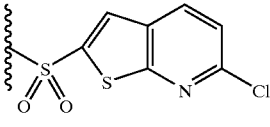

LCMS: M + H = 462

-continued
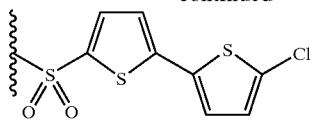
LCMS: M + H = 493
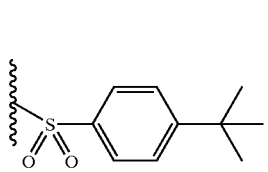
LCMS: M + H = 427
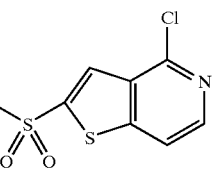
LCMS: M + H = 462
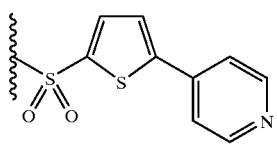
LCMS: M + H = 454
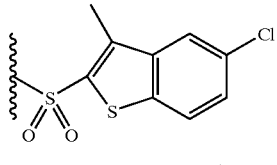
LCMS: M + H = 475
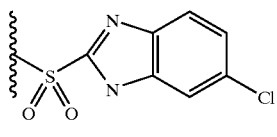
LCMS: M + H = 462
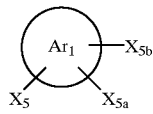
LCMS: M + H = 445
or
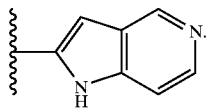
is selected from:
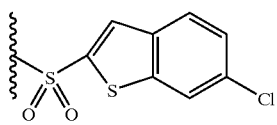
LCMS: M + H = 461
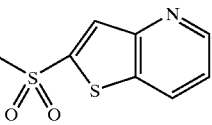
LCMS: M + H = 428
-continued
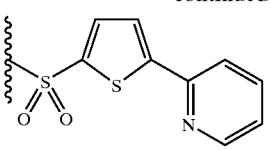
LCMS: M + H = 454
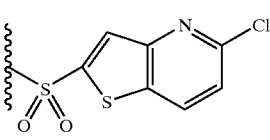
LCMS: M + H = 462
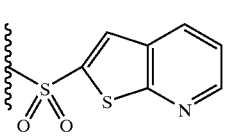
LCMS: M + H = 428
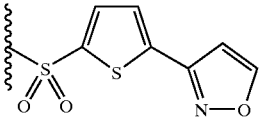
LCMS: M + H = 444
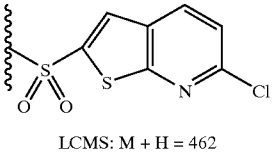
LCMS: M + H = 462
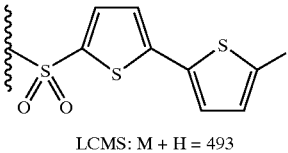
LCMS: M + H = 493
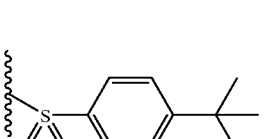
LCMS: M + H = 427
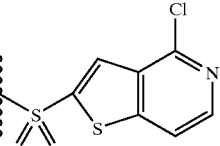
LCMS: M + H = 462
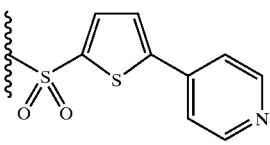
LCMS: M + H = 454
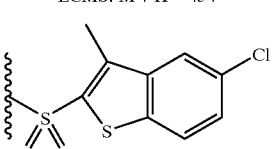
LCMS: M + H = 475
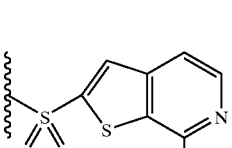
LCMS: M + H = 462
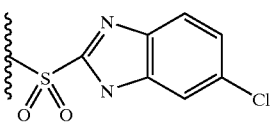
LCMS: M + H = 445
$R_1$ is H; and $R_2$ is selected from the group of formulae consisting of:

or
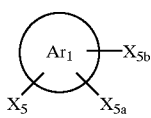
is selected from:
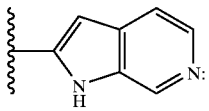
$R_1$ is H; and $R_2$ is selected from the group of formulae consisting of:
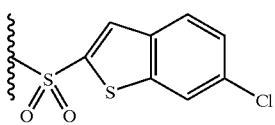
LCMS: M + H = 461
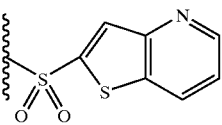
LCMS: M + H = 428
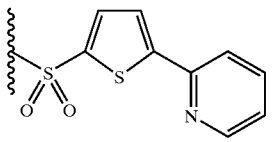
LCMS: M + H = 454
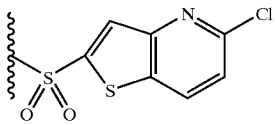
LCMS: M + H = 462
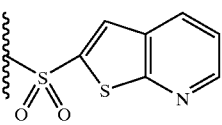
LCMS: M + H = 428
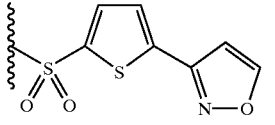
LCMS: M + H = 444
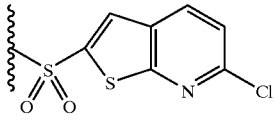
LCMS: M + H = 462
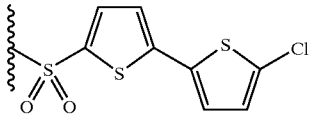
LCMS: M + H = 493
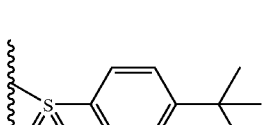
LCMS: M + H = 427
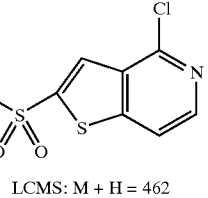
LCMS: M + H = 462
-continued
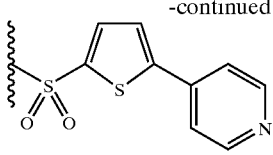
LCMS: M + H = 454
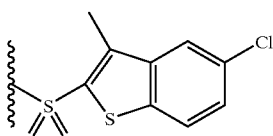
LCMS: M + H = 475
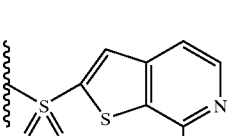
LCMS: M + H = 462
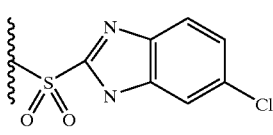
LCMS: M + H = 445
By the methods described herein compounds encompassed by the following formula:
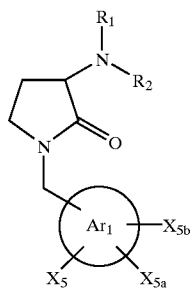
wherein
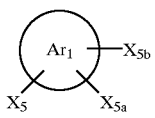
is selected from:
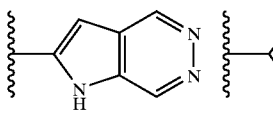
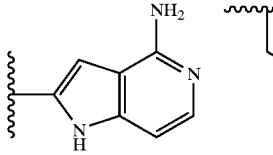
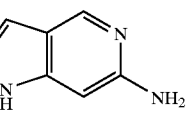
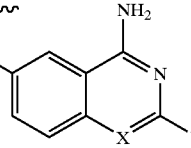
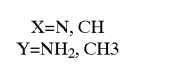
X=N, CH
Y=NH$_2$, CH3

R1 is H; and R2 is selected from the group of formulae consisting of:

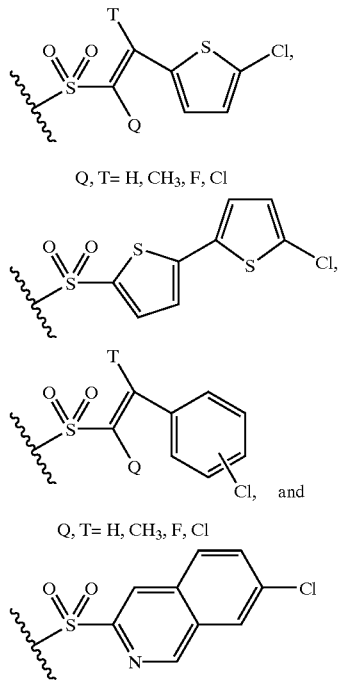

are also prepared.

The molecules described herein inhibit blood coagulation by virtue of their ability to inhibit the penultimate enzyme in the coagulation cascade, controlling the activity of Factor Xa. Both the activity of free Factor Xa and Factor Xa assembled in the prothrombinase complex (Factor Xa, Factor Va, calcium and phospholipid) are inhibited by compounds of formula I. The inhibition of the Factor Xa activity is obtained by direct complex formation between the inhibitor and the enzyme and is therefore independent of the plasma co-factor antithrombin III. Effective inhibition of the Factor Xa activity is achieved by administering the compounds either by oral administration, continuous intravenous infusion, bolus intravenous administration or any other parenteral route such that it achieves the desired effect of preventing the activity of Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of inhibitors of the activity of Factor Xa with standard heparin, low molecular weight heparin, direct thrombin inhibitors (i.e. hirudin), aspirin, fibrinogen receptor antagonists, streptokinase, urokinase and/or tissue plasminogen activator may result in greater antithrombotic or thrombolytic efficacy or efficiency. The compounds described herein may be administered to treat thrombotic complications in a variety of animals such as primates including humans. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

In addition to their use in anticoagulant therapy, inhibitors of Factor Xa activity may find utility in the treatment or prevention of other physiological conditions in which the generation of thrombin has been implicated as playing a pathologic role. For example, thrombin has been proposed to contribute to the morbidity and mortality of such chronic and degenerative diseases as arthritis, cancer, atherosclerosis, restenosis post coronary angioplasty and Alzheimer's disease by virtue of its ability to regulate many different cell types through specific cleavage and activation of a cell surface thrombin receptor. Inhibition of factor Xa activity will effectively block thrombin generation and therefore neutralize any pathologic effects of thrombin on various cell types.

According to a further feature of the invention there is provided a method for the treatment of a human or animal patient suffering from, or subject to, a physiological condition which can be ameliorated by the administration of an inhibitor of the Factor Xa activity, for example conditions as hereinbefore described, which comprises the administration to the patient of a therapeutically effective amount of compound of formula I or a composition containing a compound of formula I. "Effective amount" is meant to describe an amount of compound of the present invention effective in inhibiting the activity of Factor Xa and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

Enzyme Assays:

The ability of the compounds in the present invention to act as inhibitors of factor Xa, thrombin, trypsin, tissue-plasminogen activator (t-PA), urokinase-plasminogen activator (ti-PA), plasmin and activated protein C is evaluated by determining the concentration of inhibitor which resulted in a 50% loss in enzyme activity ($IC_{50}$) using purified enzymes.

All enzyme assays are carried out at room temperature in 96-well microtiter plates using a final enzyme concentration of 1 nM. The concentrations of factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity ($IC_{50}$). The apparent Ki values are then determined according to the Cheng-Prusoff equation (IC50= Ki [1+[S]/Km]) assuming competitive inhibition kinetics.

By way of example, 7-methoxynaphthalene-2-sulfonic acid [1-(1,6-diaminoisoquinolin-7-ylmethyl)-2-oxopyrrolidin-3-(S)-yl]amide trifluoroacetate has a Ki value of 80 nM.

An additional in vitro assay may be used to evaluate the potency of compounds according to the invention in normal human plasma. The activated partial thromboplastin time is a plasma-based clotting assay that relies on the in situ generation of factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for its in vivo anticoagulant activity.

Human Plasma Based Clotting Assay:

Activated partial thromboplastin clotting times are determined in duplicate on a MLA Electra 800 instrument. A volume of 100 ml of citrated normal human pooled plasma (George King Biomedical) is added to a cuvette containing 100 ml of a compound according to the invention in Tris/NaCl buffer (pH 7.5) and placed in the instrument. Following a 3 minute warming period the instrument automatically adds 100 ml of activated cephaloplastin reagent (Actin, Dade) followed by 100 ml of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

A compound according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental in Vivo Rabbit Venous Thrombosis Model:

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Holst, B. Lindblad, D. Bergqvist, O. Nordfang, P. B. Ostergaard, J. G. L. Petersen, G. Nielsen and U. Hedner. *Thrombosis and Haemostasis*, 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with 35 mg/kg of ketamine and 5 mg/kg xylazine in a volume of 1 ml/kg (i.m.). The right jugular vein is cannulated for infusion of anesthetic (ketamine/xylazine 17/2.5 mg/kg/hr at a rate of approximately 0.5 ml/hr) and administration of test substances. The right carotid artery is cannulated for recording arterial blood pressure and collecting blood samples. Body temperature is maintained at 39_C with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 ml of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 ml ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental in Vivo Rat Arterial Thrombosis Model:

The antithrombotic efficacy of factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. *Journal of Cardiovascular Pharmacology*, 22, 526–533 (1993); Rat Model of Arterial Thrombosis Induced by Ferric Chloride, K. D. Kurtz, B. W. Main, and G. E. Sandusky. *Thrombosis Research*, 60, 269–280 (1990); The Effect of Thrombin Inhibition in a Rat Arterial Thrombosis Model, R. J. Broersma, L. W. Kutcher and E. F. Heminger. *Thrombosis Research* 64, 405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead 11 is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95–1 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 ml of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 ml/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of formula I

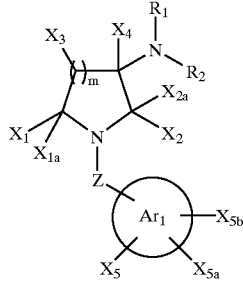

(I)

is isoquinoline;

Z is alkylenyl;

$R_1$ is hydrogen, unsubstituted or substituted alkyl, unsubstituted or substituted aralkyl, unsubstituted or substituted heteroaralkyl, $R'O(CH_2)_x$—, $R'O_2C(CH_2)_x$—, $Y^1Y^2NC(O)(CH_2)_x$—, or $Y^1Y^2N(CH_2)_x$—;

R' is hydrogen, unsubstituted or substituted alkyl, unsubstituted or substituted aralkyl or unsubstituted or substituted heteroaralkyl;

$R_2$ is $R_3S(O)_p$— or $R_3R_4NS(O)_p$—;

$R_3$ is unsubstituted or substituted alkyl, unsubstituted or substituted cycloalkyl, unsubstituted or substituted heterocyclyl, unsubstituted or substituted aryl, unsubstituted or substituted heteroaryl, unsubstituted or substituted aralkyl, unsubstituted or substituted heteroaralkyl, unsubstituted or substituted aralkenyl or unsubstituted or substituted heteroaralkenyl, or $R_1$ and $R_3$ taken together with the —N—S(O)$_p$— moiety or the —N—S(O)$_p$—NR$_4$— moiety through which $R_1$ and $R_3$ are linked form a 5 to 7 membered unsubstituted or substituted heterocyclyl; and $R_4$ is unsubstituted or substituted alkyl, unsubstituted or substituted cycloalkyl or unsubstituted or substituted aryl, unsubstituted or substituted heteroaryl, unsubstituted or substituted aralkyl or unsubstituted or substituted heteroaralkyl, or $R_3$ and $R_4$ taken together with the nitrogen to which $R_3$ and $R_4$ are attached form an unsubstituted or substituted 4 to 7 membered heterocyclyl;

$X_1$ and $X_{1a}$ are independently selected from H, unsubstituted or substituted alkyl, unsubstituted or substituted aryl, unsubstituted or substituted aralkyl, unsubstituted or substituted heteroaryl or unsubstituted or substituted heteroaralkyl, or $X_1$ and $X_{1a}$ taken together form oxo;

$X_2$ and $X_{2a}$ are H, or taken together form oxo;

$X_3$ is H, hydroxy, unsubstituted or substituted alkyl, unsubstituted or substituted aryl, unsubstituted or substituted heteroaryl, unsubstituted or substituted aralkyl or unsubstituted or substituted heteroaralkyl, or $X_3$ and one of $X_1$ and $X_{1a}$ taken together form a 4 to 7 membered cycloalkyl;

$X_4$ is H, unsubstituted or substituted alkyl, unsubstituted or substituted aralkyl, or hydroxyalkyl;

$X_5$, $X_{5a}$ and $X_{5b}$ are independently selected from H, $R_5H6N$—, (hydroxy, alkoxy or amino)HN—, $R_7O$—, $R_5R_6NCO$—, $R_5R_6NSO_2$—, $R_7CO$—, halo, cyano, nitro or $R_8(O)C(CH_2)_q$—, and one of $X_5$, $X_{5a}$ and $X_{5b}$ is H, hydroxy or (H, unsubstituted or substituted lower alkyl, hydroxy, alkoxy or amino)HN— that substitutes said isoquinoline ring at a position alpha to the nitrogen;

$Y^1$ and $Y^2$ are independently hydrogen, unsubstituted or substituted alkyl, unsubstituted or substituted aryl, unsubstituted or substituted aralkyl or unsubstituted or substituted heteroaralkyl, or $Y^1$ and $Y^2$ taken together with the N through which $Y^1$ and $Y^2$ are linked form a 4 to 7 membered heterocyclyl;

$R_5$ and $R_6$ are independently H or unsubstituted or substituted lower alkyl, or one of $R_5$ and $R_6$ is H and the other of $R_5$ and $R_6$ is $R_8(O)CCH_2$— or lower acyl;

$R_7$ is H, unsubstituted or substituted lower alkyl, lower acyl or $R_8(O)CCH_2$—;

$R_8$ is H, unsubstituted or substituted lower alkyl, alkoxy or hydroxy;

m is 0, 1, 2 or 3; p is 1 or 2; q is 0 or 1, and x is 1, 2, 3, 4, or 5, or a pharmaceutically acceptable salt thereof, an N-oxide thereof, a hydrate thereof or a solvate thereof.

2. The compound of claim 1 wherein $R_1$ is H, unsubstituted or substituted heteroaralkyl, unsubstituted or substituted aralkyl or unsubstituted or substituted alkyl.

3. The compound of claim 1 wherein $R_2$ is $R_3S(O)_p$—.

4. The compound of claim 3 wherein p is 2.

5. The compound of claim 3 wherein $R_3$ is unsubstituted or substituted phenyl, unsubstituted or substituted naphthyl, unsubstituted or substituted thienyl, unsubstituted or substituted benzothienyl, unsubstituted or substituted thienyopyridyl, unsubstituted or substituted quinolinyl, or unsubstituted or substituted isoquinolinyl.

6. The compound of claim 1 wherein Z is methylenyl, and m is 1.

7. The compound of claim 1 wherein $X_2$ and $X_{2a}$ taken together are oxo.

8. The compound of claim 1 wherein $X_1$, $X_{1a}$, $X_3$ and $X_4$ are H.

9. The compound of claim 1 wherein the isoquinolinyl is attached to Z at the 7-position thereof.

10. The compound of claim 1 wherein one of $X_5$, $X_{5a}$ and $X_{5b}$ is H, hydroxy or amino that is substituted on the proximal ring of

at a position that is adjacent to the position of the proximal ring to which Z is attached.

11. The compound of claim 10 wherein one of $X_5$, $X_{5a}$ and $X_{5b}$ is hydroxy or amino.

12. The compound of claim 1 wherein one of $X_5$, $X_{5a}$ and $X_{5b}$ that substitutes the distal ring of

at the position alpha to a nitrogen thereof is H or H(H, unsubstituted or substituted loweralkyl, hydroxy or amino) N—.

13. A compound according to claim 1 which is
7-Methoxynaphthalene-2-sulfonic acid [1-(1-aminoisoquinolin-7-yl-methyl)-2-oxopyrrolidin-3-(S)-yl]amide trifluoroacetate.

14. A compound according to claim 1 which is
7-Methoxynaphthalene-2-sulfonic acid [1-(1-aminoisoquinolin-7-yl-methyl)-2-oxopyrrolidin-3-(R)-yl]amide trifluoroacetate.

15. A compound according to claim 1 which is
7-Methoxynaphthalene-2-sulfonic acid-[1-(1-aminoisoquinolin-7-yl-methyl)-2-oxopyrrolidin-3-(S)-yl]methylamide trifluoroacetate.

16. A compound according to claim 1 which is
Benzo[b]thiophene-2-sulfonic acid [1-(1-aminoisoquinolin-7-yl-methyl)-2-oxopyrrolidin-3-(S)-yl]amide trifluoroacetate.

17. A compound according to claim 1 which is
6-Chloro-benzo[b]thiophene-2-sulfonic acid [1-(1-aminoisoquinolin-7-yl-methyl)-2-oxopyrrolidin-3-(S)-y]amide trifluoroacetate.

18. A compound according to claim 1 which is
7-Methoxynaphthalene-2-sulfonic acid-[1-(1,6-diaminoisoquinolin-7-yl-methyl)-2-oxopyrrolidin-3-(S)-yl]amide trifluoroacetate.

19. A compound according to claim 1 which is
6-Chloro-benzo[b]thiophene-2-sulfonic acid[1-(1,6-diaminoisoquinolin-7-yl-methyl)-2-oxopyrrolidin-3-(S)-yl]amide trifluoroacetate.

20. A compound according to claim 1 which is
5-Pyridin-4-yl-thiophene-2-sulfonic acid-[1-(1-aminoisoquinolin-7-yl-methyl)-2-oxopyrrolidin-3-(S)-yl]-amide trifluoroacetate.

21. A compound according to claim 1 which is
5-Pyridin-3-yl-thiophene-2-sulfonic acid-[1-(1-aminoisoquinolin-7-yl-methyl)-2-oxopyrrolidin-3-(S)-yl]-amide trifluoroacetate.

22. A compound according to claim 1 which is
7-Methoxynaphthalene-2-sulfonic acid [1-(1-aminoisoquinolin-7-yl-methyl)-2-oxopyrrolidin-3-(R,S)-yl]amide trifluoroacetate;

7-Methoxynaphthalene-2-sulfonic acid [1-(1-aminoisoquinolin-7-yl-methyl)-2-oxopyrrolidin-3-(S)-yl]amide hydrochloride;

7-Methoxynaphthalene-2-sulfonic acid [1-(1-aminoisoquinolin-7-yl-methyl)-2-oxopyrrolidin-3-(S)-yl]amide trifluoroacetate;

7-Methoxynaphthalene-2-sulfonic acid [1-(1-aminoisoquinolin-7-yl-methyl)-2-oxopyrrolidin-3-(R)-yl]amide trifluoroacetate;

7-Methoxynaphthalene-2-sulfonic acid [1-(1-hydroxyisoquinolin-7-yl-methyl)-2-oxopyrrolidin-3-(R,S)-yl]amide;

7-Methoxynaphthalene-2-sulfonic acid [1-(1-aminoisoquinolin-7-yl-methyl)-2-oxopyrrolidin-3-(R,S)-yl]methylamide trifluoroacetate;

7-Methoxynaphthalene-2-sulfonic acid [1-(1-aminoisoquinolin-7-yl-methyl)-2-oxopyrrolidin-3-(S)-yl]methyl amide trifluoroacetate;

Benzo[b]thiophene-2-sulfonic acid [1-(1-aminoisoquinolin-7-yl-methyl)-2-oxopyrrolidin-3-(S)-yl]amide trifluoroacetate;

6-Chloro-benzo[b]thiophene-2-sulfonic acid [1-(1-aminoisoquinolin-7-yl-methyl)-2-oxopyrrolidin-3-(S)-yl]amide trifluoroacetate;

7-Methoxynaphthalene-2-sulfonic acid [1-(1-amino-6-methylisoquinoline-7-yl-methyl)-2-oxo-pyrrolidin-3-(S)-yl]amide hydrochloride;

7-Methoxynaphthalene-2-sulfonic acid [1-(6-methylisoquinoline-7-yl-methyl)-2-oxopyrrolidin-3-(S)-yl]amide trifluoroacetate;

4-(2-Chloro-6-nitophenoxy) benzene sulfonic acid [1-(1-amino-6-methoxyisoquinolin-7-yl-methyl)-2-oxopyrrolidin-3-(S)-yl]amide trifluoroacetate;

7-Methoxynaphthalene-2-sulfonic acid [1-(1,6-diaminoisoquinolin-7-yl-methyl)-2-oxopyrrolidin-3-(S)-yl]amide trifluoroacetate;

6-Chloro-benzo[b]thiophene-2-sulfonic acid [1-(1,6-diaminoisoquinolin-7-yl-methyl)-2-oxo pyrrolidin-3-(S)-yl]amide trifluoroacetate;

5-Pyridin-4-yl-thiophene-2-sulfonic acid-[1-(1-aminoisoquinolin-7-yl-methyl)-2-oxopyrrolidin-3-(S)-yl]-amide trifluoroacetate;

5-Pyridin-3-yl-thiophene-2-sulfonic acid-[1-(1-aminoisoquinolin-7-yl-methyl)-2-oxopyrrolidin-3-(S)-yl]-amide trifluoroacetate;

6-Chloro-benzo[b]thiophene-2-sulfonic acid [1-(1-aminoisoquinolin-6-yl-methyl)-2-oxopyrrolidin-3-(S)-yl]-amide trifluoroacetate;

Thieno[3,2-b]pyridine-2-sulfonic acid [1-(1-aminoisoquinolin-7-yl-methyl)-2-oxopyrrolidin-3-(S)-yl]-amide;

Thieno[2,3-b]pyridine-2-sulfonic acid [1-(1-aminoisoquinolin-7-yl-methyl)-2-oxopyrrolidin-3-(S)-yl]-amide;

4-Pyridin-3-yl-thiophene-2-sulfonic acid [1-(1-aminoisoquinolin-7-yl-methyl)-2-oxopyrrolidin-3-(S)-yl]-amide;

5'-Chloro-[2,2']bithiophenyl-5-sulfonic acid [1-(1-aminoisoquinolin-7-yl-methyl)-2-oxopyrrolidin-3-(S)-yl]-amide; or 2-(5-Chloro-thiophen-2-yl)-ethenesulfonic acid [1-(1-aminoisoquinolin-7-yl-methyl)-2-oxopyrrolidin-3-(S)-yl]-amide.

23. A compound according to claim 1 which is Thieno[3,2-b]pyridine-2-sulfonic acid [1-(1-amino-isoquinolin-7-yl-methyl)-2-oxopyrrolidin-3-(S)-yl]-amide.

24. A compound according to claim 1 of the formula

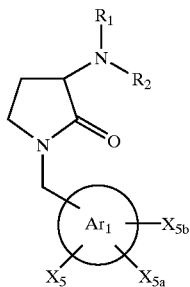

wherein

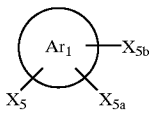

is

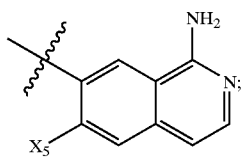

and $R_2$ is selected from the group of formulae consisting of

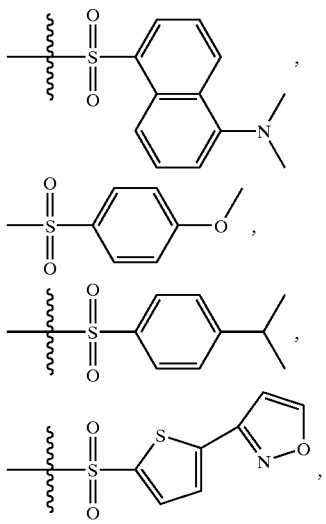

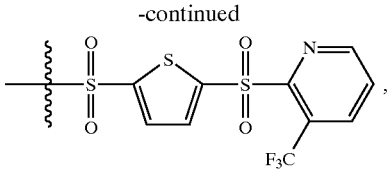

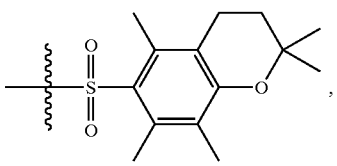

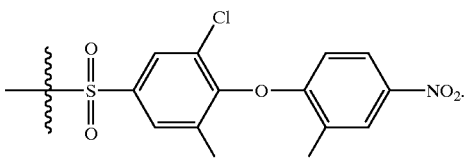

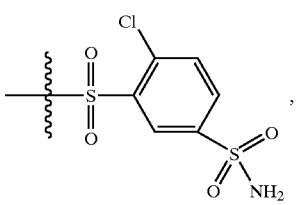

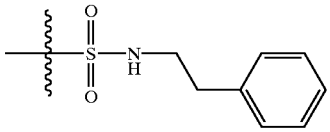

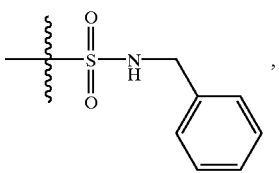

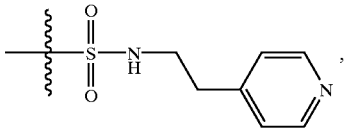

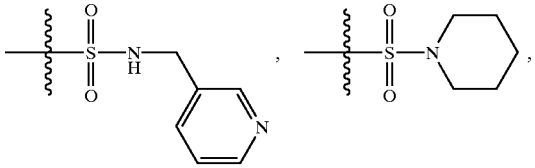

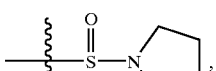

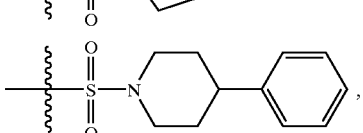

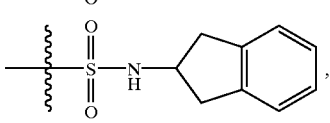

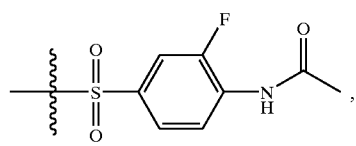
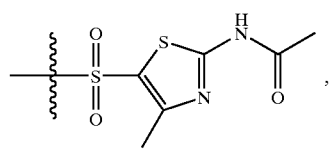
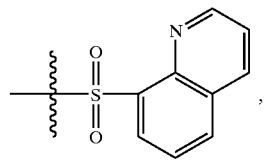
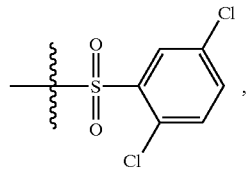
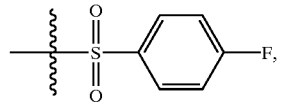
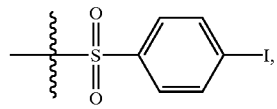
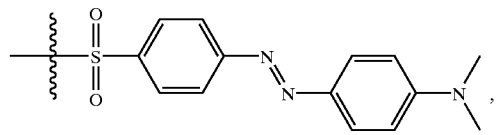
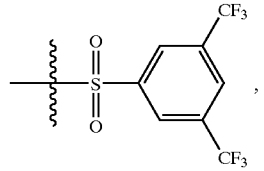
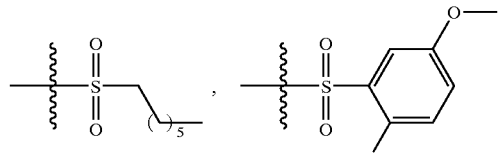
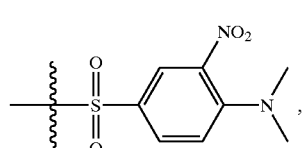
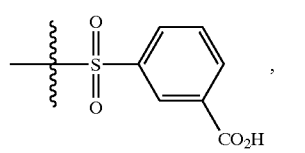
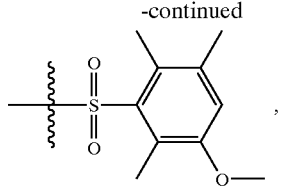
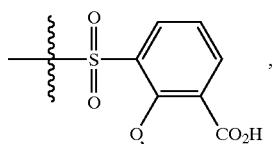
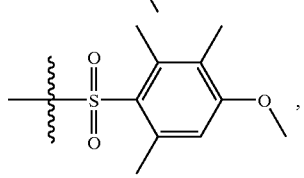
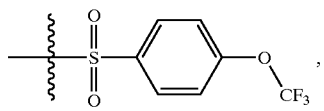
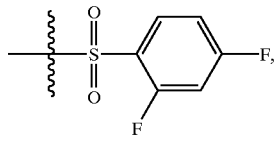
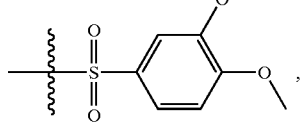
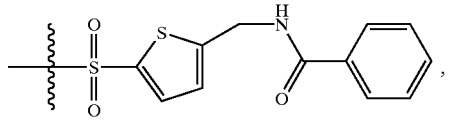
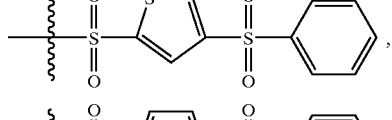
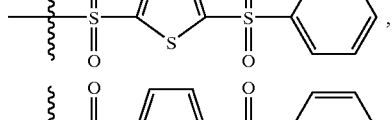
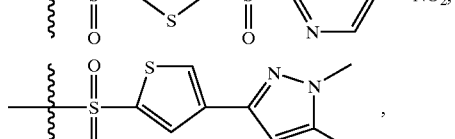
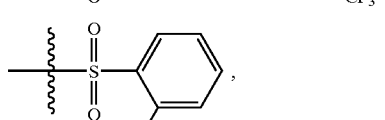
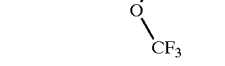

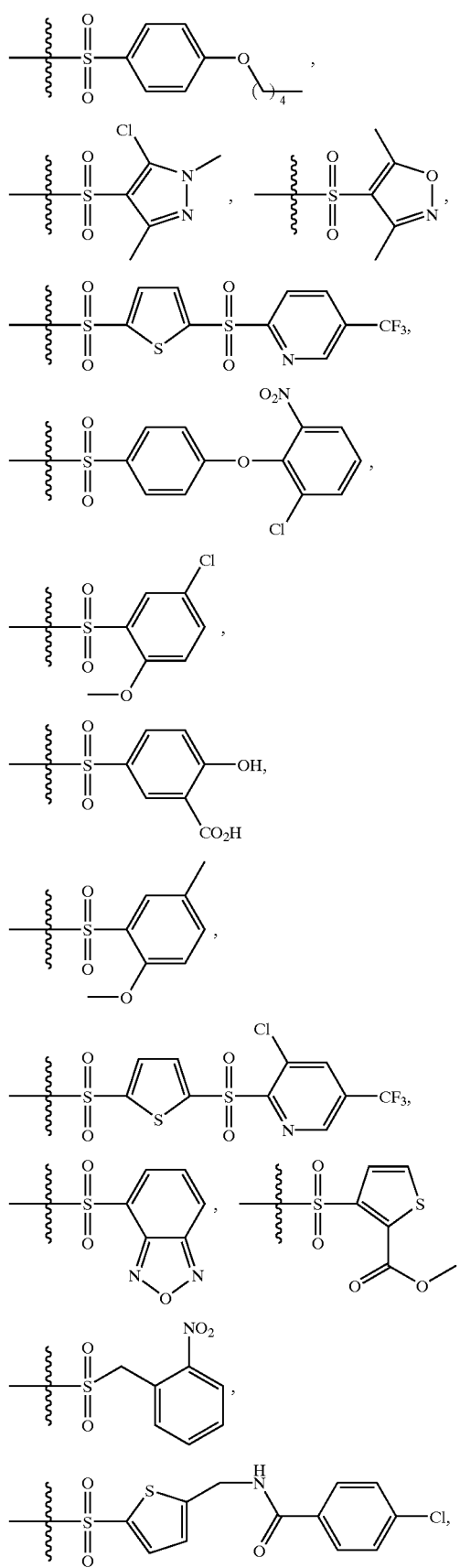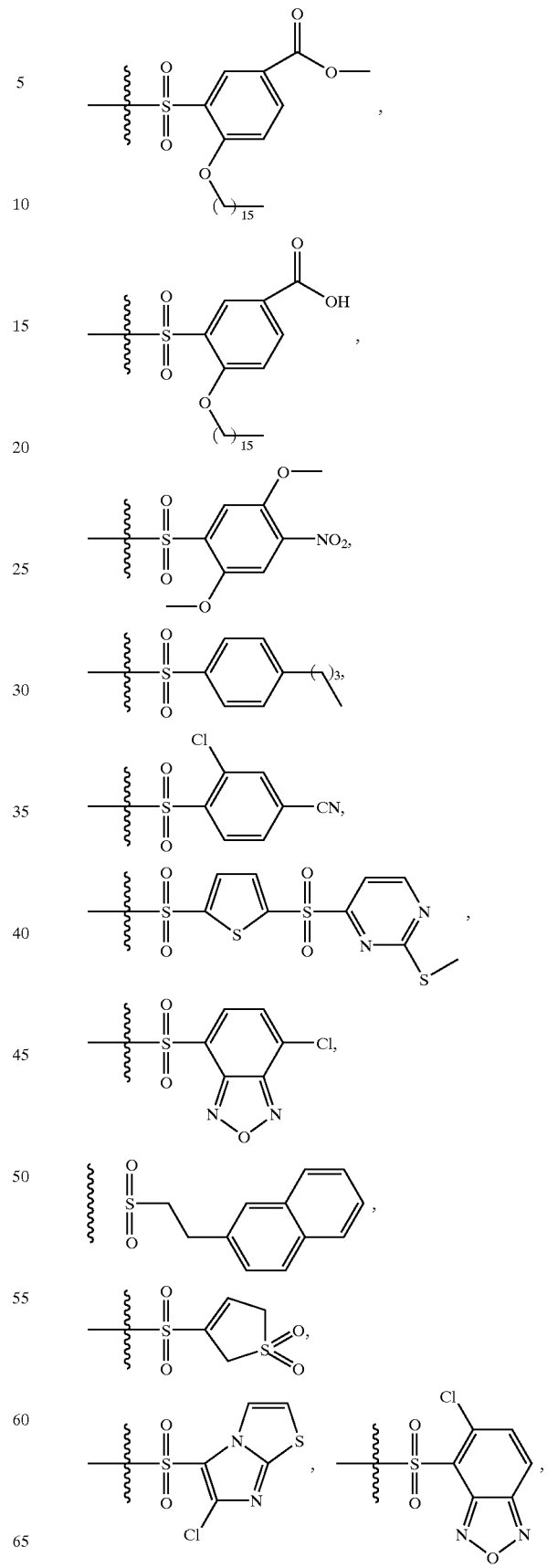

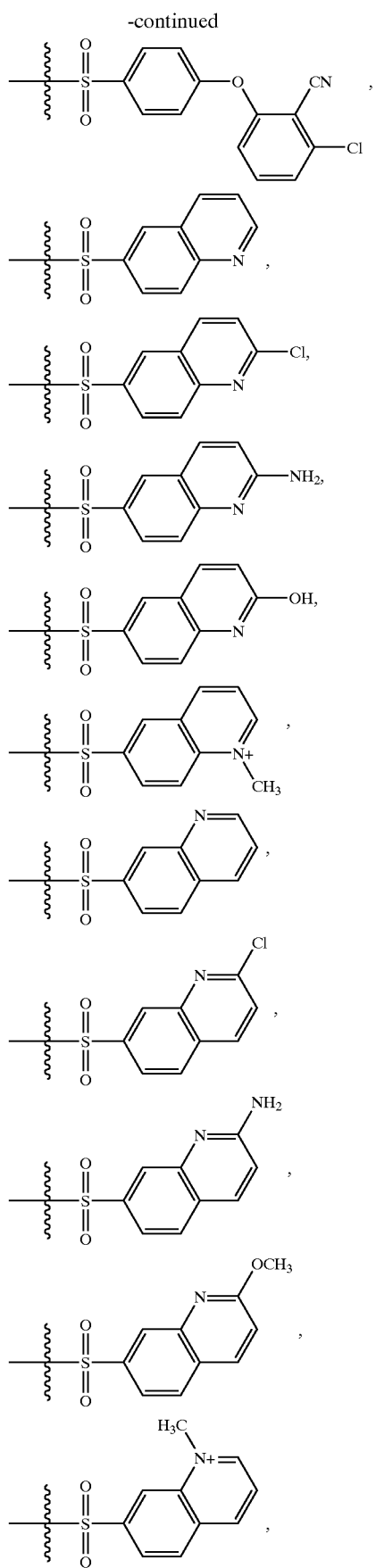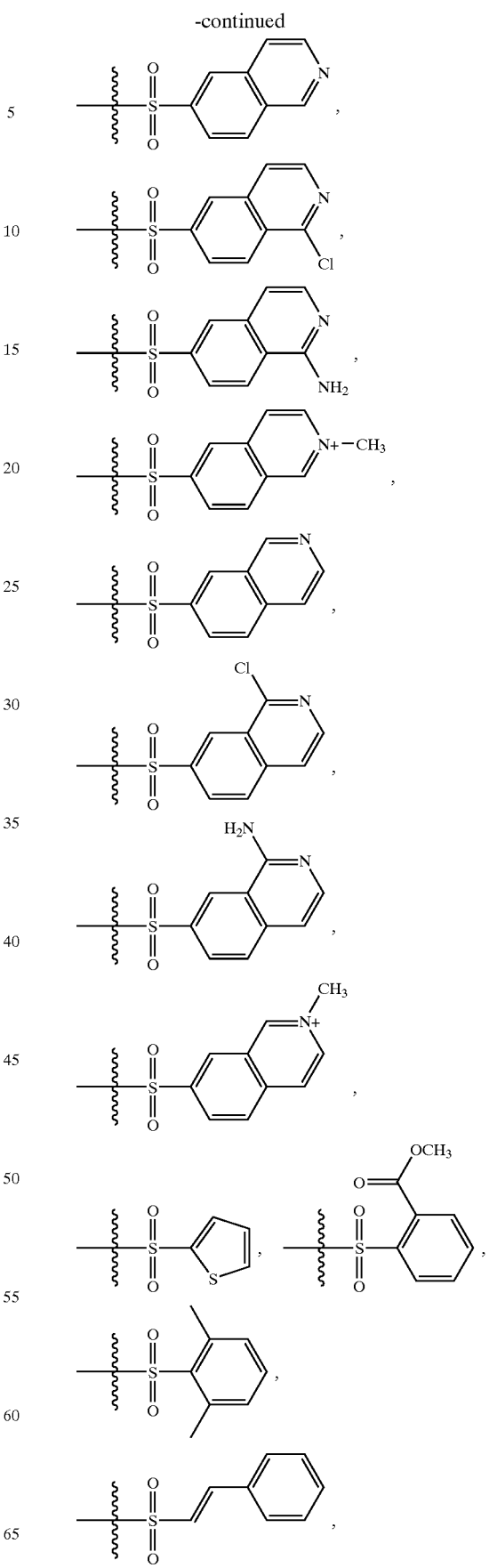

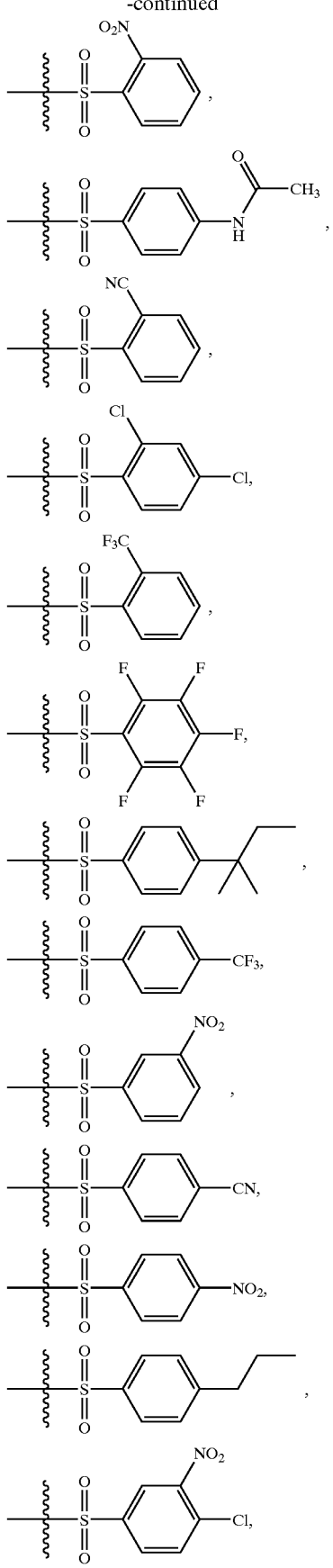
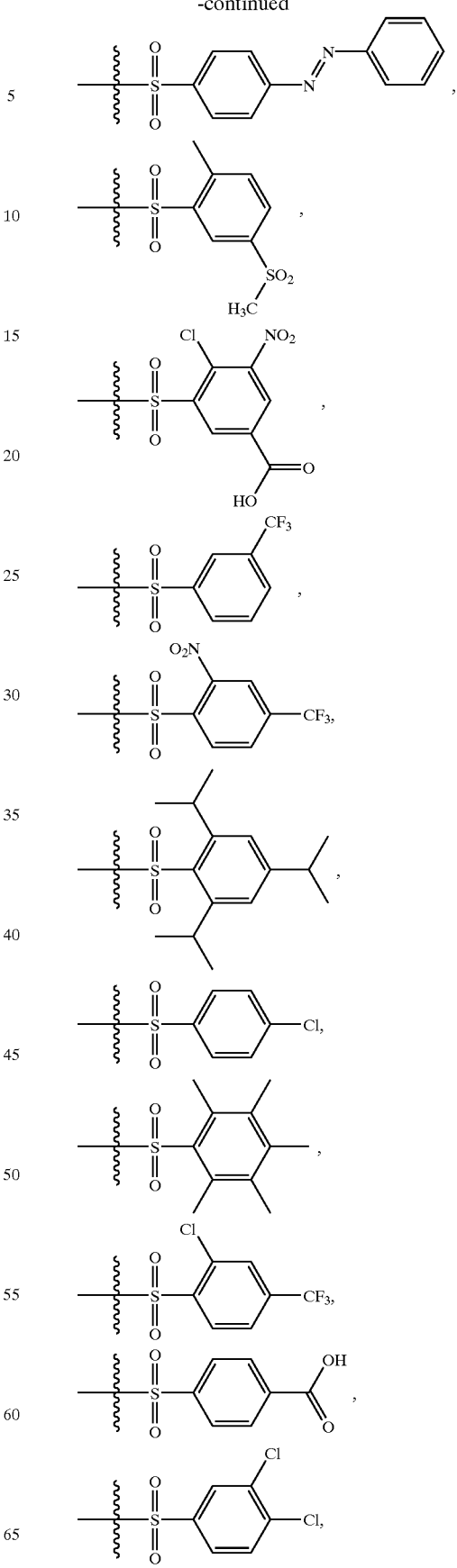

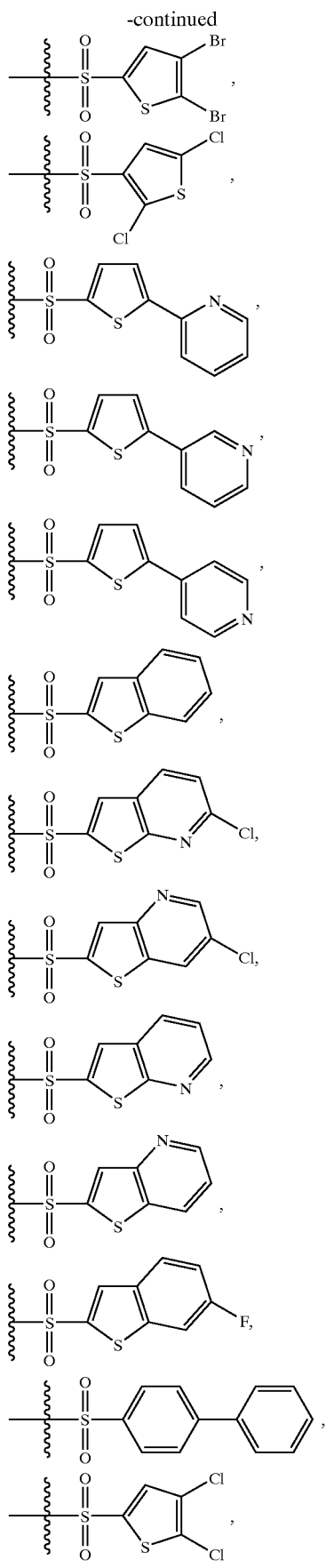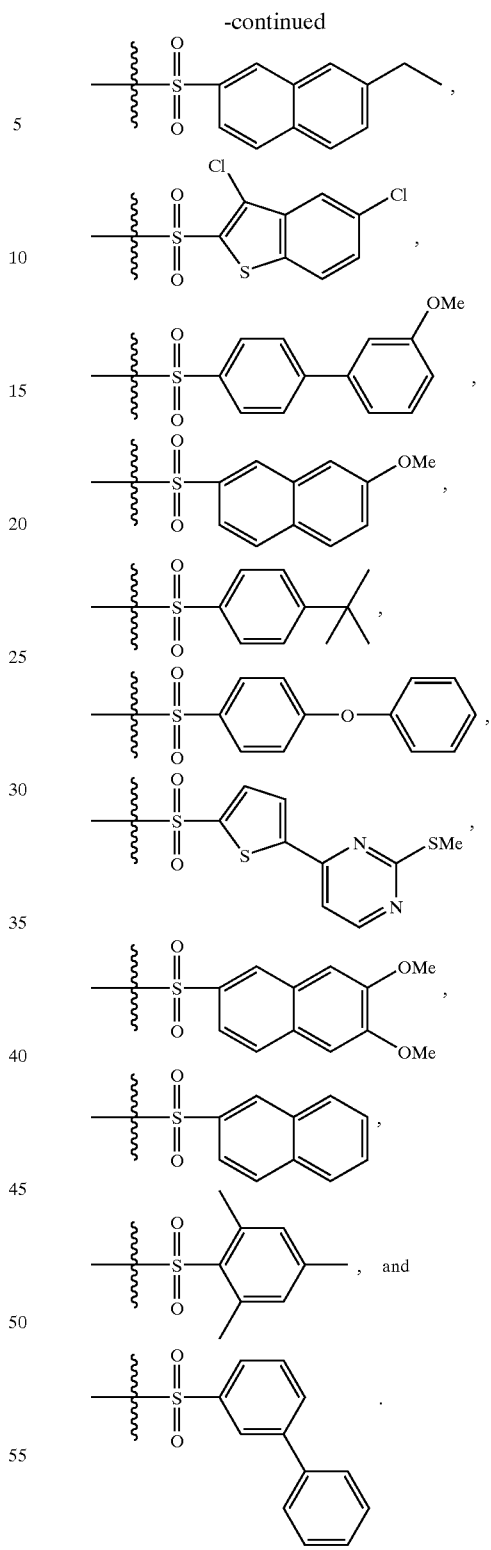

25. A pharmaceutical composition comprising a pharmaceutically acceptable amount of the compound according to claim 1 and a pharmaceutically acceptable carrier.

26. A method for treating a patient suffering from a physiological disorder which involves arterial or venous thrombosis, said method comprising the step of administering to said patient a therapeutically-effective amount of a compound according to claim 1.

27. The method according to claim 26 wherein said physiological disorder is: acute myocardial infarction; unstable angina; thromboembolism; acute vessel closure associated with thrombolytic therapy and percutaneous transluminal coronary angioplasty; transient ischemic attacks, stroke; intermittent claudication and bypass grafting of the coronary or peripheral arteries; vessel luminal narrowing that occurs following percutaneous transluminal coronary angioplasty and intermittent claudication and bypass grafting, deep vein thrombosis; or disseminated intravascular coagulopathy.

28. The method according to claim 26 wherein said physiology disorder is: stroke; vessel luminal narrowing that occurs following percutaneous transluminal coronary or venous angioplasty or intermittent claudication and bypass grafting; or disseminated intravasular coagulopathy.

29. A method for maintaining vascular access patency in long-term hemodialysis patients, said method comprising the step of administering said patient a therapeutically-effective amount of a compound according to claim 1.

30. A compound of formula:

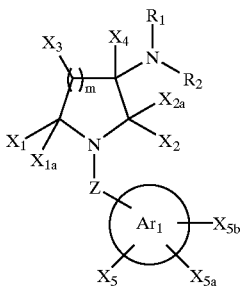

is isoquinoline;
Z is methylenyl;
$R_1$ is hydrogen;
$R_2$ is $R_3S(O)_p$—;
$R_3$ is unsubstituted or substituted (1–12C) alkyl, wherein the substitutes may be selected from a group consisting of (3–10C) cycloalkyl, (1–6C) alkoxy, OH, COOH, or halogen, unsubstituted or substituted (3–10C) cycloalkyl, wherein the substituent may be halogen, or unsubstituted or substituted (6–10C) aryl, wherein the substitutes may be selected from a group consisting of (1–6C) alkyl, (1–6C) alkoxy, OH, COOH, or halogen;
$X_1$ and $X_{1a}$ are H;
$X_2$ and $X_{2a}$ are taken together form oxo;
$X_3$ is H;
$X_4$ is H;
$X_5$, $X_{5a}$ and $X_{5b}$ are H, $R_5R_6N$—, and one of $X_5$, $X_{5a}$ and $X_{5b}$ is $H_2N$— that substitutes said isoquinoline ring at a position alpha to the nitrogen, the other two are H;
$R_5$ and $R_6$ are H;
m is 1; p is 2.

31. A compound of formula:

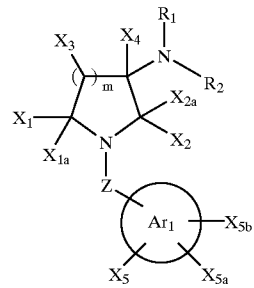

is isoquinoline,
Z is methylenyl;
$R_1$ is hydrogen;
$R_2$ is $R_3S(O)_p$—;
$R_3$ is unsubstituted or substituted phenyl or naphthyl, wherein the substitutes may be selected from a group consisting of (1–6C) alkyl, (1–6C) alkoxy, OH, COOH, or halogen;
$X_1$ and $X_{1a}$ are H;
$X_2$ and $X_{2a}$ are taken together form oxo;
$X_3$ is H;
$X_4$ is H;
$X_5$ $X_{5a}$ and $X_{1b}$ are H, $R_5R_6N$—, and one of $X_5$, $X_{5a}$ and $X_{5b}$ is $H_2N$— that substitutes said isoquinoline ring at a position alpha to the nitrogen, the other two are H;
$R_5$ and $R_6$ are H;
m is 1; p is 2.

32. A pharmaceutical composition comprising a pharmaceutically acceptable amount of the compound according to claim 30 or 31, and a pharmaceutically acceptable carrier.

33. A method for treating a patient suffering from acute myocardial infraction, stroke or deep vein thrombosis, said method comprising the step of administering to said patient a therapeutically effective amount of a compound according to claim 30 or 31.

* * * * *